US008846054B2

(12) United States Patent
Rinehart et al.

(10) Patent No.: US 8,846,054 B2
(45) Date of Patent: Sep. 30, 2014

(54) METHOD OF TREATING PREGNANT COWS AND/OR HEIFERS

(75) Inventors: Carol L. Rinehart, Saint Joseph, MO (US); Craig Jones, Saint Joseph, MO (US); Judy Myers-Kuhnhoff, Weatherby Lake, MO (US); Wayne Cole, Saint Joseph, MO (US); William Charles Ohnesorge, Saint Joseph, MO (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days.

(21) Appl. No.: 12/351,088

(22) Filed: Jan. 9, 2009

(65) Prior Publication Data

US 2010/0178301 A1 Jul. 15, 2010

(51) Int. Cl.

| | |
|---|---|
| ***A61K 39/295*** | (2006.01) |
| ***A61K 39/12*** | (2006.01) |
| ***A61K 39/102*** | (2006.01) |
| ***A61K 39/265*** | (2006.01) |
| *A61K 39/00* | (2006.01) |

(52) U.S. Cl.

CPC ....... *A61K 39/12* (2013.01); *C12N 2770/24334* (2013.01); *A61K 2039/5256* (2013.01); *A61K 2039/55* (2013.01); *A61K 39/265* (2013.01); *C12N 2760/18334* (2013.01); *C12N 2760/18634* (2013.01); *A61K 2039/5254* (2013.01); *A61K 2039/70* (2013.01); *A61K 2039/552* (2013.01); *C12N 2770/24361* (2013.01)

USPC .................................... 424/201.1; 424/202.1

(58) Field of Classification Search

None

See application file for complete search history.

(56) References Cited

U.S. PATENT DOCUMENTS

| | | | | |
|---|---|---|---|---|
| 4,719,177 | A | 1/1988 | Baltimore et al. | |
| 5,206,163 | A | 4/1993 | Renard et al. | |
| 6,001,613 | A | 12/1999 | Donis et al. | |
| 6,168,942 | B1 | 1/2001 | Cao et al. | |
| 6,610,305 | B1 | 8/2003 | Elbers et al. | |
| 7,135,561 | B2 | 11/2006 | Elbers et al. | |
| 7,179,473 | B2 | 2/2007 | Meyers | |
| 7,572,455 | B2 | 8/2009 | Meyers et al. | |
| 7,858,099 | B2 | 12/2010 | Meyers | |
| 2003/0044426 | A1 | 3/2003 | Meyers | |
| 2003/0147914 | A1 * | 8/2003 | Keich et al. | 424/201.1 |
| 2003/0165520 | A1 | 9/2003 | Cao et al. | |
| 2004/0038198 | A1 | 2/2004 | Elbers et al. | |
| 2004/0081666 | A1 | 4/2004 | Dominowski | |
| 2004/0146854 | A1 | 7/2004 | Cao et al. | |
| 2004/0185056 | A1 | 9/2004 | Jones | |
| 2004/0208901 | A1 * | 10/2004 | Ellsworth et al. | 424/229.1 |
| 2005/0002966 | A1 | 1/2005 | Meyers | |
| 2005/0053621 | A1 | 3/2005 | Welch et al. | |
| 2005/0287171 | A1 | 12/2005 | Meyers et al. | |
| 2006/0024320 | A1 | 2/2006 | Meyers | |
| 2007/0015203 | A1 | 1/2007 | Elbers et al. | |
| 2009/0004216 | A1 | 1/2009 | Meyers | |
| 2009/0068223 | A1 | 3/2009 | Meyers et al. | |
| 2009/0226488 | A1 | 9/2009 | Meyers et al. | |
| 2010/0178301 | A1 * | 7/2010 | Rinehart et al. | 424/201.1 |
| 2011/0117126 | A1 | 5/2011 | Meyers et al. | |

FOREIGN PATENT DOCUMENTS

| | | | |
|---|---|---|---|
| CA | 2363493 | A1 | 5/2002 |
| EP | 0794257 | A1 | 9/1997 |
| EP | 0982402A | A1 | 3/2000 |
| EP | 1013757 | A2 | 6/2000 |
| WO | 9964604 | A2 | 12/1999 |
| WO | 0139801 | A2 | 6/2001 |
| WO | 03023041 | A2 | 3/2003 |
| WO | 2005111201 | A1 | 11/2005 |
| WO | 2007117303 | A2 | 10/2007 |
| WO | 2009156448 | A1 | 12/2009 |

OTHER PUBLICATIONS

Kovacs et al, Veterinary Microbiology, 2003, vol. 96, pp. 117-131.*
Neill et al. (Virus Research. 2001: 59-69).*
Fulton et al. (Vaccine. 2001: 264-274).*
McClurkin et al. (Archiv für die gesamte Virusforschung. 1974; 45: 285-289).*
Platt et al. (Vaccine. May 27, 2009; 27: 4508-4519).*
Meyers et al., "Classical Swine Fever Virus: Recovery of Infectious Viruses from cDNA Constructs and Generation of Recombinant Cytopathogenic Defective Interfering Particles". Journal of Virology, vol. 70, No. 3, Mar. 1996, pp. 1588-1595.
Meyers et al., "Molecular Characterization of Pestiviruses". Advances in Virus Resarch, vol. 47, 1996, pp. 53-118.
Meyers et al., "Molecular Cloning and Nucleotide Sequence of the Genome of Hog Cholera Virus". Virology, vol. 171, 1989, pp. 555-567.
Meyers et al., "Mutations Abrogating the RNase Activity in Glycoprotein Ems of the Pestivirus Clasical Swine Fever Virus Lead to Virus Attenuation". Journal of Virology, vol. 73, No. 12, Dec. 1999, pp. 10224-10235.
Meyers et al., "Recovery of Cytopathogenic and Noncytopathogenic Bovine Viral Diarrhea Viruses from cDNA Constructs". Journal of Virology, vol. 70, No. 12, Dec. 1996, pp. 8606-8613.
Moennig et al., "The Pestiviruses". Advances in Virus Research, vol. 41, 1992, pp. 53-98.
Moormann et al., "Infectious RNA Transcribed from an Engineered Full-Length cDNA Template of the Genome of a Pestivirus". Journal of Virology, vol. 70, No. 2, Feb. 1996, pp. 763-770.
Moser et al., "A Recombinant Classical Swine Fever Virus Stably Expresses a Marker Gene". Journal of Virology, vol. 72, No. 6, Jun. 1998, pp. 5318-5322.
Murphy et al., "Flaviviridae". Veterinary Virology, Third Edition, Academic Press, San Diego, CA, 1999, pp. 564-566.
Odeon et al., "Experimental infection of calves with bovine viral diarrhea virus genotype II (NY-93)". Journal of Veterinary Diagnostic Investigation, vol. 11, 1999, pp. 221-228.

(Continued)

*Primary Examiner* — Shanon A Foley

(74) *Attorney, Agent, or Firm* — Michael P. Morris; Wendy M. Gombert

(57) ABSTRACT

The present invention relates to combination vaccines for the prophylaxis and treatment of microbiological infections in cattle which comprise an attenuated bovine viral diarrhea virus (BVDV) for the prophylaxis and treatment of BVDV caused infections. The invention also relates to a method of vaccinating a pregnant cow.

13 Claims, No Drawings

(56) References Cited

OTHER PUBLICATIONS

Paoletti et al., "Highly attenuated poxvirus vectors: NYVAC, ALVAC and TROVAC". Developments in Biological Standardization, vol. 84, 1995, pp. 159-163.
Paton et al., "Epitope Mapping of the gp53 Envelope Protein of Bovine Viral Diarrhea Virus". Virology, vol. 190, 1992, pp. 763-772.
Pellerin et al., "Identification of a New Group of Bovine Viral Diarrhea Virus Strains Associated with Severe Outbreaks and High Mortalities". Virology, vol. 203, 1994, pp. 260-268.
Racaniello et al., "Cloned Poliovirus Complementary DNA Is Infectious in Mammalian Cells". Science, vol. 214, Nov. 1981, pp. 916-919.
Ramig, R.F., "Principles of Animal Virus Genetics". in Fundamental Virology, Second Edition, Raven Press, New York, New York 1991, pp. 96-122.
Rice et al., "Transcription of infectious yellow fever RNA from full-length cDNA templates produced by in vitro ligation". The New Biologist, vol. 1, No. 3, Dec. 1989, pp. 285-296.
Rice, Charles M., "Flaviviridae: The Viruses and Their Replication " in Fields Virology (3rd Edition), Lippincott-Raven Publishers, Philadelphia, PA, 1996, pp. 931-959.
Ridpath et al., "The Genomic Sequence of a Virulent Bovine Viral Diarrhea Virus (BVDV) from the Type 2 Genotype: Detection of a Large Genomic Insertion in a Noncytopathic BVDV". Virology, vol. 212, No. 1, Sep. 1995, pp. 39-46.
Ruggli et al., "Nucleotide Sequence of Classical Swine Fever Virus Strain Alfort/187 and Transription of Infectious RNA from Stably Cloned Full-Length cDNA".Journal of Virology, vol. 70, No. 6, Jun. 1996, pp. 3478-3487.
Rümenapf et al., "N-Terminal Protease of Pestiviruses: Identification of Putative Catalytic Residues by Site-Directed Mutagenesis" Journal of Virology, vol. 72, No. 3, Mar. 1998, pp. 2544-2547.
Rümenapf et al., "Processing of the Envelope Glycoproteins of Pestiviruses". Journal of Virology, vol. 67, No. 6, Jun. 1993, pp. 3288-3294.
Schaefer et al., "Revolutions in Rapid Amplification of cDNA Ends: New Strategies for Polymerase Chain Reaction Cloning of Full-Length cDNA Ends". Analytical Biochemistry, vol. 277, 1995, pp. 255-273.
Schneider et al., "Identifitication of a Structural Glycoprotein of an RNA Virus as a Ribonuclease". Science, vol. 261, Aug. 1993, pp. 1169-1171.
Sequence Alignment Provided of SEQ ID No. 1 with GenEmbl database accession No. BVU18059, submitted Dec. 7, 1995.
Stark et al., "Processing of Pestivirus Polyprotein: Cleavage Site between Autoprotease and Nucleocapsid Protein of Classical Swine Fever Virus". Journal of Virology, vol. 67, No. 12, Dec. 1993, pp. 7088-7095.
Stedman's Medical Dictionary. 27th Edition, Internet edition. Definition of "Vaccine". http://www.pdrel.com/pdr/static.htm?path=pdrel/stedmans/v/s43000.htm., Accessed on Aug. 14, 2002.
Stoffregen et al., "Morphologic lesions in type 2 BVDV infections experimentally induced by strain BVDV2-1373 recovered from a field case". Veterinary Microbiology, vol. 77, 2000, pp. 157-162.
Sumiyoshi et al., "Infectious Japanese Encephalitis Virus RNA Can Be Synthesized from In Vitro-Ligated cDNA Templates". Journal of Virology, vol. 66, No. 9, Sep. 1992, pp. 5425-5431.
Thiel et al., "Hog Cholera Virus: Molecular Composition of Virions from a Pestivirus". Journal of Virology, vol. 65, No. 9, Sep. 1991, pp. 4705-4712.
Thiel et al., "Pestiviruses" in Fields Virology (3rd Edition), Lippincott-Raven Publishers, Philadelphia, PA, 1996, pp. 1059-1073.
Tijssen et al., "Immunodominant E2 (gp53) Sequences of Highly Virulent Bovine Viral Diarrhea Group II Viruses Indicate a Close resemblance to a Subgroup of Border Disease Viruses". Virology, vol. 217, 1996, pp. 356-361.
Topliff et al., "Virulence Markers in the 5' Untranslated Region of Genotype 2 Bovine Viral Diarrhea Virus Isolates". Virology, vol. 250, 1998, pp. 164-172.
Tratschin et al., "Classical Swine Fever Virus Leader Proteinase NPRO Is Not Required for Viral Replication in Cell Culture". Journal of Virology, vol. 72, No. 9, Sep. 1998, pp. 7681-7684.
Van Der Poel et al., "Experimental Reproduction of Respiratory Disease in Calves with Non-Cell-Culture-Passaged Bovine Respiratory Syncytial Virus". The Veterinary Quarterly, vol. 18, No. 3, Sep. 1996, pp. 81-86.
Van Gennip et al., "Experimental non-transmissible marker vaccines for classical swine fever (CSF) by trans-complementation of Ems or E2 of CSFV". Vaccine, vol. 20, Nos. 11-12, Feb. 2002, pp. 1544-1556.
Van Gennip, et al., "Dimerisation of glycoprotein Ems of classical swine fever virus is not essential for viral replication and infection". Archives of Virology, vol. 150, 2005, pp. 2271-2286.
Van Gennip, et al., "Recovery of infectious classical swine fever virus (CSFV) from full-length genomic cDNA clones by a swine kidney cell line expressing bacteriophage T7 RNA polymerase". Journal of Virological Methods, vol. 78, 1999, pp. 117-128.
Van Oirschot et al., "Vaccination of cattle against bovine viral diarrhoea". Veterinary Microbiology, vol. 64, 1999, pp. 169-183.
Van Rijn et al., "Epitope mapping of envelope glycoprotein El of hog cholera virus strain Brescia". Journal of General Virology, vol. 74, 1993, pp. 2053-2060.
Vassilev et al., "Authentic and Chimeric Full-Length Genomic cDNA Clones of Bovine Viral Diarrhea Virus That Yield Infectious Transcripts". Journal of Virology, vol. 71, No. 1, Jan. 1997, pp. 471-478.
Walker et al., "Deoxyribonucleic Acid Relatedness Among "*Haemophilus somnus*," "*Haemophilus agni*," "*Histophilus ovis*," "*Actinobacillus seminis*," and *Haemophilus influenzae*". Jan. 1985, International Journal of Systematic Bacteriology, vol. 35, No. 1, pp. 46-49.
Weiland et al., "A Second Envelope Glycoprotein Mediates Neutralization of a Pestivirus, Hog Cholera Virus". Journal of Virology, vol. 66, No. 6, Jun. 1992, pp. 3677-3682.
Weiland et al., "Development of monoclonal neutralizing antibodies against bovine viral diarrhea virus after pretreatment of mice with normal bovine cells and cyclophosphamide". Journal of Virological Methods, vol. 24, 1989, pp. 237-244.
Weiland et al., "Pestivirus Glycoprotein Which Induces Neutralizing Antibodies Forms Part of a Disulfide-Linked Heterodimer". Journal of Virology, vol. 64, No. 8, Aug. 1990, pp. 3563-3569.
Windisch et al., "RNase of Classical Swine Fever Virus: Biochemical Characterization and Inhibition by Virus-Neutralizing Monoclonal Antibodies". Journal of Virology, vol. 70, No. 1, Jan. 1996, pp. 352-358.
Yu et al., "Genetic engineering of a *Lymantria dispar* nuclear polyhedrosis virus for expression of foreign genes". Journal of General Virology, vol. 73, 1992, pp. 1509-1514.
Avalos-Ramirez, et al., "Evidence for the Presence of Two Novel Pestivirus Species". Virology, vol. 286, 2001, pp. 456-465.
Baker et al., "Bovine viral diarrhea virus: A review". Journal of the American Veterinary Medical Association, vol. 190, No. 11, Jun. 1987, pp. 1449-1458.
Becher et al., "Further Characterization of Border Disease Virus Isolates: Evidence for the Presence of More than Three Species within the Genus Pestivirus". Virology, vol. 209, 1995, pp. 200-206.
Becher et al., "Phylogenetic analysis of pestiviruses from domestic and wild ruminants". Journal of General Virology, vol. 78, 1997, pp. 1357-1366.
Beer et al., "A new inactivated BVDV genotype I and II vaccine: An immunisation and challenge study with BVDV genotype I". Veterinary Microbiology, vol. 77, 2000, pp. 195-208.
Behrens et al., "Characterization of an Autonomous Subgenomic Pestivirus RNA Replicon". Journal of Virology, vol. 72, No. 3, Mar. 1998, pp. 2364-2372.
Bolin et al., "Assessment of protection from systemic infection or disease afforded by low to intermediate titers of passively acquired neutralizing antibody against bovine viral diarrhea virus in calves". American Journal of Veterinary Research, vol. 56, 1995, pp. 755-759.
Bolin, S. R., "Control of Bovine Viral Diarrhea Infection by Use of Vaccination". Veterinary Clinics of North America: Food Animal Practice, vol. 11, No. 3, Nov. 1995, pp. 615-625.

(56) References Cited

OTHER PUBLICATIONS

Bowie et al., "Deciphering the Message in Protein Sequences: Tolerance to Amino Acid Substitutions". Science, vol. 247, 1990, pp. 1306-1310.
Boyer et al., "Infectious Transcripts and cDNA Clones of RNA Viruses". Virology, vol. 198, 1994, pp. 415-426.
Brock et al., "Nucleotide sequencing of 5' and 3' termini of bovine viral diarrhea virus by RNA ligation and PCR". Journal of Virological Methods, vol. 38, 1992, pp. 39-46.
Carman et al., "Sever acute bovine viral diarrhea in Ontario, 1993-1995". Journal of Veterinary Diagnostic Investigation, vol. 10, 1998, pp. 27-35.
Chambers et al., "Mutagenesis of the Yellow Fever Virus NS2B Protein: Effects on Proteolytic Processing, NS2B-NS3 Complex Formation, and Viral Replication". Journal of Virology, vol. 67, No. 11, Nov. 1993, pp. 6797-6807.
Chon et al., "Genetic Analysis of the Internal Ribosome Entry Segment of Bovine Viral Diarrhea Virus". Virology, vol. 251, 1998, pp. 370-382.
Chong et al., "Modulation of Protein Splicing of the *Saccharomyces cerevisiae* Vacuolar Membrane ATPase Intein*". Apr. 1998, The Journal of Biological Chemistry, vol. 272, No. 17, pp. 10567-10577.
Collett et al., "Molecular Cloning and Nucleotide Sequence of the Pestivirus Bovine Viral Diarrhea Virus". Virology, vol. 165, 1988, pp. 191-199.
Collett et al., "Proteins Encoded by Bovine Viral Diarrhea Virus: The Genomic Organization of a Pestivirus". Virology, vol. 165, 1988, pp. 200-208.
Constans et al., "Recent developments in RT-PCR technology move reverse transcription in the right direction". The Scientist-Reverse Psychology, vol. 14[17]: Sep. 29, 2000, pp. 1-4.
Cortese et al., "Clinical and immunologic responses of vaccinated and unvaccinated calves to infection with a virulent type-II isolate of bovine viral diarrhea virus". Journal of the American Veterinary Medical Association, vol. 213, No. 9, Nov. 1998, pp. 1312-1319.
Cortese et al., "Specificity and Duration of Neutralizing Antibodies Induced in Healthy Cattle After Administration of a Modified-Live Virus Vaccine Against Bovine Viral Diarrhea". American Journal of Veterinary Research, vol. 59, 1998, pp. 848-850.
Database EMBL 'Online! retrieved from EMBL Database accession No. AF145967 XP002251610.
De Smit et al., "Duration of the protection of an E2 subunit marker vaccine against classical swine fever after a single vaccination". Veterinary Microbiology, vol. 78, 2001, pp. 307-317.
Donis et al., "Neutralizing Monoclonal Antibodies to Bovine Viral Diarrhoea Virus Bind to the 56k to 58k Glycoprotein". Journal of General Virology, vol. 69, 1988, pp. 77-86.
Fekadu et al., "Immunogenicity, efficacy and safety of an oral rabies vaccine (SAG-2) in dogs". Vaccine, vol. 14, No. 6, 1996, pp. 465-468.
Fuerst et al., "Eukaryotic transient-expression system based on recombinant vaccinia virus that synthesizes bacteriophage T7 RNA polymerase". Nov. 1986, Proceedings of the National Academy of Sciences, vol. 83, pp. 8122-8126.
Fulton et al., "Bovine viral diarrhea virus types 1 and 2 antibody response in calves receiving modified live virus or inactivated vaccines". Vaccine, vol. 19, 2001, pp. 264-274.
Grebennikova et al., "Genetic Characteristics of Hog Cholera Virus Vaccine Strains: Comparative Analysis of Primary Sequences of Surface Glycoprotein Ems, E1 and E2 Genes". Mol. Gen. Mikrobiol. Virusol., vol. 2, Jan. 1999, pp. 34-40. (See Abstract at p. 40).
Greenspan et al., "Defining epitopes: It's not as easy as it seems". Nature Biotechnology, vol. 17, Oct. 1999, pp. 936-937.
Gu et al., "The RNA Helicase and Nucleotide Triphosphatase Activities of the Bovine Viral Diarrhea Virus NS3 Protein Are Essential for Viral Replication". Journal of Virology, vol. 74, No. 4, Feb. 2000, pp. 1794-1800.
Heinz, et al., "Family Flaviviridae". 2000, Virus Taxonomy: Classification and Nomenclature of Viruses, Academic Press, San Diego, pp. 859-878.
Houe et al., "Application of antibody titers against bovine viral diarrhea virus (BVDV) as a measure to detect herds with cattle persistently infected with BVDV", Journal of Veterinary Diagnostic Investigation, vol. 7, 1995, pp. 327-332.
Huang, et al., "An in vitro ligation and transfection system for inserting DNA sequences into the latency-associated transcripts (LATs) gene of herpes simplex virus type 1". Gene Therapy, vol. 1, 1994, pp. 300-306.
Hulst et al., "Glycoprotein E2 of Classical Swine Fever Virus: Expression in Insect Cells and Identification as a Ribonuclease". Virology, vol. 200, 1994, pp. 558-565.
Hulst et al., "Inactivation of the RNase Activity of Glycoprotein Ems of Classical Swine Fever Virus Results in a Cytopathogenic Virus". Journal of Virology, vol. 72, No. 1, Jan. 1998, pp. 151-157.
International Search Report and Written Opinion for PCT/EP2002/09925 mailed on Sep. 12, 2003.
International Search Report and Written Opinion for PCT/EP2005/005377 mailed Sep. 12, 2005.
International Search Report and Written Opinion for PCT/US2006/60918 mailed Nov. 19, 2007.
International Search Report for PCT/EP1999/03642 mailed Jul. 12, 1999.
Kit et al., "Sensitive glycoprotein gill blocking ELISA to distinguish between pseudorabies (Aujeszky's disease)—infected and vaccinated pigs". Veterinary Microbiology, vol. 28, 1991, pp. 141-155.
Kunkel et al., "Rapid and Efficient Site-Specific Mutagenesis without Phenotypic Selection". 1987, Methods of Enzymology, vol. 154, pp. 367-392.
Kupfermann et al., "Bovine Viral Diarrhea Virus: Characterization of a Cytopathogenic Defective Interfering Particle with Two Internal Deletions". Journal of Virology, vol. 70, No. 11, Nov. 1996, pp. 8175-8181.
Kümmerer et al., "Correlation between Point Mutations in NS2 and the Viability and Cytopathogenicity of Bovine Viral Diarrhea Virus Strain Oregon Analysed with and Infectious cDNA Clone". Journal of Virology, vol. 74, No. 1, Jan. 2000, pp. 390-400.
Lai et al., "Infectious RNA transcribed from stably cloned full-length cDNA of dengue type 4 virus". Proceedings of the National Academy of Sciences of the United States of America, vol. 8, Jun. 1991, pp. 5139-5143.
Lindenbach et al., "Flaviviridae: The Viruses and Their Replication". 2001, Fields Virology, Fourth Edition, Lippincott Williams & Wilkins, Philadelphia, pp. 991-1041.
Mayer et al., "Attenuation of classical swine fever virus by deletion of the viral Npro gene". Vaccine, vol. 22, Nos. 3-4, Jan. 2004, pp. 317-328.
Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys". Journal of Virology, vol. 70, No. 6, Jun. 1996, pp. 3930-3937.
Mendez et al., "Infectious Bovine Viral Diarrhea Virus (Strain NADL) RNA from Stable cDNA Clones: a Cellular Insert Determines NS3 pruduction and Viral Cytopathogenicity". Journal of Virology, vol. 72, No. 6, Jun. 1998, pp. 4737-4745.
Meyer et al., "Recovery of Virulent and RNase-Negative Attenuated Type 2 Bovine Viral Diarrhea Viruses from Infectious cDNA Clones". Journal of Virology, vol. 76, No. 16, Aug. 2002, pp. 8494-8503.
Meyers et al. "Rabbit Hemorrhagic Disease Virus: Genome Organization and Polyprotein Processing of a Calicivirus Studied after Transient Expression of cDNA Constructs". 2000, Virology, vol. 276, pp. 349-363.
Meyers et al., "Bovine Viral Diarrhea Virus: Prevention of Persistent Fetal Infection by a Combination of Two Mutations Affecting Erns RNase and Npro Protease". Journal of Virology, vol. 81, No. 7, Apr. 2007, pp. 3327-3338.
Langedijk et al., "A Structural Model of Pestivirus Erns Based on Disulfide Bond Connectivity and Homology Modeling Reveals an Extremely Rare Vicinal Disulfide". Journal of Virology, vol. 76, No. 20, 2002, pp. 10383-10392.
Hulst et al., "[35] Erns Protein of Pestiviruses". Methods in Enzymology, vol. 342, Ch. 35, Erns Ribonuclease, 2001, pp. 431-440.

* cited by examiner

SEQUENCE LISTING

<160> NUMBER OF SEQ ID NOS: 5

<210> SEQ ID NO 1
<211> LENGTH: 12665
<212> TYPE: DNA
<213> ORGANISM: Bovine Viral Diarrhea Virus Type I

<400> SEQUENCE: 1
gtatacgagt actttagcta atctcgtata cagattggac gttgacaaaa tattgaattg 60
aaaatgtagg gaatcttccc ctcagcgaag gccgaaaaga ggctaaccac gcccttagta 120
ggactagcaa aaggaggga ctagcggtag cagtgagttc attggatggc cgaacccctg 180
agtacagggg agtcgtcaat ggttcgacac tccttcagtt gaggagtctc gagatgccat 240
gtggacgagg gcatgcccac ggcacatctt aacccatgcg gggctgcat gggtgaaagc 300
gccattcgtg gcgttatgga cacagcctga tagggtgtag cagagacctg ctatcccgct 360
agtaaaaaaa ctctgctgta catggcacat ggagttgttt tcaaatgaac ttttatacaa 420
aacatataaa caaaaaccag aaggtgttgt ggaacctgtt tacgacatca acgggtgtcc 480
attgtttgga gagagcagcg acgtacaccc acaatccaca ctaaaactac cacacctacg 540
aggcagcggt gacatcctga ccaatgctag gtccctgccg cgtaaaggtg actgccggaa 600
aggcaacgca aatggagcgg tgagtggtat ctatatcaaa ccaggaccga tttactatca 660
ggattatgtg gggcccgtct atcatagagc cccactggaa ctatgtagag aggcaagcat 720
gtgtgaaact actaggagag ttggcagagt gaccggtagt aacgggaaat tataccacat 780
ctatatttgc atagacgggt gtatcctcct aaagagggcg actaggaacc aaccagaagt 840
cctcaaatgg gtatacaaca gattaaattg cccattgtgg gtcaccagct gctccggtga 900
agagagtaag ggtgctacaa gcaagaagca acctaagcca gataggatag aaaaaggcaa 960
gatgaaaata gcccctaaag agacagaaaa agattgcaaa accagacccc cggatgcaac 1020
cgtagtagta gaaggggtta agtaccaggt gaagaagaag ggaaaagtaa ggggaaaaaa 1080
tactcaagac gggttgtatc acaataagaa taagcccct gaatcaagaa agaaattgga 1140
gaaggcactg ctagcgtggg ccatcttagc agcggttctg cttcagctgg taacgggaga 1200
gaacattacc cagtggaact tgatggacaa cggcaccgaa ggtatacagc aarctatgtt 1260
cctgagaggg gtgaacagga gtctacatgg aatttggccc gagaagattt gcaccggagt 1320
accaactcac ttagcaacag actacgagct caaggagata gtgggaatga tggacgcgag 1380
tgagaagacc aactacacat gttgcaggtt gcaaaggcat gagtggaaca aacatggttg 1440
gtgcaattgg tttcatatag aaccgtggat atggctgatg aacaagaccc aaagcaactt 1500
gactgaagga cagccrccta gggagtgtgc tgtaacttgt aggtatgaca gggaaacaga 1560
attgaacatc gtaacacagg ctagggacag gcctacaact ctgacaggct gcaagaaagg 1620
caagaaattt tcctttgcgg gggttgtact ggatgggccc tgcaacttta aagtatcagt 1680
tgaagacgtg ctgttcaagg aacacgattg tggcaacatg ctacaggaga ccgcgataca 1740
gctactcgat ggggcaacca acaccattga gggagcaagg gcagggacgg ccaagttgac 1800
aacctggtta gggaagcaat tacggaccct tggtaggaag ttggagaata aaagcaaagc 1860
atggtttggt gcacacgcag cgagcccata ctgtgaagtg gagaggaaga tcggctacat 1920
ctggtataca aaaaactgca ctccagcttg cctgccaaga aacactaaga taataggccc 1980
cgggaagttc gataccaacg ccgaagatgg caaaatactc catgagatgg gagggcacct 2040
ctcagaattt gccctattgt ccttggtggt tctgtccgac tttgccccag aaaccgcgag 2100

-continued

```
tgtcatctac ttggttctac atttcgcgat cccgcaaagt cacattaacg tagacacatg   2160
cgacaagagc cagctaaatt taacggtcgc aactacagta gcagaagtca taccagggac   2220
agtgtggaac ctaggaaagt atgtctgcat aagaccagac tggtggccat atgaaacgac   2280
cacagtcttt gttttagagg aagcaggaca agtaattaaa ttggggctaa gggccatcag   2340
agacttaacc aggatttgga atgctgccac cacaacagcc ttcctagtct tccttgtgaa   2400
agtactgagg ggacaattaa tccaagggct attatggctg atgctaataa caggggcaca   2460
gggcttccct gaatgcaaag agggcttcca atatgccata tcaaaagaca aaaaaatagg   2520
accactgggg ccagagagtt taactacaac atggcacctt cctaccaaaa aaatagtgga   2580
ctctatggta caggtgtggt gtgatggaaa agacttgaaa atattaaaaa cgtgcacaaa   2640
ggaagagagg tacttagtgg ctgtgcacga aagagccctg tcaaccagtg ctgagttcat   2700
gcagatcagt agtgggacaa aaggcccaga agtgatagat atgcctgatg actttgaatt   2760
tgggctctgc ccttgtgatt caaaaccggt aataaggggg aagttcaatg ccagcctatt   2820
gaacggacca gctttccaga tggtatgccc acaggggtgg actggtacaa tagaatgcat   2880
cctggcgaac caagacacct tggacacaac tgtcgttagg acatatagaa gaactactcc   2940
atttcagcgg agaaaatggt gtacctatga aaagataata ggggaagata tccatgaatg   3000
cattctagga ggaaactgga catgcataac tggtgatcat agcaagttga aagatgggcc   3060
tatcaagaag tgtaagtggt gcagctacga cttcttcaat tcagaaggac tgccacacta   3120
cccaataggt aagtgcatgc tcatcaatga gagtgggtac aggtatgtag atgacacctc   3180
ttgtgatagg ggtggtgtag ccatagttca aacaggtact gtaaagtgta gaataggcaa   3240
caccacggtg caggttatcg ctactaacac tgacctggga cccatgccct gcagcccagc   3300
tgaggtgata gcaagtgaag gaccagtgga aaagacggcg tgcacgttta actattcaga   3360
gacactacct aataagtatt atgagccaag ggaccagtac ttccaacaat acatgttaaa   3420
agggaagtgg caatattggt ttgacctgga ttctatagac caccacaaag actacttttc   3480
agagttcata gtcatagcag tggtagcctt gctaggtggt aagtatgtac tgtggctctt   3540
agtaacatat atgatactgt ctgagcagat ggctatgggt gctggagtaa gtaccgaaga   3600
gatagtcatg ataggcaact tttgacaca cagtgacatc gaggttgtgg tctattttct   3660
tcttttgtac ttaataatca aagaggaact ggtgaggaaa tgggttatgc tagtgtacca   3720
catccttgta gtaaatccta tgaaaacaat aggggttayc ctactaatgc taggggggt   3780
ggtgaaggcc agcaaaatca atactgatga ccagagtgct atggacccat gttttcttct   3840
cgtaacaggc ttagtggccg ttttgatgat cgctagaaga gaacctgcca cctttccgct   3900
ggttgcagca ttactagcaa taagaacatc aggattccta ctacccgcta gcattgatat   3960
aactgtagca gtagtgctga ttgtacttct gctagctagc tacttaacag actacttcag   4020
atataaaaag tggcttcaat tttcatttag tctgatagct ggtatttttg tcataaggag   4080
tttgaaacat atcaaccaga tggaggtacc agaaatatct atgccaagtt ggagacctct   4140
agcccttgtt attttctata taatatctac agctataacc actagttggg acattgactt   4200
agcaggcttc ctgctgcaat gggcgccagc agtgatcatg atggctacca tgtgggcaga   4260
ctttttgact ctaatcatag tcctacccag ttacgagctg tctaagcttt acttcctgaa   4320
gaatgtcagg actgatgtag aaaagaactg gctcggcaag gtgaaataca gacagatcag   4380
ctcagtttat gatatctgtg acagtgaaga agcagtatac ctatttccat caaggcataa   4440
```

-continued

```
gagcgggagc agaccagatt ttgtattacc ttttttgaaa gccgtgttaa taagctgcat   4500
cagtagccaa tggcaggtgg tctacatttc ctacctaata ctggaaatta catactatat   4560
gcacaggaaa atcatagatg aggtgtcagg aggagcaaat ttcttgtcaa gacttatagc   4620
agccatcata gaattaaact gggccataga tgatgaggaa tgtaaaggac tgaagaaatt   4680
atatctctta tcagggagag taaggaattt gatagttaaa cacaaggtaa gaaatgaagc   4740
cgtccacagg tggtttggtg aggaggaaat atacggggta cccaaggtaa tcaccatcat   4800
aaaagctagt accctcagca aaagtaggca ctgcataatc tgcacaatct gtgaagggaa   4860
agattggaat ggagccaact gcccaaagtg tggaagacaa gggaaaccca taacatgcgg   4920
aatgacactc gcagactttg aggagaaaca ttacaaaaaa atatttataa gagaaggatg   4980
ccaagaagca atgaatacga tgatgtgcag ccgatgccag ggaaagcata ggaggtttga   5040
aatggaccgg gaacctaaga gtgccagata ctgtgctgag tgtaataggc tgcatcctgc   5100
tgaggaaggt gacttttggg cagagtcaag catgttgggc ctcaaaatca cctactttgc   5160
gctgatggat ggaaaggtgt atgatatcac agagtgggct ggatgccagc gtgtgggaat   5220
ctccccagat acccacagag tccctaatca catctcattt ggttcacgga tgccaggcac   5280
cagtgggcgg cagagagcta ctccagatgc ccctcctgct gaccttcagg atttcttgag   5340
ccggatcttt caagtacccc caggccacga cggacctttc agagaagagt ataagggtta   5400
tatccaatac gcagccagag ggcaactctt tctgaggaac ctaccaattc tagcgacgaa   5460
gatgaagcta ctaatggtgg ggaaccttgg cgcggaagtt ggcgacctgg agcacctggg   5520
atgggtactg agagggccag ccgtgtgcaa gaaaattacc aaccatgaga agtgccacgt   5580
aaatatcatg gacaaactaa ctgcattctt tggaattatg cctagaggca caacccctag   5640
ggcacccgtg aggttcccca cagcattact gaaagtgaga agggggctag agacgggatg   5700
ggcctacacg catcaaggag ggatcagctc ggtagaccat gtcacagctg gaaaggattt   5760
actagtgtgt gacagtatgg gtaggaccag ggttgtctgc catagtaaca ataagatgac   5820
tgatgagact gagtatggca tcaagaccga ctctgggtgt cccgaaggtg caaggtgtta   5880
cgtgttaaac ccagaagccg taaacatttc tggcacaaaa ggagctatgg tacatctcca   5940
gaaaacaggg ggggagttca catgcgtcac tgcctcaggg actccggctt tctttgacct   6000
gaaaaatcta aaaggttggt ctgggctacc aatttttgaa gcatccagtg gcagggtggt   6060
tggtagggtg aaagtcggca aaaatgagga ttccaagccc accaaactaa tgagtgggat   6120
ccagacggtg tccaagaacc agacggacct agcagacatt gtaaaaaaat tgaccagtat   6180
gaacagagga gagtttaaac agataacact ggccactggg gcaggaaaaa cgacggagct   6240
gccaaggtcc gtcatagagg agatagggag acacaaaagg gtcttagtcc tgataccatt   6300
gagagccgct gcagagtcag tgtaccaata tatgagagtg aagtacccaa gtatatcttt   6360
caatctgaga ataggagata tgaaagaagg tgacatggcc actggtatca cttatgcctc   6420
atatgggtac ttttgccagc ttcctcagcc caaactgaga gctgccatgg tagagtactc   6480
atatatattc ttagatgagt atcactgcgc tacacctgag caattagcaa taattggtaa   6540
gatacacaga tttgctgaaa atctcagagt ggtagcaatg acagcaaccc cagctggcac   6600
ggtcacgacg actggtcaga aacaccctat agaggagttt atagccccag aggtaatgaa   6660
gggtgaagat ctaggaagtg aatacttgga tattgcaggg ctgaagatac caactgaaga   6720
gatgaaaggc aacatgctcg tttttgtgcc aaccagaaat atggcagtag aaacagctaa   6780
gaaattgaag gcaaaagggt acaactctgg atactattat agtggggaaa acccagaaaa   6840
```

```
cctgagggtg gtaacatcgc aatccccgta tgtggtagta gccaccaatg ccatagagtc   6900
aggtgtgaca ttaccagact tagatacagt tgtagacact ggactaaagt gtgagaagag   6960
ggtgaggata tcttcaaaaa tgcccttcat tgtaacagga ctcaagagaa tggcagtcac   7020
tataggagag caagcccagc gcaggggtag agtaggaaga gttaagccag gtaggtacta   7080
tagaagtcag gaaacggctt cagggtcaaa agattaccat tacgacctac tacaggctca   7140
gaggtacgga atagaagatg ggattaatgt aacaaagtca ttcagggaga tgaactatga   7200
ttggagcctt tatgaggagg acagcctgat gataactcag ctcgaggtcc tcaacaacct   7260
ccttatatca gaagacctgc ctgccgcagt gaagaacatc atggctcgga ctgaccaccc   7320
agaacccata caactggcct ataacagtta tgaaaatcaa attccagtgc tattcccaaa   7380
gatyaaaaac ggtgaggtga cagacagtta tgagaattac acatacctca atgcaagaaa   7440
actaggagag gacgtaccag cgtatgtgta cgctacagag gatgaggatc tagcagtgga   7500
ccttctaggt atggattggc cggacccagg caatcagcag gtggtagaga cagggagggc   7560
attaaaacaa gtaactggct tatctacagc agagaatgcc ctcttgatag ccctattcgg   7620
ctacgtcggg taccagacac tttcaaaaag gcatatacca atgatcactg acatctatac   7680
gcttgaagac cataggctgg aggacacaac ccacctccag tttgccccga atgctataag   7740
gactgacggc aaggactcag agttgaagga attagctgtc ggagaccttg ataaatatgt   7800
ggatgcactg gtggactact ccaaacaagg gatgaagttt atcaaagtcc aagctgaaaa   7860
ggtcaaggac tcccattcca caaaggaagg cttgcaaaca atcaaggagt atgtggataa   7920
gttcatacaa tcactaatag agaacaagga ggagatcatc aggtatggac tatggggagc   7980
tcacacagca ctctacaaaa gcttggcagc gagattgggg catgaaacag ctttcgcaac   8040
tttagtggta aaatggttgg cttttggggg cgaaacggta tctgcccata tcaagcaagc   8100
agcagttgat ttactagtgt attatatcat gaacaaacca tcttttcctg gagacacaga   8160
gacccaacaa gaggggagga ggtttgtagc tagtcttttc atatctgcgc tagcgacata   8220
cacatacaaa acctggaatt acaacaatct ggcgcgggtc gttgagcctg ccttagctta   8280
cctcccatat gctacaagtg ccttgaagtt gttcacacct acaagattag agagtgtggt   8340
catactcagt tctacaatct acaagacgta cctctctata aggaagggca agagcgacgg   8400
cctactgggt acaggtataa gtgcagccat ggagatctta aaccaaaacc caatctcagt   8460
tggtatatct gtgatgctgg gggtgggtgc tattgccgcc cataatgcaa tagmatccag   8520
tgaacagaaa agaactttgt tgatgaaagt ctttgtaaaa aacttcttgg accaggcagc   8580
aacagatgag ctagtcaaag agaaccccga aaaaataatc atggctctgt ttgaagcagt   8640
ccagaccata ggcaaccccc taagactcat ctaccatctg tacggggtat actataaggg   8700
gtgggaagca aaagaactcg cagaaaaaac tgccggccgc aacttattta cactgatcat   8760
gtttgaagcc tttgaacttt taggtatgga ctcagaaggg aagataagaa acttgtcagg   8820
taactacata ctggacttga ttttcaattt rcataataaa ttaaacaagg gactcaaaaa   8880
gttggtcctt ggctgggccc cagcaccttt tagctgcgat tggacaccaa gtgatgagag   8940
gataagccta cctcacaaca actacttaag ggtggaaacc aagtgtcctt gcggctatga   9000
gatgaaggca ataaaaaacg ttgctggcaa attgacaaaa gttgaagagr aagggccctt   9060
cctttgcaga aacagattag ggagaggacc tccaaacttc aaagtaacaa aattctatga   9120
tgacaatttg atagaagtta agccagtagc taggtcagaa ggccaagtgg atctctacta   9180
```

-continued caagggagta acagcaaggt tagactatag taacgggaaa gtgctgttag ctaccaacaa 9240
gtgggaggtg gaccacgctt ttctgactag actagtaaag aagcacacag ggataggttt 9300
taaaggtgca tatttgggtg accgaccaga ccatcaagat cttgtcagta gagattgtgc 9360
aaccataact aagaactcag tacagtttct gaaaatgaag aagggttgcg cttttacata 9420
tgacctaaca atctctaacc ttgtcaggct tattgaacta gtccacaaga atgatttaca 9480
agagagagaa atcccaactg tgacagtaac tacctggctt gcttattctt ttgtcaacga 9540
agacctgggg actatcaagc ctgtgttggg ggagaaagtc atcccagaac cccccatgga 9600
gttgagtctt caacccgctt tgggactggt taccaccgaa acagcgataa ccataacagg 9660
ggaggctgaa gtgatgacga cagggatcac accagtggta gaaatgaaag aagaacctca 9720
gctgggccat cagtcaacta ccctaaaggt agggttgaag gaaggggaat tcccagggcc 9780
aggagtcaac cctaaccatt tagtagargt gatagatgaa aaagatgtca ggccttttgt 9840
cctagttatc gggaataaag gttctacctc aaatagagca aaaacagcca agaatatacg 9900
tttgtacaaa ggaaacaatc caagagagat caggtatctg atgagccaag ggagaatatt 9960
aacggttgct ctaaaagagt tggacccgga attaaaagag ttggtagatt ataaggggac 10020
ctttctcaat agggaagctt tagaagcact aagcttaggt aaaccaatca agaggaaaac 10080
cacaacagca atgatcagga ggttgataga gccagaggtt gaggaggaac taccagattg 10140
gttccaagcg gaagaacccc tatttttgga agcaagaatc maggctgaca tttatcacct 10200
agtgggcagt gttgacagta taaaaagcaa agcaaaggaa ttgggggcca cagataacac 10260
aaagrttgtg aaggaggtcg gggctaggac ctatactatg aaattgagca gttggagtac 10320
acaagttacc aaaaaacaaa tgagtctagy cccccttttt gaagagctgt tattaaagtg 10380
tcctccatgt agcaaaattt caaagggaca tatggtgtca gcataccaac tggcccaagg 10440
aaactgggaa cccctcgggt gtggggttta tatggggact gtaccagcta ggcgtctcaa 10500
gatccaccct tacgaggctt acctcaaact caaagagctg gtggaaggtg aactttcaag 10560
ggttaccgca agagaatcca tcataagaga acataacact tggattttgc ggaaagtgag 10620
acacgaaggg aacctaagaa ctaaatcaat gattaaccct gggaaagtat cagaacagtt 10680
gtgcagagaa ggacacaaaa gaaacatata caacaagatt ataggctcaa caatggcctc 10740
tactggtatc aggctggaga aactgccaat agtccgagcc caaactgata caaccagttt 10800
ccaccaagct ataagagaga aaattgataa gccagaaaac aagcaaaccc ctgaattgca 10860
tgaagagcta aagaaggttt ttgactgctt aaagatcccg gagctgaagg aatcgtatga 10920
tgaagtttca tgggaacaat tagaagccgg gataaaccgc aagggagcag ccggttttct 10980
agagagtaag aacatagggg aggtgctgga cacggaaaaa cacatagtag aacaattaat 11040
cagggatctg aggcagggga agaagatcag gtattatgaa acagccatcc ccaagaatga 11100
gaagagagat gtcagtgacg actgggaagc cggagaattt gttgatgaga agaaaccaag 11160
agtaatccag tacccagatg ccaaggtgag actggccatc acaaaagtaa tgtacaagtg 11220
ggtgaagcaa caaccagtgg tgatacccgg ctatgagggt aaaacaccgc tatttgatat 11280
attcaacaag gtgaagaagg aatgggattc attccaggac cctgtagcgg tgagctttga 11340
caccaaagcc tgggatacac aagttactag tagagaccta atgttgataa gggacatcca 11400
gaaatattat ttcaagagaa acatacacaa atttttagat acaataacag aacacatggt 11460
ggaggtaccc gtcattacag cagacggtga agtttacata aggaatggtc agaggggtag 11520
tggccaaccc gacacaagtg ctggtaacag tatgttgaat gtcctaacca tgatatatgc 11580

```
cttctgtaaa agcacaggta taccttacag gggattcagc agagtggcaa gaatccatgt  11640
gtgtggtgat gatggctttt tgataacaga aagagggctg gggttgaaat tctctgagaa  11700
gggtatgcag atattacatg aggccgggaa gccccagaaa ataactgaag gggacaaaat  11760
gaaagtggca tacagattcg aggacattga gttctgttcc catactcctg tgccagtcag  11820
atgggcagat aacaccagta gttacatggc agggaggagt acagctacta tactagctaa  11880
gatggcaacc aggctggatt ccagcggaga gaggggtagc acagcttatg agaaggccgt  11940
agcctttagc ttcctttga tgtactcatg gaatccggtg gttagaagga tctgcttaat  12000
ggtgttgtca cagtatccgg aagtatcccc atccaaacat acaatatact actaccaagg  12060
ggatcccata gctgcataca gagaagtgat agggagacag ctgtgtgaac tgaaaagaac  12120
aggatttgag aagctagcta gcctgaacct gagtatgacc actctaggca tctggacaaa  12180
acatactagt aaaagactaa tccaagactg tgtagaaata ggtaagagag aaggtaattg  12240
gttagttaat gctgacagac tgatttcagg aaagactggg aagttttata tcccaaacac  12300
tggtgtcacg ctattgggaa aacattatga ggaaattaac ttaaagcaaa aggcggcaca  12360
accgccgacg gaaggggttg acagatataa gttgggcccc atagttaata ttattttgag  12420
aagattgagg gtaatgctaa tgacagtggc cagcggaaac tggtaaacct gtccagagcg  12480
cagcgctctc actcaaggta tttaattgta aatattgtaa atagacagct aagatattta  12540
ttgtagttgg aaagtaatat agtgatagca aataccccaa tctaacacta cctccaacgc  12600
actaagcact ttagctgtgt gaggttaact cgacgtccat ggttggacta gaggragcct  12660
ctagc                                                              12665
```

```
<210> SEQ ID NO 2
<211> LENGTH: 12229
<212> TYPE: DNA
<213> ORGANISM: Bovine Viral Diarrhea Virus Type II

<400> SEQUENCE: 2

gagagccttt tctaattctc gtatacrtat tgggcaatta aaataataat taggcctagg     60
gaacaaaagt ccccctcagc gaaggccgaa aagaggctag ccatgccctt agtaggacta    120
gcataaagag gggggtagca gcagtggtga gttcgttgga tggcttaagc cctgagtaca    180
gggtagtcgt cagtggttcg acgccttgga ataaaggtct cgagatgcca cgtggacgag    240
ggcatgccca aagcacatct taacctgagc gggggtcgcc caggtaaaag cagttctaac    300
cgactgttac gaatacagcc tgatagggtg ctgcagaggc ccactgttct gctactaaaa    360
atctctgctg tacatggcac atggagttga tcacaaatga acttttatac aaaacttaca    420
aacaaaaacc cgtcagggtg gaagaacctg tttatgatca ggcaggtgat cccttatttg    480
gtgaaagggg agcagtccac cctcaatcga cgttaaagct cccacacaag agaggggaat    540
gcgatgtacc catcaacttg gcatctttac caaaaagggg tgactgcagg tcgggtaata    600
gcagaggacc tgtgagcggg atctacttga agccagggcc actattttac caggactata    660
agggtcccgt ctatcacagg gccccgctgg agctctttga agagggaacc atgtgtgaaa    720
cgactaaacg gatagggaga gtaactggaa gtgacggaaa gttgtaccac atttatgtgt    780
gtatagatgg atgtataata ataaaaagtg ccacaagaag tcaccaaagg gtgcttaggt    840
gggtccataa taggcttaac tgccctctat gggtcacaag ttgctcagac acgaaagaag    900
agggagcaac aaaaaagaaa acacagaaac ccgacagact agagaagggg aagatgaaaa    960
```

-continued

```
tagtgcccag agaatccgaa aaagacagca aaactaaacc tccggatgct acaatagtgg   1020
tagatggagt taaataccag gtgaagaaga agggaaaaat caagagtaag aacactcagg   1080
acggcttgta ccataacaaa aacaaaccgc cggaatcacg taagaaactg gaaaaagcat   1140
tgctggcatg ggcaataata actatagttt tgtttcaagt tacaatggga gaaaacataa   1200
cacagtggaa cctacaagac aatgggacgg aagggataca acgggcaatg tttcaaaggg   1260
gtgtgaatag aagtctacat ggaatctggc cagagaaaat ctgtactggt gtcccttccc   1320
atctagccac cgatatggaa ctaaaaacaa tccatggtat gatggatgca agtgagaaga   1380
ccaactacac gtgttgcaga cttcaacgcc atgagtggaa caagcatggt tggtgcaact   1440
ggtacaatat tgaaccctgg attctagtca tgaatagaac ccaagccaat cttactgagg   1500
gacaaccacc aagggagtgc gcagtcactt gcaggtatga tagggatagt gacttaaacg   1560
tagtaacaca agctagagat agccccacac tcttgacagg ttgcaagaaa ggaaagaact   1620
tctcctttgc aggcatactg acgcggggtc cctgcaactt tgaaatagct gcgagtgatg   1680
tattattcaa agaacatgac tgcactagta tgttccagga tactgctcat taccttgttg   1740
acgggatgac caactcctta gaaaatgcca gacaaggaac cgctaaactg acaacctggt   1800
taggcaagca gctcgggata ctagggaaaa agttggaaaa caagagtaag acgtggtttg   1860
gagcatacgc ggcttccccc tactgtgatg tcgatcgaaa gattggctac atatggtata   1920
caaaaaattg taccccctgcc tgcttgccca agaacacaaa aattgtcggc cctgggaagt   1980
ttgacaccaa cgcagaggaa ggcaagatac tacatgagat ggggggccac ttgtcggagg   2040
tactactact ttctttagtg gtgctgtccg acttcgcacc ggaaacagcc agcgcaatgt   2100
acctaatcct acatttttcc atcccacaaa gtcacgttga cataatggaa tgtgataaga   2160
cccagttgaa cctcacagtg gagcttacaa cagctgatgt aataccagga tcagtctgga   2220
acctaggcaa atgggtatgt ataagaccaa attggtggcc ttatgagaca actgtggtgt   2280
tggcatttga agaggtgagc caggtggtga agttagtgtt gagggcactc agagatttga   2340
cacgcatttg gaacgctgca acaactactg ctttcttaat atgccttgtt aagatagtca   2400
ggggccagat ggtacagggc attctgtggc tactactgat aacaggggta caaggggact   2460
tgcattgcaa acctgaattc tcatatgcca tagcaaggga tgaaagaatt ggtcaactgg   2520
gggctgaagg ccttactacc acttggaagg attactcgcc tgaaatgaaa ctggaagaca   2580
caatggtcat agcttggtgc aaagatggta agtttacgta cctcccaagg tgcacgagag   2640
aaaccagata tctcgcgatc ttgcatacaa gggccttacc gaccagtgtg gtattcaaaa   2700
aactttttga tgggcgaaag caagaggatg tagtcgaaat ggacgacaac tttgaatttg   2760
gactctgccc atgtgatgcc aaacccatag taagagggaa attcaataca acgctgctga   2820
acggaccggc cttccagatg gtatgcccca taggatggac agggactgta agctgtatgt   2880
cattcaatat ggacacctta gccacaaccg tgatacggac atatagaagg tccaaaccat   2940
ttcctcatag gcaaggctgt atcacccaaa agactctggg ggaggatctc cataactgca   3000
tcctcggagg aaattggact tgtgtgcctg gagacatgct attatacaaa gggggctcta   3060
ttgaatcctg caagtggtgt ggttatcaat ttaaagagag cgagggacta ccacactacc   3120
ccattggcaa gtgtagatta gagaatgaga ctggttacag actagtagac gatacctctt   3180
gtaatagaga aggtgtggcc atagtaccac aagggacatt acggtgcaag ataggaaaaa   3240
ctactataca ggtcatagct atggatacca aactcgggcc tatgccttgc agaccatatg   3300
aaataatatc aagtgagggg cctgtagaaa ggacagcgtg taccttcaac tacactaaaa   3360
```

```
cattaaaaaa taagtatttt gagcccagag acagctactt ccagcaatac atgctaaaag   3420
gagagtatca atactggttt gacctggagg taaccgacca tcaccgggat tactttgccg   3480
agtccatatt agtggtggtg gtagccctcc tgggtggcag atatgtactt tggttactag   3540
ttacatacat ggtcttatca gaacagaagg cctcagggac tcagtatgga gcaggggaag   3600
tagtgatgat gggcaacttg ctaacccata atgacattga agtggtgaca tacttcttgc   3660
tgttgtacct actgctgagg gaagagagcg taaagaagtg ggtcttactt ttataccaca   3720
tcttagtgtc acacccaatc aaatctgtaa ctgtgatcct attgatgatt ggggatgtgg   3780
taaaggcaga ctcagggggc caagggtact ttgggcaaat agacctctgt tttacaatag   3840
ttgtactaat catcataggt ttaatcatag ccaggcgtga cccaactata gtgccactag   3900
taacaataat ggcagcactg agggtcactg gattgaccta ccagcctgga gttgacgtcg   3960
ctatggcagt catgaccata accctactga tggttagcta tgtgacagat tactttagat   4020
ataaaagatg gttacagtgc gttctcagcc tggtgtcagg ggtgttcttg ataagaagcc   4080
taatgcacct aggtagaata gaggtgccag aggtaaccat cccaaactgg agaccactaa   4140
ctttaatact gttatatttg atctcaacaa caattgtaac aatgtggaag gttgacatcg   4200
ctggcttgtt gttgcaatgc ctgcctatct tattactggc cacaaccttg tgggccgact   4260
tcttaaccct catactgatc ctgcctacct atgaattggt taaattatac tacctgaaaa   4320
ctgttaggac tgatatagaa agaagttggc caggggggat agactgtaca agagttgact   4380
ccatctacga cattgatgag agtggagagg gcgtatatct ctttccatca aggcagaaag   4440
gacagaggag cttttccata ctcttgcccc ttgtcaaagc aacactgata agttgcgtca   4500
gcagtaaatg gcagctaata tacatgagtt acctaacttt ggactttatg tactacatgc   4560
acaggaaagt tatagaagag atatcaggag gcaccaacat gatatccagg ttagtagcgg   4620
cactcataga gctgaactgg tccatggaag aagaggagag caaaggccta aagaagtttt   4680
atctattatc tggaaggttg agaaacctaa taataaaaca taaagtaaga aatgagaccg   4740
tggcttcttg gtacggggag gaggaagtct acggtatgcc aaagatcatg acaataatca   4800
aggccagtac gctgagtaag agcaagcact gcatgatatg cactgtatgt gagagccgag   4860
agtggaaagg cggcacctgc ccaaaatgtg gacgccatgg gaagccgata atgtgtggga   4920
tgtcgctagc ggattttgaa gaaagacact ataaaagaat ctttataagg gaaggtaact   4980
ttgagggtcc tttcaggcaa gaatacaatg gctttgtaca atataccgct agggggcaat   5040
tacttgtgag aaacttgccc gtactggcaa ctaaagtaaa aatgctcatg gtaggcaacc   5100
ttggagaaga aattggtgat ctggaacatc ttgggtggat cctaaggggg cctgccgtgt   5160
gtaagaagat cacagagcac gaaaaatgcc acatcaatat actggataaa ctaactgcat   5220
ttttcgggat catgccgagg gggactacac ccagagcccc ggtgaggttc cctacgagct   5280
tactaaaagt gaggaggggc ctggagactg gctgggctta cacacaccaa ggtgggataa   5340
gttcagtcga ccatgtaacc gccggaaaag acctattggt ctgtgacagc atgggacgga   5400
ctagagtggt ttgccaaagc aacaacaggt tgaccgatga gacagaatat ggcgtcaaga   5460
ctgactcagg atgcccagac ggtgccagat gttatgtgtt aaatccagag gctgtcaaca   5520
tatcaggatc caaggggggca gtcgtccacc tccaaaagac aggtggagaa ttcacgtgtg   5580
tcaccgcatc aggcacaccg gcctttttcg acctaaaaaa cttgaaagga tggtcaggat   5640
tgcctatatt cgaagcctcc agcgggaggg tggttggcag agtcaaagta gggaagaatg   5700
```

-continued

```
aagagtctaa acctacaaaa ataatgagtg gaatccagac cgtctcaaag aacacagcag   5760
atctaactga gatggtcaag aagataacca gcatgaacag gggagacttc aagcagatta   5820
ctttggcaac aggggcagga aaaaccacag aactcccaaa agcagttata gaggaaatag   5880
gaagacacaa gagagtatta gttcttatac cattaagggc agcggcagag tcagtttacc   5940
agtatatgag attaaaacac ccaagcatct cttttaacct aaggataggg gacatgaaag   6000
agggggacat ggcaacgggg ataacctatg catcatacgg gtacttctgc caaatgcccc   6060
aaccaaagct cagagctgct atggtagaat actcatacat attcttagat gaataccatt   6120
gtgccactcc tgaacaactg gcaattatcg gaaagatcca cagattttca gagagtataa   6180
gagtcgtcgc catgactgcc acgccggcag ggtcggtgac cacaacaggt caaaagcacc   6240
caatagagga attcatagcc cccgaggtaa tgaaagggga ggatcttggt agtcagttcc   6300
ttgatatagc agggttaaaa ataccagtgg atgagatgaa aggtaatatg ttggtttttg   6360
tacccacgag aaacatggca gtagaggtgg caaagaagct aaaagctaag ggctataatt   6420
ctggatacta ttacagtgga gaggatccag ccaatctgag agttgtaaca tcgcagtctc   6480
cctatgtaat cgtggccaca aatgctattg aatcaggagt gacactacca gatttggaca   6540
cggttgtaga cacggggctg aaatgtgaaa agagggtgag ggtatcatca aagataccct   6600
tcatcgtaac aggtcttaag aggatggccg tgactgtggg tgagcaggct cagcgtaggg   6660
gcagagtagg tagaatgaaa cccgggagat attatagaag ccaggaaaca gcaaccgggt   6720
caaaggacta ccactatgac ctcttgcagg cacaaagata cgggattgag gatggaatca   6780
acgtaacgaa gtcctttagg gagatgaatt acgattggag cctatacgag gaggacagcc   6840
tactaataac ccagttggaa atactaaata atctactcat ctcagaagac ttgccagccg   6900
ctgttaagaa tataatggcc aggacagatc acccagagcc aatccaactt gcatacaaca   6960
gctatgaagt ccaggtcccg gtcctgttcc caaaaaataag gaatggagaa gtcacagaca   7020
cctacgaaaa ttactcgttt ctaaacgcca gaaagttagg ggaggatgta cccgtgtata   7080
tctatgccac tgaagatgag gatctggcag ttgacctctt agggctagac tggccagatc   7140
ctgggaacca gcaggtagtg gagactggca aagcactgaa gcaagtgacc gggttgtcct   7200
cggctgaaaa tgccctacta gtggctttat ttgggtacgt aggttatcag gctctctcaa   7260
agaggcatgt cccaatgata acagacatat ataccatcga ggaccagaga ctagaagaca   7320
ccacccacct ccagtatgca cccaacgcca taaaaaccga agggacagag actgaactga   7380
aagaactggc gtcgggtgac gtggaaaaaa tcatgggagt catttcagat tatgcagccg   7440
ggggactgga gtttgtgaaa tcccaagcag aaaagataaa aacagcacct ttgtttaaag   7500
aaaacgtaga agctgcaaaa gggtacgtcc aaaaattcat tgactcatta attgaaaata   7560
aagatgcaat aatcagatat ggtttgtggg gaacacacac tgcactatac aaaagcatag   7620
ctgcaagact ggggcacgaa acagcgtttg ccacactggt gttaaaatgg ctagcttttg   7680
gaggggaatc agtgccagac cacatcaagc aggcggcagt tgatttagtg gtctattatg   7740
tgatgaataa gccttccttc ccaggcgaca ccgaaacaca gcaagaaggg aggcgattcg   7800
tcgctagcct gttcatctcc gcactggcaa cctacacata caaaacttgg aattaccaca   7860
atctctctaa agtggtggaa ccagccttgg cttacctccc ctatgctacc agcgcattaa   7920
aaatgttcac cccaacgcgg ctagagagcg tggtgatact gagcaccacg atatacaaaa   7980
catacctctc cataaggaag gggaagagtg atggattgct gggcacgggg atcagtgcag   8040
ccatggaaat cctgtcacaa aacccagtgt cggtgggtat atctgtgatg ttgggggtag   8100
```

```
gggccattgc tgcgcacaac gctattgagt ccagtgaaca gaaaaggacc ctacttatga   8160
aggtgttcgt aaagaacttc ttggatcagg ctgcaacgga tgagctggta aaagaaaacc   8220
cagagaaaat tataatggcc ttatttgaag cagtccagac aattggtaac cccctgagac   8280
taatatacca cctgtatggg gtttactaca aaggttggga ggccaaggaa ctatctgaga   8340
ggacagcagg cagaaactta ttcacattga taatgtttga agccttcgag ttattaggga   8400
tggactcaga aggaaaaata aggaacctgt ccggaaatta catcttggat ctgatatacg   8460
gcctacacaa gcagatcaac agagggctga agaaaatagt actggggtgg gctcctgcac   8520
cctttagttg tgactggacc cctagcgacg agaggatcag attgccaaca gacaactatt   8580
tgagggtaga aaccaggtgc ccatgtggtt atgagatgaa agcgttcaaa aatgtaggtg   8640
gcaagcttac caaagtggag gagagcgggc ctttcctatg tagaaacaga cctggtaggg   8700
gaccagtcaa ctacagagtc accaagtatt acgatgacaa cctcagagag atagaaccag   8760
tagcaaagtt ggaaggacag gtggagcact actataaagg ggtcacagca aaaattgact   8820
acagtaaagg aaaaacgctc ttggctactg acaagtggga ggtagaacat ggtgtcatga   8880
ccaggttagc taagagatat actggggttg ggttcaatgg tgcatactta ggtgatgagc   8940
ccaatcaccg tgatctagtg gagaggaact gtgcgactat aaccaaaaac acagtacagt   9000
ttctaaaaat gaagaagggg tgtgcattca cctatgacct gaccatctcc aatctgacca   9060
ggcttattga actagtacac aggaacaatc ttgaagagaa ggaaataccc accgttacag   9120
tcaccacatg gctagcttac accttcgtga atgaagacgt agggactata aaaccagtac   9180
taggagagag ggtaatcccc gaccctgtag ttgatgtcaa cttacaacca gaggtccaag   9240
tggatacatc agaggtcggg atcacaataa ttggaaggga aaccctgatg acaacggggg   9300
tgacacctgt attggaaaaa gtagagcctg acgctagcaa caaccaaagc tcagtgaaga   9360
ttgggttgga taagggtaat tacccagggc ctggaataca gacacataca ctaacagaag   9420
aaatacacga cagggatgca agacccttca tcatgatcct gggctcaaag aattccatgt   9480
caaatagggc aaagactgct agaaacataa atctgtacac aggaaatgac cccagggaaa   9540
taagagactt gatggctgca gggcgcatgt tagtagtagc actgagggat gtcgaccctg   9600
agctttctga aatggtcgac ttcaagggga ccttcttaga tagggaggcc ctggaggctc   9660
taagtctcgg gcaacctaaa cctaagcagg tcaccaaggc agctattagg gatttgattg   9720
aacaggaaaa acaggtggag atccctaact ggtttacatc agatgaccca gtatttttgg   9780
aagtggccat aagaaatgat aagtactact tagtaggaga tgttggagag gtaaaagatc   9840
aagctaaaac acttggggcc acggatcaga caagaattgt aaaggaggta ggctcaagga   9900
cgtataccat gaagctatct agttggttcc tccaagcatc aaaaaaacag ataagtttaa   9960
ctccactgtt tgaggaattg ttgctacggt gcccacctgc aactaagagc aataaggggc  10020
acatggcatc agcttaccaa ttggcacagg gtaactggga gcccctcggt tgcggggtgc  10080
acctaggtac cataccagct agaagggtga agatacaccc atatgaagct tacctgaggt  10140
tgaaagattt catagaagaa gaagagaaga aacctagggt taaggataca gtaataagag  10200
agcacaacaa atggatactt aaaaaaataa ggtttcaagg aaacctcaac accaagaaaa  10260
tgctcaaccc cgggaaacta tctgaacagt tggacaggga ggggcgcaaa aggaacatct  10320
acaaccacca gattggtacc ataatgtcaa gtgcaggcat aaggctggag aaattgccaa  10380
tagtaagggc ccaaaccgac actaaaacct ttcatgaggc aataagagat aagatagaca  10440
```

-continued

```
agagtgagaa ccggcaaaat ccagaattgc acaacaaatt gttggagatt tttcacacaa  10500

tagcccaacc cgccctgaaa cacacttacg gtgaggtgac gtgggagcaa cttgaggcag  10560

ggataaatag aaaaggggca gcaggctttc tggagaagaa gaacatcggg gaagtattgg  10620

attcagaaaa acacctggtg gaacaattgg tcagggatct gaaggccggg agaaagataa  10680

aatattatga aactgcaata ccaaaaaatg agaaaagaga tgtcagcgat gactggcagg  10740

caggggacct ggtggatgag aagaggccaa gagttattca ataccctgaa gccaagacaa  10800

ggctagccat cactaaggtc atgtataact gggtgaaaca gcagcccgtt gtgattccag  10860

gatatgaagg aaagacccct ttgttcaaca tctttgataa agtgagaaag gaatgggact  10920

tgttcaatga gccagtggcc gtaagttttg ataccaaagc ctgggacaca caagtgacta  10980

gtagggatct gcaacttatc ggagaaatcc agaaatatta ctataggaag gagtggcaca  11040

agttcattga caccatcacc gaccacatga cagaagtgcc agttataaca gcagatggtg  11100

aagtatatat aagaaatggg cagagaggta gtggccaacc agacacaagt gcaggcaaca  11160

gcatgttaaa tgtcctaaca atgatgtacg ctttctgcga aagcacaggg gtcccgtaca  11220

agagtttcaa cagggtggca aggatccatg tctgtgggga tgatggcttc ttaataactg  11280

aaaaagggtt agggctgaaa tttgctaaca aagggatgca gattcttcac gaagcaggca  11340

aacctcagaa gataacggaa ggggaaaaga tgaaagttgc ctatagattt gaggacatag  11400

agttctgttc ccataccccca gtccctgtta ggtggtccga caataccagt agtcacatgg  11460

ccgggagaga caccgctgtg atactatcaa agatggctac aagattggat tcaagtggag  11520

agaggggtac cacagcatat gaaaaagcgg tagccttcag tttcttgctg atgtattcct  11580

ggaacccgct tgttaggagg atttgcctgt tggtactttc gcaacagcca gagacagacc  11640

catccaaaca ggccacttat tattacaaag gtgatccaat aggggcctat aaagatgtga  11700

taggtcggaa tctaagtgaa ctaaagagaa caggcttcga gaaattggca aatctaaacc  11760

taagcctgtc cacattaggg atctggacta agcacacaag caaaagaata attaatgact  11820

gtgttgccat tgggaaagaa gaaggcaact ggctagttaa cgccgacagg ctgatatcca  11880

gcaaaactgg ccacttatac atacctgata agggctttac attacaagga aagcattatg  11940

agcaactaca gctaagaaca gagacaaacc cggtcatggg ggtcgggact gagagataca  12000

agttaggtcc catagtcaat ctgctgctga gaaggttgaa agttctgctc atgacggccg  12060

tcggtgccag cagctgagac aagtgtatat attgtaaata aattaaccca tgtacatatt  12120

gtatataaat atagttggga tcgtccacct caagaagacg acacacccaa cacgcacagc  12180

taaacagtag ttaagattat ctacctcaag ataacactac atttaatgc             12229
```

<210> SEQ ID NO 3
<211> LENGTH: 11105
<212> TYPE: DNA
<213> ORGANISM: Bovine herpesvirus 1
<220> FEATURE:
<221> NAME/KEY: misc_feature
<223> OTHER INFORMATION: IRL Region

<400> SEQUENCE: 3

```
gccccgagac ccccggccct gaggccctgg ggcggggccc gactgtcccc ttcccccctc     60

ccccccgtcc gcccgcgagt aaaggctgtc taattttttc cgcacgcccg cgcctgtctt    120

cttagggagg ggaaggaggg gagggagggg aaggagggga ttcgggccgg ccgaggattc    180

gggccggccg agcgagcggg ccaaagctcc ggctccccct tccccctccc gccccgcggg    240
```

-continued

```
cgaataaaac aactagaacc acaagatata gagaggcaag gcgcgcctgc gcgcggcgtt    300
ttatttaaaa aaatatgaca agggccgggg agagggcggg agagggggcc gcggggcccc    360
gcccccctaa actcgctggc ggcgcttggc cggcgcgggc cgcgcccggg cgcgaccgga    420
gggcgagccc cccggcgacg ggtatggcga ggagcccggc gaggagccgg aggaccagcg    480
ccagcagggc gcgggccggc gccggcccgc gcgcgcgggg gggccgccgg cgccgggccc    540
ggcgccggcc gggcgcgggt ccccgggccc ggggaagaac acgtcgtcgt cgccgtccga    600
ggcggagaac gaggacagcg acgacgagga ggtggaagag gacgcggtgg gcgacgagac    660
gaaggagacg gccgaggccg cgggcgaggc ggaggagagg accgcggctc gcgcgcggca    720
ccgggggcg ctttcggcgg cggccccctc gccgccgttc tcctccccct cctcgtccgc    780
ctcctcgtcc tcctcgtagt cttcgctgct ggagtcgctg ccgctcacgt cgcactcggc    840
tccgaaaagc gggcccggca ggcgcgccgg gggcgacagc gggcgcgccc tgggcccggc    900
ggcggcggcg gcgcgcaaaa gccggcgcag cgggccggcc tgctcgggcg agagctgcag    960
cagcgcctcc cagcacgcgt ccgtgggcgt ggcgcccgtg tagccgagca ggaagaagcc   1020
gacgagcgcg cggcgcagcg cgcgcgtgtc ggccgtgacg aacgcggagc cggtggcgat   1080
gcagcggaag agggtgttga cgtcgatggc gaggcgcagc gcctcggggc gccagtcctc   1140
ggggcagaag gcgcccgggc cgcggcgagc gtgctcgtcc gcgggggcgg ggcccgagac   1200
cacgcggtcg ggcgagcggc agaggcggca ggagccgtcg caggtggggc aaggctggcc   1260
gtggctcatg gcggcggcgg gccgggccgg tctgccggga caaagggggc gggacagaga   1320
agaggaggag cggtaagcgg gcgccccggg gcagggcccg cccggtcgcg tggcaagcga   1380
gtggccgcgc agggcgcgtc cggggagggc gggcttgccc cgggcgggcg agggatcggg   1440
gggatggggg cgagggatcg ggaggatggg ggcgagggat cggggggatg gggggcgaggg   1500
atcgggggga tgggggcgag ggatcggggg gatgggggcg agggatcggg gggatgggga   1560
tgggggggcga ggggaacctg gcttacctcg caatgtcgcc ctggtccacc ggcgcggtcc   1620
tgggtttcag ctctgggggg tcgccgccgg ggttctgcaa gagcatggct gggctgggct   1680
gggctggggt gggctgggct gggctgggct ggggtgggct ggggtgggct gggctgggct   1740
ggggtgggct gggctgggct gggctgggct ggggtgggct ggggtgggct gggctgggct   1800
gggctgggct ggggtgggct gggctgggct ggggtgggct gggctggggt gggctgggct   1860
ggggtgggct gggctggggt gggctgggct ggggtgggct gggctgggct ggggtgggct   1920
gggctgggct ggggtgggct gggctgggct ggggtgggct gggctgacct tgcggcaggt   1980
ccctaggtgc agtcgaggtg cggttcctgg aggtgctcgt caagccggct gcgatggagc   2040
gctgcacggg ggggtggggg cggagcacag gagctcgggt ggggtcccga gtgagctccg   2100
cccacccagc ccccaccccc gtctgcccgc ccccgggccc gagatgaggg tgggggctgg   2160
gtgggcggag ctcacttggc ggggtcgtcg gcggggcgtc cggggtcgtc ggcggggcgt   2220
ccggggtcgt cggcgagttc ctatggaagc aacccacctg agctcgagga agcggttcgc   2280
tcgagctcgg gtgggggtgg gggtgagcga gaaaaaaaaa aaaaaaaaaa aagggccccg   2340
gccccggggc ggatgcgctt accttgcctt tgccggggct ggggatcggt gaaggttctg   2400
cagtgcgccg cgctcctcta gctccccgtg tgtgggcttg ggcgcgatg tcgcgcgctt   2460
atatgtcttt gagtagggcg ctcctccccc cgcccccggc cgagcgccgc ccctggcccg   2520
gcctgatttg cctgtgccct cccaccgtcc cggtagccct ctcgggaccc cacgtgagaa   2580
cactggcaga atgccagggg gcccacgtaa ggggccccgc ccccggccga gcgccgcccc   2640
```

-continued

```
cggcccggcg ccgcctccga cccggcgccg cctccgaccc gacatgattt gcatatgccc   2700
tcccactatc ccggcagccc catcgaaacc cggcgttggt ggttgccatg ggcaggcttg   2760
gcgccagtcc cagaattcgc actcgggcta ataatatata tatacttatt gagttttgtg   2820
cgaacgctgg cattctgcca gcgttctcac gggcacggtc gtgagagctg gcgcgggtcc   2880
cagggctcgc actcgggcca ataatatata tataaactta ttgagctttg tgcgaacgct   2940
ggaggccagc caagcagccc cgcgaggctc gtcggcccgc ccgccccgcg gttgtagggg   3000
tcacgtgggt cggcgcctcg ccgtggtgga caggcccccc cgctggcgca aaaatacaat   3060
agctctcgat tatccgccat tggatttttt gcccgcgcgg gggcgctgtc caggtggagg   3120
ggggcccgag cagggcccta aaaacccgca tggcgcgaag tccggcgcgg cgcgcgcggg   3180
agggtcttcc tctcttcata atcaatccgc caatcgattt gggtctggcg gcccaaacgg   3240
cccgatacat cgatcgcgct tacagatcaa tcgtattgat ttaatctgat ggcccgatac   3300
caatctatca atatcggtta gatcgattgc caattgtaca accggccgca tatgcgcccc   3360
gttaatcgat cgaccctcgc cgatatttat tttcgccgat tggactttaa agtttcagct   3420
attgatcatc tattgaccga aactgtgtgt cgatatccct ctctgtggtc cctccacccc   3480
ccaccccgca tcaatccagc cgcgcccgag taacaggggg gaggggaggg gggcataaaa   3540
ggacgaatag aaactcaggg ggggctacga cccgagtggg aggggatggc gccatctggt   3600
ggcgacgcgc aaaataacgg cacccaaaaa gggtgcgggt cgctgcaagt acgccccccc   3660
ccataaaggt acagcagctg cggcggcttg cccagcaggt ggcgcagcaa cagagccatc   3720
aatacagatc tttttttttt gtttcgcccc gcctctccgt gcacttacac agctaaaccg   3780
caaggcggag caaggaacga tggggggggg caggggcaag ctgagcgagc aagcgagcgc   3840
agagagaaga gagcgggcgg cggccgcggc tgcctggagc cgaagcggat gaaccgcccg   3900
ggcgagcgag cacgacacgc ccaaaggggg gggcaagacc ggcaaggtgg gctgcggctt   3960
gcatgcaagg acacgggata gtgggctggg ggtatgcccg gcaagggggt cagcagcggg   4020
gtgggaagct gcggtggtcg tccacagggg cgcgggtgtg catatacaaa ctacccacgc   4080
cggcaagctg atggcagggg gcggcggcgg ggcggagggg gaccgcggaa gcactgcggg   4140
ccagggggct atgcaaatta aaccgggcag gggcgagcca aatgcaaaag cgcaaggcgg   4200
gccaaagcaa gcgccacccc ccaactcccc gcttttgtta tcgccgcgcc tgcttgctct   4260
ccctttttttt ggtttttttt taaaaaaagg ggggttgtca ggttacggtt agtttcctcc   4320
cccgccattt tcttttcgcc tctgctgctc ctttttcctc ctccccattt tcctcctcct   4380
tccccccccc cccgctagca caggcttgag ggaacactgt gttcctcgca taaggcgccg   4440
cggctgggcc cttcacacag gcaaaagtgg ggaagcaggg ccgcggcgag taatttgcgg   4500
ttagaacagg tcgcgccctc gcaccggcgg ctgtggctca ggcttttccc cttgggacac   4560
acgcccggag gcaactggta cactgtgtgg cgatctcgca aatgcagcaa gggaggagga   4620
gcggggtgcg gggtgcgagg gggagggggg gtggtggccg tggagagaat ggagcggcta   4680
gggccaaagg gggcagcggg cggtcagacc agggcgggcg ggcgggcgcg caggcgcgca   4740
caaaaagggc caaccaccaa aactaaatgc cgcgcaaata ggcaaaagga aaaggcgggc   4800
tcgaaggcaa tgctgggggc ggagggagca gtggcgctgg gcaggaagcg gggagtccca   4860
atggggaggg ggtaggcaaa tgagcctgga cacaattgcc gcgcctccct gctcgctcac   4920
cgccggggtc ctgggcggga agcggggagt cccaatgggg agggggtagg caaatgagcc   4980
```

-continued

```
tggacacaat tgccgcgcct ccctgctcgc tcaccgccgg ggtcctcccg ccaatcgcga   5040
aagggagaag ggtggggggc ggccgtgagc aagcggggaa gaagggggaa gggggaagga   5100
ggggaggcta gaagcagcgg gcgggacgcg cgtcggtccg gccggcccca tcccgcctag   5160
cgggctggcc agaccaacgc gcgcgaggca ggggcgggaa tggggagggg aactggtagg   5220
ggcgggcctg gtgcaaggcg ggcctgccgg gcgcggggcc gggggcgttc ggccatgctt   5280
tcatgcaaat gagccccgac agccgctcct attataatga gcttggcggc gaaccgcccc   5340
gcgggcaggt aggccctccc aggcgcacct gaactgccgg gtctgggcgg ccccggccgg   5400
cccaccttcg cgcctgggcg ggccttcaaa gggtttataa ggctagcacc gtcgccaccg   5460
actgtacctc cgccgctgcg cgctttttga cacccgtact gcaacacctg ccgctgccgc   5520
cgctgctgcc gccgccggtg cgaggaagga ggagacggcc aagaaagaag ctcgcggaac   5580
aagaaagagg cgcggggaaa ggagagagac gcggccgcga ccgccgtcgg gcaacacgca   5640
gggggagcga gcgagaaaag gaagagccag cggggacgaa ggagcagaaa gccggccagc   5700
cagagagaca gacatccagc cgcggccggc tagctagctc cgaccggccg gccttctgcc   5760
aggaccctcg ccgtcgcgct cgccgtaccc ccgtccccgg gtctccggat ctaaaggtga   5820
gcagcaagca aaccctttgc cgcgcgcgcc ccgccagccg ccgcggcgag agagccggcg   5880
agggcttctc ccgcgccgcg gtaaaacaaa aaaaaaaggg cacgcgcggg ggtgggggga   5940
agggagggaa gggaaagaga aggaggggaa ggggaaggag aaggcgccgc actgccgccc   6000
gctcccggcc cgccgtccgt cccgtcggag ccgccgccgg tcgcccgagc ttcccctccg   6060
cgccgccgcc gccggcggct ttgccgcggc cgccgcagcc ccagctgccc ccccggcgcg   6120
cgcgatagcg aggttgctcg ggggggcgct gttgccgccg cggccgcggt cggtgtcgtt   6180
cgcagcggcg cgggggccct gccgctgccc gccgcccccc cccctcccct gcgttttgac   6240
ggccggccga cccacccgcc cccctacccc gtctccccca ggccaccgca cgcacccacg   6300
gccggtcatg tcgtcgcccg gcaggctcga gctggccacg ctcgacctgt acgacctcat   6360
cgagtccgcg gacctcggcc cgacgggggg ctcggaggag gacccggccc tgctcgacgc   6420
ggcgcgtcgg gctgaggcgc gcgagcgccg gcgggccgcc cgcgccgagc tggccgagct   6480
gtggcggatg gtgggcgggg aggacgcgga gagcagcgag gacgacggcg ccggagacgc   6540
gggggccacc gagggcgccg aggccgagga cgcggagatc ggcgaggacg ccggcgccgg   6600
agacgcgggg ggcgccgagg acgcggacgt cgcggagtgc gccgaggccg agggggcgga   6660
gggcgcggag gacgcggaca gcgcctgggc cgcggcgcgc gcgctcgcgg tcgcggtgga   6720
ggcagccgcg gccggggcgg aggcggccgc ggccgaagcg gccgtcatag ccgccgccat   6780
cgaagccgag gcgggggcgg cgcccctcaa ggccgaagcg gggaccgagg cggggggcgg   6840
cggtgccgtc ggggccagga ccgaggccgg cgatgttggg cccgaggact gcagcgatgc   6900
cgggtccgag gacagcgggc ccgaggacag cagcgatgcc gggcccgagg acgatggggg   6960
cgaggcccgg gaggggagca ccgacgccga cgccgacgcc gacgctgagg ccgaggccgg   7020
gactggggcc gggaccagaa ccaaagcggc cccgcgaaag gcgggcgccg ggcccggcgc   7080
cccgcggggc cgcgcgcccg ggcccccggc gccctcgccg ccggagacgg cgcccccccc   7140
gccgcggcgc cagcgcgggc gcgcaaccgg cgcccgcgct ggctacgccg cggcgccgcg   7200
cgacgggccg ccgccgctgg agggcccgct gctgacgcct tctggcgagg cgtggcccgg   7260
cagcgcgccg ccgccgcccg gccgcgtgcg cttcggcggc gcgggcgaca ctcgcgaggg   7320
cctctgggac tgccccgaga tccgcgaggc ggccgcgcgc tacgcggcgg ccgcgggccc   7380
```

cgcggccgtg ttcgtgccgg agatggggga cgcggggaag cagtacgcgg cgctggtgga 7440
cctggtgtac gcgcgccgcg acgccatggc ctggctgcag agcgcgaagc tcgcgggccc 7500
ggacctgcag ctggcgcgcc tgctgcagcg gcgcgtgcag ggctgccggg gccacagctc 7560
gttcatcacc gggagcgtga cggcgccgct gccgccggtc ggggacgcca tggccgcgca 7620
gaacgcgctg tgggcgctgc cgcacgtggc ggcctgcgtg gccatgagcc gccgctacga 7680
ctgcgaccag aagctgttcc tcctgcagag cctgcggcgc gcgtacgcgc ccatggccta 7740
cccggaggcc ggcgccggcg gcagcggcgc ccgcgccgcg ctcgccgagc tgcgcgccgt 7800
gctcgccggc cgcgcggcgc cggcgcccct gccgccggcg agcacggcgc gggcggcgcg 7860
cgagcggctg cgcgagctgg cggaccgctg cgccgtcgcc tgccgcgagg cgctggaggc 7920
ggcccgccgc gccgccggcg ccgccgggct cccggtgctc tcggccgcgg cgggccgcgg 7980
cctgccggcc gcggcctgcg cgccggacgc gctggcggcg cacccggagc gcgtgctccg 8040
ggccgccgag ctgctcggcg cggcccgcga cgcggtggag cgcgcgcggc tccagcgcgc 8100
ggccccggcg gcgctgcgcg ccgaggcggc tgccgcgctg gaggcggccg cgctggcggc 8160
gcggaccgtg gccccgctcg cgcggtactc aacgcgcggc gcggcagccc gcgcgtcggc 8220
ctgggcgctg gcgcgcgcgc tgttcagccc gccggcggag gtaccggcgc ggctggcggc 8280
cgcgctcgcg gccctggagg ccgccggcgg aggcgctggc gccggcgcgg ccgcgccggg 8340
ccgggggccg gtggaagtgg aggtggagga catgagggcc ggggcgccgc gggcggaccc 8400
ggaggacggg tccgaggcgg aggatgagga ggctgaggag gacggggagg acgaagaggc 8460
ggaagaggag gaagaggagg aaggggacgg ggaggacgaa gaggcggaag aggaggaaga 8520
ggaggaaaag ggccgccccg gcccggcggc gctcccgccg ccgggtccga gggaaggaag 8580
aagggccgag gaggaggagg aggaggagga ggaggaagaa ggggacgggg acggggacgg 8640
cgaggcggcg gccctgccgg ccgccgcggg gggcccctcg ggggaggacg actctgggcc 8700
gaggcgccgg cgaaaagccg ccgccgccga cgcggccggg ccggcgcggc gggagccgcc 8760
gctgcccgcc cgcgtgctgg ggcccatgcc gcccggcggc cccgccgccg acggcggctt 8820
ccgccgcgtg ccgcccgggg actaccacac gcccgcgccc agcgccgcgg cgctggcggc 8880
ctactgccgc cccgaggtcg cggcgcggct cgcggaccac ccgctcttcc ccgagccctg 8940
gcgcccggcg ctcgccttcg accccgaggc gctggccgag atcgcggccc gccgccgcgc 9000
gggccccgcg ggcgcgctcg ccgccagcgc gccgctgcgg cggcgcgtgg cctggatgtc 9060
gcagatcgcg gaccccgagg acgtgcgcgt ggtggtgctc tacgacccgc tgcccgggga 9120
ggcgctggcg gcgccgcccg gcgaggacga gcgccggcgg cccgagtggc cgccgcgccg 9180
cggcgggctc tcgcacgcgc tcgcggcgct gggcaaccgg ctgctgctga gcgccgactc 9240
gcacgcctgg gccgggcgct ggacgggcgc gccggacgtg agcgcgctcg gcgcgcaggg 9300
cgtgctgctg ctctcgacgc gggacctggc cttccgcggc gcggtggagt acctctgcgc 9360
gcggctggcc gcggcgcggc ggcggctgat cgtgctcgac gccgtggacc ccgagaactg 9420
gccgcgcgac ggcccggccg tcgggcaggc gcacgtgtac ctgcgcgccg cggtgctgcc 9480
cgcggcgcag tgcgccgcgc gctggcccga gcggcgcgcg ctggcgcgcg ccgtgctggc 9540
ctcgcggcgc gtcttcggcc cgggcgcctt cgcgcgcgcc gaggccgcct acgcgcggct 9600
ctaccccgag gcgccgccgc tgcggctctg ccgcggcggc aacgtgcgct acacggtggc 9660
cacgcgcctg ggcccgcgca ccgcggtgcc cgtgccgccg cgcgagtacc ggcagcgcgt 9720

-continued

```
gctgccggcg ctcgacgggc gcaaggacat ggccgcgcag ggcgcggcgc tggggctcgg   9780

ggagccggac ttcgtggagg gcgaggcggc cagccaccgc gccgccaacc gctgggggct   9840

cggcgcgccg ctgcggccgg tgtacctggc ctgcgggcgg cgcgcgctgg agctggcgcc   9900

cgacgagctg ccggccgcgg cggtggcctt ctgcgcggcc gcgctgccgg agccgcgcgc   9960

cgaggcgccg ccgctggtgc tggaggccgc ggcggcgccg cccgcggccg cggcgcccgg  10020

cgtggactgg gacgcggacc agggcccgcg ggagacgctc gtgctgctgc ggcgcgccgc  10080

gggcggcggc ctggtggagc gcgtgccgcc gccggcggcg gaagccccgc cggcccgggt  10140

gccggcgcag tcgtccccgg gcgcgggctc gggcttcccg gcgccggcgg gcggcggccg  10200

gcggccgcgg cggccccggc acgggccgcc gccgcgcgtg gaggtgctct cctcctcctc  10260

ctccgcctcc tcgtccgcgg cgtcgtcccc cgcctcgtcg gacgacgacg aggccggcgc  10320

cgccggcggc gggccggcct cgccctaggg gggcccgcgg gaagggaggg agggggcgcg  10380

acggcggcaa taaagacgag tctgtgcgaa cacacgcggt ccgagtgcgg ctctttcttc  10440

attgtcgggc ctcgggggcg gggggaggcg cgggccgcgc gccgctgcgg agcggccgcg  10500

gagggccagg acccggcgcc ggagacgcgg cgctggcgtc cgccgccacg ttccccgcgt  10560

cgggcacttg ccctccgcgg acaagggggt tggcgcgcgg ccgcccgcc gccgccgctg  10620

ctgccgccgc cgccgccgcc gccgccgctg ctgccgccgc cgccgccgcc cgcccgcccc  10680

aggccctcgg tctcggtcgg agcgcggtcc ggcgcgcggc gcgcggggca ggccccgggg  10740

cgcgaagccc gggagggacg cgggcgtgga gcgcgaagct ccggcggggc gcggggacag  10800

cgcccgcgcg gggctcgccg gcccccgggc tcgggcccct gggcgccggg ggtcggggcg  10860

cgaggcccgg gctcgggccc ccgggcgccg ggggcggggg cgggggcggg ggccccgggg  10920

gccaagacgc agaaccccgg ccccccggcc ggggcccgag gcccgcgggc ggggccgggg  10980

cgcggggcgc cggacccagg ggcggagccc agagcgggtc cgggcccgcc gcgccgaaat  11040

ttccgccccc ccccaaaaac acccccccgg ggttgcaagg ggcccgcgcg gcgcggcgcg  11100

gaggg                                                              11105
```

<210> SEQ ID NO 4
<211> LENGTH: 102478
<212> TYPE: DNA
<213> ORGANISM: Bovine herpesvirus 1
<220> FEATURE:
<221> NAME/KEY: misc_feature
<223> OTHER INFORMATION: Unique Region - Long

<400> SEQUENCE: 4

```
gcccagcccc cgcgcggggg gcgcagagaa aaaaaaaatt tttttcgcgc ggcgcgtgca     60

ttgcggcggg cgggggcggg gtgggggatg ggcgcggagc gcgagggtag ggttggcaca    120

cggccaagat caccgagcat gtgcgcggcc atcttgcttc caaactcatt agcatacccc    180

gcccagtatt ccattctcat ttgcataccc accgtcgcac atgccgccat attgctcctc    240

ctccctcgct cctcctccct cgctcctcct ccctcgctcc tcctccctcg ctcctcctcc    300

ctcgctcctc ctccctcgct cctcctccct cgctcctcct ccctcgctcc tcctccctcg    360

ctcctcctcc ctcgctcctc ctccctcgct cctcctccct cgctcctcct ccctcgctcc    420

tcctccctcg ctcctcctca aaacactacc gcgggcgtcc gctcccacta gcttcggcgc    480

cgtcatgggt gcccgtgcct ccgcgcctgc tgccggtccg cccccagccc acgctgttct    540

actagatgcg ctctccgggc gcacgatcga cctgcccggc ggcgacgagg ccgtctttgt    600
```

-continued

```
gtcctgcccg acgacgcgcc ccgtgcacca ccacatgcgc cgcggccgca cggcccacac    660
tacacccgtg cacttcgttg gccgcgccta tgccatcttg ccctgccgca agtttatgct    720
gtatctgatg cgcggtggtg ccgtttacgg ctacgagccc accactggcc tgcaccgcct    780
cgccgattca ctgcacgact ttcttactac tgccggacta cagcagcgag acctacactg    840
cctcgatgtc acggtgcttg acgcgcagat ggacccggtg acgttcacca cccctgagat    900
cctcatcgag ctcgaggcgg acccggcctt cccaccgcca ccctcggccc gcgcgcgccg    960
ctccacgctg cgccgggcgt ctatgcgccg gcccgcacgc accttctgcc cccaccagct   1020
agcagagggc tccattctgg acctctgctc gccagagcaa gcggcggcgc cgggctgttc   1080
gctgctcccc gcctgtgact ctggagacgc cgcgtgcccc tgcgacgctg gcgagaccgc   1140
ccgtgactgt actgccgatg ccgcgcccgc tcccagcccc ggcgccttat ctcgctatag   1200
ctccgtgcgc tcggtgttct tttagcgcgc gggcgcccgt gtgggacata cattaataaa   1260
tgcagcgttt cttactctac tgtagtggct ggccgtttgc ttctttttgg gattggcaat   1320
ttagcgttcc gtcgacgcca catcttttgc ctctctgttt cccgttgcgt gcgcgcgtgt   1380
cgccgagccg acttgccccg acaacacagg caggcacgcg gccccgcgcc ccgccaggca   1440
ctatttgcgc tcgggtgcat tgagcttgac tttgactcgc ttttgtgccg acgcccaatt   1500
atttgccttg gcccgttgtg tccccccgc gcgcgcttgt gccgcccaag tccgcccgcc   1560
cgatagcgcg cccgcgcctg tgtccccaac aagtactata cacactcgag tatatcgggt   1620
tcaaatcaat gttgacttta ttagcttaga agatctcgtt gcagtaaaag tattttccgt   1680
gcatgtacac gggaaccagg gtgaaattag cgacgagctt gcacgtcatg ctgtcgcagg   1740
cctgtttgtg tgtgtccagg gcatcgatga gccccgccac gcaggccccg gggatgtact   1800
cctcaaaagg cgcgtcgccc acagtcacct ccaacagcgg cacgcactct gcgccggagc   1860
gcaccgcgcg gcttagacgc gccaacatca cgaacatgta cgatgcgggg caggtggcga   1920
ggcttagccg gcgcgcagcg cagagctcct ccagcgaggg tagcccgcgc ccgcgcaggt   1980
agcagcgcag aaaaggcgct agcttcagcc gcaggttttc cagcacggcg ccggccgtgg   2040
ccacgatagg gtctttggtg cgcaggcgca agttcttggt ggcgatgaac ttgcaccacg   2100
ttaggcactc gtcggccgag gccagtgcgt ctaccaggtt ttcgttgcgc agcaccaggt   2160
ctcgcagcgc ccgcgccgcc tgggcggcgt gcgagcgcac ctcaaacatg cggtagaggt   2220
cgcggccgtg gaacatgagc gtctcccagg tgacgcggcg gccctcggga acgaattgct   2280
ccgcgccaaa gtccaagacg gctgcccatg gcgacacgcc cgctgcgcgg aacccgccgt   2340
tttgcacggg ccgcatgagg tccagtcgcg cgcccgcgaa gacggcggtg acgcgctcgg   2400
ccgtggctcg ctgcgccgct tcggccaagc ttcgcgcgag ccgcagcgag ctcccgatcg   2460
agcgggcggc ggcgcccccg ccgccgtgtg aagacgtcgc gagggccgcc tcgcgctttg   2520
ctgccgggcc gcgggaccgc tgctctccgg cgggctgcct tcggcgcggg cgcctgcgcg   2580
gccgccgcgg ccgcacgcga gcccgccgcg ccggaggtgc ttcggcggga ccgccgtcgc   2640
cgcttgcggc gccttcgccc ggcggctcgg ccggcatcgg ctcgtcctcc gcgccctcca   2700
gcttgcgctt gcgaacctgc cccaccacgg agcgcagggc gggagcgagc gagggcgcct   2760
cgtcgtcttc ttcgcggtca gagccgaaga ggctcaagtc gtcgctctcg ctggccgtgc   2820
tgagggttgc gatctcgggg tccgccatgc cgctgcgact cgcgggcgtc gtcgtcgggc   2880
cgggtgcgtc gccgttcggg ccggacggtg tctcgcgttt ctaaaagagg gctcgcactc   2940
cggcgccgtg ttcgcactga gaccggcatt ttatgttcgc tggccccacc ctgcgcggca   3000
```

-continued

```
gcagcgccgc ccaatagggg cggtcacgtc tgcgcgccca gcagccgcag gcgcaggttg   3060
tgctcgtagt gcagcagcgc gatgacgccc cccacgatag cggccaggta gagcgccttt   3120
acgagcagcc ccgcgagcag cgtggagcag cagttcacgc acacctttct gatcccgctc   3180
tcgccgccat cgccgccatc gccggcgacg gcgctgcccc cgcgccgccg cgcgggcttg   3240
cggtatagca gcgagaccag ttccaatccg gcaaagaggg cgacgtgaac ccacgcccag   3300
attttcaggt acagcgggta ggcggccgcg cagggcgcgt gcgttatgcc gacgctgctg   3360
gccgccgcaa tccgcgcgcc gagccgcgcc aagccctccg caagcagcgg gagcagcagc   3420
cccgggcggc gccaagcgca gcccaggggg tcgaggcgga agttgacagc aagcgcgcgc   3480
cggcgcgccg agagctcgca catgagccgc gcgagcttcg tgtacgggcc gtggccgact   3540
acggccgcga gcgcggcggc agcgtagttg agggtgtagc cgccggggct gaggaagtcg   3600
gcgtcgttgc ggcaaatgcc gaacatgcgc cgctcctggc gcaggtacac gaacgcgacg   3660
tacagcagcc atgccagcag cgcgctgcga gcctgcgcgg accacaggta ggcgcggcaa   3720
tcgcgcgcgc cggccacggc gcgcacgcgg ccgtgcagcg cttcgtcgcc gtcgagcagc   3780
ccgggcggga tgtgctgcac gacggcgtgc cggcacgggg cgtcggccgc gagcgtggcg   3840
ttgttcgcgc cgcccccagac gtagacggcg ccggggtcgc gcagctccca gcggagcgag   3900
ccgttggcgc cggtggcgcg gacggcgagc gcacagcgct cgcgcagcgg cgcggcgagc   3960
gcggcccaca gcgccagcgc gaggtgggcc gtgagcagcg ccagcgcggc caagttaaca   4020
gtccgccccc cgagcagcat accgcgccgc gcgccccgag agatccacgg tgaacacggt   4080
accgaggcgg ttgctgccgc acttggtagc gaagcactgc tggatgagcg aggcacacag   4140
gcggtcgtgc gagtcgacac tgagggacac cagcgagcgg gccttgtttt gggccgcgcg   4200
cccgtgggcc gcgcgcaggc agccaaagcc ctgcgcggtg ccggcgcgcg cgcgcgccgg   4260
cacgagctgc gccagcagcc agtcggcttt ggcggccacg aggcgcgcgc cggcgccttg   4320
gtactcgcgc gccgcctgcg ggtagtgctc cgccatgtag ggcgccagct cggcctcgat   4380
tacgtcagca ataaactctt cgacggcgcc acggtcgccg ccgtcgacgc cgacggcggc   4440
gagcgcgcgc cgcagggaaa cgcgcacgcc gtgaaaggcc gcgcggttga cggcggcctt   4500
gcgctcaaaa aagctaacgt attcgccgcc aacgctgcgc agcacgtgcg tgcgcggcgg   4560
cgcgcccgcg ggtggcgcgg cgtggaagtg gaagtggtgc gggtcgcggt gcgcggcgac   4620
gaaggcggcc acgtcgtcgc agcgctctgg gaccacgtag aagggcagga gccaccgccc   4680
gacgttgctt gcggcgtctg gcttgccaaa aaagggcaaa cgcaggctgt gcccgtgcgt   4740
gtagacagcc gcgtcaacga aggcaaagtc gcgcaagtag cggctcatgg cctcggcgaa   4800
ggggcgttcc agcatgacgg catgctggac gaggcgcgcg atgcccttga gcgtggggcc   4860
gccggcgata atgtatggcg ccgggacggg cacagccacg cggaagccca ttttgtcgtc   4920
gcatccgcac gcggtcgtta gggccgccgc gcttcccgcg ccctccgcgc cgcccgtctc   4980
ttcaggccgg gcgcccgcgg ggtcgctgac gtcctcgcag ctgtattgcg cctcgccctc   5040
gcgcgcgagg gcgctctcgt actcgtccca gcccgcgtcg cggtcgggcg cggcccagga   5100
cggcgacgcg tcgccgtcgc ctaggttgct agcggcggcc gaagggcacg cgctcttgta   5160
gaagaagcag gggtgtgcgg gccaggcatc ggcggcgatt tcggggaaca gcgccgcgag   5220
cgcggcaagc gcgccgcgac ggaagctgcg catggctccg tgcaggtctc cgcgggggag   5280
ggggcgcttg aggcgaaagt ccacgtccag gacgatgttg gttacggcga ggcgggcgtt   5340
```

gaacagctcg ttgcggttca cgtagtactg gtcgcgcggc gcggccgggc ccaggctccg 5400
gcggtccgag cggccggcgg cacaggccgc gcgctcagtg aggagcgcgg ttagccgcgc 5460
gtctcgctcc acaagcgcgt cccggccgct ctctgcggcg gcggcagcgg ccgccgcaac 5520
ctcgaccgcc acttcgtcgg ggtctagggc ggcgacgctc gtgacggcgg cccagtcgtc 5580
gccgtccgcg acggcaaatg cctggtggcc gcgcggtagc tccactcggt agacgggcgt 5640
gggcgccgcg gtcccgcgcg cgccaaagag cccgtccagc ggatgcgcgc cgtcgcgcgc 5700
ggcggcggcc gccagctcaa gtagccgctt ggacaccccg cagcaggcgg gcgtcgcatc 5760
aggggacgca ccgccgtccg gcgcgccaag cgcaagcgcg gcgtctagcc ccgggcccgg 5820
caccgcgctt gcgcttggcg cgccgggtgc gtgcagcacc cacccgaagc gagccgcctg 5880
gccctcgagg tggtccagcg ctgcgcgcag ggcggccgcg ccgtcgcaga ttgtgcgccc 5940
gggcccatta gcggtcgccg cgagcaagcg cgcgtacgta cgcgcgcgcg cgtaagcctc 6000
ggctgttgcg gggggcagcc gaacaacggc gaccgccacg ttctgttcga tgtagctttg 6060
gacgttaaac tgcgcgcgca cgtgccgaaa aaaagcgtca acggcgcgct cgcggaggcg 6120
cgagacgccc gcgaggcgcg gcgcgagcgc ctcgccgcca tcggggggct cggtggcggt 6180
gacggcgcgc aggtgctcgg tgatctgccg gcgattaaag ccctcaaagt aggccaagta 6240
tacgtaggcc acgaactccg ggtcggccac tttaagactg cgacggtcgt ggtcgatgta 6300
ctcgcgcagg cagcggacct cggcgaggtc ggcctcgatg cgcgcggcca cgtacgcggg 6360
tgccccggcg gcaaccgcgc cgcgggcgta gccgctgcgg cagcagaagg cggcaagcgc 6420
cgcgaaggaa accaagtcgg ggaaggcgag tcccgagggg ttaggcggcg cggcgacggc 6480
gtacgtggcc aggcagtccc gcacggcctg caggtcgtag gtagcggcgt cgccggcgcg 6540
ctcagcctgg aacacgtaga agcgcgtggc caacaccaag gtttttttcgc cgggcccaaa 6600
cttggagagg aaccagaagg gagtcgcacc gctgttggcg taaagccgcc ggtaggcggc 6660
gaccgttttg tgctcgtggt ggatgtagag cgaggctagg ccgcggcggc cggccgggcg 6720
cgcgcgcagg gccgagcgca ctgtagtctg gccctcaaca tagcgggcgt cgtctgcggt 6780
gcggccggtg cgaggcgcca gctgctccgt ggccaccagc agcgcggtga tcatgtccgc 6840
gtgcagcgca aaggtgacgt cctcggcgag gtgctcgagc agcacgcgcg cgggtagggc 6900
cttgccgagg agcagtgcgt cggcgagcgc gcgcgcgccc tgcgcgctgt tgaaggtgca 6960
cacgaagacg ggccaggcgc ggggtcgcgc ggcggcgctt ccgcccggcg ggccgcccag 7020
cagataaaac gcgacgagcg gccgcgcatc cgccagcgcc agcgccacgt cgtttgggct 7080
ttcgccacca aggcacgcgg cgagccgccc gggccagttg taggagacca cgtaggcgcc 7140
acggccgggc tcctcctggc ccgtgagcag catcagcgaa aacccgatcg cgcagccgtc 7200
ggtggcgtac aggatttgga gcgcgtcctc gagcgcggct gggccgtcca tggcgctgca 7260
gcggctggtc gggtggctgt gcgggcgcgg cgggggcacg cgagacgctc cgcagtacga 7320
gccgctggcg cggcgcctga gcggaccgac gctatttcgc ctgcaagaag cggtggtagc 7380
cgtcagcgcg ctgctgccgg cgccgctgac agtggaggac gtggcgcgct cggcagacgg 7440
cacgcggcgg cttgccaagg cgcagtcgct agcgcggacc tactacatct gccagcggaa 7500
catcgagtgc ctctcaaagc accaggccgc gtgtagtgac gcaagcatca ccgccgtcgt 7560
gacgaagcac atacaggatg ctcagcgcat gcgcgacacc tgcctggccg ccttgcttca 7620
aatgtaccac tcggtgggcg ctgtggaggg cacgacggac agcatggtgg accaggccat 7680
ccgcatggcg gccgaaagca acattgtaat ggccgatgtt gcggtgctgg agcgcgcctt 7740

```
gggcattcag gcgcagggcg cgggcgcgga ggcggcggcc agggcaagcc cgacggccgt   7800
tggtgccgag gctcgggccc cgccgcccct gccgcggcag ccggccgcct cggcgccggt   7860
cgccgtgtct ccggcaccgc cggtggcgcc tgcagaggcg gccgccacaa aaccacctag   7920
ccgcgcgggg cgcgcggcgg ccgccgcttc ttcccccgcc gttttgcagc ttgcggcgta   7980
gcccggtgca ataaaagcaa aataagtata cgcaaaacac gtgtgtggtg gagtcggtgt   8040
actttaatgt gctttgtttt acagcccggt ggacccaaag ccgcgcggcc cgcgcgcaga   8100
ggggggcacc gccgcggcga gatcggcgac gcggcgccag cgcaggcgcg gggccccagg   8160
ggcgggcggt gctgcgcgag ggctagttgg gaagggctcg cggtcgttga ggccggacgg   8220
aagccactcg aggcgccgtg ccagcagaag cagctgcgcc acgcgctggc ctgcggcagc   8280
aacgagcggt tcctgcgtga cgtttcgcaa gacaaagcgg cagggctccc cggggggcca   8340
ggctgtcggc aggacgatca gcccccgaag gttgcaggac gatcgaccaa acacgtaggg   8400
cgcggcagcg tgggcgtctg ccgcgtaggc tacgggcagc cgcacgtgta aattttcccc   8460
gggtgccaag acggccgtgt atggcatggc aatatcgtac ccggcgtcct cgtcgcgttt   8520
gggggcgaac gtggcaaaga agggcacttc gacgcccgcc tctgtcccgg cgtttgcgtc   8580
gtcgtcgacg gcgatgaggc gaggcagcgt ggtggttagc cgcgcgagcg tcagccgcag   8640
cgcaagcccc gccgggggag cggccgctgc ggactcgggc gcccagacga tggcgcgcaa   8700
gatccccgag tagcccgagt cgacgatgcc gacggccacg gctggtgggc ggggcatgtg   8760
tgtgtcaccc gagcgcattt gcgacattat aatggcatat ccgccgggcg cggccgcctt   8820
catgtttaaa ttaatcagcc ggctataaag gagagatccc gacggggctg tttcatctcg   8880
ctttgctgct ggcgcaattg ggccccagag cgccagcgag tcgggctcac agcagctttc   8940
caaccgccag gggccgcct ccgcgttgag ctctacgacg aggatgccgc ggtcgccgct   9000
catcgttgcg gttgtggccg ccgcgctgtt tgccatcgtg cgcggccgcg accccctgct   9060
agacgcgatg cggcgcgagg gggcaatgga cttttggagc gcaggctgct acgcgcgcgg   9120
ggtgccgctc tcggagccac cgcaggccct ggttgttttt tacgtggccc tgaccgcggt   9180
aatggtcgcc gtggccctgt acgcgtacgg gctttgcttt aggctcatgg gcgccagcgg   9240
gcccaataaa aaggagtcgc gggggcgggg ctgattgacc gcaacgctgc ggagtaactt   9300
gtatataaag ctcgcggtcc cggcgaccgc tgccttttc gcactcggcc cgacccgctt   9360
tgagctgcac gcccgccggc ccgccgactc gcttgccatg gcccggttcc acaggccctc   9420
cgaagacgag gacgattacg agtacagcga cctttgggtg cgagaaaaca gcctctatga   9480
ctacgagtcc ggctcggatg accacgtata cgaagagctg cgcgccgcga cgagcggacc   9540
cgagccgagc gggcggcgcg ctagcgtccg tgcgtgcgcc agcgctgcag ccgtccagcc   9600
cgccgcccgc ggccgcgatc gagccgcagc cgcggggacg accgtagctg cgcccgccgc   9660
cgcgccggcc cgccgctcga gcagccgggc gtcctcgcgc ccgccgcgag ctgccgccga   9720
cccgcccgtc ctccggccag ccacgcgcgg gtcctccggc ggcgccgggg cagtcgccgt   9780
cggtccacct cgacctcgcg cgcccccgg tgctaatgct gttgcgtctg gccggccgct   9840
ggcgttcagc gcggctccga aaacgcccaa ggcgccctgg tgtggaccga cgcacgccta   9900
caaccgaacg atcttttgcg aggccgtcgc gctcgtggcc gccgagtacg cccggcaggc   9960
ggctgccagc gtctgggact cggacccccc aaagagcaac gagcgattgg atcgcatgtt  10020
gaagtcggcg gcaattcgca tcctcgtgtg cgagggctcc gggcttctcg ccgccgcgaa  10080
```

-continued cgacatcttg gccgcgcggg cccagcgccc cgccgcgcgc gggagcacaa gcggcgggga 10140
aagccgcctt cgcggcgagc gggcccggcc gtagcgcgag cgggagggct ttttcgacgc 10200
gcgcggctta agcagcgcgc tgctgtgcta gtatgaaaat aaacgcttgt taattaaaca 10260
caccaagccg agttgcgttg tctttgggat gagcgggcgc ataaaaaccg cgggccgcgc 10320
gctcgccagt cagtgcggcg gtgctgcggc ggcaaccatg gacccgtacg acgccattga 10380
agcgttcgat gactccctgc tcgggtcgcc gctcgcggcg gggccgcttt atgacggccc 10440
gtcccccgcg cggttcgcgc tgccgccccc gcgcccggct cccctggccg cgttgctgga 10500
gcgaatgcag gccgagctgg gcttccccga cggccccgcg ctgctgcggg ccatggagcg 10560
gtggaacgag gacttattct cgtgtctgcc gaccaacgca gacctgtacg cagacgccgc 10620
gctgctctcg gcagacgcag acgcggtagt gggcgccatg tacctagcgg tgcctgggga 10680
cgcggagcgc ttggacttga acgcgcacgc gaaccagccg cttcccgcac cgccggcctc 10740
ggaggagggc ctcccggagt atgtggccgg cgtacaggcg cattttctgg cagagctgcg 10800
cgcgcgggaa gagcggtacg cgggcctgtt tttgggctac tgccgcgcgc tgctgcagca 10860
cctgcgcgcg acggcggcgc gtggccgagg cgcggcgggc gcgggcgccc aggcagaccg 10920
cctgcggcag ctggtggcgg cgcggtacta ccgcgaggcg agcgcgctgg cgcggctggc 10980
ctttgcgcat atgtacgtgg cgacggcgcg cgaagtctct tggcgcctgc actcccagca 11040
gagccaggcg cagggcgtgt tcgtttcgct gtactatgct tggccgcagc ggcggcagtt 11100
cacctgcctg ttccaccccg tgctgttcaa ccacggcgtc gtggcgctgg aggacggctt 11160
cttggacgcg gcggagctgc ggcggctaaa ctaccggcgt cgggagctgg ggctgccgct 11220
ggtccgcgcg gggctggtcg aggttgaagt ggggcctctg gtggaggagc cgccgttttc 11280
gggaagcttg ccgcgggcgc tgggcttcct gaattaccaa gtacgcgcga agatgggcgc 11340
gcccgccgag gccggcgggc ggctggcgcc ggagcgggag cactcgtacg cgcggccgcg 11400
cggcgcgatc aactacggga cgactccaga ggccatgttg cggcccccgt cgccgagcga 11460
agtgctgccg tgcgaccccg cgccagcggc taccgtgcgc gtggcgagcc ccgccacaca 11520
tctggctcag gcgccttcag ccaagggcgc cgcccccggcc gagtttgccg ccttggctgg 11580
gcttgcaagg cccggtccgg ccccgctcgc ggcggccccg gcccaagccc cgttcgcagc 11640
ggccttggcc ttagccgagc ccgcggcagc cctggccccg gccccgcttg cggcggcccc 11700
agccgagccc gcggcggccg tcgccgggcc aagcccggca aacccattcg gcggcacgta 11760
tgacgcgctg ctgggggacc gcctcaacca gctgctggac ttctaagggc gggcgggcag 11820
tggcgctttc gacccggcgc gtggcgtttg cgaggcctcc ctctggcgta aggcctctgg 11880
cgccgccctg cgggcggcgc gagcgtataa aagccacttg ggtctacacg ggatttagtt 11940
ttcgcgcccg cggctttcta ggcgccctta gacgccatgg acgccgctag ggatgggcgg 12000
cctgagcgcc gcccgcgccg ctccggaacg taccgcacgc acccgttcca gcgcccctct 12060
gcccggcgga gcctgctgga cgccctgcgc gctgcggacg ccgaggccgc ggagcgcccg 12120
cgggtccggc gcccgcggcc tgacttccag cggcccccgg acgaggacac cagtgaggac 12180
gagaacgtgt atgattacat cgacggcgat agcagcgaca gcgccgacga ctatgatagc 12240
gattatttta ctgctaaccg cggccccaat cacggcgccg gcgatgctat ggacacagac 12300
gcaccacccg agcgcgcccc ggaagggggt gccccgcaag actacttgac ggcccacctg 12360
cgcgccatcg aggccctgcc cgagtcagcg ccccaccgga gcctgctgga gcgcacggcc 12420
cggaccgtgt atgcgcagca gtttcccccg cgcgatttga gtgcgggctc cagggcgccg 12480

-continued

```
gcacagcgcg cgcggcggag cctccgcggc ttcccgcgtg gcggcggggg cggccaggaa  12540
cccgggccag acgacgaagg cgacgacgcc gcagacctgc gcgaggacct tgtgccagat  12600
gaggcctacg cgcacctaga gcgcgacgag cggctgtcgg aagggccccc gctcctcaac  12660
atggaggcgg ccgctgcggc tgcgggggag aggagcgtgg tggaggagct gtttacgtac  12720
gcccctgccc agcctcaggt agaggtgccg ctgcccagga ttttggaggg ccgggtgcgg  12780
cccagcgcct tcttcgcgca gatgccgctg gacgcgctgt gccgcacgcc gcccaacgat  12840
cagcgcgtgg tgcgcgagcg gcgcgcttgg gagatggccg gtacgccgca tgggctccta  12900
ataaccacgt ggagcacggt ggacccggaa ttctcgatcg gcggcatgta cgtgggcgcc  12960
cctgagggca cccggccccg gctagtgtgg cggcgcgcga tgaagcaggc catggcgctg  13020
cagtaccggc tgggggtggg gggcctgtgc cgagcagtag acggcgcagc aatgccgccc  13080
actgaggcgc tgctcttttt ggcggacgcg ctgctgcgcg tagtgcgcaa ctgccatttt  13140
ttgtcgcggc cggggcgcgc gggcggcgcc gcgcggcgcc tgcccgcggc ggcggttggg  13200
ctgctggcag ccacgcagtt cacgccaccg gacgcgtccc cccacgcgac gctctttcgc  13260
ggctcaatgg gctccctgat ttactggcac gagctgcgcg tgatgctgac tgcggtgccg  13320
gccctgtgcg cgcgctacgc gggcgccggg ctgcagtcgg ccgagctgta cctgctggcg  13380
ctagcgcact cagaggcgcc cggctacacg gcaaatgagc gctacgcgct ctcggcgtac  13440
ctgacgctgt ttgtagcgct cgcggagcgg gcgctgcgct ggctgtatct agcgggcgcg  13500
cacctgctcg ggccgcaccc cacagcggcg gccttccgcg aagtgcgcgc caagatcccg  13560
tacgagcggc tgccgctagg cagcgcgacg ctgcacgacg ccgaagtgga gacggtggac  13620
tcggccacct tccaggaggc cctggctttt agcgcgctgg cacatgttta cggggaggcc  13680
tacgtagcgg tgcggaccgc gacgacgctg ctgatggccg agtacgcggc ccacgctgag  13740
cgccgggacg tgcgcgagat gacagcggcc ttcctgggcg tggggctgat cgcgcagcgg  13800
ctgatgggca gcctgaacct gctgctgaac tgcgtagccg gcgcagcggt gtacgggggc  13860
cggcgtgtga cggtgcgcga gggcacgctc gcgcggtaca gcctgctagc ggacgcggca  13920
ctgccgctgg tgcgcccggt gtccctggtg gagttctggg aggcccgcga cggcgtcatg  13980
cgcgagctgc ggctgcggcc cgtggcgagc ccgcccctgg ccggcaagcg gcgggtcatg  14040
gagctgtacc tctcgctgga cagcatagag gcgctggtcg gccgcgagcc gctaggttcg  14100
cggccggtgc ttgggccgct cgtggacatc gcggaggcgc tggcggacca cccgcacctc  14160
gtcacgggcg atgggcgggg cccgcgcctg ggcggccgct aggcggcagg ccgcgcttac  14220
gcggcggctg ggtccgccca catcagccac cacgcccgcg cgcccgcccc gccctcgtat  14280
gcctatatag ccatcacgct tgaatgccaa gcgccacttt cccgccgcgg cgaaatggcg  14340
tggccggccg cctctcgggg cctcatcgag cggcgggcag agaaggggtg cctgctgccg  14400
acgctcgcag atgccacggc cgcggccgtg gtggccttgc aggaggcgac cgagcctctg  14460
tgcggggctc cgctgtttgg cgccgagcgc gcggccgcgc tgctcggcgt gcgctccaac  14520
gccgtcccgg aggcgctggt tctgtcggac tcggcgaaag acgccgacga cgagtaccgg  14580
ctggagtatg accgcgccgc agcgcgggtg ctggcgggcg cgcggctctc taaggacgcc  14640
gtctggcgcg cggtcatcgg ctcgtactgg aagtacctga aggcctcgag cggcgctgac  14700
gtgaacatcg acggcgcggc cggcggcgcg gcgatggagc aggcgcagct gacgaacgtg  14760
atgctctttg cgcccacata cgcgcgccgg gcctcgcgct cgccgttcaa gcacaagcag  14820
```

-continued

```
gacaacgcgg cgtacaaaac cgcagcggcg gagctgcgcg gcgccctgcg cgcggtggaa  14880
aagtatatgt attacatgcg gccgggcgac cccatggtcg aaagccccga cacggaagcc  14940
cgcctgcagg aaattttggc gtacgccgcg acggcctacc gctggctgct gtggttcatg  15000
gacgcgctcg atggcacggt gctgcgcaag cttggcaagc gcccctcggc cgcggtgggg  15060
ccgcgcgagc cgcagccgcc gggcgagctg tgcgagcgcc atctgaccgg cggcccgggg  15120
atcgcctgcg gcagcggggc cgcgctcatg ctgacggccc tgacggcggc ggtgctggcc  15180
ttgctactgc gcgtcggggc cgcttggacg gaatcgtcat ggaagagcaa tacgcagggc  15240
gtgacgggag ccatcgtcgc cgcggtcgag ctggcgtcgg ccgtacacca ccacctgcag  15300
tacctgctca acatggcctt tgtggggtac gcctgctggc tgcgcgcggg cgtgcgcgac  15360
ccgtacatga tcgcggccat ccgcgcgcag tgccgcttcg ctcactttac ggggcagctg  15420
atgccgacca tgacttccgc cagctgggcg gccctggagc gcggcacggc gagctggttt  15480
aagctggcgc tgctgaaaag cgtggcggcg cacggcgcgc agacgcgcta ctactccaac  15540
atcgtggagt cgatgcggct cggcgggagc cgcgggctgc tggcgccggt gcgcgcgcgg  15600
ccgtcgggcc gcggccgccg ctgcccgcag agtctggccg cgcgcccctt gcccagcctg  15660
ccggccgcgg ccgccgcccc tccgggctcg ggctcgggct cgggctcggg ctctgactct  15720
gactccgacc tggatctcgg ctttgccccc gccgtcggcg tctatgcctc gatgcgcaac  15780
ctggagggcg cctatgccga cgcgggcggc ccgctttcgc cggcggcaag cgccgcgcgg  15840
cgggaggcgg cggtgtacga aaacgaaggc gagggcgaat tcgcgccttt gccctcggcg  15900
ttcgccgaag acggcagctc cgacagcgcc gacgagctcg ctatcgacgg ccccatgcct  15960
gccccgccgc cccgcggtgg ccgcggcgcc gacgagctcg ccatcgacgg tcccatgcct  16020
gccccgccgc cccgcggcgg ccgcggcgcc gacgagctcg ccatcgacgg ccccatgcct  16080
gccccgccgc cccgcggcgg ccgcggcgcc tctgctgggc gcctccagta cgctgatttg  16140
tgcgccgtct cgagtgacga cgacgaggac gagggcaagg acgaggacga gaacaaggcc  16200
ggggcgaccg ccccgttggc cgcggacccc gaatcggaac tggcccgcgc catgcggcgt  16260
tgcagcctcc gcgtcccggc ctcggccccg gccccggccc cggccccgtg caccgagcgc  16320
ccgggtaatc caacccggtc ttactcgcgc tcgcgccctc ggctccgcgc cctagacgac  16380
cggcacggcc tggaggcgct ggcggctgcc ggtgccgctc acaccgcgcg ccacaaccgc  16440
gacgtgtggc agcgcttttc ccgcgtctgc gaggccggcg acgactacga aaactacgac  16500
gaggcccgcg gcgcagagcg cggacacctc tcttgcgcct cccgcgcgcg gcctgaggtg  16560
gagagggtaa cgtcgctgta aaggcgccca ccgcaaacgc tgtaacacac acacaataaa  16620
aagtttgttt tagtttatta tgaaattgta catgcgtggt ctttgggggg ggggcgcggc  16680
ggctttgccg tcggggcccc gcgcctacag gcgcgcccgg gccttgcgcc gcaggcacga  16740
ggccgccacc agcaggagcc ccacggcgcc gagaccgcag gcgacggcca cgacgctgac  16800
gaggacgggg cttccgatta ggccgggcga ggcgtcgtac gtggcggtcg cggagaactc  16860
gggcagcggt gccgggtagc cagtggcggt gcaggtgtag tcgacgggcc cgtcggttgt  16920
agaaagcagg cgcacgccgc gcaggtttac cagcccgggc cgctcggcgc agacgccggt  16980
ctgctcagtg cgcgacgggg cgatgccgtc gcgcaccgtc cagcgcaggg agacgcgccc  17040
ctcggggacg cagcgcgcct cgcagacggc ctcgccgccc tcgaagtaca cgcgcagctc  17100
gggcgggcgg taaacggccg gcgtgccagc cgcgtaaaag cggcgctcca tgttagcgct  17160
ctggaaccag gagacgtcgc agcgcaggtt gggcgggtgg gcggttggcg tcgcgtcctc  17220
```

```
gagcgtaagg acggacgtgc gcgaaaagag cccggagtcg tcgaccgtaa agacgtcgcg  17280
cgcgtgccga gcctccacgg ggtagccgtt gcggaaccag tgcaggcgcg tggagcgcgg  17340
cgggtagtac tcggcggcgc ggcacacggc cgcgtagccg gcgccttcta gcgctggctg  17400
gggttcgacg gaaacagcgg gcgcgcggtg cgtcgtgacg gtcacgacct tgcgctgtga  17460
cttggtgccc atgtcgcggc gccaagtgta cacgccctcg gtggcggccg tcagggagcg  17520
cacggtcagg ggcaagttgc gggggtcggc gggcgaaggg aaaatatagt tgtcgcccag  17580
ctccgcgcta cggtacgcga tcgagccgtt ctgggctacg aacagcagca cgggcggggc  17640
ccgcggaaag gggttgcgca cggcctcgtc gtcgccgcgc gtggagcgga acctgcccac  17700
gcgctgaaac cagagctcca ggcgcgcacc gccagtggcg ttgtcggcca cgccgcagtg  17760
cacgtacagc ggctcggcgt acgaggcggc cacggcctcg cgctcgcaga gcatccactt  17820
gcgctccttc ggcggggctt tgctcggccg cggggggcga ggccgccccc cgccgctagg  17880
tcgcccatcg cggctcgcgt tgccagcgcc gccgggtcgc ccgtcctcgg gcggggcggg  17940
cggcggcgtg ctgttggtaa cgggcgggtc gtgctcggac acggacggcg gctccggcgt  18000
ccccacgggc gtagtagcac cgggcgtgct gtcctctggc gtagcgtcgg ggctgttggg  18060
cgtggggggc gttgcgccgg tggtcccagc ggagctttcc gtctcggttg gggacgggga  18120
gggcggaggc gagggcgagg cttccgcctc ctcggcgagc cccgccgggg cagacaggag  18180
cgcccaggcg aaaatagctg cgatcagcca cgctcgcccc agcgggccca tggcggacgc  18240
gcggcgaggt ctcgggctgg cggtctctcg gcggtcgtgc gcgcgggtgg atccaagatg  18300
gccgcgaccg cggcgcgggc tacattttta agggcgtccg ttttgtgctt tcgtggtccg  18360
ggattgagca cacgcgcggc tgcaggcgcg ttaccgtcgg cggcagccgt tcattcgtcg  18420
gcgcagaccc agcaggcccc gacgcagaag cacagcgcgg cgtgcagggc cttggccacg  18480
tgcgccgcgg ccagccgtgc ggtgccgcgc ccgcagcgcc ggacccacac gcaggccacc  18540
agcgtgcccg cggctgccga ggccagcgct gcgggcgcgc cgccgtccgc gccgcagagc  18600
ggcagcgctg cgcccagagc gcagatgccc acgtgcgcca ttagcgcgcc gtccgcggcg  18660
tcggcgcgcg cgtagcgcag gcagaggtgc tcggcgagcg cgacgccgtg cccgcccgcg  18720
acgctgagca gaaccgcgcc gcgcgtgcgc cagcgcccac cgccctcgag cccaagcgcg  18780
cggcccgggg cccagagcgc cgccgccgcg gctaaggcgg cggccgacag cgcgagctcc  18840
gcggcggcgg cgcgcgccag cgcgcgcatg ggcacggcgt cctcgcgcgc gccgcacggg  18900
tcagcggggc acgctgcctc gccgagcggc gccagagtcc gcagcgccgc gtaccgccag  18960
atcttgtagt ggcaggtgtc ttccagcgcc gccgcggcgt ccgtggcggc gacgaccagc  19020
gcggccgcgg cgcccgcggc cgccagcgcc tcgggccgcg cgccccagcg cccggccgaa  19080
aggccgagaa gcagcccgca ggtcatggtc agtagcgccg tgcgaaagtg cgccccggtg  19140
cccgaggctg ccgtcacaaa gtgcgcgcag tgcaccggca caccgcagac gacgtaggca  19200
gcggccgcgc ccgttgttac cccgcgcagc acggcggggg cggggtctgt ggcccagacg  19260
gcgagtgccg ctgcgacagc cagcgcctgc gcgagccggc caagcggcgc gagccggcgg  19320
cgcagcgtct gtgcggcggg ccgccaacaa acgagcgcgg ccgcggccgt ggctgttaac  19380
gcaagcgccg cggccgggtc ttgcgcgcgc ccgacggtgg ccagggccgc cgccatcaag  19440
ccggtgtgtg tgcccatggc caccagcgcg cccgtggcgg caagcgcaca cgggccgcag  19500
ccggctctcg cccccgcgca gccgctcacc cgcacggacg cgaacatgga tggtcccggt  19560
```

tccccaaata acgcaacgtg gcccaggatc gtcttttatc ggcctttatt gtttttcgct 19620
taaggagttt cgcccccctc cccgccccga tccgggcccg agctcgggcc cggggcgccg 19680
gcgtcggcgc gcggccgctt gcgggcccgg ccgccggaaa ctgcgaccgg gtgcgcgccg 19740
tcggtttgaa tgccggctcc ggccccgcga cgaggttggc cggacgcggc gggccgctta 19800
gcgggaaggc ggggtgcggg ctcggcgcag tcatcagcat cgtcggcgga ggcggtggcg 19860
gtggcggggc ggcagaaaaa gaacacagtc agcccctccg gcgccgctgt ggacacgctc 19920
atcatggcgg cgctggcggg cgcgaggtag aagcgcagca gggcgtcgcc gccgacctgc 19980
cgcacctttt gcagcagccg ccggaatccc gagggggact ccaactccag ccgaaagtca 20040
ggcgccccgc cagagcagcg cacttccaat agggcggccc tgcggccgcc gccctgggcg 20100
cgggcaaaaa tgcgctcgct gcctgcgctc ggggcgagcg ccagctggag ctctgccccg 20160
gactcgccgc cctcatggcg cgcggcgaac gaagctcggc ccgatgcgga ctcggcgctc 20220
aggcaacggg cgcgccggta tgcgaatacc accgcctcgt tgggatcttt ggcaactgcc 20280
tgcagctttg agagctgcgg ccgcgagagc gagacggcga ggtcggcgcc gcgcgtcgga 20340
agcatgattg agtactcgcc tagctcgtgc ttgaccaggc tggcctgcga tagggcatcg 20400
gcctcccgaa agtaggtaac ttgcgttagc acgctcgcgg gtggctcacc ggtgattaga 20460
aaggccacgt tctgcactgt ccgtgtcttg tcggcgcgga aggcgtccag caggccgcgg 20520
cggctgtcga cgttggcgag gaagacggct cgcgcgtcgt cgcgggcggg ggcccactgg 20580
aaggacgtga acttctcggc ggggacggcc acgtacactt gctcgtcgta gaggccgctg 20640
tgtaccagca tgccctcgcg gctaaagacc aaaaaggcgt ttcgcagcga ggcgccaaag 20700
gggctcagca gggcggagac gtccgccagc tggcggccga taagcgaggc gctcgcgatt 20760
gggttgccgt tgccgccgtc ggacagaccg gcggtgaggc gggcctcgcc ttcgtcggcg 20820
cgcagatgcg aggggggctg cagcatcgcg gcgggtgctt cggcggcgct ttcgctcgcc 20880
tcttacgcgc gcggtcgcaa agcgagtctg cgctgcggcg gcgctcttta tactgggcgg 20940
acgcccccgc agcggcaaaa cacacactcg gcggcctcag cgtatcaaac ggcgacacgt 21000
ttaagtttcg acgcctataa gcgggcgcgc gcactaggcc tcccaatcgg caccgcgcgc 21060
ggctgtgcgg gcgaccctgc gcagagagag atggggctct tcaagctact gcgttacgcg 21120
tacggcaatc ggctggtaaa gcacgacgcc atcaccacgc cgccgggcgt gatgaccccg 21180
atcgcggtcg acctgtggaa cgtgatgtat acgctcctgg agcgcttctg cggcgacgcg 21240
cccggcggcg taggagacgc cgccgcgacc gcgcgctgct tcctctcgct gctgcggatg 21300
ctgctcaagc gctcctacta cccgatcttt gtagcggacc gcggcatcca cggggaccgg 21360
cgcgccacgc ggggtgccaa ggccattgtg gcgcagacga tgcgcgccgt cggcggctcg 21420
ggccgcctcg ggcggctcgt cagcgacgat tatacctcgg aggacgaggt gctgggcgcg 21480
tacgagtacc ccgtcccgca cgcggacgcg gcagccgacg acgacgagga ggcaacggcg 21540
aaggaatttg ccgggcgcgc ctcggcgggg gccgcgcggg ccaacgcgcc caagctggca 21600
catcgcgtgt gcgtgagcct catccgcttt ttgggctacg cgtacgtcga cgccgctgag 21660
atggaggcag acgacgtctg cgcaaacctc ttccacacaa acaccgtggc gcacatctac 21720
acgacggaca cggacatgat ccttatgggc tgtgacctga ttttggacgc ggcgccgttg 21780
ttccccccga cgctacgctg ccgcgacgtg ctggcgtcgc tggggctcac gtacggccag 21840
ttcctcgcga cgttcgtgcg ctgccacacc gacttgcacc agccgccaat gttgcgctcg 21900
gtgcagcagg tggtgcgggg gctgcggcgc gctgccgagg ccgagcccgc gactaccgag 21960

```
acggagtctg gctccgagcg cgagccggag tccgagctcg gtcgtccggg cgctgggccg  22020
cggcgccggt tgccgcccgc ggtcgacgac ccgctgaaaa ctacgacgcc ggcgaccgtg  22080
gaagcgcaca gcgtgcgcat gaagtataca tctcggtacc ctccgattgc gcagacgtgc  22140
gccgacgcgc tgcggctgct gccggcgtcc cagacgcgcg gcggcgtgct ggagcgcaaa  22200
tttgtaaagc acgtggtgga cacgatcgcg ccgcgaatgc gcgggcgctg ggccgtgctg  22260
aagcgcgtgc ccatcgcaca ggacgccccc gaccctcggc tcgtgtacga caccatcgtg  22320
agcgccgtag gcagcgccgc cgaggccgac acgctgatgg ggctcttctg gaagcacatc  22380
cccactccac ccccatttgc cagggtgctg gcagactact gggacgaggc ccccgcgggg  22440
ccggggtcgc gacggacaac ccgccaataa aaacgcgcgc atacgcgaga ctggctttcg  22500
ttgacatgga acatttttta ttcgcggcgt gggggtgaga aggaggagga aaggcggggc  22560
gctctggcag ggcagcgggg gtgccctaca ggtcgttgat tacggtgcct gtgtagttgg  22620
tgctgcggcg ctcaaagaag ttcgtgtgct tctcggcagt catcagggcc aaaggaaaat  22680
cggtcccagg aggcggggtg ccaaacagag gaggcagctg gatagcagcg agcaggcggt  22740
ccgcgctgta ctcaacgtac gcagaaatag cctccacgtc aagtatatga ctgccgcgcg  22800
gcgcgcgtga ccaaataaac tcgcgctcaa tttccacagc ttcgcggaac agctcgtaga  22860
tgcgggccgg cggcggccgc tccccgccga ggtagttgtt gaagatgcag cacgacgcgg  22920
ccgtgtgcac ggcttcgtcg cggctgatga ggtcgttggt ttggcacgtc acgacgaaaa  22980
ggttgtgggt gcgcaggtag gcaatcgccg caaacgagga ggagaaaaaa atgccctcga  23040
ttagaatcat gagcacgtac ttttcggcca ccgactctgc cgcggccacg cgccgctcga  23100
gccagtccac cttgcgccgg accgccgggt cgccgagggc gccctctacg tagcccgcgc  23160
gcgccaccgc gtcgtttcta aagagcagca gctgtatggc gctgtacacc cgcgagtgca  23220
ccacttcgat ggactcctgc tcgatatagt aatgcaggat gtctttttgg gtgaacagct  23280
cggacaggtc cccgaggttg acgttcacga ggtcatcggc ggccgagagg aacgcgaaca  23340
gaaagcggta aaactccagc tcggcgccgc tgagccgcgc cacgtccttg gcgtcgtccg  23400
ccaggggaaa ctcggtctcc agccagcggt ttgcgacgct gagcgaccgc aagtgatcta  23460
ggtcggggca ctcggtctcg taaaagtatt tgtatttacg cgtgagggtc gccgcgtccg  23520
ccgcctcggc catcgcgctc ggcgcgtcgt cgctacaggt ggcacccaga gcacacgagg  23580
tcgccgcccg tgaagacgcc gttgttggtg gccttgcgga tcttgcagta gtagagtccc  23640
gtcttaaggc ccttcttata ggcgtacacc aggaggttca tgatctggga ggcgggcacc  23700
tttccgtcca ttggctcggt cacgaagagc gacattgact ggctctggtc cacgaacggg  23760
gcgcggtcgg cgcagaggtc gatcaggcgc tcctggtcgt actcgaaggc cgtcttgaac  23820
ttggccagcg gatgcccggg cgcgaggtcg cccagcgcgg cggccaccga ccactgctcg  23880
cggtccagcg cgcgcacggc cccgagccgg ctggcctcgc gcgtaaagtg ctttcgcagc  23940
gcgcgcatca gcggcaggtt cgggcgcagc agctcgccgc tcatcgtgac cttgctgaac  24000
atgttggtga agacgggcga gaagccctcg ctgccctccg tcacctgcga cgaggacacg  24060
gtcggcataa gggcgacaaa ctgcgcgttg tacagcccgt gccgcgcgac cttctcgcgc  24120
agccgggccc aggcccgcgg cagcgagagg accacgccct cgtagccgtc gaacggcatg  24180
agcccgcgcg cgaacttgct gcgcgcaaag tcctcgaacg gcgcgcagcc gtactcgcac  24240
agcgtggcgc tggtggccat gacggccagg agcaggcgct cggcgatctc cacgttcagc  24300
```

-continued

```
cgccgcgcgg cgggcgagag catgtccatg ccgagctcca ggaggagcgt gtgcaggccc  24360
tggaagccga tgcccagcga gcggtggcgc gccacgccgc gcgcggcctt ttcggtaggg  24420
tactgtccgc ctagcatcat agcgttgaca aaaatggcgg ccgtggcggc cgccgtggac  24480
agagcggcaa agtcaaaggc gagcgcgccg ccctcaccct cgcgcacgca gcgcggcagg  24540
ttgacgctgg ccaggttgca cacgccgtgg gcgtcggggc tcgcgcgctg cacgatttcc  24600
gtgcagaggt tggagcccgt tagcgcgtcc ccggccgtgt ccatgtggta atggcggtta  24660
cacgcgtcct tgaacatgac gaaggggctc cccgtcatga cgatgcttcg gacgatgagg  24720
aaagccaggt cctgcacggg cacggtctcg acgcctagcc cctcgcgctc cagtcgctcg  24780
tactcggccg taaaggccgg gccgtgcagc cggctgaggt gcgacgcgcg gtcgtcgaag  24840
agcgtccaca caacgccctc gcggccttcg aggtgggcga ggtagcggtc aaagagcagg  24900
tccggcaccc agaggcagct gaacaggttg tcgcagcgcg tcgactcgtc ccgggcgagc  24960
aggccgcgca tgtttagcac ggcccgcacg tcgcagtgcc agggctcgag gtacacgcag  25020
atgcccgtcg ggcgctcgct gtcgctgttg atggccatgg ccatcgagtc cagcagcttc  25080
agcgccccca tgatgccacg cttgcagtcg cgcgagaccg cccggttgaa gctctggaag  25140
gagattccga tcccaccgcg gttgagcaag attcgcgcga cctccgtggt gatcgcctcc  25200
acggcctccg tactgctgga cacctgcgga ttgagcaggt agcagctggc cagcgagccc  25260
cgcgcgcggc cggcaaagag catgatcggc gtcgcgggga caacgagctg ccggtacagc  25320
gcggtcaggt aggcgttgaa caccgcgcac cacgtggcgc cctcgccgac gagggcgcgc  25380
ccaaaggccg gctcccgcat cgtccacgtg gcggcggtcg cggcgatccg cacgaagaac  25440
tggcccatag actcgatcgc cccgccctcg agcttggcca ggtacatctc ttcgtacttc  25500
agcgccgact gcaggccgag cgcgcgcagg gtggcgtact cggtaagctc gaagtatcgg  25560
agcgagacct ccacgaaggc gcggttggcg cgcacgcgct ccgcgacctc ggacacgagc  25620
gcgagctcgg ccgatgtaag ccagtcgtcc agaggcacgc tccgagcacg cacgcgcaag  25680
tgcacgagtt gcccgcactt tacgtacacg cgttcgtcgg cccgcgactg cgccttcatg  25740
cgatccacga cctcgccgac gtaagccgcc actgcggccc gagaaggacg agaagcggcg  25800
gcgggcggcg gcggcacggc accgcagccc agctgcgccc attccgcgtg ctcggcctcg  25860
agctgctccg ccgcgtcggc cgggcaggct gtctgcatga acgcgtcgct cgccatcttg  25920
ctcgcccccc tcgcttgcag cccgcccctg ccgacccgct ggctttttgt ctttcgcccg  25980
ccgacccgcc ggcgcttggt ctgcccgatc gcacccgccc cgacgccttg ggaacaagcg  26040
cgcggccggc tctggctccc cggagataaa aaccgagcgt atggcggcag caaaaggtgc  26100
gggccaggtg ctcgctcggc aggcaacctg ggcccggcag cagagatatt taacggcggt  26160
ttgaggggcg tggcggccct tccctgttga tttatggcat cgcacacaac ggtgtttgcg  26220
gaacacattt tatttaaaac gacagcgccc ccttgtgtca gtaaaagcac tccacccagt  26280
ccccggttcc ccacaccaag ccctcgatct tgacgacggg cacgtcgcaa gactggtagc  26340
gctcgctgcg gcaagtgact cgcggcgagt cgtggggcag cgtccccagg cgcgcgaagg  26400
cggcgtacat gcagctctcc cgggtgggcc gcccggcagc gtccggcgcc cagcgcggca  26460
ggaacgccgt cgcgtcgcag tcgcccagcc gcgagacggg gcagcggtag gccgcgcggc  26520
tgttcgccag cgcggggagc ggaaactcgt ccgcggcccc ggccacttct gcagcgtcgc  26580
ccgccgtccc ccggagcacg ttttcggcgc gcgtgcggtg cagcaagtag ctcagcccgc  26640
tggcgaatgt ggtttcgtta agcttgctga cggccacgtg ggcgcgaaag ccctcgtgct  26700
```

```
ccaagcgctg cgtgtacacg aagaccaggt acacaaattt gacgccggcg ggctccagcc  26760
gcagctcggc gtccacgtcc aggaacgcgc aggcgggcac gtgggccgta gagcgcgggt  26820
gcgcggcctg gtcagtgcgc gcgccctcct gcgcgccgca gacgacggcc gtgacgctgg  26880
ccagcttgtc ttgcgtggtc cacgagagca gtccgcccag gcacccgagt gcctgatgcg  26940
ggaacgcgcg gcagcggatc atggcctgca ggcaggcgta gaagcggtct agccgcaatg  27000
ccatgcggcg gtcgccggag ttggaaatga ggtgcgcgcg cagcgcgtct gcggcggcgc  27060
ggttgccgta ctcggcggcg caggcggctg ccagaaagga aaaggataca agagaggccc  27120
gcagcccccc gggcggcacc gcgcccacgc tggaggcgtc gccgaggtcg cgccaagcct  27180
cttcgacgtc gcgaaactgc cgtccggggg gcgcagccgc ggcggccagc ccaataatgt  27240
cggcggggtg cttcagcgtt aggacgggcg cgccggggcg ctcgagctgc gggtcgcaaa  27300
agtccgtcag ggtaacctgc cgcgagagcc ggatgtgagg ctgcccgccg ggcgagagga  27360
cggcggtgcc ggcgggcgtg tccacggcaa tctgccgggg cgtgacgatt tgaatccccg  27420
acatgttctg gatggttacc gttgcgtcag acacgtgcag catcccgccg gcccaagggt  27480
tgtagccccg gggtgcccgc ccgcgagcgc cgccaaccgc aggcgccgtc actgactgca  27540
cgccggcttc ggcggcagag gcctcggccg ccgccgcggc ggcggcgggg acgcccgaga  27600
acggcggcgc ggcggctggg agccgcatcc gcaagtggtt gccgatttga atgtaactcg  27660
agctcccgtt aggcgcggcc atcgttcctc gtccgctcgg cactcgcgct cgggtcgggt  27720
gttatagggt ggcggattcg agctgccttt atagcgccgg cgcacgcggc gggggcaagg  27780
gcgtcagcgg cggaagccgc ggcggcggtt gcggcggggg gctgtgcggg gcgtacaata  27840
aactgcgcgg cgggtgcggg ctctggccat tcgcgccccg gcgcacgcgc ggctgacatg  27900
agcggagacc ccgtgcgggc cctgtgggcc gcgctcgagc ggttggatgg cgaggtcgcc  27960
ggcccggccg cgcttgcgga ggccagggcg gccgtctcgg agttcctcct cgcgtccggg  28020
cccagctcgc tagacttcgt ggcgccgcgc tgggccgcgc tgcagcgcgc ggcgtgccgc  28080
gcttacgagc gcctgcacac gccagacgcg gcgctgctgg cggaaaacct gcccggtctg  28140
gtgctgtggc gcctgcccgg ggccgcgcgc gacaccgccg atttcatggc cggcgttcgg  28200
gacctggcca acagcatgat cgccgaggcg ccgttgggtt acctggcggc cgcgcgcctg  28260
cgcgccacgg cggcgttcgg cccggtgaac atgcagcgcg tggtggtgga gtgggcctcg  28320
ctctttttgg agatctacgc acgcgaggac gcggcgtgcg tgggtgtgtt aggccccgac  28380
cctgcgtgcc gctcgccggc gggcagcgcg gccgtcatcc gcccgctgct gcagagccgc  28440
ttccgcctgc tgtatgacat gcccttttt caggcggggc ttagcgccct ggcgcacgcc  28500
gccaactgga aagtgcctat ggccgccgtg gcacgacgcg ccgcggacgc cgcggcgccg  28560
ccgctagcgc gcgcgctttt tgccgtggcg cttgtcgacg agtactttcc cgagccagac  28620
gacgaggaca cggcgccggg gctggctgag gcgtttgcgg aaattgctga cttggtgccg  28680
cccgaggcgc tagtgcccgc gggtgaggct aacgcttttg cgcgctcgtc gcacgacgtg  28740
cgcgtatcgg cggcgctggc ctaccgggac ccctttgtgc gcggcgcggc cgcgggcagc  28800
gtcgccgcgc gcgtgcgtgc cgacgcgggc cttctcgccg acgacacgtt gctcggccgg  28860
gacgccgtcg ccgttcacgc aggcgcggtg gtgcggctgc tagaacgcgc ggccgcggcc  28920
gcgcccgcga cgccggcggc gctggggcga gttgcagagc acgcggccgc cgtttgggac  28980
gccgtgcagg cgagcgccac gccagaccaa gccgtggaga cgctggccgc ggcggggttt  29040
```

-continued

```
acgccgggaa cgtgcgccat gctagagcgc gccgtgctgg cgcagctatc gcgcccagag  29100
ccgcgcgcgc cggcagacgt gctgcaggcg gtgggctgcg tggcggtggc gggcggcgtg  29160
ctgtttaaac tctttgacgc gtacgggccc agtgcggact acctcgcgca ctacacggcc  29220
actatcgcaa acctgcaccc gtactacgcg gacgtgctgc cgttgctggg gctgcccgac  29280
ggcgggctgg agcagacgat ccgccactgc atggccccgc ggccgcgcac ggactacgtg  29340
gcggcgattc gcgcggcgct ggcggcagag gccgcggccg cggacaagcg agccgcgagc  29400
gcgagtgcgc gggcggccgt tgaaaacagc ggcgaccgcg cggcggccgg agctgccgcg  29460
cgcgaggccc tcctaacctg gtttgacctg cgcgccagcg agcgctgggg cgtggcgccg  29520
cccgcggccg aagcgccgcc cgcggccgag gcggcacgct ctccggccgc gggcggcgct  29580
tcggccgcag agctcgcccg cgcggcgcgg gcgctcgagt tcccccgcac ggacgccgtg  29640
ccggctgccg tcttgcgaga cccggccttt gcgccccact tcgccgccgc cgtgctgtcg  29700
gacgtgctgg tggctgcgga cgcgctgccc ttcagcgcaa acggcgtggc gcagctgatg  29760
gcgctgatcg cttgggcgcg agactgcggc gcgggagcgg tggccaacgt agacggctac  29820
cggacaaaac tgtcggccct ggcggccggg ctctggccgt ttgtggacgc gagcgccccg  29880
gcgcccacga cgacgcaggt ccgcaacgcg gaggctgtgc tgggcgagct gcacacggta  29940
gctacgaccg cggcggagtg cctgccgccc gaagtgcgcc cgcctgtgcc cgcgcgcccg  30000
cgggtgggcg gttgtgtctt cttagcgagc atgtacctgc acgccgcctt cgcgcggctg  30060
cagggctatg tcgccgagac ggaagcgctg gccgcgtcta tggccgcggc cgtgggcgac  30120
gttgccggcg cggtggcgcg gctgggagtg ctgttcgact gccactttgc gtcggtgccg  30180
gggcagcaga tgctggcgat atacgcgacg cgcggcgcgc cgtgcgccct gggtgcgtgg  30240
cgctcggcgg acctggccga cgcggtgcgc ggcgcgcgcg ccgaagccga gcgcgcccgg  30300
gccgaggtgc gcgtgtcgct ggcggcgttg cagcgcgccg cggcgcagac gacacaagcg  30360
ctgcaggagt gtgaagctgc ggacgcccgc ccccccggcg gcgggctgga cgacgagcac  30420
cgcgcgttgc tggcgggcca ctcggcgctg gtgcgggcgc agacggcgct ggcgctggcc  30480
gccggcaagc tcgtggcggg cgcggaggcg ccggggctgc acgaggtggg ccgctttctg  30540
cagcgctggg acgcgatcgg cgcggccctc gggcgcgcgc tagacgacag tgccggcgag  30600
cgcgacgtcg ccgagctcgt cgcgcggctc cgcggcgtct gggacgaggt ccaggaggac  30660
cgccgcgtag cggccccggg gccgccgcgc agcgccgcaa acgcggcggc cgccgaagag  30720
gcggtgctgg cgctgttgga gggctacccg gaggttcggg gagacgaggg cagcccggcg  30780
ctcctggacg cccgcgcgga cgtggccgac tgggcgggcg tagaccgcgg cccgctgcag  30840
cgccgcgcgt ctgcgggcgc ggacgccgcc gcgtctgccg ccgcggcaaa cacggcggcg  30900
gggccgtggc ttacgacgga agacctgctc gccgaagtcg atggcgtttg cgccagtcgc  30960
ccggccgcag cccggtgagg cgcgcgccgg cggtgcggcg ggaggccttc gcataaacgg  31020
cgctgcgcgc gcggtgcccc ctagtacccc tgtggagcag cgaagcggca ccatgtccgg  31080
cgttgccggc gcgcgcgcgc cggcaacgcc ggccgacgtc gcggtcgccg ctgtgggttt  31140
tcgcaaccag tacgacgcgg cgctggggcc gggcagcgcg gtggcatgcc ttcggtcctc  31200
gctgtcgttt ctgcggctgg ccttcgcggg cggcgtcgac gccgcgctgg gcgccgacgc  31260
catcgacggt gctctcgctg agggcgcggc gtgggcgcgc gaaagcgggg cgcgcccgga  31320
aatgtgctcg atcgtgcacc tgccaaaccg catcaccgac caggcgggcg cggggagcgg  31380
gctctgctgc gtgttttcgc gcgtgtatgg ggagtgcggc ttctacacgc cgccggcgga  31440
```

```
gcgcgccctg agcacccaag tcccagcgcg cgaattcgtg gacgccgtct ggcagccgcg  31500
gcggacgtcg ctggcgctgg tgatcgtggg cgccatgggc gtcggtgtct ttcgcgccgg  31560
cgacgcggtc tacctcttcg acccgcatgg gagcggggac gtgccccagg cgtttgtcgc  31620
gcgcatgcgc cccgaggccc tctacgcgta cctagctctg cgcgcgtgtg gccagcccga  31680
gtcccggtgg gcgggcgcgc tagtgcactt tgtttcggcg ggcccggagc ccgcgcgccc  31740
cgaggagcta agggcggccg tgtctgcgct gtacggcgcg agcgagacat acctggacga  31800
cgagccctat gtcgagcggc gcgtggtcag cgtgcacccg cgcgcgccgg ccaacacggc  31860
ctgccttacg gccgtggcgg tgggcggcgc gggggcagag tgcgaggacc ctacgttcgc  31920
gcgcccgggc tcgccggcgt tgctgccggc ggagcccgtc gcgcggatgc cgccgcagat  31980
cacggccgcg gccgcggctc gcgcggcggg taagcggacg agcctgccgc ggcggcggcg  32040
ggccccgtgg acgccgccct cgagccgcga ggaccttcgc gcgccggcgg cccgcgctcg  32100
cgcggggaag cccccgcgaa aggtccgggg cgcggagacg gcgggggccg gggaagattg  32160
gggggagggg ggaaacgcgg ctgcggcccg cccgccgccg gcgctgggcg ccgccgcgcc  32220
cgcgcacgcc gcgacggcgt gcgcggcgga gcttggcgcg cgcgcggcgg aggttaccgc  32280
ggccttggac gccgtccagg cgcacgcggc gtcgatagcc gctgacgcag acgcgtgcgt  32340
ggctcgcgcc gtccgcgtgg cgcggccccg cgacgccgcc gcggaacggg acccgctgga  32400
acacgcgatc gcgggcctgt ttgagcgggt gctggccttt ttggtgcaga acggcgcgcg  32460
cacgcggcac gacgccccgt cggccgtcca gccgcttttc ggggcggtgg cccaggcgct  32520
gccgcagcac acgcccgcca gcgcgttcat cacatcttcc gggatggtgc tcgaggggct  32580
ggccgcgtac acgcggctgt cggaggcgat gcgcgcgcag ccctcggcgc tgggcgacct  32640
ggcggacgcc aagctgcgcc tagtcgcggc cgccgtcgcg gccgacacgg agcggctgca  32700
cgacgccgtg gacgagctgg agggcgaggt ggacggcgcc ggcggcgcgg gcccgctcga  32760
gctgtgcggc gccgtctcgg cgcgcttcat ggagcgcctc tcggcctccg gccggcggct  32820
attttcgcgg gcggcgcttc gcgacggccg gccgctggac gcgcgagtcc gagcgctctt  32880
tgagcgcgcg cgagcgcgcg aggcccgcgt ggccgccgag accgcggcgc tcgcgcgcga  32940
gatcctggcg ctggagggca cggtgcgcgc cgcgcgcgag cgcctggacg ccgtcccgcc  33000
cgacgacccg cgcgcggtgc ccgcggacag cgcggtggcc gacttggcgg ctgagcttgc  33060
ggcgggccgc gccgccgtgg tcgcgcggag tgccgccgcc ctctccgccg agctggacgc  33120
gctcgcggcc gaggcgctgc ggcagtactt tctgcgcggc gcgcagtaca gcgctcgcgc  33180
catcctggcc gaccgcggcg gcggcgagcg cttccgcgtg gcgagcgcgg cggttgcgcc  33240
gctgcagcgg ctggccggct ctgcgcccga cttggcggcg cgggtggctc ggcttggcgc  33300
cgcgccgggc gccgcggcgc ctccgctgcc gcggtccgcg cgcaaaggcg agctcctccg  33360
cgacctgctc gcggcaggcg caacggcgca caccgaagac ggcctcgcgg cctgggtggc  33420
gctgctgcac gaggcgcagg cggaaggcgc tgccgccaag aaggagctgg acgccgtgct  33480
gagtgacgtg gccgccataa acgggcgctc ggcgtcgcgg gcgtcgctgg aggcgagcat  33540
ggctcgcttc gaggcgatgt ccgcggcggc ggcgcgggcg gcggcgggcg ccgccgcgga  33600
ggcgccgggc gcgggcgccg aagaggcggc agacgccgcg gaggcggccg tgcgcggtgc  33660
cgacgacgtc ctgcgccagc tggacgccct ggcgacgggc gcggcggctg accgcgaggc  33720
gcgcgcgcgc gtggccgcgg cccgcgcggg gctagaggcg caggcgctcg cggcgcggcg  33780
```

-continued

```
gcgcgtggcc gagctggggg agcgacgcgc agagctgtac cagcgcctgg acgcgctgtt  33840
gctgccgctg cagggcttcg cggggctgcg cgcggcgccc ggcgcgctgg agcggctgtg  33900
cgcagacgcg ggcgcgcaga gcgcagagga ctgcgcgcgc ttcttgcagg aggcgccgcc  33960
gcgcgtggcc gcgggcgtgc aggaccgcct gtggcagctc ttcggccggt accgcgaggc  34020
gctggagaac ccgagcgcgc tggcgccggg cgcgctggcc gggctgggcc cagccttcgc  34080
ggcggtgctg ggcaccgcgc tggccaggc gatgggcccc gcggcgcgcg cgtttttcga  34140
ggggcacgcg gagcgcgtgg cggccgccgt ggctcgcgcg gcggcggagc ctgcggcgcc  34200
tgccgcggtg gccgccgcgg cgagcgcgct gcgcgaggcg gctgaggcgc tgcgggccgg  34260
gggcgcgcag ctcccgcccg agtttgcgtt tttggacgcg ctgcaggccc agtacgcggc  34320
gcggcgcgag gcgcagaccg gcgcgcggcg gctgggcgcc gcgctcgcgg ccgtcagcga  34380
ggcttcgggc gcgcttgcgt ctgcggcgag cgcactaaaa aacgccatga cggcgggcgc  34440
tgatgcggcc gaaacaacgg cggccgccgc cgcggcagac gcggcgctgg gggcggcgga  34500
agaagtactt cgggccgcgg acgaggccgc ggtggccgcc ggcggcgagg atgcggacgg  34560
cggcgaggat gcgagcgagg ccgacgcgga cggcgccggc gatgcgccgc ccgccgggcg  34620
cttggggcca caggccgcca agctgcacgc cgacctgcgc aaggcccggg cgctggcgcg  34680
gcggcgcgcc gaggaagtcc ggcgcctgcg cgccgaggcc gagcggcgcg ccgagggggc  34740
ggccgcgcag cggcaggagg agcgctggcg cgaggacttg cgcgccgcgc tggagcgcgt  34800
cgaggcgaac tccgccttcg acgcggccga gctggcgcgg ctgcgcgccg cggccgcggc  34860
gcgcggctac gacccgcggc cgctggcgcg gcaggccgac cgagcgctgg aggcgagcgc  34920
gcagcgggcg acggcagcca tcgaggccgt gctcgcgttc aacccgcacg cgcccgagaa  34980
cgcgaagatc gatgtcccgc cgccgctggc gcagctgcgc ggcatcgcgt ggtgggacgc  35040
gttttccctg gcggcccccg cgctgtcggc cctcttcccg gccgcggacg tgggccagct  35100
gacgcggttg atgcacatcg cgacggggct gctgacgttc gccgcctcgg gaggcggcga  35160
gcctcgctac tacgacgccg taacgtacct ggagggcgac ctggcggccg tgcctcggct  35220
cgccaagtac gtggccttct accgccgggg gcacgcggcc ttcgaggagg agcgcgcgcg  35280
gctgggcgcc ctgcgcgcgg acgtgctgca ggcggccggc gggcgcgcgg cggagatcag  35340
ccgcgcgcta gaagaggtaa cgtacgtgcg cagccccgcc gaggcggcgc gcgcgctgga  35400
agcgggcgtg cgcctggagc tgccgagcga ggctctgatc gcgagcgcgc tggcgcagct  35460
ggagcgcttt gaccacgctc gctttgccgg ctcggcctac gaggcgcaga tgctgagcac  35520
ggtgcggcgc gacgcggccg cggcgcgaga ggcgctagag gcggcaaagg cggcgcgcgc  35580
ggaggccacg gcgcgcgccg agcgcatcct cggcgaggtc gtggctgccg aggcggcgcg  35640
cgaccgcgac gagggcgccg ggctggccaa cctcaagaac ctgctgcgca tcacgccgcc  35700
gccggcggcg ctggggccag cgctggaccg cgccgcctcg gcggccgacg tcgtgacgca  35760
agcggcgctg ctgctggcgg ccgtggagga ggcgccggag ctggacgtgg ccgcggtgga  35820
gtggctgcag caagcgcgct ctatcatcga ctcgcacccg ctaacggcgc gcatcgacga  35880
ccgcgggccc atggagccct ttgcggagcg catcgacgcg ctgcgcgagc tgaggcgcca  35940
cctcgacgcg ctgcggcggc agctggagtc ggcggcggcg gcgtgggacg gcgcgtggga  36000
gctctttgtg gcggcgcgcc gccgcgcggc cgcctcgcgc gaggaccacg agggcgccaa  36060
ggcgcgcgca gccgcgctgc aggcggccgc gggcgtggtg ctggggctgc gcgcggacga  36120
gcactacgcg cggctgccgg ccgcgttcac aggcgcgctg gacgcgcggc tggcggagcg  36180
```

-continued

```
cggcgacgcg ctgggcgcct tccacgaagc cgcgcgcgcc gcggacgcgg gcctgcagcg  36240
gctgcaggca acgcttgcgg cggtgcgcgg cgaggccgcg tacgaggggc tgcgcgccct  36300
cctggcggcc ttcgacgcgc aggttgccga gctcccggcc tgggccgccc aggcgcacgc  36360
gcccttccgg gatctgctgg tgctgcggat gcgcctctac gaagcctact ttaagctcgt  36420
gccgcgcgcc gcggcgcgcg cacgcggcgc cgccgcggcc cgggcagcgc gcgccgcggc  36480
gacggtgcac tcgcgcgcag accctgcgac gcgcgccgta gcggcgcgcg cggcgcggct  36540
gtgtgagcgg gacctgcacc tgcgcgggcg cgtggcggcc cttctgggcg acgaagcggc  36600
ggtgtgcacg ctgcgcgagg cggattcgga gattgacgcg ctggcgccgc gcgcctacct  36660
ggacgccgac ggcacgccgc tctgctaccg ggtgtgctac cgcgcggtgg gcgacaagct  36720
ggctgtggcg ctgtgctcgc aggtgggggc ttcgatgcgc cccccgctgg acgagagcgg  36780
cgtggtggag gcggcttcgg tcgccgccgt gaacgtgtta aacgagattg tgaacctgcg  36840
cctggagatc gagcgcgccc gcgacgcgga ctttggggcg ttttgccgct tcgtgcgcca  36900
ccggcgcgcc gactgggggc tggcggacgt gcgctcggcg gcggccgagc tctacgcggg  36960
gctgctggcg actacgctgc cccgccgcca cggcgtcgcc tccctgggcg cgctgtgctt  37020
ctcgctggcc gagcgggggc tgcggccagc gcgggcgccg gcgagcgggc ccgcgccgag  37080
cggcggcggc gcgctcgagc tgacgcccgc ggacctggtc gtggccgcgc tcatgggcgc  37140
cttcatgcac ctggtaaact tcacgcgcct ggacctcgtg cagaagcagg agtacatgtg  37200
caagacgttg gacggcgttc tgaccgaggc gcttacgagc cgagtggcgg tcaacagcct  37260
cgcgccggga gagcccggtg cgaggcgccc ggtgccgctt ggcggcggcg cggacgaccc  37320
ggcggacggc gcgctgttcg ccatccgcgc cgccgactgg gacgcgggcc gcctttcccc  37380
gtccgacgtg ctagccgtgt ggcggcacgc gcccgacgcg gccacgcgcg cgaccgtggc  37440
ggagctggcg cgtctcatcc ccggcggtgc gctgacaacg atcagcgtgc tggcgcgcat  37500
gtgcattccg ggcgacttgc tggcggcgct gtggacgaca ctcgcggtgg actcgctggg  37560
cgcacagacc cagagctacg acgccttttt ggcgcgccgc ctggacgcac cctcgacggt  37620
gcacgcgacg ggcggccctt cggaagacgc ggcggcgctg gccgctgcgg ctgcggcggc  37680
cgggggccgg cccgcgctct tttgcccgac ggggagcagc gtgacgttta cgctcgtgcg  37740
gcagccgccc agcgaggtgc agaccgtcaa cgcgctggac ctcgtcacgt gcgcgctgct  37800
gctgggcgcg ccggttgtcg tggccatgga gaacccggac gtgttctcgg agggctcgcg  37860
cctgatcatg tgcctgcggc tgtttgacac gcggccgggc gggcgcgacg ccgacgcgcc  37920
tgccgccgtg tcatcggacc taaactcgtg gggggagcgg ctgctggcgc tcgacgagaa  37980
cattatcgaa aacgcgtgcc tgacggcgca gctggagcag ctgtcggcgc tgatcgcgag  38040
caagccgcta cgcagcgcgc cgccctgcct cattatgctg gatacgcatc tgcagctcgc  38100
gcgggtgctg tgggcgcgcg ccgccgcgcc gccgctcgca atgttgaaga ttgccgaaga  38160
cgacgtgctc cgggacttgc ccagcctgac gctagactac gaggacgcgc tgcccccgc  38220
ggccagcgcc gccgacccgc tcttcacgca catcatcagc gagaacaacg tcccggactt  38280
tgccgccgct agcggcgacc cgctatacgc gcacccccc gtgttccagc acgccaccga  38340
caatttattt ccgcacgcgc gggcggcggc aggtggcggc agcggcaacc gtgtagccaa  38400
cgcccgcgcg gtcgccgccg ctgcgcgccc cccgacccca gcttcagccc cagcgccggc  38460
accggcactg gcaccggctt cggcggagcc tgctctcgct tggggggccg acgagtggct  38520
```

-continued agacgacgag attggcgacg cgtacccgcc ggcccccgcg cacgacgcgt acccgccggc 38580
ccccgcgcac gcgcaaggaa aacccgcgtt actggcagcg cctgctgccg gagccgcgga 38640
ggctcctggc gttgagcgcg cgcgtcgcct gacgcgccgt actggaccac ggaagtccat 38700
gcccgccgcg ttgccgtggc gacgcccgcc gcccgcaagc ctggtctccg cagcgcctcc 38760
agtgcctccg gggccgcgcc tgccgccggc cccgccattg ccgccgccgg ccccgccatt 38820
gccgccgccg gccccgccat tgccaccgcc ggccccgcca ttgccgccgc cggccccgcc 38880
attgccgccg ccggccccgc cattgccgcc gccggccccg agtacggccc cggttccggc 38940
cccgccattg ccgccgccgg ccctgactcc ggccctgact ccagccctga ctccggcccc 39000
gactccggcc ccgccattgc cgccgccggc cccgagtacg gccccggttc cggccccgcc 39060
attgccgccg ccggccctga ctccggccct gactccggcc ccgactccgg ccccgactcc 39120
ggccccgcca ttgccgctgc cggccccgat tacggttttg gttccggccc cggttccggc 39180
tccggccccg attccggctc cggccccgac tccggctccg gccccgactc cggctccgcc 39240
attgccgccg ccggctccag atggggccat gggagcgctt agcgcaacgc ggcggccgac 39300
gcgccgcgct ggggctcgaa aatcgctgcc ggccgcgcag ccgcggcagc ggctgctgcg 39360
ctcacgctcg cccgccagcg ttccggcgcc gggctcagag ctcgttccac caccgtcagg 39420
cggtgcgctt ggctcgcccc cttctttcgt gccgtccaga ccgcctagct tggagcccgt 39480
gcctggcttg cccctgccgc cgagccgggt ccaagcacca gtagatgcgc ccgcgccgcc 39540
ccccgcgcca gagcggcccg cgccgccccc cgcgccagag cggcccgcgc cgcccccgc 39600
gccagagcgg cccgcgccgc cccccgcgcc agagcggccc gcgccgcccc ccgcgccaga 39660
gcggcccgcg ccgcccccg cgccagagcg gcccgccaca gcggtccaga gtggttcaaa 39720
aattccagca ccgtcgaatg ctttggtggg ccaggtggcc ccagcgctgc tgcggcgcgg 39780
ccccagcccc aggggcaagc ctggcgcgcc cgccaggccc acgggcggcg caaatattgc 39840
gcggaaaaac acccgggccg ttgaccctac cgttatcgga tctggctctg cgctgtcggg 39900
ccttggctcc gccgaggagg atgctgactt tggagcgtcg ggcatgtatg ttgcgccgcc 39960
tggccccgct cccctggctg cgccccctgc gccttcggcc ctgccggcgc cgcgcctgga 40020
ggcgccagcg gccgcaagct tgccggcgcc cccgatcgcg cccccgatcg cgcccccgat 40080
cgcgcccccg atcgcgcccc cgatcgcgcc cccgatcgcg cccccgatcg cgcccccgat 40140
cgcgcccccg atcgcgcccc cgatcgcgcc ccccgccatg ccggcacccc caagcgcagc 40200
gccggcgact gcaggctcgt ccgcgccccc aatcgcgccc cccgccacgc cagcgcctct 40260
aattgcaccc cttgccgcgc cggtgcctcg gttggtaggt gcggctgcgc gtgggcgagt 40320
gattggacac atgcgcgcag ctgcgccaaa gccgcggggg ctgcgcgcgg cggaacggcc 40380
gccgatgcgg tcgtgggcgt ctcggggtaa cctccacacg caagatttac tggcaagcgc 40440
cgaagcgcgg atttgcgagc tgcccgcgcc ccccaaggtc cccctcggcg cagactccga 40500
cgccaccgat agctccctgg acggaagcgg gccggaaacg gaagaggaga cagaagcgga 40560
agcggggggc gacggccccg gccaagacgc gcccaaagcc cgagtggtgc ctgccaactc 40620
gctgctgaag cgccagtact tgcgcggcac gggcataagc gtcctggccc tcttgctgga 40680
ggcctgcgaa aaaattgccc ggcggctgcg cgcgacgcgc gacgtgctgc ggcagcgcgc 40740
cgctgaagtc acggctgaca tatttgcgct gcgcttgctt ttggggtagc gctcgccctt 40800
tcccctcggt ccctcccttt cccccacgtc cgccgcgcct cgcggccttc tgtactttgc 40860
cgcacaataa acaccgcaac gcaaaatttc atgagcacaa aactgtttta ttattgcgat 40920

```
cgcacaattg cgccgatccg aaaaaagcgt cacgtgcgcg cggcagacgc cgccgcgcca  40980
gcgtcctcct cgtattcggg ggggagctgc accacccggg ggaggaaggt ccgcttcagt  41040
ccgattgtcg ggcgcgccca atgcgcgtgg tcgtaggtcg caaacatggg cacgcgcggc  41100
acaacggcct tttcgtgccg ccgccgcagg tcgaccatgg ccagcgacgt gccgacgagc  41160
aggttgcgcc gggccgcgct cacctgctcc ggcgtcgtgc cgtcctgcaa cgggcgcgcc  41220
gcggcgttta gcacatgcaa aatctgcacg ggcagcaagt cccgcagggt gtcgggggtg  41280
atggtagccg gcgcactagg gtcgatcccg gcaggcgcgg acatggcgtc gtcgaaccgc  41340
gagtgagcgc gcggcgcggg cgcgcgtgtt aagagggcgc ccagaaaagg cgcagtatcg  41400
cgagaatgcc gcaaactccg cccacaagtg ttgcaagggc tgccattttt tgccggcgcg  41460
cggtcagcag cgcgccggcg tagtgcgcga cgtttccggc gccgccggcc ggttcgagct  41520
ctcgctcgct gtgaccgcac gcgcttgcgc gccgagagcg cacgtcacgc tcgctcagcc  41580
gctcccggac cgcgcggtct agcagccggc cggtgcgatg cgagtcgccg gggcccatga  41640
accggaacga gagctgcacg cgcggcatgc gcacgaagca gctcacggac atcatggcgc  41700
gaaagggccg tgggtctatg ccgccgcggg ccttgatctt ctccagcgcc gacaggctca  41760
ggcccgtgct ttgcgtcgag gccagcgtgg cgttgttctg ctccgccgtg atggccgcga  41820
gcggcgcgcc ggggggccgc gagaagtacc cctggaagag cacggacacg cccgtgttct  41880
ggacccggac gtaggggtcg cagtccgtct gcgcccagct ggccattagc cgcaagatgt  41940
actccagggg gaaggactcg ttgcttccgt cctggccgtt gaactggaag acgcaccgcg  42000
cgggcgggcg gcgcgggtcc cagggctggg gcacgtcccc ctcgccacat tgcaggttgc  42060
cggcgaccag caggcgaatg cgggccataa gactccggga agaaccctcg ccctcgccct  42120
cgccgtcgca gtcgcgctcg cggccgtgca tagtgggcgg cagtctgtct cgccgagcgc  42180
tgcgtcggcg cggaacgaag ctgcgccgtg ccggcgcggc gcctttatag cccgccccgc  42240
tttgcggggc gggcccgggg cctacgcgtc gtgcagaatc tggtgtaggt ccagaaattt  42300
gttgatcacc gtcgcaaagc gctccttcct cgcctccagc gctcgcgtgt ggctgcacgc  42360
cgcccgcccg cccgagccgt gtgcgatcgt cgaggccagg cgcgccgaaa aggccaaata  42420
gttcaccttg gcgtcggtgg tgggcagcag cacctcgagc tcgcgcggcg ccacgtcctc  42480
gaaccaaatt tctacggcgg cgccttcgct ttggaggtag cggcgctcca gctcggccac  42540
gtcctcggtg gccagcgcct cggggggat gagctcgcgg agccgcatgt tcgcgcgcgc  42600
tgacgacggc gccggtggcg gcgatggcgc gcgctcgtgg gcagagggtg cgttccgcgc  42660
cccgtacgtc gcgtttgacc cggcgctgtt gaaggaaaac ggccagctcc ttgaggagct  42720
cgtctttgcg gcccatttaa tggaggtgcc aagccctcga gacgacgggg acgaggacgg  42780
gggtggtgac agggacggcg ccgccgcgga ggggggcggc agcgccgacg tcgtgccctt  42840
tgtcgaagag gccgccgccg cgctggccat cgaccggccc tgcgccgtgt gtcgcacgat  42900
tgatgcttac cggcgcgagt tcgggctggc gccccccctgg gtggccgact acgccatgct  42960
ctgcgctaaa agcctcgcgg cgccgccctg tgccgtggcc atcgtggttg ccgcctttga  43020
gttcgtctac ctgatggacc ggcacttcct agccgcgcac cgcgccacgc tagtgggcgc  43080
ctttgcgact cgggtgctga cgctggtgga tgtacacaag catttcttcc tccacgtgtg  43140
cttccgcacg gacggcggcg ttcccggcaa caacgccggg aacgccgccg gggggcgcg  43200
ccgggccgcc gaaaaggtgc gctactccaa ctactccttc ctcatccaat cggcaacgcg  43260
```

-continued

```
ggcgctgctg gcctcggcgg cggagcgccc ggaggcgccg gcggtgcccg cagacggcgc  43320
gggcccgcgg gcgctgcgcc cgcagtcgct ggcgactgcg ctgctgagtt ggaaagagtg  43380
cgcgcgcctc gtggattgct cggcgccgtt gcccggcggc ggtgggggcg cgcgggcggc  43440
gcggcgcccg gggggcacct gctgcgacgc cgcgcgtgcg cgggctgcgg agtacgaagc  43500
gcgcgctgcc gtgctgccat cgccgcgcgg cggcgacgcc gacgaagcgt ccgcggccag  43560
cgccgccgac ggagcgcccg cggaccgatg ggcgtacgcg gacctcgcgc tgctgctgct  43620
ggccggcgtc gcgacccggg gcgacggcgc ggtcgccgag cgcgcgatcg cgtcccgccg  43680
cgccgccgtc gatcgctact gggcggcgcg cgcgggcttc ctcgcggcca acacggcgcc  43740
gcggtttgcg cgcttcgccg cgggcgacgc gcgccccagc gtggcgctgg ggccggtgct  43800
ggccacggcc ctcaagcaca ttacagggcg cgggcgcacg acgggcgagt gtgtgctctg  43860
caatcttctg ctcacgccgg cgcactggcg tgctttgcgc gcgctgcgcg cggacgtggt  43920
ggcgcactct gccaacaacg cgggcctctt cgactgcatc ctgccggtgc tggacgcgcg  43980
cgccggcgcg ccggtcgagg gcgacggcgg ccgcttcttt gccgcgctgg cgctgctgga  44040
gcccgaggct gtgtataagc acctattttg cgaccccatg tgcgccgcgt gcgagctgca  44100
ggcggacccc gaagtgttgt tcgcattttc cgacggcgac gcgcgcgacg cggacgagct  44160
ggatctatat aaggcgcgcg tggccagcga gaatagtttt gagggccgcg tgtgtgcggg  44220
cttgtgggcg ctcgcgtacg cttttaaaac gtaccagcgg ttccccccaa agccgaccgc  44280
gtgtgcggcc tttgtccgag acgccgggca gctgctccgc cggcacggcg tggctctcgt  44340
ctcgctggag cacaccctct gccactatgt ctgaccgcgg ggagcgccgc cgagctagag  44400
agccaagccc agactttggg tgcgggcgtg gggctgagcg cgccggcgac tgggcaacgg  44460
ccccggcctc gacaccagcc ccggccccgg ggcgccgctc gctgatctcg ccccgccttt  44520
gctctcgctc tcgctctcgc tctcgctctc gctcccgctc gccgtttgcg cctcaagggc  44580
gctcccgctc ccggggcccg gccacgcgcc gcgagcggct gcgttcgcgc acgggggcgc  44640
ggcgcgcggc acgcgcgcga gacagctacc tgatgtactt caggtttttg gcctcctccc  44700
ccgctgacga gctggccgcc gtccgcgagc tcgcggtgcc gcttatccga acgacgcccg  44760
tggtgctccc gttcgacctc tcgcggacgg tcgccgataa ttgcctatcg ctttcgggca  44820
tgggctacta tctgggcatc ggaggctgct gccccgcctg caccgtgacc ggcgagccgc  44880
ggatgggccg cgcggaccgc gcggcgctta ttttggccta cgtgcaacag ctgagcaaca  44940
tctacgagta ccgggccttc ctggcctcca tccgcgcgct tggcgggacg gacgacggcg  45000
gctttggcgg ctgcgccccc ggccccggcg gccccaccga acgcgcgctc gccgaggttt  45060
tggcccaacc cgagctcttt ttcgcctacc acgtgctgcg ggacgggggc gtgcgcgacg  45120
cgcgcgtgct gttttaccga gacctggact gctcgggctt tatgatgtac gtggtgttcc  45180
cgggcaaagc catccacctg caccaccgcc tgctggacca cctgttaacg gcttgtgccg  45240
ggtacaagat cgtcgcccac gtgtggcaga cgatgtttgt gctcgtggtg cgccgggacg  45300
ggggtggggg cagacaacag agcgcgacag acgccgaggt gccggcggtg agcgcggggg  45360
acctttattg caaaatgtcg gacctcaact ttgatgggga gctgctgcta gaataccgaa  45420
ggctgtacgc agcgtttgac gactttgcgc cgccggcgtg agcgcggcga agcccgccgc  45480
ggcgagccgg ccttgcagcc ggcggtcgca ggcgcgcgtt tccggaataa agcgcttgag  45540
caggttctcc gtggtccgcg tgtcgtttcc aaacagggcc ttgaaggtgg cgccgacggt  45600
gcctaggagg tgggaaaagt agtagtctgt gttgaggggc acggcatggg cccgcgcata  45660
```

```
ccccgggtcc tcggccatgt ccgagattag caaacgcccg gggcgggcgc cgccgccggg  45720
cggcgcggac ggggccgtgc cgcgcagcgc gttcaccgcg gcggcgtcgc gctccacgcc  45780
ctcgccgggc gcgacgatca cgtaggggat gcggtccttg acgttggggc gggcctcgct  45840
gcgcagcagg agtttgtagt acacggtcag atgcgcgatg cgcttgttgg cgtaggcctc  45900
cggtgggcgg ctcagctccg ccgtcatgac gaagtcgcca atgtccagcg ccgggtcggc  45960
gatcttggcg tgagcttcgg ccaacacagc tccgaagcgc gcaaagcccg gcgggagctg  46020
ccgcccgggc cactcgctgg gcggcacggc cgaggcctcg gccgcggcgc gcgaaacagc  46080
gtcgtcgtgc ataagcacgt cgaccaagcg ccgcgcgtag gcgttgataa agcggcagtt  46140
gtttttgcgc acgaggtcca cgcctttcat gagcatcttg ccgccgccga caaggccgag  46200
gtactttttt tttgtgatga gcagcagctt ggcaaaggtt ttctcgcact cgagcttgat  46260
gggcgggcga aagagcgccg ccgaaacccg gcgcgccatg ccgtcgccca gtgcgcacac  46320
ggcgtcgtag ggcatccccg cgaacttgac aaagaccgag tccgtgtcgc cgtaaaccac  46380
gcgcacgcgg tagcgcgcgc cggcggcggc cgccgccggc gcggccgcgg ggaaatctcg  46440
caccagtgcc tcgggtgtgg cccagcgctc gtgtatgtac cgccgcgtct cgagcagcat  46500
gtcgcgcccg atggtcgtta cggtggccgc gaccgccagg caaggcagta gtccgttgga  46560
cacgccggtg aagccgtaca ccgagttgca cacgaccttg atggcggcct gctgcttatc  46620
gagcagcaca gcctcctcgg gcgcggcggt ggggatgcgc gcgcggatgg ccttgcgcat  46680
ggccagccag tcgcgcaaca gcacgctgag caggctctcg cgcacgtgcg cgcgcacaaa  46740
gtggagcgcg cgcccgccca cgtcgaacgt cgcgtagtcc gcgccgggcg tcagccccgc  46800
cggcgcggcc tcgccgcgca cgagcgtggt gaagcacagg ttgtgcgcct gaatgatgct  46860
ggggtagagg ctggcaaagt ccagcaccat gacggggtcg acgtgaaagc ccgactcggg  46920
gtccaaaacc ttggcccccct ggtacccgac ggcgcgcccg cccgccgcgc ggggccggtc  46980
cgccgcgccc gcgccccccct cgttcccccc gtcttcttct cccccctcgt cctcctcttc  47040
ctcctcgccg cgagccgcgt cggcccagca ggcgaatgcc cccccgtccc cgcccggcgc  47100
cccggccgcg ccggcctcgg ctccggcgag gcgcttttgg gtgtccggca gcagaaagcc  47160
ccgctcccgg gccaagcgca gcaggcaggt gaatacgcga atctgctgcc cgtcaaaaat  47220
ggcgcgcgac accgtgattc cggccagccg cgccaccgcc gacagctcca ggtggggcaa  47280
gtacttgaag aacagctttc cgaccagcgc cgaatcttgg atgcagtact cgccgatgac  47340
gccgcgcccc tcgggcccgg ccgcaaagtg ccgagggatg tccttgtagt ccaggtccac  47400
cttccgctcc cgcagggcct cctcggccac ggcgttgagc ttgtagctgg gcagcttgag  47460
cttctccacg gccgtgcggt acatgtccag ggaaaccacg ccgttaatct tcaccttgct  47520
ctgcttctga aagcggtttt ggcccgcgtc gaagacgcgg aagaggccgc cccggtttag  47580
cttcccgtag ccgtcgagcc gcacgtcgta gacggccgtg agcttctccg agatgtacgc  47640
ccagtcgaag ttgacgatgt tgtacccggt gacgaactcg ggcgagtact gcttgaggaa  47700
cgtcatgaag gccagcagca gctcgaactc gctgtcaaac tccagcacgg cgggcgcggg  47760
gagcccggcg gccgcgcacg cgccgaggaa ggccggcggc aggtcgcagg atcccagcga  47820
aaacaaaagc gtgtgctcgt ggcgctgagt gcgcagcgag tacgtcagac acgagatctg  47880
gacgacgagg tcctcggcgt tggcggccgc cgggaacgcc agcccgtcgc ccgcgcacga  47940
caggcactca atgtcaaagc acagcagctt gtagtcgggc cacgcgtcgg cctcggcgcc  48000
```

-continued

```
cgcgatcggc tccaggttgt ccgcggtgca gttgacttcc acgtcgcagg aggtcgcgtg  48060
ctgcgcgggc gcgcgcagcg ccacgcgcgc gcccgcgcgc ccggggcgca gccggtacca  48120
gccgaagctg gtgaagcctt cgttgtccag caaaaagcgc gtcgtcacgt ccacgtggcc  48180
ctcatacttg gtcacgccgg ggaggaagtt gtcgcagagg tagcccccga gccgcgcgct  48240
ggccgaagac accttgtaga aaagctgcgg gcgcgtgtcg tagaagtaca cgtccgctgc  48300
ctcgaccacc gcgaccgaaa ggctgtcccg cgaggcgcgg cccaggtaac cgccgggccg  48360
gcgcgcgccg gcccggccgg cggcgtcctg ctgtgccgcg ccggcggcca gggccgagga  48420
gcgcagcgcc gccaccatgg cgtcgatcag ctggccctcg tcgcgcaccc cgcaggctag  48480
gtcgacggcg gccttctcca tgtaaaaata gtgccgcacg ccgtacacgt gcaccgccac  48540
gcgcttgccg tcctccgaca tgcccagcag cgtcacgacc gtggcgccgc cgggccgggc  48600
ctcggcggca aagcgggacg cgtcgccggc gctcgggtac tcggtcgtct ccacgatgtc  48660
gtacacgtga aagcgctcaa agcgcgggtc gagcgcggcg cgctccgggg cggcgcggcc  48720
cgcccacacg cttacgcggc gcggccagca gcaatggccc gcaaagtcca ggatgtcgtg  48780
ctcctcgccg tcgaggtata ccttgggcgc gcgctcggcc gtgccgatgt gaacgccgcg  48840
gcggcggggc gccgccgccc ccgcagcctc gtcgtccgtg ccgccgtcgg cgccgtcggc  48900
gtccaggcag cgcggcgcga tgaagcggaa ggacgaggcg gcggtgcagt atgactcagc  48960
cgcgcgcccg ccgccgcggc ccgccgcctc gtctgcgggc gcctcgccgg cgccatcggg  49020
gatgtccggg ccttgccgcg cgggggcgcc tcggccgcgc ggcgcgaggt acgggttgaa  49080
aaacccagcg cgcgggggcg cagtgccctg ttcgcagtct ctgtccatag cctggcgggc  49140
gcaggcgcgc gactggaccg cccccggtgc cgtcagacgc tttaacggcc tcaccggggg  49200
aggggccggc gcgaggttaa ataccagatc tgccagcggc gagccgtggt ggcgcgcagc  49260
tcacggccgc gggcggcggc agccgacaag ccaacagaca gtgcgtccgg ccggcttgtc  49320
ctcctcgcgc tcccgccgcg ccccgccttt tttgagttgt tgccgcgccg cgtctgccga  49380
ccatggacgc ggcggccaag acggtagccc tcgcgccggg gcccgcgggc ttcgtgtacg  49440
tctgcgacgc ggctcgcctg gacctcgaca agctcgcgct gctcgccgcg cggagccgcg  49500
actcgccgct ggcggtgctg cccctggtgc gcgggctcac tgtggagacg gcattcgcgc  49560
caaacgtcgc ggtggtcgcc ggcactaaga ctaccggcct gggtggcgcg gggctgacgg  49620
ccaagctaac gcccagccac taccacccga acgtgtttgt ctttcacggc ggcgagcgcc  49680
tgcgcgccag cacggccgcg ccaaacctga cgcgcgcctg cgagcaagcg cgccggcgct  49740
ttggctttag cgcctttgcc ggcgcgcccg tcgacggcgc cgttgagacg acggccgagg  49800
acatttgccg cgcagtaggc gcgagtcccg aaacggccct ggtcttcctc gcgacgacgg  49860
aggctttcaa ggagacggtg tacatgtgca acaccttcct gcactacggg ggcgcggcgc  49920
ccgtgcaagt gggcgccggc gaggcggtgc gcgtgccgct gtaccccgtg cagctgtaca  49980
tgcccgacgt gaaccgcgtg aacctagagc cctttaacgc gcgccagcgg gccatcggcg  50040
agcagcttgc gtatccgcgg cccttctaca acgccgcact ctgcgagctg ctgcacggct  50100
acgtgctggg cccggccgcg gtggcgctgc gcgtgcgcag cttggacgcc gtggcgcgcg  50160
gtgccgcgca cctagccttc gacgagagcc acgagggcgc cgtgttgccg ccggatgtgt  50220
gcttcacggt ctttgaccag cccgcggggc gcggtggcgg ccgcgggtcc gcgcgcggcg  50280
cggacccggg cgcggccaag gctgccgcgc cgggcggcgt agagcgccgg ctggcctcgg  50340
tgatggcggc ggacacggcc gtgtcgatcg aggcggccat gagcacgagc gtgttcgacg  50400
```

aggacgtcgc gtgcgtggac gactggccga tgctgcaggg cgcggcagac gacgcggcga 50460
agctggacgc gctgggcgcg tacgtgggcc gcctagccgg gctagtgggc gccatggtgt 50520
ttagctcaaa ctcggtgctg cacatgacgg aggtggacga cggcggcgcg gccgacgcca 50580
aggacggcgc cgccgccggc ttccaccgct tctaccagat cgccgccccc tacgctgccg 50640
ggaacccgcg ctgcgacaag gacggcaagc cgctgccgca gaccggcgcc ggtccggccg 50700
tatctatcaa cggcgcgggc caggagttcg cgctggacca cctggcgctg gcgtgcgggt 50760
tttgcccgca gctgctggcg cgcatgctgt tctacctgga gcgctgcgac gcgggcgcct 50820
tcgccgggcg caacgacatg gacgcgctga agtatgtggc cagcacgctg gagggcgacg 50880
tgccctgcgg gctgtgctcg cgcgacgacc ggcacgcgtg cgcacacacg acgctgcacc 50940
ggctgcggca ccggctgccc cggtttggcg cgccaacgcg gagcccgctc ggcgtcttcg 51000
ggaccatgaa cagcgcgtac agcgactgcg acgtgctggg gaactacgcg tcgtacagcg 51060
cgcttcggcg cccgggcgcc gacgagaacg ccaggagcat catgcaggcc acgtaccgcg 51120
cggccgtgga aaacgtgctc gcggagctgg accagcagcg gctgctggcg cacgacgccc 51180
agtcggcggc gcagctcgag cgcgcgatta cggaccacgc cagctttcgc ggcgctctgg 51240
ctgcgatcca aaacacggtc gagcaggcca ccgaggcgtt cgtgcgcggg ctggtcgagg 51300
accgcgactt caagatgcgc gaggcgctgt acgaggccaa ccacacgctc tcgctggcgc 51360
tggacccgta ctcgacggcc gtttgcccgg cgacggcctt cctgtttcgg cgctcggtgc 51420
tggccgtggt gcaagatcta gcgctcagcc agtgccacgg catcttctgc gggcagccgg 51480
tggacgggcg caactttcgc gcgcaattcc agcccgtgct gcggcggcgc ttcatggacc 51540
tgctcaacgg cggcttcctc acgacgcgga ccgtgacggt gacgctcgcg gaggccgcgg 51600
tcgcggcgcc gaaccttgcg gcggcgcaga cggagccgcc cgcgcgcgac atggacggcg 51660
acatctcgaa ggtaagcctg gaggtcttca aggagatgcg cgtgaagaac cgcgtgatgt 51720
tctcggcggg caacgccaac atgtcggagg ctgcgcgcgc gcgcgtgctc gggctcgcgg 51780
gcgcctacca gaagcccgag agcggcggcg tgaacattct cagcgggccg ctgggcttcc 51840
tggtgaagca gttccaccgc aagcttttc ccaacgggaa gccgcccggg agcccgacgc 51900
ccaacccca gtggttctgg acgctgctgc agcgcaacca aatgccggcg cggctgctct 51960
ccaaggagga catcgagacg atcggcgccg tgaagcgctt ttcggacgcg tacgcggcca 52020
tcaactacgt caacctcacg ccgggcaacg tggccgagct ggcgcagttt tacatggcca 52080
acctggtgct gcgccactgc gaccacaagc agttctacat caacgggctc acggcgatcg 52140
tggccggggc gcgacggccg cgcgaccccg cggcagtgat gcactgggtg cgccggcgca 52200
tcgcggacgc gcccgacgcc gcggcggccg ccgaggaggt gctacgcgag gcggaggccc 52260
gcccggaggt gtgggcgggc accttcgccg ccagcaacct cgtgcgctcg gtcatggcca 52320
cgcggcccgc ggtagtgctg ggcctcagca tcagcaagta caacggcagc gcgggcaaca 52380
atcgcgtctt ccaggcgggc aactggagcg gcctcaacgg gggcaagaac gtgtgccccc 52440
tgctgtgctt tgacaagacg cgccgcttcg tgctcgcgtg cccgcgcgcc ggctttgtgt 52500
gcgcgaccgc gggcgcgggc ggcgccaacc gggacaacac gctggtggaa gcgctccgcg 52560
agattatcaa cggcagcaac ggcgcgctgg cgcagacggc cgtctacggc gccgtgctcc 52620
aggcgctggg cccgcgcgtg gagcacatgg acctggacga ctgggcggcc ctggtggagg 52680
acgagttctt cgcccagagc atggtggagc tgacggagcg cgcggccgcg cggcccgggg 52740

-continued

```
gatggtcgcc ggagggcgcg gccgacatgc tgcgagagct ggagctcgag gcggcggccg  52800
aggccgagcc cgcgggcggc gcctttgact tcggcgcgtg cgcgagcgcc gcgccagacg  52860
cgacctacgc cttcggcggc cccgtggccg gggccgccgc cgcgcctgga gccaagcgcc  52920
ccgacctgga cgagctgttt gagatgggcg tcccggacaa gcggcccgcc ctgaccattg  52980
acatggtgta gcgcggcggc gacatgggcg gggctatagg tcgctcgtcg ccggcgaccc  53040
cgcccgcatt ctcccgcccc ggtaacagat atatacatgc gccgtttgcc gcgaaataaa  53100
aggataatat cgttgcacat tattcgtgtt tttgtctggc gcggttcgac cgaggccgcg  53160
gcgtctttgg ccgtgaaggg ggggggaag ggggacgcgc aggcatggcg gagccgacag  53220
cggcggccgc tgcgcgctcg ggcctcggct ccgagcctgg ccccgcgctt ggcccagacg  53280
ccgagcccgg ctcagcgttc ggcggggcgg cggcccgcca gcggctgctt gccatcctcg  53340
ggcaggtaca gacgtacaac ttccagctgg cgctgctcgg gcgctgcgac ccggctgtgg  53400
cgcgccgcca cctcgacgcc gtcaagctga acgccctcat ggtgcgctgg ctgcggcgcc  53460
gcctcggcgg ggcgctgcgc gcccaggcgc gcgtccgcct cacgccgctg acgtacgcgc  53520
tggacctcgc gctggaccac gccgcagcgg aaagcgacgc gctgctggcg gccgcgggca  53580
ccgcgagcgc gcctgccgag ttttttgcgc gcaccatggg gctggagggc gcgtgccgct  53640
tccaccggcg cgcgcgcctg gcgctctacg gcggcgagac gatcgacatc gagatccagt  53700
tcttgcacga cgtggaaaac tttttgaagc agcttaactt tgcccacttg ctcgcctcaa  53760
ccgacgccgc gctcgccgcg ctgggcgacg tggatgcctt tttgcgggcc acggtggcgg  53820
gcggcggggt ggcaccgccc gagctgcacg attttgcgca gccgtgtctg gtgtgcttcg  53880
aggagctttg cgtcaccgcg aaccagggcg agtctgtggg ccggcggctg gcgctgtgcg  53940
cctgcgacca tgtcacgcgg cagctgcgag tgcgcaccga gctatgcagc gtgggccagt  54000
acctgccgca cgtgcaaggc gtgtcgcggg cgcggctggc ggcggcagcg gcggcgctgg  54060
cggcgctggc ggcgccgacc gccgcggggg cgggcgggcc ccccgtcctc gcgacggccc  54120
cgcccggagg cgacggcgac ggcggctctg tgcgcgaggc ggccgcctct gtgctcgacg  54180
cgcaccacgt cttccgcccg gcgccgcgtt ggctctacgc ggtcagcgag ctgcagttct  54240
ggatgtcctc gtcggcgcgc ggcgaggccg ccgccagcgc cgtcgccgcc ttcgccggca  54300
acctagaggc gctcgccgcg cgggaggcgc agcaccggct gcaagtggcc gcggcggaga  54360
tggcgctctt tggccgctcc ccggagcact ttgaccgcgc gctcgcggac aagctggcgc  54420
agctggacgg cgtggactgt ctgctcgtgg gcagcgctgc ggtggcgccc gacgagcggc  54480
tcgaggcgct catccgcgcg tgctacgacc accacatgtc ggcctcgctg atccggcgcc  54540
tcacgcgccc ggaccagcgc aacgaggacg cgctgcgcga gctgctgcgg cgggcggccg  54600
cgggcgaggc gggcgccgcc gcggttggcc tcggcggccc gggcagagac gagggggcg  54660
gggacgagcc cgaggaggag ggcgggacgg acaacgacgg cggcgccggg gccggggtgg  54720
ggggcggtgg ggcggggccg tccgggggcg cagacggcgg gggcggcgcg gaggacgacg  54780
gccccgcggg ctgggcggcg ctggcggcgc gcgcccgcgc cgatgccgac gtgcgccgac  54840
agcgctatgc cgagcggctc tcgaagcgct cgatggacag cctcgggcgg tgcatccgcg  54900
accagcggcg ggagctggaa aagaccctgc gcgtgagcgt ctacggggac gtgctgctca  54960
acgtgtacgt ggcggtgcat aatgggtttt gcgcacgccg cgccttccgc gccgcgctgg  55020
cgagcgcggg cacggtggtg gacaaccgcg cctcggacgc cacctttgac gcgcaccgct  55080
tcatgaagga ggccctgctg cggcacgccg tcgacccggc aacgtggccc gcgttgacgc  55140
```

```
accagttctt cgacctagtt aacgggccgc tctttgacgg cagcgcgcac aacttcgcgc  55200
agccgccaaa caccgcgctg tactttagcg tggaaaacgt gggcctgctc ccgcacctca  55260
aggaggagct ggccgcgttt atgctggcgg ccgcgggggg cgggtgggcg gtaagcgact  55320
tccagcagtt tttttgcttc gcatccgcgc gggcgcgggg cgtcaccgcc gcgcagcggc  55380
tcgcctggca atatatccgc gagctcgttc tggcccgcgc cgtctttgcg tccgtcttcc  55440
actgcggacg cgtcccgctg ctgcgtgcgg accgaacggc gccgggcccg gacgggcggc  55500
agtcgtgtcc cagcggcgtc tacctgacct acgaggagtc atggccgctc gcggcggtgc  55560
tgaacgcgcc gcgggcgccg gagacggtcg gcgaggacag cgtcgtcatc tacgaccggg  55620
acgtgttctc gctgctctac gcggtcctgc agcgcctggc gccggcgggg cgcgcgccgc  55680
gctagccgct gccctgctat gggcgacgtg ggccctgctg ctggcggcgc ccgccgcggg  55740
gcgaccggcg acaacgcccc cggcgccccc gcccgaagag gccgcgagcc cggcgccccc  55800
cgcgagcccc agccccccg gccccgacgg cgacgacgcc gccagccccg acaacagcac  55860
agacgtgcgc gccgcgctcc ggctcgcgca ggcggccggg gaaaactcgc gcttcttcgt  55920
gtgcccgccg ccctcgggcg ccacggtggt ccggctcgcg cccgcgcggc cgtgccctga  55980
gtacgggctc gggcggaact acacggaggg catcggcgtc atttacaagg agaacatcgc  56040
gccgtacacg ttcaaggcct acatttacta caaaaacgtg atcgtgacca cgacctgggc  56100
gggcagcacg tacgcggcca ttacaaacca gtacacggac cgcgtgcccg tgggcatggg  56160
cgagatcacg gacctggtgg acaagaagtg gcgctgcctt tcgaaagccg agtacctgcg  56220
cagcgggcgc aaggtggtgg cctttgaccg cgacgacgac ccctgggagg cgccgctgaa  56280
gcctgcgcgg ctgagcgcgc ccggggtgcg gggctggcac acgacggacg atgtgtacac  56340
ggcgctgggc tcggcggggc tctaccgcac gggcacctct gtgaactgca tcgtggaaga  56400
agtggaggcg cgctcggtgt acccgtacga ctcgttcgcg ctctcgaccg gggacattat  56460
ctacatgtcg ccctttacg ggctgcgcga gggcgcgcac cgcgagcaca ccagctactc  56520
gccggagcgc ttccagcaga tcgagggcta ctacaagcgc gacatggcca cgggccggcg  56580
cctcaaggag ccggtctcgc ggaacttttt gcgtacacag cacgtgacgg tagcctggga  56640
ctgggtgccc aagcgcaaaa acgtgtgctc gctggccaag tggcgcgagg cggacgaaat  56700
gctgcgagac gagagccgcg ggaacttccg cttcacggcc cgctcgctct cggcgacctt  56760
tgtgagcgac agccacacct tcgcgttgca gaatgtgccg ctgagcgact gcgtgatcga  56820
agaggccgag gccgcggtcg agcgcgtcta ccgcgagcgc tacaacggca cgcacgtgct  56880
gtcgggcagc ttggagacgt acctggcgcg cggcggcttt gtcgtggcct tccggccgat  56940
gctcagcaac gagctggcca agctgtacct gcaggagctg gcgcgctcga acggcacgct  57000
cgaggggctg ttcgccgccg cggcgcccaa gccgggcccg cggcgcgcgc gccgcgccgc  57060
gccgtctgcg cccggcggcc cgggcgcggc caacgggccc gccggcgacg gcgacgccgg  57120
cgggcgggtg actaccgtga gctcggccga gtttgcggcg ctgcagttca cctacgacca  57180
catccaggac cacgtgaaca ccatgttcag ccgcctggcc acgtcctggt gcctgctgca  57240
gaacaaggag cgcgccctgt gggccgaggc ggctaagctc aaccccagcg cggcggccag  57300
cgctgcgctg gaccgccgcg ccgccgcgcg catgttgggg gacgccatgg ccgtgacgta  57360
ctgccacgag ctgggcgagg ggcgcgtgtt catcgagaac tcgatgcgcg cgcccggcgg  57420
cgtttgctac agccgcccgc cggtctcctt tgccttcggc aacgagagcg agccggtgga  57480
```

-continued

```
gggccagctc ggcgaggaca acgagctgct gccgggccgc gagctcgtgg agccctgcac  57540
cgccaaccac aagcgctact tccgctttgg cgcggactac gtgtactacg agaactacgc  57600
gtacgtgcgg cgggtcccgc tcgcggagct ggaggtgatc agcacctttg tggacctaaa  57660
cctcacggtt ctggaggacc gcgagttctt gccgctagaa gtgtacacgc gcgccgagct  57720
cgccgacacg ggtctgctcg actacagcga gatacagcgc cgcaaccagc tgcacgagct  57780
ccggttctac gacattgacc gcgtggtcaa gacggacggc aatatggcca tcatgcgagg  57840
gctcgccaac ttctttcagg gcctgggcgc cgtcgggcag gcggtgggca cggtggtgct  57900
gggcgccgcg ggtgccgcgc tctcgaccgt gtcgggcatc gcctcgttta ttgcgaaccc  57960
gttcggcgcg ctggccacgg ggctgctggt gctcgccggg ctggtggccg ctttcctggc  58020
gtaccggtac atttcccgcc tccgcagcaa ccccatgaag gcgctgtacc cgatcaccac  58080
gcgcgcgctc aaggacgacg cccggggcgc aaccgccccg ggcgaggaag aggaggagtt  58140
tgacgcggcc aaactggagc aggcccgcga gatgatcaag tatatgtcgc tcgtgtcagc  58200
ggtcgagcgg caagagcaca aggcgaaaaa gagcaacaag ggcggcccgc tgctggcgac  58260
ccggctgacg cagctcgcgc ttcggcggcg agcgccgccg gagtaccagc agcttccgat  58320
ggccgacgtc ggggggggcat gaggcctatg tatgggcagt tcgggtgcca ataataaatt  58380
ttgcgcgaat cttatttaag tgcacaccgt gttatttgcg gctgtttgtt tttcctggag  58440
gcgggacgct gcgcgcgagc tcggccggat tagggttcgg cgccacccgg gcacggcagg  58500
gcgccctta cttatgtttg gcgcgcggtg gctccggcac cggtctctgt ggccctcccc  58560
ccgcctttgc gtttattgtc ccagctgtgt tcccgccttt gcgtgccccc cgcccgaccg  58620
cccgaccgtc cttccccgcc cgaccgtcct tcccggcgcg cctcctcccg cgccacaaag  58680
cacatttgac cccaaaagta atgcaaaata tacatttatt gtgggcgcgg ggcgcccgag  58740
gtaccgcatt gtttgttgtg tccgtgtgta aacatcctcg acttgccggc cagctaagcg  58800
ggccgctttg cgcgcgggct cgcctttcgc tagcgctgcc gcatcatctg ggccacgaag  58860
atttccgccg ggtcgcacgc ttgcggcggt tgggcgggcg gcaggctggc catggcgctg  58920
gcatccaccg tcgcggccac cccgggctcc tccggcggcc cgacagcggc ggcggccgcg  58980
acggtcgctg gtgctgcagc tacggcagga acggacagcg cctgcgccgg cgcctgggcc  59040
ggtgcgaggg tcggcacttg ggccgggccc gcacctaccc ggggcggggc agtgtactgc  59100
tgcggcaagc acggcaaatg cgccgcgggc gggtgttgcg cagcagcgaa ggcaggaccg  59160
taggggtagc cggccctcag ctggctcacc tcctgctgca gcgaggacac ggcggaggcg  59220
agcttggaaa gagcgtgcga cggtggcggg tgcggcggcg gaggagagtg gtggtgaggc  59280
ggcagctcgg ctggcgcgcc ctcgcccggg tagtaggcct cgtcgtcgtc gccgccgccg  59340
ctccggccgc gcgggtggtc ccagttgtac cggcgccgct tggccagggg gcggcggtcg  59400
agggggccgt cgtagcccga gccgtccgcg ccgtgcgctt gcacgcgtcg gccgtcggcg  59460
atggcgccgg ccagggccat gatttggctc tcgagccccg gcggcgggaa accgtaccca  59520
gggtgccagg gcgcggcgcc ggcggcgccg taccagcccg gcatcggggg cggagcggcg  59580
gcggcagcgg cggcggccgg caaaaaatac ggagccggcg gaggcgcggc ggtcatcgct  59640
gcgccccggg cctggctgac gaccaactgg ttgtactgag cagtcggcac gtacacgtag  59700
tccccagccg gcagggggtg cgccgaggcc gcaccggctt ggtgcgctgc gctcatggca  59760
ggcggtgggg gcggcggggg cggtgccggc ggaagctctg gctggcgtgc gcgtccgccc  59820
gcgacgggaa gcgcaatgca gacgccgccc gcgaccgcgc tcttttgagc ccgctcgcgc  59880
```

```
ccgcccgtgc gctctggccc ctcccccccg gtcggcagcg ggaacaccgc gctcgcctgc  59940
aggtacgtgt ggcccgcgat gcccgcctcg cggcggcgac gcgagacggt gtcccacttg  60000
tcccggacga gcatgttgtt cacggcggtc gagagcagcg tttgcgccag cgcctcgcgg  60060
ggcaccggcc aggcgcggtc gccgagggcc gcgcgcgcgg cctccgcgtt ggcgaggagg  60120
gcggcgcgcg cgcgcggcga gagccggcgg aagggcgcca cgcaagcgtc cggcgtggcg  60180
tcgtacgtga cgatggtccc gacgcggcgg cctagcacgc acagcgcgac gtgggcaaag  60240
agcgtgccgt cggcctcttc gtcgggcgcg aggcggcgcg aagagagcga cacggagggc  60300
aagtagttgc tgacgaggta caggaagcgc tcgcgcggcg tgagcgaggg ggcgtcggcg  60360
ccgaagaacg cggggtgcgc cacgcccgcg agcgtgtcgg ccagttgcgg gcagttgatg  60420
acgccgacga aaaacagccc ggcgtcgtcg tcggcgaggg ctagcacggc gccgacttcg  60480
caggcgcttg cgtggtcaat gttgatcggc agcggggcgg cgggcggcag cgcgcgcgcc  60540
acctgctcgc gcgtgaggac gagctctcct tcgtcgccca tgccgtagag ggcaaggtac  60600
ccgcccacat agacgggcat gctcgcgcgc gcaagcgccg aaggctcggc gtccacgcgc  60660
gcgtcggcgc tgcccccgtc gggcgcgtcc gccatggcgc cgccgctttg tgcgcgcgcg  60720
ggccggcggg cctttttatg gccgcggcac cgctcacacc gcggaggtga acagcggcac  60780
gaagcccaga cacaaaaagt acagcaagtc gtagtcgctg gcgacgttaa actgactcaa  60840
gcgccgcgtc tcgtccagcg cgcggcgcag gcgcggctgc tgcatcaaca cgcccagccc  60900
ccgctcgtac tgcagcgcca cggcgtcgtg cgccgccacg acctccacga cgggcgcggg  60960
cgcggcgcgg tggcggtttt ccagctccag cgccacgagg cgcagcagcc caccttggtg  61020
gcgcccgcca gacacactga tggcgcgagg ggcgcccgcg gcgctgcgcg gcgccagggc  61080
gtccagcgcg agggcggccg cgcccgggaa gagttgcgtg acctccacct cggggcaggc  61140
ttcgtacacg cgagccacat agcgcgcgca gaggaacgtc aggttggcgt ccccgctgcg  61200
cgcgcccacg gcgccgtcga ggccgccatc ggcgccgcgc gtcacatccc cgggcgcggc  61260
cgccccgggc accagcgtgc caatctggaa gttgttccgg agcttgtcgg cgtacacgtt  61320
gccgttccac agcaggcggc gcaccaggag caaggcggtg atagtgtcga ccgtagcgcg  61380
cagcaagctc tggtcctcgg cgaggaaaag gttttgcgcg cgcgccaggt acgcgccggc  61440
tgcgcggtga acgtcgtcca cgtacgcaac gccgtccgcg tccgcggcgc gcgcgggcgc  61500
cgcgccgccg cctagcgcgc caggaatcgc cggcaggacg cgcagccgct gcagcgcggc  61560
gaccacggcg tgcgcttcca gcgccccgcg ctcgtagcgg cccgcgccgc cgcccggcgc  61620
ttggaactgc cctcgcggga ggcgctcgag gtcaaacgcg tactgcacgc gccgggccgc  61680
gccttcatcg atggcgcggg ccagggcgtc caggtacgcc gggatctgct ccacgaggcc  61740
gacaaaggtc acggggctct gcgagccgcc ggcaacggca cggtgcgcga ggtgcagaca  61800
cagcaccgcg cactcaaagg ccgagtacgc gcggttgccc acgtacatgc gcccgctgga  61860
ctgcagcgcc gccaccgcgg ccgccatgaa ggttcgagac atgcgcccat cgcggtagtc  61920
catgccgcgc gtcgccagag ggcgctcggc aatcagccga tcctgcaacg tgcgatacca  61980
ggtcccgaag acaatgcccg ccgacccccc gccggcacgc gcggtgtaca ccattgccaa  62040
caggtcggcg gccagggtgg tgtcgtactc caggggcggg tcgttttttg ctatttgcac  62100
tcggcgtgcg cgcacggcct cgagcgcgcc cgcgccgccg ccccccctcct ccgcgtcagc  62160
ggcggcgcgg cccgcgcggg ccgactccgc cgccgcgtcc gcctcctccg cccggcgcgc  62220
```

-continued

```
cgcctcctcc aggtccgcga gcacggcggc tacctccgcc acccgggcct caatgggccg  62280
gatgcgcgcg tcgacttccg cgcccgcggc gcgttgcttc gccagcaggt tgtccgcggc  62340
cgctgccgcg gcctggttcc gcgcccgcgc tgcggccagc tcccgcgcgg gcgcgtccgc  62400
gtccccaatc cgcgcgaaga cgggctcgtc ccagaagcgc agcggaaagg ccggcgctat  62460
aaaatttcgc tcgtccggta caaagacgcg gtccgcgact gcgtggatgt ccacgcccag  62520
gcaagcaaac tctaaacgcc cgagcgccat ggccccgatg ccgccacaaa gagcgccgaa  62580
atttcgccca ggcacgccgc gccgcccgac gcgtctttag cgcacccgcc ggcgctgttg  62640
cccgcgtgcc tgctgccgcc caccgggcgg ccgctctccc cggcctcagc agggccgggg  62700
tcgccggcgg gcggccgcgg ggtggcggcc acagccgccc ttttgcccgt agccagggga  62760
agcggctgcc ccttctgccg ccgcggccgc ggttgctcgg ctttgcgttt gccccgcggc  62820
gatcgccccg ctcgccgcga acgcgcgcgc gcgaatgggg cgtactcggc gagcccggct  62880
attatagcct caaggcgcgc cgcgttgcta gcgatcgtct gggccggcag gcgcgtcact  62940
ctgagcacgc gcatgccccg ctgggagacg aacaccagca ccggcgctag gaccaccggg  63000
tctgggcccg ggggggcgag atcgcgcaca agccgggccg agtcgcgcag ctgccgcagc  63060
cccccgaggc gctggtccat cttgctgggc gtgttcatgt tcgttgaaaa acggcacgtc  63120
ttcagctcca cgataagaca gacggcccgg gcgtgccctg cctccgcgac ccggagtagg  63180
cacacgcaat cgggccgccg gctttgcagg tttacctcaa agctcagaga cacgcccacg  63240
acctgcttaa aaacctccgg ggcgccaaac ttgcccaaaa gctgggcgag gcgcgggcgc  63300
agcttctgcg cgccaaccgc cgcgcgtgcg tcgcaagcca gcgcctcgta aaagcggctg  63360
tggcaccgga tcccggcgcg caggcgcgca cgtcggtcgc ggtcgcgcgc catggccgag  63420
cccgcgcgcg ctctccgcgt cgtgcgtatc tacctggacg gcgcgcacgg gctgggaaag  63480
acaacaacgg gccgcgcgct cgcggccgct tccaccgctg gggagggcgt gctctttttc  63540
ccggagccga tggcgtactg gcgcacgatg tttggtacgg acgccttaag tgggatcctc  63600
gcggcgtctg cgcgatgcgc cgcagcctcg cacgggagcg cacgcggcgc cggcgggccg  63660
gcgcaccgcg cagacgcgga cgcggcgggc ctggttgcgt actaccaggc caggttcgcg  63720
gccccgtact taattttgca cgcgcgcgtg tccgcgctgc tggcgccgcc tgggccggcg  63780
ccgggcggca ctgtgaccct cgtgttcgac cgccaccccg tggccgcgtg cctctgctac  63840
cccttcgccc gctactgcct ccgcgagatc aacgcggaag atctgctcat gctcgcggcc  63900
gccatgcccc cggaagcgcc cggggccaac ctcgtcgtgt gcaccctccc cccggccgag  63960
caacagcgcc gcctggcggc gcgggccagg cccggagacc gcgcggacgc gggctttctg  64020
gtcgctgtgc gcaatgctta tgcgctcctg gtgaacacgt gcgctttcct gcgcgcgggg  64080
ggcgcatggc gcgacggctg ggacgcgctg gagtgggcgg acgcaaatgc attggccgcg  64140
ctcgcagacc ccagttgtga tgaatgcaaa atggcgccgg cgccggcgct gcgcgacacc  64200
ctgttcgcgg cgctcaagtg ccgcgagctc tacccgggcg gcgggacggg cttgcccgcg  64260
gttcacgcct gggcgctgga cgccctggcc ggccgcctcg ccgccctcga ggtgttcgtg  64320
ctggacgtgt ccgcggcgcc agacgcgtgc gcggccgccg tactggacat gcggcccgcc  64380
atgcaggccg cttgcgcgga cggggcggcg ggcgcgacgc tggcgaccct ggcgcgtcag  64440
ttcgcgctag agatggcggg ggaggccacg gcgggcccta ggggactata aagctgcccc  64500
tgcgctcgct cgctcgctgc atttgcgccc cgatcgcctt acggggactc ggcgctcggc  64560
ggatcccctc ccggccccgc cgcgaagcga gccgccagac aaaaaaatgc ggcgcccgct  64620
```

ctgcgcggcg ctattggcag cggctgtcct cgcgctcgcc gcgggcgccc ccgccgccgc 64680
ccgcggcggc gcggggggcc gaagcaggga gcacagagac gcccgatacg aaatcgaaga 64740
gtgggaaatg gtggtcggag ccgggccggc cgtgcacacg ttcaccatcc gctgcctcgg 64800
gccgcggggc attgagcgcg tggcccacat tgcaaacctc agccggctgc tggacgggta 64860
catagcggtc cacgttgacg ttgcgcgcac ctctggcctg cgggacacca tgtttttcct 64920
gccgcgcgcg gccgtcgaca acgcttcggc cgctgacatt ccggacaccc cggccgtaca 64980
gtcgcacccg gggctcttcg gggcggcctt ttcctggagc tacttgcaaa cgcgccacct 65040
cgtagactac gacctggtgc cgagccgccc cctgcaggac tggtactttt cgcaggcgcg 65100
cgccgagagc aacgccgcgc gcccgccgcc cgccccgcgc gtcacaccaa cgccggcggg 65160
gcgggtggcc gcttttgaca tcaacgacgt gctggccagc ggcccggagc acttctttgt 65220
gcctgtgcga gcggaccgca agcggcgcga gcgccacgtg gcggattttg ccgcggtgtg 65280
gcccgtgtcc tacatccccg caggacgggc agtgctaagc tgcgagcgag ccgcggctcg 65340
gctggcggtg gggctcggct tcctgagcgt ctcggtgacg tcgcgggacc tcctgcctct 65400
ggagtttatg gtcgcgcccg cggacgccaa cgtgcgcatg attaccgcct ttaacggggg 65460
cggcgctttt ccgccacccg ggcccgcggc cggtccgcag cggcgggcct acgtaatcgg 65520
ctacgggaac tcgcggctgg acagccatat gtatctgacc atgcgcgagg tggcgtcgta 65580
cgcgaacgag cccgctgact ttcgcgcgca cttgaccgcc gcgcaccggg aggctttttt 65640
gatgctccgg gaggcggcag ccgcgcgccg cggaccgagc gccggccccg cgcccaacgc 65700
tgcctaccac gcgtaccggg tcgcggcgcg gctgggactc gcgctctccg cgctcaccga 65760
gggggcgctc gcggacggct acgtgctcgc ggaggagcta gtcgaccttg actaccacct 65820
caagctgctg tcgcgcgtgc tgctcggcgc agggcttggc tgcgccgcca acggccgcgt 65880
gcgcgcccgc accatcgcgc agctggccgt gccccgcgag ctacgcccgg acgcgttcat 65940
cccagagccc gccggggcgg cgctcgagag cgtggtggcc cgcgggcgca agctgcgcgc 66000
cgtgtacgct ttttcgggtc cggacgctcc gctagctgcg cggctgctgg cccacggcgt 66060
ggtgtcggac ctctacgacg ccttcctgcg cggcgagctg acgtgggggc cgcccatgcg 66120
ccacgcgctt tttttcgccg tcgcggcgtc ggcgttcccc gcggacgccc aggcgctgga 66180
gctcgcgcgg gacgtgacgc gcaagtgcac ggctatgtgc accgccgggc acgccacggc 66240
ggccgcgctg gacctggagg aggtatacgc gcacgtcggc ggcggcgccg ggggcgacgc 66300
gggctttgag ctgctggatg ccttctcgcc gtgcatggcc tctttccgcc tggacttgct 66360
cgaggaggcg cacgtgctgg acgtgctctc ggccgtgccc gcgcgggccg cgctggacgc 66420
ctggctggag gcgcagcccg cggccgccgc gccgaacctc agcgcggcgg cgctcggcat 66480
gctgggccgg ggaggcctct tcggcccggc gcacgccgcc gcgctcgcgc ccgagctctt 66540
cgcggcgccc tgcggcgggt ggggcgcggg cgccgccgtg gcgatcgtcc ccgtggcgcc 66600
gaacgctagc tatgtcatca cgcgcgcaca tccgcggcgc gggctgacgt acaccctcca 66660
gggaattgac gtcgctaacc ccctgctggt gacttttgtg cgcggcacgt cgtgcgtgtc 66720
ggccagcggc gcggtggagg cgcgccgcct tgcggtcccc ggcccgctgg acgcgtgcgc 66780
ctactgcggc agcgtgttcg tgcgatactt gccctcgggc gcggttatgg acatcgtgct 66840
cattgcggac aagcgcaccg aggttgagtt ctcgcgcggc gccaactcta gcatgcccgt 66900
cttcaaccct cgcctccaca gcgggcgctc ccgcgccatg ctgctgttcc ccaacgggac 66960

-continued

```
ggtcgtaagc gtcctggcct tcgccgggca cgaagcgccg acgttttcgc cggcgtacgt  67020
ctgggcgtcg gtaggcgggg cgctggtcgc gggtaccacg atatacgcca tcgcgaagat  67080
gctgtgcagc tcggtcccgc tcgcgcgcgg gtactcgtcg gtcccggtgt tttagcgcgc  67140
gcgttgccct cccccccttc ccccttttca cgtctccccg ccaataaaga cgcctccaac  67200
aaatctcaca cgcgcgcccg gttttggttt tttgtaaggg tatattattg attgccgcgt  67260
cgccgccctt gtggcacgct gagcctaggg ttcagtgccg gctccagctt ccccttctcc  67320
ctccccttcg ccgtcgctgt tgccgtcctc atactcactg tccgacggcg gcgtaatacc  67380
ggccgcccca agccgccggt cgacaagggc gcgcaggtag cacacgccgt gccgagcggc  67440
gggcgcgcgg tcgaacgccg tgagctgctc cgcctccatg agggttacgt ggggtgccgc  67500
cgttcccagc gcgtgcgcga gcgcgcgcgc cagcgccggc agcccgccgc cggcgtatag  67560
gtgcagcagc atcgcgcgga cgtggccctc ggctctccgt agctcgtccg cgctgcccgt  67620
ctccacaatg cgccggcgcg tgtgccgaga ggccaggctc aagacggcgg tcatctcgag  67680
gtccagcgcg cgcgcggcgg ccgcggcgtc gtcgcagtca cagtcgtaat cgtagccgcc  67740
gccgtctccg ccggcgccgc ctttttccgc aggcgcgggc ggttctccca gatcggcgcg  67800
ggccaaagcc tcggcgaacc gccccagtac gcacagctct cggaggatgt cgttggccgc  67860
gtccgcgacc gtgccctcgt cgagggggcgc ggcggcgcgg tgcggataat tggcggcata  67920
gctctcggcg aggtgctcga gcgcgccgta gcagctggcc atgccccagc gcgacagcaa  67980
gaactggcac agtgcgaagc gctggcagaa gctgaacccg tagtccgcca cggattcgcc  68040
gacaaagccg cggcgtccgc gcggcccaaa aagggccgtc gccgcggcca ccaagtcccc  68100
gcgcgcctcg tttagcgttt cgtcgatgcc ggcccagtgg tcgctcttca ggacgacggc  68160
gtccgcgcag cgcacgacgg cacacagccg cggcaggggg tcgccgccgc agagcggggg  68220
gcctgtcatg gcccaggcat tgtaggtccg cgggatgagc cgcacctgca caaagctcga  68280
cacggcggcc tcgcggcgcg cctgcggcgc gcggcgaacg cccgcggcgc gagcggtggt  68340
gacgatgact tcggtggtcg cgggcgagcg cgcgtctgcc ccttctccgg cgccgccgcc  68400
gcagcccgcc tctgcagcga cgcgctcaaa aagcccgcac agtagggggc gcacgggcgc  68460
cggcggggcc ggcaagcacg cttgcatcag cgcgaagcac tcccggttgg gcgcgtacac  68520
gaagcccgag agcgcgttgg tgatcgtggg cacgtcaaac aggtgcagaa cgcgccgctc  68580
ggcgtcgtgg tagccggtcg tgagcacgag ccccgaagcg acgccgagcg acacgaagca  68640
ctcggccagg taagggtcgc caaccggcac gtcgaagcgg ccgcagaggt ccgcgcccgc  68700
ggccggggcc ccgccgcgcg ggcgcaagcg cgccaggcag tccacaaacg cgcccccgcc  68760
gtcgggatcg tcctcgccgt cggttgcgcc agaaggggcg aggggaaccg cgcgcgcgag  68820
ttccgcgcgc acgtagttgg ctacggcgcg gtcgctgcgc ccccagccgc gcagctccag  68880
cccaaacttc accgcctccc cgcccctgcg ggcgactgag actaccgtgc ccgcatagac  68940
aaagtacgcg acgtcccccg cggccgagac gtagaaggaa accccgttgt gcgcgacgac  69000
gctgtggtag gcgagctcca tcgccgcggc ggccgcgcga gcgggccgac ggggggaaca  69060
atgacgcaaa agggccccgg gcgctgagtt aaatgcggcg cctactcgcg ccgcccggga  69120
gtcgccgcga gcatgctcgg cccggagagt gcagcccttt tgcgcgcgcc cgagccgccg  69180
ctgggcggcg ccgatgcgga agagggggcg gccggcgcca gcccgggaga cagcggctcg  69240
gacgacgagg aggatgagct gctgcggtgc gtcgcgctgt cggcgtacgg gggcgacgtg  69300
gactttctaa cgcgctcgcc gcgtctggcg ccgcgcgcgg acgggcgggc cgcgttctcg  69360
```

-continued gcgtacgtgg tctttggcgc ggcgtccgcc ttcgggctga atcccgcctg ctgcctgctg 69420
ttcttatact actaccggac gtttggcgac gcgacgtttg ccgtcgccgg cgccgcggca 69480
acgctggcct actacgcgcg gctggcggcg gccgcgggct tcctctacgc gggcgtgcgg 69540
gcggaccggc tgccttttgg gcgcgggcct cgggcgctgc tggcggcgct ggtgctggcg 69600
cgcgcggcgg tctttgcggc ggtggcgctg ccggcggcct ttgcgggccc ggcgctgttc 69660
ctgcggctca gcgcggcggt ggcggacggc ggcgcgcgcg cggcggcggc ggggctcctg 69720
ctggccgggc tggcggcgta cacggcggat ctcgtttgtg acgtcatcgg gtttttcgcg 69780
ccccgggcgt ggatgcgcgt gtgcctgggg ggccacgtgg ccgtgtgacg ccaccgcgtg 69840
agtataaaac gagcggcgcg gccgggcggc cgcactgcgc gcgccgcccc acaccgcgcc 69900
atggaccgcc agagcgagcc tccgcgcgcg cccgcctaca cgggcgggct ggtctccggt 69960
caagtgctgt cgaacatcga agtggcctgc caccgcgcgc tgttcagctt tttccagcag 70020
gtgcgatcgg acgacaacgg cctgtacgcg gccgcctttg acgccctctt gggcacgtac 70080
tgcaacacgc tgacactagt gcgctttctg gagctcgggc tctcggtggc gtgcgtgtgc 70140
accaagttcc cggagctgaa ctacgtgcac gagggcacga tccaatttga ggtgcagcag 70200
cccatgatcg cgcgcgatgg gccacatccg gtggaccagc ccgtgcataa ctacatggtg 70260
aagcggatta accggcgctc gctgagcgcg gccttctcga tcgccgccga agcgctggga 70320
ctgctcgcgg aggaggcgtc cgacgggacg caggtttcgt cggccatgcg catgcgcgcc 70380
atccagcagc tcgcgcgcaa cgtgcagacg gtgctggatt cgttcgagcg cggcacggcg 70440
gaccagctgc tgcgcgtgct gctggagaag gcgccgccga tgtcgctgct ggtgccgctc 70500
tcgctgtacc gcgaggacgc gcgcctggcg gggtcggcgg cgcgcgccgc gctggtctcg 70560
gagctgaagc gccgcgtgcg cgacgacgcc ttcttcttga acaagagcga gggggcgccg 70620
gggcgcgagc tcgcgctggc caagattacg gacctcgtgg gctgcacggc cgcgtcggtg 70680
gcggtgccgc gcctgacgca ctgcgacagc cgcgggcgcc cggtggatgg cgtgctggtg 70740
acgacggcgg gcatcaagca gcggctgctg ggcggcgtgc tggcgctggc cgactcggag 70800
gcggacgtgc ccgtgacgta cggcgagttc gtgatctcgg ggctgaactt ggtgacggcg 70860
ctaacgatgg gcaaggcgct gcgcgggctg gatgacgtgg ccgcgcatct gctggggctg 70920
gaggggaccg cgggcccggg gctggccgtg gccgccgact acgacgcgcc ggcagaggcg 70980
cgcgtaaagg cggacctggt ggccgttggg gaccggctag tgtttttgga ggccctagag 71040
aagcgcgtgt accaggccac gcgggtgccc tacccgctgg taggcaacat ggacctgacg 71100
tttgtcatgc cgctggggct gtacaaaccg cctgcggacc gctactcgcg gcactcgggc 71160
agcttcgcgc cgccgcccgg gcaccccgac ccgcgcatgt tcccgccgcg gtcggtgttt 71220
tttttcaaca aggacggcgc gctgacggag gtttcgttcg gcgcggccat gggcacgctc 71280
tgtcacccgt cctttctgga cgtggacccg gtgctggcgg cgctgcgcgc cggcgcgcgc 71340
cagaggcgag aggcggagtg gtgcctcttc ggcgcgtacg tcgccgaccc cggcgagcag 71400
gagctcgcgg accaggtgcg gcacttcctg gacgcctggc acgcgctgct gcccgcgcgg 71460
ccgcgctggg tgatggagtg tgccatgacg ccggaacaga tggtggcgcc cggcaaccca 71520
aacatgccgc tcgagctgca cccggcgttt gacttctttt tggggcccgc ggacgtggag 71580
ctgccagggc cacccaaccc accacaggtg atgccggcca tgcaggcgat gccccgtatc 71640
atcaacggca acatcccggt gccgctgtgt ccggtggact ttcgcgacgg gcgcggcttt 71700

-continued gagctgagcg tggaccggca ccggctgagc ccggcaacgg tggcggcggt gcgcggtgcc 71760
tttcgggacc cgaactaccc catggccttc tacatcattg aggcggtcat ccacggcagc 71820
gagcgcacct tttgcgcgct ggcgcggctg gtgatgcaat gcgtgaccag ctactggcgc 71880
aactcgcgct gcgccgcctt tgtgaacagc ttccccatgg tgatgtacat caacgcgtac 71940
ctgggcaacg gcgagctgcc cgaggactgc acggcggtct acaaggacct gctggagcac 72000
ttgcacgcgc tgcggcggct cgtggacgag tacacagtgc cgcacgcgcc cctgggcggc 72060
gagcaggagc acgccgcgct gaaccacgcg ctgctggacc cggtgcttcc gccgccgctc 72120
atctgggact gcgacgcggt gatggcgctg cagcgcgcgg acccggcgcg cggcgcgcgc 72180
gcacgcgtaa acggcgccgc gccgcacgtc gtggcgcggc gcgagctggc cgaagccaac 72240
ttccgcaacg tcgggcccga cctggtgcac aaccgacccg tgcgcggcgg cggccccggg 72300
gcgtacccgg tcccgcacca tggcgacgag tggctggtgc tggctaagat cttctactac 72360
gccgtggtcc cggccttcgc gcgcggcgcg tgctgcagca tgggcgtgca ctacgaccgc 72420
gtgtacccgc tggtgcagtc ggtcgtggtg ccggatctgc cccccgacga ggagccgccc 72480
gcgggccccg agcacccgcg ccacccgctg cacccgacga acctggtggc caactccttc 72540
aacgtgctgc tgcacaacgc gcgcgtggcg gtggacgcgg acgcgctgct ggtgctgcag 72600
gaagccgtga ccaacatggc cgagcgcacc tcggtggtgg tggtggacgc gggccccgac 72660
gcggggacgg ccacggccgc aacgcggaac atgcgcacgc tggacgcggc gctgcaccac 72720
ggcgtgctga tgatggcgta ccagcggaac gacgaaacgc tgctggacgg ggccttcttc 72780
tacccggcgc ccgtgcacgc gctctttgcc tgcccggacc acctgcacgc gatgcgcggg 72840
ctgggccaaa acgcgctgct ggccgcgcgg cacgtgccgc ccgtgccgca ctttgtgggc 72900
gccaactact acgccaccgt gcggcagcct gtggcacacc acgcggcgca gagccgcgcc 72960
gacgaaaaca cgctcaccta cgcgctgatg ggcggatact tcaagctgag tccgctggcg 73020
ctgacgcacc agctgcgcac ggggctgcac cccggcttcg ggctcacggt cgtgcgacaa 73080
gaccgcttcg ccacggagaa catgctcttt gcggagaaag cttcagagtc gtactttgtc 73140
gggcagctgc aggtggcgcg ccacgaggcg gtcggcggcg tcgggtttac gctcacgcag 73200
ccgcgcgcgc acgtggacct cggcgtgggc tacacggcgg cctacgccgc cgcggccatg 73260
cgcacgccgc tcacagacct gggcaacacg ccgcagaacc tgtacatgac gcgcggcgac 73320
ccgcccatgg tgaacgggga cgcggacggc ttcgtgcgcg acagcgtcaa cgccgggagc 73380
cgcatccggc cgcagggccc cgcgccgctc ttcgggccca ttatgcccgc cgcgccggcg 73440
ggcacggcgc gcgggcaggc tgcggtctgc gagttcatcg cgacgcctgt ctcggcggac 73500
ctcgcgtact tccgctcgcc gtgcaacccc cgcgggcgct cggcaggcgc ggcctacgcc 73560
ggcgacggcg agtcggacgc cgacgacctc atgttcgacc atggccaggg cgacccggcc 73620
cacccgcacc gcgccaccgt taacccgtgg gcctcgcagc gacactcgta cggcgaccgg 73680
ctctacaacg ggcagtacaa catgagcggc gcctcgccgg tgtacagccc ctgcttcaag 73740
ttcttcacgc cggcggaggt gtcggccaag gaccgctgca tgagccggct gattgcggag 73800
gtgggcgcgg gcgtgtcgcg gagcacgtcg gacacggagc tgcagttcaa gcagcccccc 73860
ggcaccgggg agctcgtaga agacccgtgc gcgctgtttc aggaggcgta cccgccgctg 73920
tgcgccagcg acgcggcgct gctgcgcgac cgcctcgccg cgcccggcgg cgcggccgcg 73980
ggcgtcgagg gccggctgga ggagggccac tttgcgcagt acctgatccg cgacgcctcg 74040
ccggtgcggg gctgcctgcc ggtgggctag gcgcgcccgc cccgccccgc gcacccgcgc 74100
ataaaaacgc cgccgcggtg cgcggggcgc gtcagttccg ccggcgcccc gcgcagcgat 74160
ggcccagccc gaagcgttcg aggtggagat tgtgctcccc ggagacctct ctcacggcga 74220
cctagccgcc ctccagaagt gcgagggcaa ggtggtattc tttaccacgc tgcgccggcg 74280
cgtgccgctg gcggacgtgg cgctggcctc cttctcggtc aacggcgtcg cgccagacac 74340
cctggggctg atggccgcgt accgctgccg gttcccggcc gtggtgctgc gcgtggcgcc 74400
ggggcgaatg atggcggcgc ctctcggcgt ggggcccatg ccgcgcggcg ccttcctgca 74460
aaacacgggc ccctttgacc tctgcaacgg ggacgcggta tgcctgctgc cgccgctgct 74520
ggggcccggc gaccggctcg cgctggcctc ggcgggcgcg gagctgctgt ttcccatgac 74580
ggtgccgctg ccgcaggcgc gcgagctggt ggcgcgcgtg gtggcgcgcg cggtagaggc 74640
gctgggggac cgcgcggccg ccgcgcgccc gcgggccgcc gacgtaatgt accacaacgg 74700
gcgccgctac caggtgacgc cggacgtgct gtgccgcgag ggcgcggacg cggccgcgcg 74760
caccctcgtg ctgaacatgg tcttcaacgt caacgagggg agcttgctgc tgctgtcgct 74820
gatccccaac ctgctgacgc agggcctgca ggacggcgtg gccaacgcca tcgtgcagct 74880
gggcagcgcc tcgcgcgagg cggggcagct gctgcgcctg gagccggccg agccgcggca 74940
ggacggcggc cggcgctttt gcctgtacgg ggcgctggcg gcctggatta gctcggcgac 75000
ccggctggga gacgcggtcg gcgcgcgccc cctggcgaag gtgtgcacgt tcgacgggcc 75060
ctcggtagtg cgtgtgggcg aaaaggcgcc catcgtggtg ccgctttagg ggcggctgtg 75120
gtggcggctc ccctccccc tcaccggtgt taatacgcac gacaataaat gagctgacac 75180
acgctcgcac atacacagtt tgtttgccgt ttatttgttt attggggaca gcgacggggc 75240
ggggcgccag gctcagtccg ccggcgggcg gggggccagc gggcagaagg cgccgtcggt 75300
gggcgggagg ctgcccacga acacggccat cactagcgcc accattagat cgtcggcggc 75360
gccccggcgc ttgcccgaga aggcccgggc cccgccgggg ccggcggtgc tctcggttag 75420
gttttgcagt tgctcaaaga ggtactccac ggggtctgtc tgcaggcgca cggtcagcga 75480
ggccaggtcc tgggaggcaa ccacgcgccc ggagttgaat aagcggatga agtggtcaaa 75540
ggcggccgtc ttctgcttct gcagcaaaaa aaaggggtag gccaccgcgc tcccgggcgg 75600
gcggcagtgg taaaagcgcg tctcggcggg catgggcacg gcaccggacg cggccagcga 75660
gtcgagctcg cgccggacgc cgagcgcgat cgcgaccgcg gagtcctggc tgctgttgcc 75720
ctcgacggcg acaaagaggc cgtcgaggcg gcgccggtgc acggccatga cctgcgcgaa 75780
gcagcgcacg gcgcaccgcg cgatctcggc ggccgagctg cccgtgagcg ccggcaaaaa 75840
aaagtgctcc aggcccagca ccagccagct gccgcgatgc cgccccacga cggcgatgcc 75900
ggagccggag gcgcgggcgt tgctcgtgaa ggccgggtcg atgtacatgt agagccgctc 75960
gggccacggg ccgcgggccg ccgccgtgga tggccgatag agcagaaact gctcgcccgc 76020
cgcgcgggtg aacacggccg cgggctcggc gcggcgcgcg acctcgccgc cgccaatgat 76080
ctcctgcatg aacgagttgg gcaggaaggt ctcggcggtg ttgcgcgcgg cggcgtccat 76140
ggtgatgaag acgggcttgt tgaggacgta acacgagcac gcggtggcgc cgccgtgcgc 76200
cgccacacgc ggcgtgtgct cgttgcatat atacgtcacc acgttgagca gcccgtcaga 76260
ggcgcccttg aggttgtaga ggaagctcgt gctggccttg ccggtgttgg tcgaggagac 76320
gaagattatc ttgcagctgg cctggttcag gaacccgact atcgtctgga cggcctcggg 76380
gcggataaag ttggcctcgt ccacgaagag gaggttgaag tcttgcccgc ggatgccctg 76440

-continued cgagacgcaa ataatagaaa aagaggcgtg agcagcgcgc gtgccgacct cgtcccgacc 76500
cgacgccatg gaggcgcacc tcgccaacga gactaagcac tgcctggcgc gcggacgcag 76560
cgccgcgggc accgtcgtcc acctaatcat atcgagcgac tgcctacggg ccgccggggc 76620
ggaccccggt cgcctcttca cggcctcggg gggggcgccg ggggccgcgg cgggggcacc 76680
ccgcggcggg agcgcgcgcg cggacttttc cgccgcggca cagacgcgct tccacggcag 76740
cggcgcctgc agcgcctggg agcccgtgtt cgcggcctac gtccccgcgg gcgcgctggc 76800
cagcgtgtta ctgcccacgc agccggcggc ccggcccccg atcttcgccg ccgctggcgg 76860
cggcgaagac cgcggcggcc tcttcgtgtc cctgcccgtc gccctgcccg agggcgggga 76920
gggcgccttt ttcgacccgt tcacgcgcgc ggcgctgcgg ctggaaatgg ccgacggcga 76980
gctcgtcgac ttgctcttcg cctacgaaga gctgctgccc gccggcaccc gctacgaggc 77040
cgacgtcccg cgcctggccg ccctctgctg gcagtttgtg cactatacgc ggcgccatgc 77100
cggcctgccg gccgccgccg tcgccgcggc cgagcacatg gaggcctgcc tgacggaggg 77160
cggtcgcgcg ccgccgctgc cgcccggcgg gcagatccgc ccggagcgcc tgctggccga 77220
aggcggcttt gacgaccccg ccgcggtcgc ccgcctcgag gacagcgacc aggaggtcct 77280
ggcgctcatc cgccgcgccg cagaagtagt agcggcgcgg cacccgctgc ggcgcgcgcg 77340
cgcgccaatc ggcggcccgc gcgcggtagc ggcggggctg cttcaaggcg cgcgcgcgac 77400
cgccgccgcc tgcgccgcca ccgcgccggt cctgcctccc gacgccgcga ccgcgctgct 77460
gcccgcgacg gagccgcggg ccgccgggcc cggacttggc gcggtcgcgc gggcgctggc 77520
gggcgacacc ctcgtggcga cggcggcgac ccgacaggcc cgcacactga ccgagtggtt 77580
cgacgcgggg cactgcgcgc tgctgggcgg cgacacgccg tgcgacgcgt ggcgccggcg 77640
cccgctctcg ctcgtggccc ggcggcacta cgagacgggc gagggcttcg tcgtcgtggc 77700
gtacgagcag tcggcgggct ggggcgggcg ccgggcgccc ggcccggccc gccggcccga 77760
gtcggtggcc ggggagctcg cgcgtgcctg cgagcgcgag ggcgtggcgc accctcgtgc 77820
gctttccgcg gccgcgcggg ccgagctcgc acggcggcac ccgtttctgg cggcgccgct 77880
gggcgaggac ggcgcgccgc ccgtggaggc cttcgacgcg ggcgccgagg tactgctggc 77940
cgagcgcttc aaggcggcgt gcgcgcgcgc gctggtgcgc gcgcttgcgc gcgcgtgcga 78000
ggcccgcccg gacctacccc agcggttcca ctacgacgtg cgggaggccc agcgcggatg 78060
tctggaggac gtggcgcggc gcgtgccggc ctttttgcgc gcactggcca gcgcgctggg 78120
ggcgctctcg gcccgggagt ttttgaacag cgcgctctgc gcggcggcgg tggcgcacct 78180
ctcggcgacg agccccggcg gccggggcgt cctgccgtat catcgcgcgt gcttttcgct 78240
gctggcgggc ggcgagcgcg ccctgctgtt tgattacttc agctttggcg gggaggtcat 78300
aaaggtctcg cgctcgcccc tcgcggccac gacggcgcag gagtccgggc ggcggccggg 78360
ctcgatccgc ctcttggacg cgggcgccaa aagcgggcgc gcgccggcct gcggctcata 78420
cgcacccggc gagtcgtacg cgtacgcgtg cgtaggcttc tcgcggcggc tgcggtgcac 78480
cgtcgtgttc ccgggcgggt tcgccctgga ggccgacgtc gccgcgcacc tggactggcc 78540
tgcgcgcctc tgcgaggcgg tgctcgggcg gctgggccgc cccctccccg cgcccccagg 78600
cgcgccggcc ccgtgagcgc gacgaacggc gggcgggcaa gcgcggcgca tggccgagga 78660
ccccgccgct gcgggcgcgc tgctggcgcg cgcgctgacg gaggagctgg gctgcctgca 78720
cctcgtgcgc agcgactcgc gcgtaaagat ttacgtggcg gtggccacgc tcggccggct 78780
gctcgcgcgg ctggtgtcgc cggaagacgc gagtcccggc gctgccgttc gcgtcaccct 78840

```
ctacatcacg cggccgcgct ccctggagct gccgccgcgg cacttccacg tcctggtgct  78900
ttttggcggc gcggtcgcgc gcgcctgcgt cgccggcgtg cgcacgcggg cgctggtgcc  78960
gggcagcacg cgagtgcggg cggtcttccg cgacgcggtg gctgtccccg cgccggccga  79020
cctccccgac ccgagcgccg aggtcgtgcc gcccgcgccc gcggagcatg tggacccctt  79080
cgcctttacg gccttcgcgc gcccgccgcg cgacgccgca gactgcttcc agctggcgcc  79140
gggcgtgtgg tggtcgtacg cagaccggcg cctctacctc gtgcagatgg acgaagccct  79200
gctggccctg tgccccgcag gctggcgctc gcgcagcctc gggggcgtgc tcgggcggct  79260
gctgagccac ccggagggct gcgcggcgtg caccgccaaa tggcacatcg acgcgcttaa  79320
cgcggcgccg gagccgggcg cgtgcgacgt gtgcccgtgc gccgcgccgt gcctgtggaa  79380
gaaggcccgc cgccaggacg tgcccgtcgc gggggactcg agcctgtttc gagtgctttt  79440
tacggacgcg gtcgcgcggg tgcgcattct gggctcgcga cgccggccgc ggatcacggg  79500
cgcgctcccc gagctgctag ccggcgtcgg gccgcgcggc gaagccgtgc cggtgaacgg  79560
cgccggctgg cagctgcgcg tcatggacga cgacgtcacg cgactgctcg cgagcagctg  79620
ccgcgcgatg cgaagcgtgt gcggcagcgc gcggctcgcc gtggggctga gcgcgtacta  79680
ggaccgccgt gcccgctctg tcgccccctc gcgccgtttg cacgcacccc ctttttttcc  79740
aaaataccaa gataccaata aacaacacac ttgttagcct atttcgcgcg tgcgcgtttt  79800
ctgtgtactt acgtttgtgt tgtggctgga tgcaaacacg atcgtgctgc gggcgccgtc  79860
cgggaacgaa aaggagatca cttccccctt gacgtggtct acgcgctcgc cgccgaacca  79920
ctgccggagc cgcgccacga tctcctcgaa tacgggctcg gtggctttgc ggatgtgcgc  79980
cgtgtatccg attttgatgc ccttgaacgt ggcgagcgcc agcgcgatca gcggcaccag  80040
aaaccaggtc ttgccgtgcc gccgtggtac caggaacacc gtggcccgct gccggaagtg  80100
ggcgaccgcg gcgtctgaga agtccggcgt gttgaaggcc acgcgcaaaa aggcgccaat  80160
gcgctcggcg tggtccccca acagcgtcgc cgccacgaag tacgtcgcgt gcatcagaat  80220
catcttttgg aaaagctcca gcgcgccccg cgtctggccg ctggggggct ctacgcgcgc  80280
gcgtttggcg cgggggggt cggcgtcatc gccgccgccg aggtgcgaga acgacgtgcc  80340
caccagccgg ctgaaccgcg cgacgaacgc ggccacctgc gcaaacgcgc ccgacgcgcg  80400
catggactcc agcgccgcca tgacgctgtg gtacgcgttg cagtgcgccg ccgcctctgc  80460
gggcgggtgc gccacgaagc gcagggcgct caagaccccc gcgagctccc gggaaacgtg  80520
cgcctcgccg gtgccggtat ttaacccggc ttcggcgcgc gccatgctcg tcagtagcag  80580
gcgagaggcc gtggcggcaa acagcggcgc cagctcgcag tacccgtgca gcgtgcccac  80640
gcctgggacg accgtctggt ggcgcttggg ggccgcaacg gcaaagtcga ggaaggggac  80700
ccgcgcgtcg tcctccccgc gggcgccgcc gccgccgtcg ggccgcgctc cccgttccgc  80760
agcgcggcgc tgccgctcgc gcaacagccg ctgaaagtag cgggcggatt gctcgcccac  80820
ggcgcccccg aacatcgctc gcgcgcgtca cgggcgcgac tgcgtcttcc ccgcccccgc  80880
ccccgccgcg gttgccgatg gcgacggcgg cgctcgcggg agacccggcg ccggggagcc  80940
gaacggctgc gcgccggcgg cggctgcggc tggaagaagc acaccggagg gaggcgatct  81000
tcaagtcgcg cgtcgtggac ttggtccgcg ccggcgcgga ccgggacgac ccggccttta  81060
tacacgcctt tacggcggcg aaggccgcgc gccgcgactt gggggggcag atccgggcgg  81120
cggcgcgcgt cgaggccgtc cggcagcacg cccgcgacat agagacacgc gtggccgccc  81180
```

```
aagcggccgt ggccgccgtg ctggccgaaa atcgccgctt tttgcgcggc gactttctgc  81240
gcgcgtttga cgacgcggag gacgcgctgc tggaccagga ggagcgcatg ggcgacgccg  81300
ccgcggactg cgggggcgac gtgggcgtgg gcggggcctg gctggacggg gacgacgaaa  81360
gcctgctcgc ccagtggctg ctccagagcg cgccgcgcgt cggaccggac gtgttaagcg  81420
acgactggcc cgccgcgccg ctcggagggc tcgcggcggc gccagccggc gcgcgcgtag  81480
atgcaggctc ggcggcagcg gcggcgggcc aggctgggcc tgccgctgct ttccgggaga  81540
gacggccgcc ccacagcacc ccctgacccc ccgcgccggc tcttcagcgc ccccgcctcc  81600
ggcgcgccag gggcgcaga cctcctcgcg gcggctgcgg tgctgccgcc ctcgccgcct  81660
cgggccgccg gatccgcgct acgccgcgcg ccgatccgcc ccgcgagccg ccggcggcgg  81720
cgctcgcgcg cgcacatctt gcggctggcg gcagttgagc ggcccgggtg cccggtcttt  81780
gtcgcggacg cgagtctgcg catgccttcg gcggccgagc tcgccggccc cgcgcagctg  81840
cgcggggccg gcggctacgg gagcgtcgtt gtgcacgagg ccgccggcgt ggccgtaaag  81900
acctttgcga gtgccgccga cttcgagcac gagctgctcg tgacgctgct cgcgggcgag  81960
tgctcgctgc gcgcgctgcg gcacgcgcgc gccgacgcca tcatccggcc gtgcgggttc  82020
agcctgcggc gccggcagct agccctgccc gcgtatgacg cggacctggt ggcctacgcg  82080
gaggcggcgg ggcgcgccgt cctgtcgccc gccgcactgg cggcgatcga gcgcgcgttc  82140
gtcggactcg gccgcgcggt cgtgtttcta aacgcgagct gcggcctcgc gcacctggac  82200
atcaagggcg gcaacatatt cgttaacacc gcgggcgcgc tcatcacgcg ggcggtgctc  82260
ggagacttca gcttgatgac gctcaccgcg cagtcggcgc tggccgacgc ggagtttctc  82320
gtgtcgacgg acgacggcaa cagcgacggc gcgtctgacg ccgtcgccgg agggcgcctg  82380
cgtttgcgcc tgccgcccga cgcccggatg ccagaccctg aaattgttat gggccactgc  82440
gcgacgcggc cctcggagat gctcctcgac ttccttaacc ggcacggcct tcgcgggcgc  82500
cccgagccgc tgcccgcgga cctaggactg gccatcgacc tgtacgcgct cggccacgcc  82560
ttgctggagc tggtgttaac cggcgcccgc gaaacgcccg aggtccagtg tgcgcggcgc  82620
cagggcgcac tgcacatgag cgcgcgccgc gtgacctgcg ggctggtcat cggcattctg  82680
gcgcaccggt gcgcgctcct cccccttggtc ttcccggcaa ccccgcgcac ggccgcgtgc  82740
ggcgtgccgt gggacgagcc cgcggccgtg cgggcggcca tcggcaacgt ggcgatccgc  82800
gcggccttcg accgcactac cgaagcgcac cgcgcgcggt acacggagcg cgtgcgcgaa  82860
gcgctcgcgg cggcgcctgt gcgccgcgcg ctggagcttg ccgcgctctt ttgccacccg  82920
aacccgcgag cgcggcgcgc cgcgctcgtg ctgtggtcat gagtcgggcg ccgctcgcga  82980
agcgggcccg cttcgagctc gacagcgcgc gcgccgcgct ggagcgcttg ccggaagggc  83040
ttatggagag cagcatggac gagtttctgg ccgaggcggc gggcgaaggc gacggcgacg  83100
acccggtcgt ttgccgcgcg gcgtacgtcc ggcacgtgct cgcccgtgcg ggcgcgccgc  83160
agccagccgc ggcgcgcggc gcccgggggc tttttctcgc tgtcgaggcc gcgacccgcg  83220
gccaggccgc ctgcgatctg tggtggctgc tccggcggag cctggccacg gcctcgtcgg  83280
tccgctgggg cgccgccggc ccgcggccgc tagtgcgctt gggccgcggc gcggccgaag  83340
agcgcaacac ggcagccacg gccttcgggc gcgataatga gcccctggcg cgagcgctag  83400
tgcgcgcctg ctgcgtcccg cccggcgacc tcccaacgcc cgacgggctg gcggacggcg  83460
gggggcgcgc agacgagctt gggcccgtgt ttgtgtttga cgccgcggcc ggggcggcgg  83520
ccgaaagcgc ggcgggggcg ggcgcagagg cgcacacctg cggcctcctg atcgacccgc  83580
```

gcacgggggc gcttggcgcc tccatcgaca tgctggtctg cgaccgggac gcgcggggcg 83640
agctggcgcc gcatcccacc cagaccgcgt tgggggtctt tgagattaag tgccgcgcca 83700
agtacgcgtt cgaccccgac gacggcggcg cgacggcgcg cgcgtacgcc gccctgttgg 83760
cggcgcgcag cgccgcggcg ctgcgtgcct tcctgcggtc cgtgcgccgc cccggggtgg 83820
agcactgccc tcccgacggc tgccccggcg ccgcggaagc gctggcgagc tgcgccgacg 83880
cctgggcgcc gccccgcct gccggcgccg caccggcgcg gcgctgctcc gagtttgact 83940
ggcgccacct ggcgctgaac cggagcgtga cgtcgcgcgt gtggctattt aacgagcccg 84000
ccgctcactc gggcgctatt ggactcgcca cgtgggacac cggcgaggca gccctcgaag 84060
cgcccctgtt cgccaacccg cggcacgcga acttcaagca gatcctcgtg cagagctacg 84120
tcctcgcggg ccacttcccc gagcgcgccg cggcgctgca tctcgtcact ttcatcggcc 84180
ggcagcggcg cgcccgcgag cagggcccgc tcgaagtgcg cgcggggccg ggggcggaga 84240
cgtgtaccgt accgcgcgaa ggcgccgtcc ccgttctgct gatcgccacg cctgtggtgg 84300
tcgacggcga gctcgcgcgc gagtcgctag agcagccggc ccgggaagcg tttcgggcgg 84360
ccgtcaagga gtcatgggac aggcggcgtc gtgcagccga tgccgccgca accgcatctt 84420
gacgcgcgcc ggggacctcg tagccctaga cgcggccgcc tttgaggact tcagcctcga 84480
cgacctgcag gccctgacgg ccggggccgc cgcgggggag gagggcggcg aggacaaaaa 84540
aaacgccgac gacgactggt ccgacgtcat caccagcgcc ccccggcgcg ggcagcgccc 84600
ccccgtaaaa ccgtaccggc cgcagcgccg cgaggtgtat tgagcggccg cggacccgcg 84660
gcagacccgc gacaataaac acacgcaaag aattacacga tttgatagca tctttatttg 84720
acgtgcgcgg ggggtgggga gcgggggggg gggcgggggt gtgaacgcgg gagtggggga 84780
cctccggtct ccttagcggt atggttggcg ggcggggcgg gcgtccgcct cgtacacggc 84840
ctcctcgtcg tcagaggcga cgccgcggtc cagcagcgcc gctgcgtcgc cttcgagcgg 84900
ggccatgccg cggctgctgc gcgctcgggc gatgtagcgc gccgcttgct gtcgcgcggc 84960
gctcacgtgg ccgtagaagg cgctgccttt gcgccggtgg tgcaggcagg cgcgcaccaa 85020
ccgcagcacg agcatggcca cggccagcag ggcgacgccg gccagcgcca gctttacgcc 85080
tagcggcagc ccgggggcct gcgtgcgcac aaccccccgc agctggtgga agtagtcgtg 85140
cgaggcgacc gcgatgcagc tagctgccac cagcgttcca aaggccggcc cgggcagcac 85200
ttgcgtgtag cgcgacagga ctagctcggt cagtaccaaa aagagcacgg cggcgaggca 85260
gaagaccgtc acgccggcga cgaccgtttg tgccagcgac agccccagcc cggcccccag 85320
cagctggccg agcatcaggg gcgcggtgcc aatgatcagc gccagcaggc cgccggccag 85380
gttgatcatc acggcgcgcc cggggcccag caggcggtgg gcgcgcgggc tcctctcgcg 85440
gagggcgtgc acggcctgcg cgtactcggc gccgggcagc ccggcggtgc aaaagagccc 85500
gacgaaggcg gcggcggcgc cagcgtgcgc gaggtaggtg gccgcggcca agaccatgat 85560
cttgtgggac agcagcagca cggccgcctg cagcgtccag gccgccagcg cgcccagcag 85620
cagcgcaccc gggggcgtgg caagcgtcgc cagcgcgttc atatgatacg ccgccgcaaa 85680
accccctgag ttttcgcggc gaatgattat agcggccgcg acgtcaaagg cggcgacggc 85740
gagcagaact acggccgtgt acgcggagaa ggccgctgtg gtcggcgtct ccaaaaacag 85800
cgccgggtgg cgcgcgccga gctcccgctg cgcccaggcg ccgccgtcgg ccgagaggtt 85860
ccgcgcattg taattaacta tggccgcgta gaagcagggg agccccgcgc ccggcgaagc 85920

-continued

```
ggcgccgatc agggtgatca gcagcagcag cgccagcgcg gcgaagacgc cgacctgagc  85980
gagccacaag cgccagtgca cggcggcagg ctgcgcggag cccgccatga cggcaacgcc  86040
gggggcagcg gccgatgcgg tgcgcgtcga gggtgcgggc gcgtgcagcg acgggggcga  86100
agaagcgcgt tatgcgtcga gcgcgtcgct ggcgcggatg ttatacggcg cggacctgag  86160
cgagcgcgtt cgccggcgcc accccgccgt ttgcgtggag caccaatcag gacgccccgt  86220
cgcgttgccg tccccgcttg cagcggacgc ccggcgcgtg accgtggtcc gcgcgccgat  86280
gggctcgggc aagacgacgg cactgctgcg ctggttgggc gaggcgctgg gggccacgga  86340
tgcgagcgtc ctcgtggtct cctgtcggcg cagctttacg cgcacgctgc acgagcggct  86400
ccgcgacgcg gggctgccgg ctttcgcgac gtactttgac gcgcggagct acgtgatgac  86460
gggcgcggcc taccggcggc tgctggtgca agtggagagc ctgcaccgag tggacgagga  86520
gctgctgggc gactacgata tactagtgtt ggacgaagtt atgtccaccc tggcccagtt  86580
gtattcgccg acgatggggc gcttgcaccg ggttgacgcg ctgctgcacc ggctgttgcg  86640
gcggtgcccg cggattgtgg cgatggacgc gacggtgaac gcgcagctcg tggatttgtt  86700
ggcggcgctg cgcggcgcgg gcagcgtgca cgtggtcatc tgcgattatg cgtcggcggg  86760
cttctcgcag cggcgctgca ccgtcgcgcg gcggctgggc gcccgcgtgc tggcggcgcg  86820
gcttaagggg gacgccgagg acggcgccga agacggcggc gcttcgttct ttacgcggct  86880
ccgggcgcgc ctcgaggcgg gccacaacgt ctgcgtcttc tcctcgacgg tgctcttctc  86940
ggagctcgcc gcgcgctttt gcctcacctt cacgccctcg gtgctggtgc tcaactccac  87000
gcggcccgcg gagggcgatg tgtcgcgctg gcgtgacgtt cgcgtgctca tctacacgac  87060
ggtcattacc gtcggcctca gctttgacca cagctacttc cacgcgatgt tcgcctacgt  87120
caagcccatg agccacggcc ccgacatggt ctcggtgtac cagtcgctcg ggcgcatccg  87180
ctcgctcgtc gacaacgagc tctgcgtgta cttcgacagc agcgccgcgc gccccgagcc  87240
cgtgttcacg cccatgctgc taaatcacgt ggtggctgag gacggcggct ggcccgcgac  87300
tttctcggag gtcaccaacc tcctctgctg cagcttccgc gcggcgtgcg cccccgcctt  87360
tcgcggcgcg cgcggactcg cgctgtttcc gcgcttcaag tacaagcacc tctttgagcg  87420
ctgcacgctg gccagcgcga gcgacagcct caacatcctc cacgcgctgc tggagaacaa  87480
ccgcgtcggg ttccaactgg aaggctgcgc agcgctcacc gccgcgggat tctgccgctt  87540
tctcgcggac gtgcgcgccg acgcggccgc ggccgcggcc gatttgcgcg cattggccgc  87600
cggcatcccg tccccggtgt cggccgaggg cctggccgag cacccggccg tggccgcctt  87660
cgcggacaag tacttgcgcg cgggcggggc cccgcccgcc gcgctcgaag agctgctgcg  87720
cgcgctcaac tgccccgcgg cgcgcgcccg cttcgtaaac ttggccgtgc tcggcggctg  87780
cttgcacgtg cccgccgccg ccgaaagcct ggaagtattc gcgggcatct accgccacta  87840
cgcctcgggc gaggtgcccg tgctcaccga ggccggcgcc gttgagacgg cggctttggc  87900
gcccgggctc gcgctggagg ccaactggcg gctgtttggg ggctgcgccc gcatggcccg  87960
ggcgctgggg ctgctgcgcc gccgcggcgg cggcgaagcc gacgacgtcg cagacgccgc  88020
ccacggcctc acggagccgg cgatcgtcga gctcgtcggg ccgccggggg ggcacgacta  88080
cgcgcagtgc ttactggaaa tcgcccgctg caacatcacg ccggcgggcg tgatggcccg  88140
cgggcctgtg gtcgctgtgg ccgcgcggct ttctgggcgg ggctttgcac aggggcgggg  88200
cgtggggctg ggcgcggccg cgcacgcggt gagcgtgttc aaagtgatat gggaagaggt  88260
gttcggggcc cggctgcaga agagcacgca aaccttcccg ggccacgcgc gcgttaagaa  88320
```

-continued cctgcgcaaa catgaaatcg tcgccctgct ggacttggct ggcatcgacc gcgccggccg 88380
cgacacgcac cgcgagttgt atcgcctgct gatgagccac aaggcgcgct tcgcgagccc 88440
caagtacagc ctgcgcctcc caaagtgggg ccggctcctt ggcttcgccg cacgcggccc 88500
ggagcccggg cccgacgcgc cccccgaagc ctcgctggaa gcggcgctcg cacgcgtccc 88560
ggctttgcac tggccttgcg ccgcgggggc ggtcgacttt tgcgcgcttt agccgcgcgg 88620
gcctgtgctc gtctgccgta gccctccccc cccccccct ctttaccgcg ccatgccggt 88680
ttcgcacagc aacggctgtg tgtgcggggt ctcgctttat tcggcgtggg ccgcgggccc 88740
cgaccgcgcg cgcgtgctgc tcgccctact ctgccgaatg gacgacggcg gctgcgacgc 88800
caagttcgcc ctcgtaaacg tgtgtgcgcg tggcgtgacc gcgctcgcgc gcggcgcgag 88860
agatgtaacg gccgcgcggc tggaggacct cgcgcgcgcc gccgccgccc cccgagcgct 88920
gccgctggca acgctcggcc acgctgcgac gtggaaggcc ctgtacgtaa gtgccctggc 88980
ggcgctgcgc gcgcagattg ggccctttcg cttttatcga gagacgcgct ttggagtaga 89040
caacgacacc gggttgctgg tgtccgccga ggagcccccc gatgccgccg acgcggcccc 89100
gcgggcggcc gtgctgcgct cggcgctacg gctggccgta gaggaagacg cggtgcgcgc 89160
ggcggcggcg gcggctcccg ccgggggcgg ctcccttgcg cgcgcgcggc tctgcgccat 89220
gcgcgacgga cacgccgacc tctccgcgcc cgggaacgtc gtcgaattcg agctgactac 89280
aaagacggcc cgcttctacc gaatctttgc cgacatcgcc cagcccccgc ggaagcgggc 89340
cgggcgcctg gcggacgtgt ttgcccaccg ggagtaccgc gtgcgcacag aaggcagcgc 89400
cgccccggtg gtcgtgcgcg cgctcgtgcc cgtcaacttt gactgcgtcg tcgccgacgc 89460
gcgcgccttt tcgccgatgg ccgccatgct tgtgtttgcg cagtggcacg cggcgctctt 89520
taccgacgga ccggcgcagg tcctcggctt tctggggccc cagctgaacc ccggcggcga 89580
agagcgcgac tactgcttct tgctggggtt tccgggcgtc ccgctagtag tctcggccgc 89640
cgacgccggc gccgtgcgcg atgacttaga cgcgcacgtt ctcacggacg ggctctggcc 89700
cgccttcggc gtgcacgtgt accacgcgct cggcccgtgg aactttttgg acggcgccgc 89760
cgtcgcaagc ctgaaccgcc gcattgcggc agcgcgcgcc gcgctgccgc cgggcggcag 89820
cgacgggtca gattggcccg cgggccgcgt gagcaccatc ttgaacagcc ccgcctgcgt 89880
gcgcgggctc tggctggcca agttcgactt ttcggccttt tttcccaccc tgtacgccca 89940
tcttgttccc gagaacgcgc gactggcgcg cgctatttgc gcgcgccgcg acgggcgccc 90000
tgggctcaag ccttcgctct tgaccttttt tggcgggctg cggcacgtgc acgcgccggc 90060
gtacgaggcc gtcatcgcgc tggcgaacgc cgtggcagcc gccgtggagc gcgcggccaa 90120
cgcgcgaaac tttgccgtgt gcacgtacgt caaggatggc ttttggggcg ccttcgggga 90180
cgcggcgccc gaggttgtgc cgcgcgaggc cgcgctcgcg gcggcgctcg cgctgcgaga 90240
cgactgccag cgcgcggcgg aagcggtgct gcgcgccgcg gggctgcacc ccgcagaagg 90300
cgccgagctg cacctgcgct tcgagggcct gttcacgcat gccgtttcgt ggtcggccaa 90360
caaatactgg ctctgggacg ccaccgcggg gggcgctgag ggtgagctct ttgtgggatt 90420
cccctgccgg actgagttcg ggcgcatggc caagcgcagc cttgcggggc tgctgcggcg 90480
cgccgtcgcc cagcccgagc gccccagcga cacggtcgcg gccgccgccg cggcctgtga 90540
cgcgctcgtt cacgcggcct ttgagcggcg cggcgacgtg cgtttttgga gcgcgaccgc 90600
gcccattgcc gactggggcg cggtgccgcg ctcggcgctt tcgggcggcg acctgctgga 90660

-continued

```
cgcggaccac ggcccccggc cgtacgtgct tgtggcgggc cacgaggcgg cgcccttccc  90720
gctaccctgg gctctctacc gctcccccgt gttgcttccg gacatcgcct gtcgcgctca  90780
catggcgcct gtgctgcagg agctggcgcg catgctgaac ggcgccctgg cggccctcgc  90840
cgcgcgcgag ggcgacgacg agccgccaat agaagagttc gagtacaacc tggccgattt  90900
cgatttttta tttgcctgag gggatggggg ggggaaagga aacatcataa taaaagatgg  90960
tagacgatgt ctcagtcgta cgacacaaac atcttgtccg gcgtcagttt gtcggggatg  91020
cgcgtccacc aatgatacac cgcgtcgcgg aacgcctgcg cggcgagggg cccgttcagc  91080
agccccgggc gcgcgttaat cacgcccggc gggcaccgct ctggcgctgg cccgccgcgc  91140
cgcgccgcgc cgccggtgtg gtagatcgcc gtaatcaccg acggggggtt gccggccgct  91200
agcagcagcc gggcgacggc gtagtggggc aacaccagct ggctgtcgaa ggggctgtag  91260
ccggccatgc acatagccgt atttagcacg cgcatggcgc ccacgtaaag caaccggctc  91320
atcttgcgcg caggcggcgg gcgcagacgc cgcagcaggc acgacagctg cacgaacagg  91380
gcggccccga cgcgcgcctc gctgcagccc tctaaaaaca tttgcacgac gcagagggca  91440
aagtcctccc gcgttttggg gcggcacaag gccagccggt acggcagcac ggcagcgggc  91500
acggtagtgg caaagaccgc atcctccatg gcggtgagca cggcgaaggc aaagccccgg  91560
aaggccggca tggcttcgca ttcggcacgg tacgcatcgc agtccacttc ttcggcgcgg  91620
ccgtcgagcg tcagtagtag cgcgcccgtg ctcggctcta cgcgcaggtg cgtaatggac  91680
gatgacgtga acgtcggcgg ccctgctggg atctcgcgga cttcgcagac gaagcgcggg  91740
agcgcgttcc acacgaggtc gtcgagcacc tgcggcgggc cacccgagcc ctcgcgcgcg  91800
tcctgcagca ggctctccag cgtcgagccc tcaaggggca cgcccagcgt aagtccgtcg  91860
tacgcctcgg ccatcctcgc ggcgctcgcg gcggcgcttc tcctcgcggc tgcggctgcg  91920
gctgcggctc ttgcttcgcc ctctctcgcg gctgcggctg cggctgcggc tgcggctccc  91980
gcttcgctct cgggcaccgc gcgacgcaag gcccagctgc agcgccctgc gcgcgtcggc  92040
cgtgaagatc gcagcgagct ccgcgaggta cgtctccagg cgcgtttttt taaacaccgc  92100
cccgcatagc tcctcctccg acctgcacgc ctcctggtgc gcgatcagga agccgaagcg  92160
ccggacgcgc agcacagaga aaaaatacgg cgccaggatc aaggagatgg agctgttcga  92220
gtacacgacc gacacctcct ggccctggtt gttagccgtc cgggcaagct tgaagcagcg  92280
gagcagttcc tgctcccaca gccgcgagag ccgctccacg tcatcggcgt acgtggggat  92340
gtaccgcgac tgaaagctgt tggcgacgta agagtccggg cccatcagcc cagatatgtc  92400
gatgacttcg tgccccaatc cgccgtccgc ggggcccgcc gacagcgacc cgggccggcc  92460
ggcggccccg cccccccgc gcgcggcgtc ggccgcgcgc tgggcggcca gcagcgcgcg  92520
ctctcgagcc gcctgcagct cgcgctcgct ggcgcggagc ttgtcggcca ggtcgcggtt  92580
ggcgcccttt agcgattcga tggttttgaa gaggttgctg acgtagcctt ccaacatccc  92640
gttaatgctg tgcaccacag acgctcggaa ggcgtcctgg atctgctgtc cgcccgcggc  92700
cgccgcgcgg cggccgcccg ccgcgccaaa tccgggctgg gaggtgtcca cgtctgagac  92760
gtcaaagagc ccggcggccg tgtcgtctag gtacgaacgc acggtctccg agatgtcgcc  92820
gatgtgccgc atgcccttca tgttgacgat gagcttgatc aaccgcgccg ccgaggagga  92880
cgcggccgcg tcctcgccct caccgagcag cttttccacg gacggcgcgc ccggcgcgct  92940
ttcgcccgca gcgccttcgg cgcgccgccc caccagcacc ttcaggggga cggtgttaag  93000
cagctggcag agcctcgcgt gctcgcgcag cgcgtggcag gccaggacct cgccgtgcag  93060
```

-continued ccgctgcatg ggcgactcga agagtacgtc gccgccgcgc cacacgggcg cccacagcac 93120
gaaacactcg ccctcttcgc cggtgacggc gtcgcgcacg gcaaattgct ttttgcgaaa 93180
attgtagaga atctcggtgc ggtcgtagtc gaggaccgtc acggcgccgg cgcatcgcag 93240
gaggtccgct gcgaaggcct cgcattccgc cagcacccgc ccggcaacgt ccaggcgccg 93300
ggccagctct ccgccaacgg cggaagcggc ccccggcgcc tggacggtgc cggcaccgcg 93360
aggccgatgc cgccgcagcg gcaccagccc caggcacacg agccagtcta cgtaccgggc 93420
gaagctggcc gggctgccgg cgccccccgc gggaaaggcg gccgcgacgc cccgaacgca 93480
ctcaacgagc gacatctgca gcgtgcgcct ccaggtatcg aacacgtgct ccgcgagccg 93540
caccacctct gcctcgccgg cggcgccgta tcgcgccgcg atgtcggcgg cgcgcaggcc 93600
gcgcgcgcgt gtgtaggcgc gccaatcccg cgccacgtcc tcgtagcgcg cggcgtttag 93660
cgttgtgctt aggatggtgg cttgcacttg ccggatcacg gtctccgtgc agcgcacggc 93720
gctgtacacg ccctggccct cggtgtagcc cagctccccc agcaggatct ccttgaagag 93780
ccgcgtgcgc ggcgtcgggt ggatccgcac ccactcgccc ggcggccccg gagcgcccgg 93840
gtcacgtgcc gagccggcca agtttaaggc gcgctcggac acgacgcgct cgcactctgc 93900
catcgcccag gtgctccggc cggcgcggcc gcggacgtct gcacgctcgg tcatggagcg 93960
cgaggccttt tcagccgagg tcttcctgaa tttcacttcc atgcacgaga tacagccaat 94020
cgtcaagcgg atccggcagc tggcggccgc gcggctgccg gcggcggccc ggccgccgct 94080
tggctggttc cgcgcggccg cggcggccga gtccccgctg gactttgcgc cgcgcgagct 94140
gccttttgcc gcgtacctta tcacggggaa cgcgggctcg ggcaaaagca cctgcatcca 94200
aaccctcagc gagacgctcg actgcgtgat cacgggcgcg acgcgcgtcg ccgcgcaaaa 94260
cgtctaccta aagctagccg ccgcctacca cagccgtcac atcaacacca tcttccaaga 94320
gtttggcttc cgcgccaacc acgtgcaggc gcagctgggc cggcaccagt acgtttgcgc 94380
ggccagcccg cccagcatcc aggacgtgca gttccgcgac ctcgtgtact actgggaggt 94440
gctgggcgac atctcgcggc ggctgctggg cgcggccgcc tcgcgcgggc agttcgaggc 94500
gctgcgcgcg gcggagctcg cggcggggcg cccgcgcggc gccgtggagc ggctcgcgcc 94560
ctgcgtccac ggctcacttc cggcgttcgc gcgtagcaac gtgattgtca tcgacgaggc 94620
cgggctgctg ggccggcaca tcctcaccgc ggtcgtttac tgctggtggc tcatcaatgc 94680
ggcgcacgat tcggcgcagt accgcgacgg ggccatgccc gtcgtggtct gcgtgggttc 94740
gcccacgcag accgactctc tcgagtccac cttcgagcac cacaagctaa agtgccgcgt 94800
gcgctccagc gagaatgtcc tcacctgcct tatcaccaac cccacgctgc gcgagtacgc 94860
cgcgatcccg cacaattgga ccattttcat taacaacaag cgctgccagg agtacgagtt 94920
cggcgagctg ctcaaaacac tcgagtacgg cctgcccgtg acggaagagc acctcgcgct 94980
cgtggacaag tttgtcgtgc cagacgcctt cattaacaac cccgcgaacc tgcagggctg 95040
gacgcggctc tactcttcgc accgcgaggt gagcgcctac atgagccgcc tccacgcgca 95100
cctcaaggtc gccgagggcc gcagccgctt tgtggtcttt acgctacccg tgtacacctt 95160
tgtcaacatc cgcaccttcg aggactaccg caccgccacg ggccagccgg ggctgggggt 95220
ggaaaaatgg ctgcaggcca actcgggccg cattaccaac tactcgcaga gccgcgacca 95280
ggacgccagt ccaccgcact gcgaagtgtg ctcggccaag ggactcgtcg tggcgcgctc 95340
ggacgtaact tacgtgctca acagccaggt gacggtcacc acgaggctca agaagctggt 95400

-continued

```
tttcggattc agcggcacct tcgccgactt tatcgccgtg ctgcgcgacg acgggttcgt  95460
cagggcgcag agcgagacct cggtggagta cgcgtatcag tttctggccg cgctgctctt  95520
tgggggcatg atcgcctttt acaacttttt gcgcacgccc ggcctggacc cgggccgcgt  95580
ggacgaagcc taccggcggc tggcgcgcgc cacgcaggaa gcgctcgggc ccgccgcgga  95640
cgacgcggtc gactggcggg ggctggcggc ggaccgcgcc gccggctctg aggccggcgc  95700
cggggacaac gacgacgacc tcgtcttcgc ggccctggac gaggggaccc tcgacttgct  95760
ctactgcaac tacgagttcc agcgccctac gtccgcccac gaaatctacg cacagtttct  95820
gctactgaag aacttgttcg ctgcgcgctt tgacgtctgt cgaaccctgt tcggggcggc  95880
cttcgcggac gcgcccttcg aggcttacgt ggacaacctt agcttcaaag gctgcgaggt  95940
gttcaccggg agcctgcgcg gcgggctggt ctccatggca ctgcagaccg acacatacac  96000
gctgatgggc tacgcccacg cgccccccctc gctgctttcg gaggagcccg gccggcgccg  96060
gctccccgac ggcgtcgcgg agctgctgtc gacgctggac gtgcccaaca tcgtggtccg  96120
cgaccagcgc ggcttcgtgt ccgtgctgca cacgaacgtc agcgagttcg tggaggcgct  96180
ggacgacaag gagctcgaga tggctgtcag cgtcgactac ggcatcagct cgaagctggc  96240
catgaccatc gcccgctccc agggcctgag cctcgacaag gtcgccgtat gcttcgcgcg  96300
cggaaacctg cggctcaacg ccgtgtacgt agccctgtcg cgcagcgtgt cgtcccgatt  96360
tctccgaatg aacctcaacc cgctgcgcga gccccacgag cgggacacga tgatcagcga  96420
gcatatatta gccgcactcc gcgacgagaa cgtccacatc gtctactaag ccccgccgcg  96480
gccgccgcca tggcgctcgc ggcccccggg cccgggacga cgacgctcat cgcgtactcc  96540
ctatacgaaa taaagatggc ccccttgtgg gccttgcccc actgcgagca ggtggtgtgt  96600
gagtgcgccg cggggggtcg ctcggtgtcg gtgggcggcg ggctggcgtg cgacgcgctg  96660
ccggcaggga cgctcgtgct ccagcacggg cccgccgcca cgctggtcgc agtcgactgc  96720
gggtccgaat actgctcgta tgccttcacg cacgccagcg gcgtgcgcaa ctcgctgagc  96780
ttgcgcgagg gctccgtgtt cgttgtcccg ttcgacgagt gggcggcaac ggaccgcgcg  96840
cgccggctgt gcagccgcgc gcgcggtctg ctggccgtgt gcctgggcgc ccggcgagac  96900
atccacgtca ccattacggt gtacggccag agcacagcgc cggcgaccgc gccgcccccc  96960
ggcgacgtcc tcgaggctat cctgcaggag tcggagattc gcgactgcga tgcccgcccc  97020
tcgggctccc gcccctgcgg cgaagaatga gaccgaggca gttaataaac tcacagttac  97080
gctttattgg aatgtgtagt atatggttac gtcttattgg aacgtgcggt aattgggggg  97140
gaaagggcgc gtcgggggcg gcggtgggcg gcggtccgcg ctggggaggg accgccgtgc  97200
tcgcgcggga ctggcggccg cgtagaggcg cgcggcccgg gcctccgcgg gcggcaggcg  97260
ctcttcgttc gcgggtacgg ccgcttccgg tccctcgggg cggcgcgccg cgcgaagact  97320
cggtgcccgg cgcacccgcc gggcagcggc gtccgggctg ctttccccga ccgcggcggc  97380
cgccgcgcgc agcttagccg cggcggcgcg gttggccgcg agaaactgcg tgtagtccgc  97440
caccgtggcc acccgggcct ccccaaagac actgccggcg cgcacgcggg ccatggctac  97500
cggtgcggtt gctcgccggg gcgcgagtcg ggaccaagcg tgttgtcgcg gtgtatatac  97560
accgggccgg cggcagaaaa ctcgtacacg tacaccggga ccgcggggcg cgtgcctccg  97620
tccgaggagc gagtgcagta ctttcgcggt ttccgcgact ggatcaccga gtggagctga  97680
tcgcgaacgc gctgcgcatg ggcacgctgg cacagcagga acatctgcag gctcttgttg  97740
ctgcgcagcc cgcgcgccgc agcgcgcgcg gcccgcgcgc taagcccgcg ggcttgcgcg  97800
```

ccggaaaaag acgacgtctt tgtgcacgct atggtgtact tggccagcgt gcgcttgagg 97860
tccttccgga tcgtgtccgt gagctggcgc cgcccgagct cgtcgataga ggagaccata 97920
aacaaggtgt caaaggccac gcagtcgggg tttgggccca gacccgccgc tgccaggccg 97980
ggcccggcca acgcaggccc gctgctgcgc tcgccgtcgt cggcgggggc agaagcggaa 98040
gcggcggcgg cggcagatac ttgccagccg ccggccgcca gcagagagag gaccggctcg 98100
acccgccgca tgaccgcacg ccggcgctgt gctcggcgcg cgcgggctgc gcgcgcctta 98160
tacaatgctc cagtcgacgc cgccccggcc gtgctgctcc aggaacgcgt tggcctcggc 98220
aaagtgcgtg cagtgaacga agggcgctcg tgacagcggc gaggggtggc tgtacgtcag 98280
cacgaggtgc cgcttcccgg ccgccccaaa ggcccgctgg gcgtgcgcgc cccagagcat 98340
gaacaccagc gggccgctct ccgcgctcag gcgggccagt accgcgtgca ccagccgccc 98400
ccagcccagg ctagagtgcg agcccggcgc cccgctccgc acggtgagcg aggtgttaag 98460
cagcagcacg ccgcggcgcg cccagtcctc taggcagccg tgcgacggcc gcggagctcc 98520
gggaaagttc ttctgcacgg cagcgtagat gttctggagg ctgggtggga ccggaacgcc 98580
gcggttcacg ctaaaagcca agccgtgggc ctgcccgcgg ctgtgatagg ggtcctggcc 98640
cagaatgaca accttgatgt cctcgggtgc cgcgtaacgc gtccacgcga agatgtccgc 98700
tttcggaggc agcacttgct cgacgcggct ccggcgctcg tattcgcgca gcgcgtgtcg 98760
cgtgtagggc atggccagct cgggttccag cacgcgccgc caggcttcgt ggacgccaaa 98820
ttcagcggcg aatgcccccc aagtaatggc acgctggtct tctagcgctg ttacgcacgc 98880
gggaagtcca ttggggcgcc ggcgcttggg cggcgcggca cccgcaagcg gggacaaaga 98940
ctttcggcgc gtttgggccg aagccggggc cgaagccggg gccgaagccg gggccgaagc 99000
cggggccgaa gccggggccg aagccggggc cgaagccggg gccggggccg gggccggggc 99060
atcgctagcg gtagatgccg tcgccagggc cgcagggacc agtcgtgtgg tatcggggcg 99120
gcaggacgca ccctcgcggc ggcggtggca gcggcgcgcg aacttcgtgc ggcaagccga 99180
aggcgctatt gaggacttgg atggccaagt ctcgatacac tggagtgtcg gcaagcaccc 99240
gccttatatc ttcagcgagc ccacgcgcca cggcgtaggg gttggcccag tacgtctcgc 99300
cggtgtcctc gtaccacagc gctgcctcgg gcggcgagca ccgcccgcgg ataaaaatgc 99360
ccgccaggcc cggggccgcc tcttcgtgct ggggcctgtc tgcgagcaat aagttgccgc 99420
ggcaccgctc agccaagatg gattctgcgc tatccgcgcg ccttgtggcg ccagccggcg 99480
ggagccacag cagcgccgcc agcagcgccc aggcgcaagc gcgcgcgacc gccggtgcca 99540
tgccgctcgt tgtcgcagcc ggcgcgggag tatatttgcg ccggcccaca tgcgatgtat 99600
atatgcacgc ccatcgccgc ccgccggggg ccgaagctaa agggtgggcg gccgggcgga 99660
tcttggcccc tgcgacccag cctagcacac actgcgtgtg tgtaggggag aagccgcagg 99720
gtacgcggta gccgcatacg ctgcgccagc gtgggagttg cgcagcgcgc cgctcggggc 99780
caagatcagc gcgatccgcg gaaattagcc tggagtttgc gccgagcccc gcgccgcgcg 99840
ctttcgtttg cgatgtaccg cagccttgcg ccggcgccgc tccaaagcgc gcacgccaag 99900
cttggcgcgg ggctgcagtc cggcggaaaa atacaagccc cggcgcgcac gccgagcata 99960
acgcgcgccg gaccccaaag gctggctttg cggcgcgcgg cgcgggccgc cgtaaagtca 100020
gcgcgatgcg caagccgctg cgcgggtgcg ttggccggcc cggcagtgag ccgccgcggc 100080
tttgggcggg gggcagcggc ctgtggtgcg gggtcggagc ggccgggggc cgcttagtgc 100140

-continued

```
tttgcgttgc ccgcccccgc ccacgcaccg ttcttatgcc agcgtttgca ccccggcgcg 100200
aacgctctac cctcctccct cgaggcaggc gcaacggacc ccgcccagtc catcccactt 100260
cgcacaatcg ccaaattttt gtccattagc taaaagtatc tccggccata atcgatgtgt 100320
ctgagagggt aataaaacac acccagacgc tcggcactta gctctcgagt gattgcctgg 100380
ctgcttgccc cgtttgcgtg gaatgaggcc aaacaagcat ttggcccctg tttgtctaga 100440
cggggctttg tgtttttccc acccctgccc ttgcccctgg ccgcctggcc ggccggctaa 100500
agtataggcc agaccaaacc ccccgcagca gctctgctcg ctggcgagac cccaaagcgc 100560
caattgtggc atatttccgg gtctgaccgc gcctgcactt gcctttggca ttaatatttc 100620
agagtttaat attacagaca gacaaaaagc cagataatta caaagtattt gtttttattg 100680
attgcgcatg cgcgacctgg gccataaaag ccccgcgcat gcgcgagcag ttactttcgg 100740
tttggggatg acagcggcga ctgcggctcg aaagttaagt atgcaggctg ggggtcgcaa 100800
atacacggcg gtgcggtgtg gtgggctgcg ggtcgcggag tgggtgggcg gggagccggc 100860
cgcggcgatt attgccgcca ggcgctgccg ccgctgcagc ggccgagcag cccggccagg 100920
ctcgggccct ggcgaccgcc tggctgcggc gccagggccg cgctgctgcg gcggggggtc 100980
cccaggaggc tttctcgcac ccaggcggcc acttccattt cggtgcgccg cctcttctgc 101040
gccgagctct cggggccggg gtccaggtcg ccccgcgcca tggcgctcgc tggccttctc 101100
tcccggccgg ggttgccatt gcggccgacc tcggcccggg cggctccggc cagggccgga 101160
gcgccggccc gccgggggtc ggcggcaggg gcgcggccgg cgggagacgg ggtcggggct 101220
cgggtggaaa tagccgcggc ggtgctggta gccgccgcgg taacagcggg gctcggcgcc 101280
gagctccgag cgacggaagg tgccgccgcg gcggcagtta ctgccgccgc ggcggcagtt 101340
actgccgccg ccgcggccgg ggtcccaatt tgcgccccg ccgaggccgg ccccggggcc 101400
gccgcggggg ccgggtcggc ggggcgggcg ggcgcgttcg ccgtcaggtc tatcactgtg 101460
gagatgggcg cgggggctgg ggccggggcc ggggccgggg tcggggcgcg gtctaactct 101520
gtccttcttc tccggcgggc ctgcacacgg ggaggcccag cctccccgag cagcctggcc 101580
cggcgctccc ctcgtccctc ctcactgccc gccccccagc ccgcggtctc tcccgccgcg 101640
actcccaagc ccgctcccct cccctcttct ctgggctcgg ggctgcatgc gcgcgcttgc 101700
gccgcggggg ctgcccgcgg cgccgccggc aatcgggggt ctcgtctccc gccgcggctc 101760
cgagagctgg ggggcgcgga aactgccgcc gcgcggccgc aagggcggcg cgctagcgac 101820
cgaggcgccg gctgcaccgc gggtgtttgt cgacctctag tgctgacata ctgtctttcc 101880
gcaggccgcc gagcccgggc cgcgccagac gccccccgcg tgcgcctcga ctcaacctcc 101940
gcgtccgtct ccggctccgt ttccgtgtcg tcaatggcgg tcaggtcgga ggtgctgagc 102000
cccgacgacg actcttctga ctccgaccaa gagtcgtcct ccgagccctc cgagtccgag 102060
tccgaggtgt cgagaaacac caccccacgg ccgccaggag gcgcagactg ctgagggatg 102120
aggtgcgagg ggcccaccgt cacgcagcgc gccgccacga acaacaggct gcgcacaaac 102180
gcgggggcgt cgtcctcgcc aatcaggggc tccatcgcgt cggccagccc gtcgtcgtcg 102240
aagccgcact cggccagcat cgccatcacg tagtccgtca tggccgcgag ctcgcgggcc 102300
gtcacggcaa aggtgcccac cagagcgccc tcgacccact ccaccacccg ccgcaggtac 102360
ggggcgcccg gcccatgctc cggcgtgttc ggcagcaagg gcaggcgcgg gccgcgcgcg 102420
acccggtcaa taaactcctg cgccgcgtcc gcgcctcgcc ccgcgcgccc cccggccg 102478
```

-continued

<210> SEQ ID NO 5
<211> LENGTH: 9740
<212> TYPE: DNA
<213> ORGANISM: Bovine herpesvirus 1
<220> FEATURE:
<221> NAME/KEY: misc_feature
<223> OTHER INFORMATION: Unique Region - Short

<400> SEQUENCE: 5
aagcttgctc gcacgcgcgc tcggcgtgag ttcgcaccag catgcagcgg cgcgcgctca 60
ctgggcgctc gctccaaacg cagcatccgc gtgtcaatca gctcaaaaca gtcctccgtg 120
tagcgctcgc ccgcgacgcg ctcgctgccc agccgaagta catatcgacg atgtggcagg 180
ggcgttcttg ccgggccagg gactttcgct ctgagctcgc gctggaaagc gtcggggagc 240
cgagtaaagt actggctcat gtttcccacg ggcagggatt gcggatccac gtcggcgttg 300
aggtagaagc ggtccgccag cggggcctcg tcctcgtagc actcgtctgg gaagttgtgc 360
ggaagcttaa cgaatgttcc gtcgtaaagc tgacgaaaga actgcagcgg tcggcgcggc 420
gcgggaacac attcaaagtg aactgcgccc ccagttcggt cgggactcgc gccgggagcg 480
ggaactttca ccagcagggg cttggacgag ggcaccaccg gaaaatagtc cggcgggagc 540
atagcataca ggccgtcttc ttgctcgtgg cggcacgcct taaagagtcg ccagccacca 600 agcccccccct cgcatccggg accggtgccg gcggtcgcgg tcgcggtcgc ctctctgctc 660
aacggcactg tgctgatcac cacgcggttg ggggtgccct ggcggtacat ggtccctcgg 720
cgcggtcaca aagcaaatga ccaaacgccg gcgctgggtg cggcctttaa aggatagcac 780
atggcgcgcg cgggggcgag cccctggggc acgggggctc gcgtttggcg gggcggggcg 840
ccgccccgcg gtctacgact tcgtagacca gccggaaaag gacaccaccg gccaccagct 900
cagggagtgt cggggtatcg tagggcggcc acgggctagc gatggccggg ccgcgccgcg 960
ggagccgcca cgccgctccc gcaaacgtac agtccagctg cgcgtaaacc aagcgcgtcg 1020
tggcggcaat gtgcgcaaaa ataggcgcgt acaaatcggc ggcgccaaaa acccacatgt 1080
ggaagggccg agccctcgcg cggcccgagt tcagcaagtt gtagccgtcg accacgctga 1140
cccactccgc cggttggcgg tggcgggcta agccggcgcc cccgggcgcg ggccaagggc 1200
gctgtgtcga caaaagccac ccgcgccgct ggcgttgacg ttgacgtcga cgtgcagccc 1260
ttcgccgttt ttactagggc gtgatcgaag acaacgaccg tcgtccccag ccggcttgcc 1320
gtcagcgccc ggctctgctc ggcaaggaaa cgccacaccc gcgcgggcac gtctgggctt 1380
gcccctggaa gggcgccgcg cctatccgca cacgtgacta tagtcaccat ggcgaccgcc 1440
acggcaacgc ttaagtacgg gccgcggcga tcgcgggcgt cgatcgcgtg cggcttggag 1500
tccggctgcc gtttctgccg caagcgcgat cccgcgacac gacccgacgt tcttgggcac 1560
ccatggagcg cgcggcggag cggctggccc ggcagcgggc gcgcggcctt tggcgctccc 1620
gctttgcctg ctgcgtcgcc gcggagccga gcggggagcc ggctcggcca gagcgttcgc 1680
ggagccgctg cggctccgcg cgctgcgctg cggcgggctc tgcggattta tacttggccg 1740
tcaacaacga gggaccggag gtcgcgccgc cggccagaac cggtccgccg gacgcggacg 1800
ggatcgaagg gggggctgcc gtcgggaacg agcagggagg ggtcgccgct ggaaacgaga 1860
gaagagctgc catcggggac gaaaaaaaaa gcgcctccgg gggcgagaat gagagcgaaa 1920
gcgagagcga aagcgagagc gaaagcggga gcgaaagcgg ggccgacgac ggcgactggg 1980
acgacgatga cgacgccggg cctgccggcg gggtcacgcg cgaagaggcc gagggcgccg 2040
cccgtgcgct aaactttcgc attatccggc ggttgacccc cggctcggag ggacgcgtgt 2100

```
ttgaggcaac ggggcctgct cccgcgcagg agcacgtggt gctcaagatc ggggcctcgg   2160
cctctacgct ggccgaggct atgctactgc gaaccttgga ccacgccaac gtggtcaagc   2220
tgaaggccgt gctcttccac ggggagctgg tgtgcgtggt gctggcgcgc taccgcgagg   2280
acctgcacac gcacctctgg agaatcaacc gcccgctggc gctccccgcg gcgctggcgg   2340
tgacgcgggc cgtgctgcgg ggcctcgcgt acctgcactc ccgccggatc gctcaccggg   2400
acgtcaaaac ggaaaacgtc ttcctcaacg gcccaggcga cgtgtgcctg ggcgactttg   2460
gcgcggcaca cgggccggtc accgagcccc gctactacgg cctggccggc accctggaga   2520
cgaactcgcc agagctgctg gcgcgcgcgc gctacgactg ccgcacggac gtgtggagcg   2580
cgggcgtcgt cgcgtacgag atgctggcat acccgcgcgc gctgttcgac agccccgcgg   2640
gcccgcaggg cgaggacgcc gaggcatcgg gcccgccgac gatcttgggc gaccgcgact   2700
gcgcccggca gctgctccgc gtgattcgcc ggctggccgt gcacgccgaa gagtttccac   2760
ccagccccac tgaccggctg acccgcaact tcaagcgcca cgcgagcacg cgccgagagc   2820
cgcacagccc gtaccgctgc ctggcggtgc tccggctgcc ctgcgacgcc gaccgcctcc   2880
tacaccagat gctgaccttt gactttcgcg cgcgccccac cgccgcggag ctgctggagc   2940
accccgtctt cggtgcggcc tcggggtagc cccgggggtt tcccgcaaaa ctgaggcata   3000
taaggcgcgg gcaccggcaa gtttggcatc cacacttcgc gctgtggaca cgagagcgaa   3060
cgcgagcgaa cgcgagcgca agcgcgagca cacgactgcg atcatgcctg ccgcccggac   3120
cggcaccttg gccgccgtcg ccctaatcct gctctgcggg gccgccgttt tggggcgccc   3180
cgcgcccgac gacctctgtt tcgccgacgt gcgccgcact ggcatggcgc cctcccgccc   3240
gctggggccc gtcctgaacc tagcggcctc ggatttgacc tcgcgggttt cggtgcgcgc   3300
ggtggacgct tcgcgcggct gcgccctggc cctcttggac atggcggaga cggtggtgcc   3360
cggcggaccg cgagccgccg acgtcgtcga cgtcggctgg gcttaccaag acggggactg   3420
catggtgcct ctggcatatc gccagtactt taactgcacg gggggcgcgc tgcccggcca   3480
aaacgtctgc gccgggctct ctgagacccg catccgcggt ggctttggaa cctccgacta   3540
cgcgctctac gggacgtcgc tagtactgcg ccccggcctg tacgaccgcg ggacctacat   3600
ctacttcctt ggatacggcc cagacgacat ctacgtgggc agcgtcacgc tcatggtggg   3660
cgccgacatc cacaaatacc cctgcgggct ggaccgaggg ctcggtgtgg ccctgcacca   3720
caagagcgga ccggcccgac ctctgacaga ggacgacgcc accggcgact gggcctgcgg   3780
ctgcttcccc gcccttgttg aggttgacgc ggtgtggggc aacgtaagcg ccgcagagct   3840
gggcctggcc gacccgatcg actacgccga cgaagggggt gaggtcgaag tgctcgagga   3900
cgaagccggg agcgccagcg gaaacctgcc gcaggacgac cccgaccccg acctcgcaga   3960
ttgccggacc gtcgggctct ttagcgaaag cgacatgttc cggaccgcca gcgggcccga   4020
atcgctgctg atcggcgccg ttgccaagga cgtcctgacg gtgcccctca atctgccgcc   4080
cggccgctct tacgaggccc tgcgaaacgc atcgctggag tgcaactccc gcccgcgcga   4140
gaccggcgac gcagcggtgg tggtgatgtc tctccaggag cccgctcgcc tcgagcgccg   4200
ccccgatgcc cgcgccaccg atccggagtt tgggctcttt ggcctgcccg atgaccccgc   4260
cgtgcggcgc ggcattctca tcggcctcgc gatcgctctg ctggtgctgc tgttttcgct   4320
ggtgatcgtg ctcgtctgcg cctgccggct cgcccgcgca gccaaggctg cgcgacgcgc   4380
ccgcgccgcc acgttcgcca agagcaaccc cgcgtacgag ccgatgctca gcgtctgatc   4440
```

-continued

```
gccggcaccc cacgccgccc cgaccccgct gtcccgcgtt tacaataaac agttattctt   4500
accaacgttg gtgcgcctgt cgcgtgtcta ttgcgagtta aaccgagtgc cccacccagg   4560
cagggcgggg gttgggccgg gccgcagccc cggctgggta tatatccccg acgggcgact   4620
agagatacac tcgccccgcg cggctgctgc gagcgggcga acatgcaagg gccgacattg   4680
gccgtgctgg gcgcgctgct cgccgttgcg gtgagcttgc ctacacccgc gccgcgggtg   4740
acggtatacg tcgacccgcc ggcgtacccg atgccgcgat acaactacac tgaacgctgg   4800
cacactaccg ggcccatacc gtcgcccttc gcagacggcc gcgagcagcc cgtcgaggtg   4860
cgctacgcga cgagcgcggc ggcgtgcgac atgctggcgc tgatcgcaga cccgcaggtg   4920
gggcgcacgc tgtgggaagc ggtacgccgg cacgcgcgcg cgtacaacgc cacggtcata   4980
tggtacaaga tcgagagcgg gtgcgcccgg ccgctgtact acatggagta caccgagtgc   5040
gagcccagga agcactttgg gtactgccgc taccgcacac ccccgttttg ggacagcttc   5100
ctggcgggct tcgcctaccc cacggacgac gagctgggac tgattatggc ggcgcccgcg   5160
cggctcgtcg agggccagta ccgacgcgcg ctgtacatcg acggcacggt cgcctataca   5220
gatttcatgg tttcgctgcc ggccggggac tgctggttct cgaaactcgg cgcggctcgc   5280
gggtacacct ttggcgcgtg cttcccggcc cgggattacg agcaaaagaa ggttctgcgc   5340
ctgacgtatc tcacgcagta ctacccgcag gaggcacaca aggccatagt cgactactgg   5400
ttcatgcgcc acgggggcgt cgttccgccg tattttgagg agtcgaaggg ctacgagccg   5460
ccgcctgccg ccgatggggg ttcccccgcg ccacccggcg acgacgaggc ccgcgaggat   5520
gaaggggaga ccgaggacgg ggcagccggg cgggagggca acggcggccc cccaggaccc   5580
gaaggcgacg gcgagagtca gacccccgaa gccaacggag gcgccgaggg cgagccgaaa   5640
cccggcccca gccccgacgc cgaccgcccc gaaggctggc cgagcctcga agccatcacg   5700
caccccccg ctacgcccgc ggcccccgac gccgtgccgg tcagcgtcgg gatcggcatt   5760
gcggctgcgg cgatcgcgtg cgtggccgcc gccgccgccg gcgcgtactt cgtctatacg   5820
cgccggcgcg gtgcgggtcc gctgcccaga aagccaaaaa agctgccggc ctttggcaac   5880
gtcaactaca gcgcgctgcc cgggtgagcg gcctaggccc tcccccgacc gcccccttg    5940
ctcctagccc cggctcctgc cgagccgcgc ggggcgggag ataaagcgcc cgcgcgtcgg   6000
cgactcaagc cattgccgcg accttgtcct ccggcgcgct cgcgatgcgg tgcctgttgc   6060
tctggatggt ggtgctggcc gcgcgagcgg cgcccgctcg cagccttgtg tatcgcggcg   6120
aggcagtcgg cctgcgcgcg gacggccccg tagcgttcgc tgtccacccg accgacgcaa   6180
cgctcgcgct gcggggccgg ctgattttcc tggaacacca gctcccggcc gggcggcgct   6240
acaacgggac cgtcgagctg ctgcgctacc acgccgcggg cgactgcttc gttatgctgc   6300
agacgaccgc gttcgcctcc tgcccgcgcg tcgcgaacga cgcctttcgc tcctgcctgc   6360
acgccgacac gcgccccgct cgcagcgagc ggcgcgcgag cgccgcggtc gaaaaccacg   6420
tgctcttctc catcgcccat ccgcgcccaa tagactcagg gctctacttt ctgcgcgtcg   6480
gcatctacgg cggcaccgcg ggcagcgagc gccgccgaga cgtctttccc ttggccgcgt   6540
ttgtacacag cttcggtgag cccggagacc cagaggccgc ggccgcgcac cccggcgccg   6600
tcgaggcagt cgcgacccgc tgcgagcggg gcctcgacgc cagctcggcg agcctctacg   6660
accgcgcgct ggcggcgttc cccgcaggcg ccgccaccac gcccggcccc accgcgagca   6720
gcgggagcgg ggccgcgacg ccggagaggg tcgacgagac gacggaagtc aaggccgcga   6780
cgagagcggg ctcggcgttt gccctcacca cgcccccggc cggcctgacc gccagccccg   6840
```

-continued

```
ccgccagccc ctcccgtgcc tttagcgcgg ccgccccggc cgccgctgcg cagccggccg   6900
gagacacgcc cgctcgcttc cggcgccaac tggcgtcgat cctagtgcct ctgtgcgtgc   6960
tggtgctgct gctgcttgcg ctctgcgccg cgacggtaaa ctgcgcgctg cgccgccgcc   7020
tgctgccgtg ctctcggcgc gtttacaagc cgcggacgtg cgcgacatgc gggagcggca   7080
cttgcgcggg gcggcccccc tgccgcggcg cggcaccgag cgccccagcc accgtcgtgg   7140
cactgggctc ccggccaaag gcgccccccc tcgccaccat cagcgaagaa taaacgccgc   7200
gcgcggcaaa cgatctcgct cgcgtgtgtc ttggtttctg cgcggcgggc ggggtgggga   7260
gcgggcaagg cggaggaaga ccgggggcag gagctgcgtg gagggcggag ccgttgagcg   7320
gcccgaccgc cgccgggttg ttaaatgggt ctcgcgcggc tcgtggttcc acaccgcgcc   7380
ggagaaccag cgcgagcttc gctgcgtgtg tcccgcgagc tgcgttccgg ggaacggcgc   7440
acgcgagagg gttcgaaaag ggcatttggc aatgcaaccc accgcgccgc cccggcggcg   7500
gttgctgccg ctgctgctgc cgcagttatt gcttttcggg ctgatggccg aggccaagcc   7560
cgcgaccgaa accccgggct cggcttcggt cgacacggtc ttcacggcgc gcgctggcgc   7620
gcccgtcttt ctcccagggc ccgcggcgcg cccggacgtg cgcgccgttc gcggctggag   7680
cgtcctcgcg ggcgcctgct cgccgcccgt gccggagccc gtctgcctcg acgaccgcga   7740
gtgcttcacc gacgtggccc tggacgcggc ctgcctgcga accgcccgcg tggccccgct   7800
ggccatcgcg gagctcgccg agcggcccga ctcaacgggc gacaaagagt ttgttctcgc   7860
cgacccgcac gtctcggcgc agctgggtcg caacgcgacc ggggtgctga tcgcggccgc   7920
agccgaggag gacggcggcg tgtacttcct gtacgaccgg ctcatcggcg acgccggcga   7980
cgaggagacg cagttggcgc tgacgctgca ggtcgcgacg gccggcgcgc agggcgccgc   8040
gcgggacgag gagagggaac cagcgaccgg gcccaccccc ggcccgccgc cccaccgcac   8100
gacgacacgc gcgcccccgc ggcggcacgg cgcgcgcttc cgcgtgctgc cgtaccactc   8160
ccacgtatac accccgggcg attcctttct gctatcggtg cgtctgcagt ctgagttttt   8220
cgacgaggct cccttctcgg ccagcatcga ctggtacttc ctgcggacgg ccggcgactg   8280
cgcgctcatc cgcatatacg agacgtgcat cttccacccc gaggcaccgg cctgcctgca   8340
ccccgccgac gcgcagtgca gcttcgcgtc gccgtaccgc tccgagaccg tgtacagccg   8400
gctgtacgag cagtgccgcc cggaccctgc cggtcgctgg ccgcacgagt gcgagggcgc   8460
cgcgtacgcg gcgcccgttg cgcacctgcg tcccgccaat aacagcgtag acctggtctt   8520
tgacgacgcg ccggctgcgg cctccgggct ttacgtcttt gtgctgcagt acaacggcca   8580
cgtggaagct tgggactaca gcctagtcgt tacttcggac cgtttggtgc gcgcggtcac   8640
cgaccacacg cgccccgagg ccgcagccgc cgacgctccc gagccaggcc caccgctcac   8700
cagcgagccg gcgggcgcgc ccaccgggcc cgcgccctgg cttgtggtgc tggtgggcgc   8760
gcttggactc gcgggactgg tgggcatcgc agccctcgcc gttcgggtgt gcgcgcgccg   8820
cgcaagccag aagcgcacct acgacatcct caacccttc gggcccgtat acaccagctt   8880
gccgaccaac gagccgctcg acgtggtggt gccagttagc gacgacgaat tttccctcga   8940
cgaagactct tttgcggatg acgacagcga cgatgacggg cccgctagca accccccctgc   9000
ggatgcctac gacctcgccg gcgccccaga gccaactagc gggtttgcgc gagcccccgc   9060
caacggcacg cgctcgagtc gctctgggtt caaagtttgg tttagggacc cgcttgaaga   9120
cgatgccgcg ccagcgcgga ccccggccgc accagattac accgtggtag cagcgcgact   9180
```

-continued

```
caagtccatc ctccgctagg cgcccccccc ccgcgcgctg tgccgtctga cggaaagcac   9240

ccgcgtgtag ggctgcatat aaatggagcg ctcacacaaa gcctcgtgcg gctgcttcga   9300

aggcatggag agtccacgca gcgtcgtcaa cgaaaactat cgaggcgctg atgaggccga   9360

tgcagcgccc ccttcaccgc cgccggaagg ctccatcgtg tccatcccca tcctcgagct   9420

caccatcgag gacgcgccgg ccagcgcaga agcaaccggc accgcggcag ccgcacccgc   9480

tgggcgcact ccagacgcga acgcagcacc cggcggctac gtgccagttc ccgcggcgga   9540

tgtggactgc tattatagcg aaagcgacag cgagacggca ggcgagtttt tgatacgcat   9600

ggggcggcag cagcggcggc ggcatcggcg gcggcgctgc atgatagcag cggccctgac   9660

ttgcattggc ctcggggcct gcgcggcggc ggcagcggca ggcgccgtcc tggcgttgga   9720

ggtagtgccc cggccctgag                                               9740
```

METHOD OF TREATING PREGNANT COWS AND/OR HEIFERS

SEQUENCE LISTING

This application contains a sequence listing in paper format and in computer readable format, the teachings and content of which are hereby incorporated by reference.

FIELD OF THE INVENTION

The present invention relates to the field of animal health and in particular to vaccines which comprise an attenuated bovine viral diarrhea virus (BVDV). More particularly, the present invention relates to the use of modified live BVDV Type 1 and BVDV Type 2 vaccines. Still more particularly, the present invention relates to the use of such vaccines in pregnant cows/heifers. Even more particularly, the vaccines will include other antigens from bovine pathogens in addition to the BVDV Type 1 and BVDV Type 2 modified live vaccines.

BACKGROUND OF THE INVENTION

Cows are susceptible to contracting a large diversity of microbial infections. A number of effective vaccines have been developed to treat or prevent infection. Vaccines that are based on modified live viruses, however, pose a risk to the health of pregnant cows and their calves. Accordingly, there is a need for safe methods of vaccinating pregnant cows.

Bovine viral diarrhea virus (BVDV) Type 1 (BVDV-1) and Type 2 (BVDV-2) cause bovine viral diarrhea (BVD) and mucosal disease (MD) in cattle, as well as cause abortions and fetal infections that may result in persistently infected calves (Baker, 1987; Moennig and Plagemann, 1992). The division of BVDV into 2 species is based on significant differences at the level of genomic sequences (summarized in Heinz et al., 2000) which are also obvious from limited cross neutralizing antibody reactions. The viral proteins of BVDV, and any other virus of the pestivirus family, are arranged in the polyprotein in the order $NH_2$—$N^{pro}$—C-$E^{rns}$-E1-E2-p7-NS2-NS3-NS4A-NS4B—NS5A-NS5B—COOH (Lindenbach and Rice, 2001).

Present BVDV vaccines for the prevention and treatment of BVDV infections still have drawbacks. Vaccines against the classical BVDV-1 provide only partial protection from BVDV-2 infection, and vaccinated dams may produce calves that are persistently infected with virulent BVDV-2. This problem is probably due to the great antigenic diversity between type 1 and type 2 strains which is most pronounced in the glycoprotein E2, the major antigen for virus neutralization. Most monoclonal antibodies against type 1 strains fail to bind to type 2 viruses.

Currently, licensed BVDV MLV vaccines are produced using attenuated viruses obtained via repeated passage in bovine or porcine cells, or using chemically modified viruses which exhibit a temperature-sensitive phenotype. A single dose of MLV vaccine is sufficient for immunization, and duration of the immunity can last for years in vaccinated cattle. However, these vaccines, although attenuated, are often associated with safety problems. Prior art has taught that the vaccine viruses may cross the placenta of pregnant animals, e.g. cows or heifers and lead to clinical manifestations in the fetus and/or the induction of persistently infected calves. Therefore, it is recommended that they not be applied or administered to breeding herds that contain pregnant cows.

Pregnant cows have to be kept separate from vaccinated cattle to protect fetuses and must not be vaccinated themselves.

Bovine Herpesvirus (BHV-1) or Infectious bovine rhinotracheitis (IBR) virus is associated with several diseases and symptoms in cattle: Infectious bovine rhinotracheitis (IBR), infectious pustular vulvovaginitis (IPV), balanoposthitis, conjunctivitis, abortion, encephalomyelitis, and mastitis. Only a single serotype of BHV-1 is recognized; however, three subtypes of BHV-1 have been described on the basis of endonuclease cleavage patterns of viral DNA. These types are referred to as BHV-1.1 (respiratory subtype), BHV-1.2 (genital subtype), and BHV-1.3 (encephalitic subtype). Recently, BHV-1.3 has been reclassified as a distinct herpesvirus designated BHV-5. BHV-1 infections are widespread in the cattle population. In feedlot cattle, the respiratory form is most common. The viral infection alone is not life-threatening but predisposes cattle to secondary bacterial pneumonia, which may result in death. In breeding cattle, abortion or genital infections are more common. Genital infections can occur in bulls (infectious pustular balanoposthitis) and cows (IPV) within 1-3 days of mating or close contact with an infected animal. Transmission can occur in the absence of visible lesions and through artificial insemination with semen from subclinically infected bulls. Cattle with latent BHV-1 infections generally show no clinical signs when the virus is reactivated, but they do serve as a source of infection for other susceptible animals and thus perpetuate the disease. The incubation period for the respiratory and genital forms is 2-6 days. In the respiratory form, clinical signs range from mild to severe, depending on the presence of secondary bacterial pneumonia. Clinical signs include pyrexia, anorexia, coughing, excessive salivation, nasal discharge that progresses from serous to mucopurulent, conjunctivitis with lacrimal discharge, inflamed nares (hence the common name "red nose"), and dyspnea if the larynx becomes occluded with purulent material. Pustules may develop on the nasal mucosa and later form diphtheritic plaques. Conjunctivitis with corneal opacity may develop as the only manifestation of BHV-1 infection. In the absence of bacterial pneumonia, recovery generally occurs 4-5 days after the onset of clinical signs. Abortions may occur concurrently with respiratory disease but can also occur up to 100 days after infection. Abortions can occur regardless of the severity of disease in the dam. Abortions generally occur during the second half of pregnancy, but early embryonic death may also occur. The first signs of genital infections in cows are frequent urination, elevation of the tailhead, and a mild vaginal discharge. The vulva is swollen, and small papules, then erosions and ulcers, are present on the mucosal surface. If secondary bacterial infections do not occur, animals recover in 10-14 days. If bacterial infection occurs, there may be inflammation of the uterus and transient infertility, with purulent vaginal discharge for several weeks. In bulls, similar lesions occur on the penis and prepuce. BHV-1 infection can be severe in young calves and cause a generalized disease. Pyrexia, ocular and nasal discharges, respiratory distress, diarrhea, incoordination, and eventually convulsions and death may occur in a short period after generalized viral infection. IBR is rarely fatal in cattle unless complicated by bacterial pneumonia. In uncomplicated IBR infections, most lesions are restricted to the upper respiratory tract and trachea. Petechial to ecchymotic hemorrhages may be found in the mucous membranes of the nasal cavity and the paranasal sinuses. Focal areas of necrosis develop in the nose, pharynx, larynx, and trachea. The lesions may coalesce to form plaques. The sinuses are often filled with a serous or serofibrinous exudate. As the disease progresses, the pharynx becomes covered with a serofibrinous exudate, and blood-tinged fluid may be found in the trachea. The pharyngeal and pulmonary lymph nodes may be acutely swollen and hemorrhagic. The tracheitis may extend into the bronchi and bronchioles; when this occurs, epithelium is sloughed in the airways. The viral lesions are often masked by secondary bacterial infections. In young animals with generalized BHV-1 infection, erosions and ulcers overlaid with debris may be found in the nose, esophagus, and forestomachs. In addition, white foci may be found in the liver, kidney, spleen, and lymph nodes. Aborted fetuses may have pale, focal, necrotic lesions in all tissues, but which are especially visible in the liver.

Parainfluenza-3 virus (PI-3) is an RNA virus classified in the paramyxovirus family. Infections caused by PI-3 are common in cattle. Although PI-3 is capable of causing disease, it is usually associated with mild to subclinical infections. The most important role of PI-3 is to serve as an initiator that can lead to the development of secondary bacterial pneumonia. Clinical signs include pyrexia, cough, serous nasal and lacrimal discharge, increased respiratory rate, and increased breath sounds. The severity of signs worsen with the onset of bacterial pneumonia. Fatalities from uncomplicated PI-3 pneumonia are rare. Lesions include cranioventral lung consolidation, bronchiolitis, and alveolitis with marked congestion and hemorrhage. Inclusion bodies may be identified. Most fatal cases will also have a concurrent bacterial bronchopneumonia.

Bovine Respiratory Syncytial Virus (BRSV) is an RNA virus classified as a pneumovirus in the paramyxovirus family. In addition to cattle, sheep and goats can also be infected by respiratory syncytial viruses. This virus was named for its characteristic cytopathic effect—the formation of syncytial cells. Antigenic subtypes are known to exist for BRSV, and preliminary evidence suggests that there may be antigenic subtypes of BRSV. BRSV is distributed worldwide, and the virus is indigenous in the cattle population. BRSV infections associated with respiratory disease occur predominantly in young beef and dairy cattle. Passively derived immunity does not appear to prevent BRSV infections but will reduce the severity of disease. Initial exposures to the virus are associated with severe respiratory disease; subsequent exposures result in mild to subclinical disease. BRSV appears to be an important virus in the bovine respiratory disease complex because of its frequency of occurrence, predilection for the lower respiratory tract, and its ability to predispose the respiratory tract to secondary bacterial infection. In outbreaks, morbidity tends to be high, and case fatality can be 0-20%. Signs include increased rectal temperature (40-42° C.), depression, decreased feed intake, increased respiratory rate, cough, and nasal and lacrimal discharge. Generally, respiratory signs predominate. Dyspnea may become pronounced in the later stages of the disease. Subcutaneous emphysema is sometimes reported. Secondary bacterial pneumonia is a frequent occurrence. A biphasic disease pattern has been described but is not consistent. Gross lesions include a diffuse interstitial pneumonia with subpleural and interstitial emphysema along with interstitial edema. These lesions are similar to and must be differentiated from other causes of interstitial pneumonia. See also atypical interstitial pneumonia. Histologic examination reveals syncytial cells in bronchiolar epithelium and lung parenchyma, intracytoplasmic inclusion bodies, proliferation and/or degeneration of bronchiolar epithelium, alveolar epithelialization, edema, and hyaline membrane formation.

Leptospirosis is a contagious disease of animals, including man, caused by various immunologically distinct leptospiral serovars, most of which are regarded as subgroups of *Leptospira interrogans*. Infections may be asymptomatic or cause various signs, including fever, icterus, hemoglobinuria, renal failure, infertility, abortion, and death. After acute infection, leptospires frequently localize in the kidneys or reproductive organs and are shed in the urine, sometimes in large numbers for months or years. Because the organisms survive in surface waters for extended periods, the disease is often waterborne. In the USA, the disease is primarily due to the serovars *Leptospira hardjo, Leptospira pomona*, and *Leptospira grippotyphosa*. However, *Leptospira canicola* and icterohaemorrhagiae serovars also have been isolated. Calves may have fever, anorexia, and dyspnea, and in *Leptospira pomona* infections, icterus, hemoglobinuria, and anemia. Body temperature may rise suddenly to 40.5-41° C. Hemoglobinuria rarely lasts longer than 48-72 hrs. Icterus clears rapidly and is followed by anemia. The RBC's begin to increase in number by 4-5 days and return to normal 7-10 days later. However, *Leptospira hardjo* infections usually do not cause hemolytic anemia, which makes diagnosis more difficult. Morbidity and mortality are higher in calves than in adult cattle. In older cattle, signs vary greatly and diagnosis is more difficult. Enzootic *Leptospira hardjo* infections, which usually result in abnormal milk, are more obvious in dairy than in beef cattle. Signs usually are restricted to lowered milk and calf production; a hemolytic crisis does not occur. The milk is thick, yellow, and blood-tinged; it may contain clots, although there is little evidence of mammary inflammation. Milk production returns to normal in 10-14 days, even in the absence of treatment. Abortion and stillbirths, which are common in *Leptospira pomona* infections and sporadic in *Leptospira hardjo* infections, generally occur 3-10 weeks after initial infection. The abortions are more common during the third trimester. An abortion storm in a breeding herd is often the first indication that leptospirosis exists, because the mild initial signs often pass unnoticed. In endemically infected herds, abortions occur mostly in younger animals and are sporadic, rather than being manifested as abortion storms. Calves reared by previously infected cows are protected by colostral antibodies for up to 6 mos. The calves generally have an antibody titer similar to that of their dams. In the acute form, anemia, icterus, hemoglobinuria, and submucosal hemorrhages are prominent. The kidneys are swollen, with multifocal petechial and ecchymotic hemorrhages that become pale with time. The liver may be swollen, with minute areas of focal necrosis. Petechiae in other organs are seen in fulminating cases; however, in the more prevalent *Leptospira hardjo* infections, the lesions are primarily restricted to the kidneys.

*Haemophilus somnus* is being increasingly recognized as an important pathogen in BRD; these bacteria are normal inhabitants of the nasopharynx of cattle. *H. somnus* infection of the lungs results in purulent bronchopneumonia that may be followed by septicemia and infection of multiple organs. Occasionally, *H. somnus* is associated with extensive pleuritis. *H. somnus* can cause an acute, usually fatal, septicemic disease that can involve the nervous, musculoskeletal, circulatory, and respiratory systems, either singly or together. The reproductive system is often affected but usually without the other systems being clinically involved. The disease may be characterized by fever, severe depression, ataxia, weakness, blindness, coma, and death within several hours to several days. It occurs sporadically in individual beef and dairy cattle and is found nearly worldwide. *H. somnus* is a gram-negative, nonmotile, nonsporeforming, pleomorphic coccobacillus that requires an enriched medium and a microaerophilic atmosphere for culture.

DESCRIPTION OF THE INVENTION

One aspect of the present invention provides a method for safely vaccinating a pregnant cow, wherein the method generally includes or comprises the step of administering a vaccine to the pregnant cow or pregnant heifer. The vaccine preferably includes an immunological active component effective for treating or prophylaxis of an infection caused by a microbe selected from the group consisting of: Infectious Bovine Rhinotracheitis (IBR), Bovine Viral Diarrhea Virus (BVDV) Type 1, BVDV Type 2, Parainfluenza-3 Virus (PI-3), Bovine Respiratory Syncytial Virus (BRSV), and combinations thereof. The pregnant cow or heifer can be in the first, second, or third trimester of pregnancy when the vaccine is administered. In preferred forms of this vaccine, the immunological active components effective for treating or prophylaxis of infection caused by BVDV Type 1 and/or BVDV Type 2 is a modified live BVDV. In other preferred forms, the immunological active component effective for treating or prophylaxis of infection caused by IBR is a modified live IBR. Preferred vaccine compositions will include both BVDV Type 1 and BVDV Type 2 immunological active components, even more preferably both the BVDV Type 1 and BVDV Type 2 immunological active components will be modified live BVDV, still more preferably, preferred vaccine compositions will further include IBR immunological active components, preferably modified live IBR. In even further preferred vaccine compositions, PI-3 immunological active components will be included. In still further preferred vaccine compositions, BRSV immunological active components will be included. Representative vaccines that can be used in a method according to the invention including modified live BVDV Type I, modified live BVDV Type II, modified live IBR, PI-3, and BRSV that are sold under the names BREED-BACK™ FP5, EXPRESS™ FP5, and EXPRESS™ 5 (Boehringer Ingelheim Vetmedica, Inc., St. Joseph, Mo.).

According to a further aspect the present invention relates to the vaccination of pregnant cows/heifers comprising the step of administering to a pregnant cow/heifer a modified live BVDV Type 1, preferably a cytopathic modified lived BVDV Type 1, which is derived from the Singer strain, a modified live BVDV Type 2, preferably a cytopathic modified live BVDV Type 2, which is derived from the 296 strain, and/or a modified live IBR which is derived from the IBR Colorado 1 Strain. Preferably the modified live BVDV Type 1 Singer strain is the one that is included in the BREED-BACK™ FP5 vaccine. Preferably the modified live BVDV Type 2 296 strain is the one that is included in the BREED-BACK™ FP5 vaccine. Preferably the modified live IBR strain is the one that is included in the BREED-BACK™ FP5 vaccine. Preferably the vaccine is administered to prevent, or reduce the incidence of or severity of an infection in the pregnant cow and preferably its fetus with or at least the clinical signs caused by BVDV Type 1, BVDV Type 2, and/or IBR (each depending from the antigen/antigen combination that is/are used—modified live BVDV Type I, modified live BVDV Type 2, modified live IBR or any combination thereof).

In other aspect the present invention also relates to a method for vaccinating pregnant cows/heifers comprising the step of administering to said pregnant cow/heifer a vaccine which comprises a vaccine composition and/or immunological active components of *Haemophilus somnus*, preferably in a bacterin form, in addition to the modified live BVDV Type 1, modified live BVDV Type 2, and/or modified live IBR, described above. Preferably said vaccine further comprises PI-3 and BRSV immunological active components. Representative vaccines including modified live BVDV Type 1, modified live BVDV Type 2, modified live IBR, PI-3, BRSV, and *Haemophilus somnus* bacterin that can be used for the vaccination of pregnant cows as described herein are sold under the names BREED-BACK™ FP5-HS and EXPRESS™ 5-HS (Boehringer Ingelheim Vetmedica, Inc., St. Joseph, Mo.).

According to a further aspect, the vaccine composition that can be used for the vaccination of pregnant cows/heifers as described herein further comprises a vaccine composition or immunological active component effective for treating or preventing an infection caused by a *Leptospira* bacterium. In preferred forms of such vaccine composition, the immunological active component will be a *Leptospira* bacterin. Still more preferably, the bacterin will be derived from a *Leptospira* bacterium selected from the group consisting of: *Leptospira canicola, Leptospira grippotyphosa, Leptospira hardjo, Leptospira icterohaemorrhagiae, Leptospira Pomona*, and combinations thereof. Some preferred vaccine compositions will include *Leptospira* bacterin derived from *Leptospira canicola, Leptospira grippotyphosa, Leptospira hardjo, Leptospira icterohaemorrhagiae*, and *Leptospira pomona*. Representative vaccines including modified live BVDV Type 1, modified live BVDV Type 2, modified live IBR, PI-3, BRSV, *Haemophilus somnus* bacterin, and *Leptospira* bacterin derived from *Leptospira canicola, Leptospira grippotyphosa, Leptospira hardjo, Leptospira icterohaemorrhagiae*, and *Leptospira pomona* that can be used for the vaccination of pregnant cows/heifers as described herein are sold under the names BREED-BACK™ FP10-HS and EXPRESS 10-HS® (Boehringer Ingelheim Vetmedica, Inc., St. Joseph, Mo.). Representative vaccines including modified live BVDV Type 1, modified live BVDV Type 2, modified live IBR, PI-3, BRSV, and *Leptospira* bacterin derived from *Leptospira canicola, Leptospira grippotyphosa, Leptospira hardjo, Leptospira icterohaemorrhagiae*, and *Leptospira pomona* that can be used for the vaccination of pregnant cows/heifers as described herein are sold under the names BREED-BACK™ FP 10 and EXPRESS™ 10 (Boehringer Ingelheim Vetmedica, Inc., St. Joseph, Mo.).

According to a further aspect, the vaccine composition that can be used for the vaccination of pregnant cows/heifers as described herein further comprises at least one further immunological active component which can prevent the pregnant cow/heifer from microbiological infections of other cattle relevant pathogens or at least from the clinical signs caused by said other cattle relevant pathogens. A list of those pathogens and vaccine compositions which are also suitable to be used according to the present invention are disclosed in the international patent application published as WO 2007-117303, the entire teachings and content of which is incorporated herein by reference.

For all of the vaccine compositions described above and that can be used for the vaccination of pregnant cows/heifers as described herein, the modified live viruses used therein are preferably attenuated. A particularly preferred modified live BVDV Type 1 is derived from a Singer strain of BVDV. Even more preferably, the Singer strain of BVDV has been passaged at least two times in bovine turbinate cells. Most preferably the modified BVDV Singer strain is the one that is included in the BREED-BACK™ FP5 vaccine. A particularly preferred modified live BVD Type 2 is derived from BVDV Strain 296. Even more preferably, the BVDV Strain 296 has been passaged in bovine testicular cells or MDBK cells, or embryonic swine kidney cells (ESK cells). In particularly preferred forms, the BVDV Strain 296 has been passaged in bovine testicular cells at least six times and in MDBK and ESK cells at least 23 times. Most preferably the modified BVDV 296 strain is the one that is included in the BREED-BACK™ FP5 vaccine.

A particularly preferred modified live IBR strain is derived from the IBR Colorado 1 strain. Even more preferably, the IBR Colorado 1 Strain 1 has been passaged 4 times in bovine embryo kidney cells, 22 times in ovine cells and once in MDBK cells. Most preferably the modified IBR strain is the one that is included in the BREED-BACK™ FP5 vaccine. In other preferred forms of practicing the invention, in addition to the administration of any vaccine composition described above to a pregnant cow or heifer, the vaccine composition is also administered to the cow prior to the pregnancy. Preferably, such administration is performed within 12 months of the pregnancy, still more preferably within 10 months, even more preferably within 8 months, still more preferably within 7 months, even more preferably within 6 months, still more preferably within 5 months, even more preferably within 4 months, still more preferably within 3 months, even more preferably within 2 months, and most preferably between about 1 and two months prior to pregnancy.

In some preferred forms of any of the vaccine compositions described above, the composition will include at least one additional component selected from the group consisting of pharmaceutical acceptable carriers, adjuvants, diluents, preservatives, antibiotics, and combinations thereof.

“Adjuvants” as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). JohnWiley and Sons, NY, pp 51-94 (1995) and Todd et al., Vaccine 15:564-570 (1997).

For example, it is possible to use the SPT emulsion described on page 147 of “Vaccine Design, The Subunit and Adjuvant Approach” edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol (BF Goodrich, Ohio, USA) are particularly appropriate for compositions containing such adjuvants. They are cross-linked with an allyl sucrose or with allyl pentaerythritol. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide among many others.

Additionally, the composition can include one or more pharmaceutical-acceptable carriers. As used herein, “a pharmaceutical-acceptable carrier” includes any and all solvents, dispersion media, coatings, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin and alkalisalts of ethylendiamintetracetic acid, among others.

A “protectant” or “preservative” as used herein, refers to an anti-microbiological active agent, such as for example Neomycin, Amphoteracin B, Gentamycin, Merthiolate, and the like. Of these, Neomycin and/or Amphoteracin B are particularly preferred In particular adding a protectant is most preferred for the preparation of a multi-dose composition. Those anti-microbiological active agents are added in concentrations effective to prevent the composition of interest from any microbiological contamination or for inhibition of any microbiological growth within the composition of interest.

Moreover, this method can also comprise the addition of any stabilizing agent, such as for example saccharides, trehalose, mannitol, saccharose and the like, to increase and/or maintain product shelf-life.

In preferred forms, administration of any vaccine composition noted above will be safe for the animal receiving the composition both before and during pregnancy. “Safe” as used herein, shall refer to a comparison in animals receiving the composition with animals not receiving the composition wherein the abortion rates of the vaccinated pregnant cows/heifers are less than 10% higher, more preferably less than 5% higher, still more preferably less than 4% higher, even more preferably less than 3% higher, still more preferably less than 2% higher, even more preferably less than 1% higher, and most preferably no higher than unvaccinated cows/heifers. Additionally, administration of any vaccine composition noted above to a pregnant cow/heifer will not cause fetal infection by any pathogen having an immunological active component in the vaccine in more than 10%, more preferably 5%, still more preferably 4%, even more preferably 3%, still more preferably 2%, even more preferably 1% and most preferably no higher than unvaccinated cows/heifers.

Thus according a further aspect the present invention also relates to method for the treatment or prophylaxis of a pregnant cow/heifer and its fetus against infections, or at least the clinical signs, caused by caused by BVDV comprising the step administering to said pregnant cow/heifer a vaccine comprising modified live bovine viral diarrhea virus as described above. Preferably the live bovine viral diarrhea virus is a modified live BVDV Type 1 strain derived from the Singer strain and/or a modified live BVDV Type 2 derived from the 296 strain. Preferably the modified live BVDV Type 1 Singer strain is the one that is included in the BREED-BACK™ FP5 vaccine. Preferably the modified live BVDV Type 2 296 strain is the one that is included in the BREED-BACK™ FP5 vaccine. Repesentative vaccines are also sold under the names BREED-BACK™ FP5-HS, EXPRESS™ 5-HS, BREED-BACK™ FP10-HS and EXPRESS 10-HS®.

According a further aspect, the present invention also relates to a method for the treatment or prophylaxis of pregnant cow/heifer and its fetus against infections, or at least the clinical signs, caused by IBR comprising the step administering to said pregnant cow/heifer a vaccine comprising modified live IBR as described above. Preferably the modified IBR strain is the one that is included in the BREED-BACK™ FP5 vaccine. Repesentative vaccines are also sold under the names BREED-BACK™ FP5-HS, EXPRESS™ 5-HS, BREED-BACK™ FP10-HS and EXPRESS 10-HS®.

Thus according to a further aspect, the present invention also relates to method for the treatment or prophylaxis of a pregnant cow/heifer and its fetus against infections, or at least the clinical signs, caused by BVDV and IBR comprising the step administering to said pregnant cow/heifer a vaccine comprising modified live bovine viral diarrhea virus and modified live IBR as described above. Preferably the live bovine viral diarrhea virus is a modified live BVDV Type 1 strain derived from the Singer strain and/or a modified live BVDV Type 2 derived from the 296 strain. Preferably the modified live BVDV Type 1 Singer strain is the one that is included in the BREED-BACK™ FP5 vaccine. Preferably the modified live BVDV Type 2 296 strain is the one that is included in the BREED-BACK™ FP5 vaccine. Preferably the modified IBR strain is the one that is included in the BREED-BACK™ FP5 vaccine. Repesentative vaccines are also sold under the names BREED-BACK™ FP5-HS, EXPRESS™ FP5, EXPRESS™ 5-HS, BREED-BACK™ FP10-HS and EXPRESS 10-HS®.

In preferred methods of the present invention, pregnant cows/heifers receiving an administration of any of the vaccine compositions described above will experience "treatment or prophylaxis" in the form of a decrease or reduction in the incidence of or severity of clinical, pathological, and histopathological signs of infection from any of the pathogens having an immunological active component included in the administered vaccine. "Decrease" or "reduction in the incidence of or severity of clinical, pathological, and/or histopathological signs" shall mean that clinical signs are reduced in incidence or severity in animals receiving an administration of the vaccine in comparison with a "control group" of animals when both have been infected with or challenged by the pathogen from which the immunological active component(s) in the vaccine are derived and wherein the control group has not received an administration of the vaccine. In this context, the term "decrease" or "reduction" means a reduction of at least 10%, preferably 25%, even more preferably 50%, most preferably of more than 100% in the vaccinated group as compared to the control group as defined above.

"Clinical signs" shall refer to signs of infection from a pathogen that are directly observable from a live animal such as symptoms. Representative examples will depend on the pathogen selected but can include things such as nasal discharge, lethargy, coughing, elevated fever, weight gain or loss, dehydration, diarrhea, swelling, lameness, and the like.

"Pathological" signs shall refer to signs of infection that are observable at the microscopic or molecular level, through biochemical testing, or with the naked eye upon necropsy.

"Histopathological" signs shall refer to signs of tissue changes resulting from infection.

Administration of any of the vaccine compositions described herein can occur in any conventional manner or fashion known in the art with intramuscularly and subcutaneously being particularly preferred, and with subcutaneous administration being the most preferred.

In another aspect of the present invention, a method of treatment or prophylaxis of pregnant cows or heifers of clinical signs or symptoms of infection caused by bovine viral diarrhea virus is provided. Generally, the method comprises the step of administering an immunogenic composition to a pregnant cow/heifer, wherein the immunogenic composition comprises a modified live bovine viral diarrhea virus. Preferably the live bovine viral diarrhea virus is a modified live BVDV Type 1 strain derived from the Singer strain and/or a modified live BVDV Type 2 derived from the 296 strain. Preferably the modified live BVDV Type 1 Singer strain is the one that is included in the BREED-BACK™ FP5 vaccine. Preferably the modified live BVDV Type 2 296 strain is the one that is included in the BREED-BACK™ FP5 vaccine. Repesentative vaccines are also sold under the names BREED-BACK™ FP5-HS, EXPRESS™ 5-HS, BREED-BACK™ FP10-HS and EXPRESS 10-HS®. In preferred forms, the immunogenic composition, routes of administration, timing of administration, and variations noted above in describing the vaccine compositions are the same for the immunogenic composition and methods of this aspect.

In another aspect of the present invention, the vaccine or immunogenic composition as described herein is administered to healthy susceptible cows and replacement heifers prior to breeding wherein such administration prevents persistently infected calves due to BVD Types 1 and 2.

In another aspect of the present invention, the vaccine or immunogenic composition as described herein aids in the reduction of respiratory diseases caused by IBR virus, BVDV Types 1 and 2, PI-3 virus, and BRSV when administered to pregnant females or calves nursing pregnant females that had been vaccinated with the same vaccine or immunogenic composition prior to breeding or being artificially inseminated. In preferred forms of this aspect, for cows and heifers and using aseptic techniques, annually inject a 2 mL dose intramuscularly or subcutaneously at or about four weeks prior to breeding. Pregnant cows and nursing calves may be vaccinated following the pre-breeding vaccination.

For the aspects of the invention described herein, attenuated modified live BVDV Type 1 and 2 strains are grown in MDBK-cells until a $TCID_{50}$ of about $10^{5.0}$ to $10^{8.1}$ per ml cell culture fluid. A modified live attenuated strain of IBR is grown in MDBK cells until a $TCID_{50}$ of about $10^{5.0}$ to $10^{8.6}$ per ml cell culture fluid. A live attenuated strain of BRSV is grown in MDBK cells until a $TCID_{50}$ of about $10^{5.0}$ to $10^{7.2}$ per ml cell culture fluid. A live attenuated strain of PI-3 is grown in MDBK cells until a $TCID_{50}$ of about $10^{4.2}$ to $10^{6.5}$ per ml cell culture fluid. *Leptospira* bacterium, and especially those described above, are separately cultivated until reaching $10^{8.0}$ to $10^{11.0}$ cells per ml culture. The bacteria cultures are inactivated and the culture fluids are lyophilized or freeze dried. *H. somnus* is cultivated until achieving $10^{7.1}$ to $10^{9.2}$ cells per ml culture. The bacteria culture is inactivated and the culture fluid is lyophilized or freeze dried.

For any of the vaccine compositions described herein, final dosage amounts for the individual components is as follows: IBR ($10^{5.0}$ to $10^{8.6}$ $TCID_{50}$), BVDV-1 ($10^{5.8}$ to $10^{8.1}$ $TCID_{50}$), BVDV-2 ($10^{5.0}$ to $10^{8.1}$ $TCID_{50}$), BRSV ($10^{5.0}$ to $10^{7.2}$ $TCID_{50}$) PI3 ($10^{4.2}$ to $10^{6.5}$ $TCID_{50}$), each selected *Leptospira* bacteria $10^{8.0}$ to $10^{11.0}$ cells per ml culture, and *Haemophilus somnus* $10^{7.1}$ to $10^{9.2}$ cells per ml culture. Still more preferably, the dosage amounts are as found in a product selected from the group consisting of BREED-BACK™ 5, EXPRESS™ 5, BREED-BACK™ FP5, EXPRESS™ FP5, BREED-BACK™ 5HS, EXPRESS™ 5HS, BREED-BACK™ FP5-HS, EXPRESS™ FP5-HS, BREED-BACK™ 10, EXPRESS™10, BREED-BACK™FP10, EXPRESS™FP10, BREEDBACK™ FP10-HS, EXPRESS FP10-HS®, BREED-BACK™ 10HS, EXPRESS™ FP3-VL5, and EXPRESS™ FP5-VL5. It is noted that the BREED-BACK product line has been replaced by the EXPRESS product line. However, this change was in name only as all components therein remained the same.

Further Definitions:

It must be noted that as used herein and in the appended claims, the singular forms "a", "an", and "the" include plural reference unless the context clearly dictates otherwise. Thus, for example, reference to "a BVDV" includes a plurality of such BVDV, reference to the "cell" is a reference to one or more cells and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference in their entireties including for the purpose of describing and disclosing the cell lines, vectors, and methodologies as reported in the publications, which might be used in connection with the invention. Nothing herein is to be construed as an admission that the invention is not entitled to antedate such disclosure by virtue of prior invention.

The term "BVDV" as used herein refers to all viruses belonging to species bovine viral diarrhea virus (BVDV) type 1 (BVDV-1) and BVDV type 2 (BVDV-2), including any sub-species such as 1a, 1b, 2a, 2,b, and the like in the genus Pestivirus within the family Flaviviridae (Heinz et al., 2000). The more classical BVDV type 1 strains and the more recently recognized BVDV type 2 strains display some limited but distinctive differences in nucleotide and amino acid sequences. Preferably the term BVDV as used herein refers to the modified BVDV. Even more preferably the modified BVDV as used herein refers to a cytopathic modified live BVDV Type 1 strain derived from the Singer strain and/or a cytopathic modified live BVDV Type 2 derived from the 296 strain. Preferably the modified live BVDV Type 1 Singer strain refers to the one that is included in the BREED-BACK™ FP5 vaccine. Preferably the modified live BVDV Type 2 296 strain refers to the one that is included in the BREED-BACK™ FP5 vaccine.

"A modified live BVDV" as used herein means that there is a statistically significant difference between the virulence of modified live BVDV of the present invention, and wild-type BVDV isolates including those from which said modified live BVDV have been derived, for the predominant clinical parameters, in case of BVDV for diarrhea, pyrexia and lethality in animals infected with the same dose, which may be $6\times10^{6}$ $TCID_{50}$. Thus, said modified live BVDV have a reduced incidence of or severity of clinical, pathological, and histopathological signs associated with BVDV infection, including diarrhea, pyrexia and lethality.

"Immunological active component" or "immunologically active component" as used herein means a component that induces or stimulates the immune response in an animal to which said component is administered. Said immune response may be directed to said component or to a microorganism comprising said component. The immunological active component may be an attenuated microorganism, including modified live virus (MLV), a killed-microorganism or at least an immunological active part of a microorganism.

"Immunological active part of a microorganism" as used herein means a protein-, sugar-, and or glycoprotein containing fraction of a microorganism that comprises at least one antigen that induces or stimulates the immune response in an animal to which said component is administered. Said immune response may be directed to said immunological active part of a microorganism or to a microorganism comprising said immunological active part.

The term "vaccine" as used herein refers to a pharmaceutical composition comprising at least one immunologically active component that induces an immunological response in an animal and possibly, but not necessarily, one or more additional components that enhance the immunological activity of said active component. A vaccine may additionally comprise further components typical to pharmaceutical compositions. The immunologically active component of a vaccine may comprise complete virus particles in either their original form or as attenuated particles in a so-called modified live vaccine (MLV) or particles inactivated by appropriate methods in a so-called killed vaccine (KV). In another form, the immunologically active component of a vaccine may comprise appropriate elements of said organisms (subunit vaccines) whereby these elements are generated either by destroying the whole particle or the growth cultures containing such particles and optionally, subsequent purification steps yielding the desired structure(s), or by synthetic processes including an appropriate manipulation by use of a suitable system based on, for example, bacteria, insects, mammalian or other species, plus optionally subsequent isolation and purification procedures, or by induction of said synthetic processes in the animal needing a vaccine by direct incorporation of genetic material using suitable pharmaceutical compositions (polynucleotide vaccination). A vaccine may comprise one or simultaneously more than one of the elements described above. The term "vaccine" as understood herein is a vaccine for veterinary use comprising antigenic substances and is administered for the purpose of inducing a specific and active immunity against a disease provoked by a microbiological infection, such as by a BVDV infection. The BVDV as described herein, confer active immunity that may be transferred passively via maternal antibodies against the immunogens it contains and sometimes also against antigenically related organisms. A vaccine of the invention refers to a vaccine as defined above, wherein one immunologically active component is a BVDV or derived from a nucleotide sequence that is more than 70% homologous to any known BVDV sequence (sense or antisense).

The term "live vaccine" refers to a vaccine comprising a replication competent, in particular, a replication compentent viral active component.

A "pharmaceutical composition" essentially consists of one or more ingredients capable of modifying physiological e.g. immunological functions of the organism it is administered to, or of organisms living in or on the organism. The term includes, but is not restricted to, antibiotics or antiparasitics, as well as other constituents commonly used to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, and controlled release properties. One non-limiting example of such a pharmaceutical composition, solely given for demonstration purposes, could be prepared as follows: Cell culture supernatant of an infected cell culture is mixed with a stabilizer (e.g. spermidine and/or BSA (bovine serum albumin)) and the mixture is subsequently lyophilized or dehydrated by other methods. Prior to vaccination, said mixture is then rehydrated in aqueous (e.g. saline, PBS (phosphate buffered saline)) or non-aqueous solutions (e.g. oil emulsion, aluminum-based adjuvant).

EXAMPLE

The following example serves to further illustrate the present invention; but the same should not be construed as limiting the scope of the invention disclosed herein.

Example 1

Safety of Administering IBR, BVD1, BVD2, $PI_3$, and BRSV Combination Virus Vaccine to Pregnant Cows and Their Calves 1. Summary The objective of this study was to demonstrate the safety of modified live Infectious Bovine Rhinotracheitis (IBR) and Bovine Viral Diarrhea (BVD) Type 1 and 2 vaccine components as part of booster vaccines for use in previously vaccinated first, second and third trimester pregnant cows and heifers. The study monitored the following primary parameters: Pregnancy outcome from all three trimesters and postnatal health of the calves; Pre-colostral serological status of selected calves from the second and third trimesters.

Cows and heifers from three cow/calf ranches in north-central Nebraska were enrolled to determine calving outcome and calf health status. Cows from a cow/calf ranch in Alberta Canada were also enrolled.

a. Nebraska Sites:

For the Nebraska sites, all cows and heifers were given a pre-breeding vaccination of 10-way vaccine (IBR, BVD 1, BVD 2, PI3, BRSV MLV rehydrated with 5-way *Leptospira* bacterin) (BREED-BACK™ FP10) one to two months prior to breeding. Booster vaccinations (Test vaccine Group A, 10-way vaccine (BREED-BACK™ FP10), Product Code 4469.23 or Placebo vaccine Group B, 5-way *Leptospira* bacterin, Product Code 2665.00) were administered to the cows and heifers, with the timing of administration based upon trimester assignment. Pregnancy status was confirmed prior to the booster vaccination, with the pregnant cattle randomly assigned to either Group A or Group B. Cows and heifers located at the Raymond ranch, along with a supplemental set of cows from the A&K ranch, were revaccinated during the first trimester. Cows and heifers located at the A&K ranch were assigned to vaccination during the second trimester. Cows and heifers located at the Williams ranch were assigned to vaccination during the third trimester.

All cows and heifers were followed through calving and the calving outcome recorded for each case. Calving outcome was recorded as either Open (heifer or cow diagnosed as not pregnant, with no calf), Dead (calving resulted in a dead calf not diagnosed as dystocia), or Live (calving resulted in a live calf diagnosed as normal at calving). Calves that died at or immediately after calving due to calving difficulties (dystocia), weather related deaths (frozen in blizzard) or other non-study related causes (calf crushed when stepped on by dam) were removed from the trial. The animals that were removed were not included in the final study results. The Open and Dead cases were combined under the category Fetal Losses.

The resulting calves were observed for four weeks postpartum. The postpartum treatment rates and deaths were recorded.

The results of the study are summarized as follows: For First Trimester Group A, 306 cows/heifers qualified for enrollment and there were 7 fetal losses for a 2.3% loss rate; For First Trimester Group B, 274 cows/heifers qualified for enrollment and there were 6 fetal losses for a 2.2% loss rate. For Second Trimester Group A, 237 cows/heifers qualified for enrollment and there was 1 fetal loss for a 0.4% loss rate; For Second Trimester Group B, 235 cows/heifers qualified for enrollment and there were 3 fetal losses for a 1.3% loss rate. For Third Trimester Group A, 267 cows/heifers qualified for enrollment and there were 5 fetal losses for a 1.9% loss rate; For Third Trimester Group B, 267 cows/heifers qualified for enrollment and there were 6 fetal losses for a 2.2% loss rate.

A full necropsy was performed on all available fetuses (including dystocia, hypothermia, etc. cases). Tissues and body fluid samples, as available, were submitted to the Animal Disease Research & Diagnostic (ADRD) Laboratory, South Dakota State University for analysis. Tests specific for detection of Infectious Bovine Rhinotracheitis (IBR) and Bovine Viral Diarrhea Virus (BVD) were performed. In addition, Rural Technologies Inc. (RTI) performed virus isolations on all submitted tissues. All tests for viral detection and isolation on all fetal tissues were negative.

Heart blood and other body fluids, as available at necropsy, were tested for antibody to IBR, BVD 1 and BVD 2 by the ADRD laboratory. There were a total of six fetuses that tested positive for antibody, however, due to either site practices (forced feeding of colostrum) or testing problems due to sample toxicity/contamination resulting in the lack of confirmation of the test results, these results did not impact the outcome of the study.

Post-calving observations showed that the enrolled calves had low treatment and death rates. Treatments were necessary in the second and third trimester herds due to a mild outbreak of scours. The observations indicated that the majority of cases cleared in 24 to 48 hours. Few post calving deaths occurred. Necropsy results were negative for virus pathogens in the post calving deaths.

b. Alberta Site:

The trial to examine criteria was performed at a cow/calf ranch near Fort Macleod in south central Alberta, Canada. Cows that had been vaccinated pre-breeding were given booster vaccinations in either the second or third trimester. Valid pre-colostral blood samples were successfully taken from a total of 61 calves from the second trimester vaccinated cows and from 59 calves in the third trimester cows. All valid pre-colostral serum samples tested negative for antibody to IBR, BVD 1 and BVD 2. In addition, all serum samples were tested for IBR virus by virus isolation and for BVD 1 and 2 by RT PCR. All serum samples were negative for the presence of virus.

2. Final Results

The results of this study have shown no indication that vaccination of previously vaccinated pregnant cattle in the first, second or third trimester with the modified live IBR and BVD Type 1 and 2 components would result in deleterious effects to either the pregnant cow/heifer or the calves.

3. Introduction

Combination vaccines containing modified live virus (MLV) IBR and modified live BVD Types 1 and 2 have been developed and registered for use in cattle. Efficacy trials have proven the IBR, BVD 1 and BVD 2 combination vaccines (Express™ and Breed-Back FP 5™, Bovine Rhinotracheitis-Viral Diarrhea-Parainfluenza$_3$-Respiratory Syncytial Virus Vaccine, Modified Live Virus, and combinations; Boehringer Ingelheim Vetmedica) to be effective in preventing BVD Type 1 and 2 persistent fetal infection when administered prior to breeding. Due to safety issues with the use of the IBR and BVD viruses in naive pregnant cattle, these conventionally attenuated virus vaccines have label warnings against the use of the vaccines in pregnant cattle or in calves nursing pregnant cattle. To remove these warnings from the labels for products which contain the same modified live IBR and BVD 1 and BVD 2 components, safety studies were completed in pregnant cattle.

4. Objectives

The objectives of this study were to perform a field safety trial in order to determine the pregnancy outcome in pregnant cows and heifers when vaccinated prior to breeding and subsequently vaccinated in the first, second or third trimester of pregnancy with a product containing the IBR and BVD Types 1 and 2 components of BIVI fetal protection product; to determine the health of the calves born to the enrolled cows and heifers by post-partum observations for a total of four weeks; and determine pre-colostral serological status for IBR, BVD 1, BVD 2 in calves born from cows and heifers vaccinated in the second and third trimester of pregnancy.

The results of this study provides proof of safety of the use of the modified live viral products containing IBR and BVD 1 and BVD 2 components and permit revision of the labeled safety precautions regarding use of the vaccines in previously vaccinated pregnant cattle and in calves nursing pregnant cattle.

5. Materials and Methods a. Start of Study:

Nebraska:

The study was considered to be officially started on Day 0 for the first trimester herd enrollment pregnancy check/vaccination which was performed on Day 0. However, the pre-breeding vaccinations for the enrolled cattle started on Day −140, with the first vaccinations occurring in the Raymond herd.

Alberta:

The study was considered to be officially started on Day 0 for the vaccination of Group 1, Third Trimester.

b. End of Study:

Nebraska:

The animal portion of the study was completed with the final observation of the calves on Day 295. The laboratory portion of the study ended on Day 399 with receipt of the final BVD serology testing results from Benchmark BioLabs Inc.

Alberta:

The animal portion of the study was completed with the sampling of the final calf on Day 433. The laboratory portion of the tests was completed between Day 487 and Day 517.

6. Study Design a. General Description:

This large field safety study was designed to determine the safety of the administration of vaccines containing MLV IBR and BVD 1 and 2 components to previously vaccinated pregnant cows and heifers. This trial consisted of two separate segments, the first being a large field safety trial, conducted in Nebraska that investigated calving outcome and post-partum calf health. The second segment, conducted in Alberta, Canada, involved vaccinations of previously vaccinated pregnant cattle in the second and third trimesters, and obtaining pre-colostral serum samples to determine levels of antibody to IBR and BVD 1 and BVD 2. The Nebraska treatment groups are outlined in Tables B, C, and D and the Alberta Canada treatment groups are outlined in Tables E and F.

TABLE B

General Trial Design, Nebraska First Trimester

| GROUP | SUBGROUP | MINIMUM NUMBER VACCINATED | TREATMENT 1 (Pre-Breeding) | TREATMENT 2 |
|---|---|---|---|---|
| First Trimester | Group A MLV Vaccine Vaccinates | 200 | IBR-BVD1-BVD2-PI3-BRSV MLV, LEPTO 5 | IBR-BVD1-BVD2-PI3-BRSV MLV, LEPTO 5 |
| | Group B Placebo Controls | 200 | IBR-BVD1-BVD2-PI3-BRSV MLV, LEPTO 5 | Lepto 5 Bacterin |

TABLE C

General Trial Design, Nebraska Second Trimester

| GROUP | SUBGROUP | MINIMUM NUMBER VACCINATED | TREATMENT 1 (Pre-Breeding) | TREATMENT 2 |
|---|---|---|---|---|
| Second Trimester | Group A MLV Vaccine Vaccinates | 200 | IBR-BVD1-BVD2-PI3-BRSV MLV, LEPTO 5 | IBR-BVD1-BVD2-PI3-BRSV MLV, LEPTO 5 |

TABLE C-continued

| General Trial Design, Nebraska Second Trimester | | | | |
|---|---|---|---|---|
| GROUP | SUBGROUP | MINIMUM NUMBER VACCINATED | TREATMENT 1 (Pre-Breeding) | TREATMENT 2 |
| | Group B Placebo Controls | 200 | IBR-BVD1-BVD2-PI3-BRSV MLV, LEPTO 5 | Lepto 5 Bacterin |

TABLE D

| General Trial Design, Nebraska Third Trimester | | | | |
|---|---|---|---|---|
| GROUP | SUBGROUP | MINIMUM NUMBER VACCINATED | TREATMENT 1 (Pre-Breeding) | TREATMENT 2 |
| Third Trimester | Group A MLV Vaccine Vaccinates | 200 | IBR-BVD1-BVD2-PI3-BRSV MLV, LEPTO 5 | IBR-BVD1-BVD2-PI3-BRSV MLV, LEPTO 5 |
| | Group B Placebo Controls | 200 | IBR-BVD1-BVD2-PI3-BRSV MLV, LEPTO 5 | Lepto 5 Bacterin |

TABLE E

| General Trial Design, Alberta Second Trimester | | | | |
|---|---|---|---|---|
| GROUP | SUBGROUP | MINIMUM NUMBER VACCINATED | TREATMENT 1 (Pre-Breeding) | TREATMENT 2 |
| Second Trimester | MLV Vaccine Vaccinates | 65 | IBR-BVD1-BVD2-PI3-BRSV MLV | IBR-BVD1-BVD2-PI3-BRSV MLV |

TABLE F

| General Trial Design, Alberta Third Trimester | | | | |
|---|---|---|---|---|
| GROUP | SUBGROUP | MINIMUM NUMBER VACCINATED | TREATMENT 1 (Pre-Breeding) | TREATMENT 2 |
| Third Trimester | Group A MLV Vaccine Vaccinates | 65 | IBR-BVD1-BVD2-PI3-BRSV MLV | IBR-BVD1-BVD2-PI3-BRSV MLV |

b. Nebraska Sites:

Trial Sites:

Three working cow-calf production ranches located in the rural Ainsworth/Johnstown Nebr. area were identified as having normally low (between 3 to 5%) calving losses. The chosen ranches did not have recent history of either IBR or BVD abortions. With the exception of 82 additional cows enrolled in the first trimester, each trimester consisted of animals from a single herd. Parity of the animals enrolled varied from first calf heifers up to cows with histories of 10 or more pregnancies.

Cows and heifers at the Raymond/Finney Ranch (included Raymond and Walking Y Ranch cows and heifers) were enrolled in the study as first trimester test animals. In addition, a portion of the cows from the A&K herd were also enrolled as first trimester test animals.

Cows and heifers at the A&K Ranch were enrolled in the study as second trimester test animals.

Cows and heifers at the Williams & Williams (W&W) Ranch were enrolled in the study as third trimester test animals.

Animal Selection and Identification:

All heifers and cows enrolled into the study were physically normal, healthy breeding age female Angus or Angus-cross beef cattle. To prevent enrollment of BVD persistently infected (PI) cattle, all heifers in all three herds were ear notched prior to enrollment. Similarly, the calves of the cows of that year available for enrollment were ear notched. The ear notch samples were submitted to the University of Nebraska Veterinary Diagnostic Laboratory (UNVDL), Lincoln, Nebr. for testing by immunohistochemistry. The semen from bulls used for breeding or the semen used for artificial insemination was tested for the presence of BVD by PCR at UNVDL. In addition, all bulls used for breeding were ear notched.

All enrolled heifers and cows were identified using one or two plastic ear tags, a metal Nebraska state ear tag and an electronic identification device (EID). All forms of identification were confirmed each time the animal was handled. Any missing identification was replaced.

A total of two thousand sixty-three (2,063) cows/heifers completed the pre-breeding vaccinations which occurred between Day −140 and Day −67. Six hundred ten (610) cows/heifers were vaccinated for the first trimester (T1). Seven-hundred seven (707) cows/heifers were vaccinated for the second trimester (T2). Seven-hundred forty-six (746) cows/heifers were vaccinated for the third trimester (T3). These animals were bred and pregnancy checked just prior to the trimester enrollment vaccination. The number of animals available for enrollment at the time of trimester vaccinations was reduced from the initial number due to normal expected losses that included non-pregnant (open) animals, lameness, lightning strikes, etc.

Animal Management and Housing:

All three herds were managed according to their normal husbandry practices, with the exception that cows/heifers from Treatment Group A and Treatment Group B were housed as separate groups (no nose to nose contact between Groups A and B) for a minimum of 30 days after the assigned trimester vaccination. In each case, initial housing was located at the home pastures.

In the case of the A&K cows that were assigned to T1, the 82 cows were separated from the remaining A&K herd for 30 days after the T1 vaccination, after which the cows were allowed to rejoin the main A&K cow herd. Once again, at the time of the T2 vaccination, the cows/heifers enrolled in Treatment Group A were isolated from the remainder of the herd for 30 days.

All herds were fed according to their normal herd practices, as appropriate for age, weight, and pregnancy status. All heifers and cows enrolled in the study were pastured according to a rotation schedule determined by each producer throughout the trial. This included movement of the herd to corn stock pastures for the winter months. Details, including area maps for each herd, are filed with the raw data for the study. Feed for the heifers and cows were supplemented with a protein and mineral supplement (cake) and ground hay during the winter months as deemed necessary by each producer. All rations and supplements were pre-approved by the Investigators and Study Monitor.

Daily herd observations were performed starting on Day −123 and continued through Day 280 for T1, Day 276 for T2 and Day 295 for T3 at which time all enrolled calves were at least 30 days of age. Any abnormalities or other observations or comments were recorded in the notes section of the Clinical Assessment Forms. These are included in the raw data files for the study.

Breeding:

T1 and T3 trial sites used bull breeding. For T2, the heifers and majority of the cows were artificially inseminated, followed by the use of clean up bulls.

Enrollment Pregnancy Checks:

The Raymond/Finney heifers for T1 were ultrasounded for verification of pregnancy status on Day 0. Sixty-one (61) heifers were determined to be between 40 to 70 days of gestation. Cows from the Raymond/Finney herd for T1 were ultrasounded for verification of pregnancy status on Day 14 and Day 15. A total of 458 cows were determined to be between 40 to 70 days gestation and eligible for enrollment in the trial.

The A&K cows enrolled as T1 on Day 16 had been ultrasounded on Day −4 and determined to be between 40 and 70 days of gestation.

The A&K heifers for enrollment in T2 were ultrasounded for verification of pregnancy on Day −6. At that time, 95 heifers were determined to be between 40 to 70 days gestation.

The A&K cows were ultrasounded on Days −5, −4, −1, and 1 for verification of pregnancy status. At that time, 476 cows were determined to be between 40 to 70 days gestation. As noted above, 82 of the animals ultrasounded on Day −4 were enrolled as T1 animals on Day 16.

All A&K cows and heifers determined to be pregnant and within the gestation window required for enrollment in the study were palpated to confirm pregnancy status immediately prior to vaccination enrollment on Day 79 for the heifers and on Days 92 and 93 for the cows. Animals determined to be open or to have health issues at that time were not enrolled in the trial.

The W&W heifers for enrollment in T3 were initially ultrasounded on Day 13. At that time, 132 heifers were determined to be between 40 and 70 days gestation.

The W&W cows for enrollment in T3 were initially ultrasounded on Days 28, 29, and 30. At that time, 428 were determined to be between 40 to 70 days gestation.

The W&W cows and heifers determined to be pregnant and within the gestation window required for enrollment in the study were palpated to confirm pregnancy status immediately prior to vaccination enrollment on Day 177 for the heifers and on Days 196 and 197 for the cows. Animals determined to be open or have health issues at that time were not enrolled in the trial.

Randomization:

The T1 Raymond heifers, T1 A&K cows, T2 A&K cows and heifers, and the T3 W&W cows and heifers were assigned to treatment group A or B utilizing randomization software. For each set of vaccinations, two series of random numbers were generated. If the higher random number was listed in the first column of numbers, the assignment was to Group A. If the higher random number was in the second column of numbers, the assignment was to Group B. The heifer or cow was then allotted to the next assigned treatment group on the spreadsheet as the animals were worked through the chute. In the case that all slots on the spreadsheet were not used or additional group assignments were necessary, the last few animals coming through the chute were randomized to group based upon coin toss.

For the T1 cows, these animals were housed in two separate but adjacent pastures. Assignment of the pasture as a group to Treatment A or B was done by coin toss.

Enrollment Vaccinations:

The Test Vaccine (IBR, BVD 1 BVD Type 2, PI3, BRSV, Lepto 5 Serial # MK-270A or MK-270B) was administered to the cows and heifers enrolled in Treatment A. The Placebo Vaccine (Lepto 5 Bacterin, Serial Number 184-089) was administered to the cows and heifers enrolled in Treatment B. Lepto 5 Bacterin contains all of the *Leptospira* strains, *Leptospira canicola, Leptospira grippotyphosa, Leptospira hardjo, Leptospira icterohaemorrhagiae*, and *Leptospira Pomona*, as are found in the EXPRESS™ and BREEDBACK™ products including, but not limited to EXPRESS™10, BREEDBACK™ 10, BREEDBACK™ FP10, and EXPRESS™ FP10. The use of this placebo was a deviation to the protocol. The protocol stated that the placebo would be sterile water.

T1 Vaccinations:

On Days 0, 14, and 15, 61 heifers, 244 cows and 214 cows, respectively, from the Raymond/Finney herd were determined to meet the enrollment criteria for pregnancy status. These heifers and cows were bled and the assigned vaccine product was administered according to the randomization process. On Day 16, 82 additional cows from the A&K herd were administered appropriate vaccine product or placebo based upon the assigned group. The pregnancy checks for the 82 A&K cows were performed on Day −4, which was a deviation to the protocol which stated that the pregnancy checks would be performed within 7 days of the enrollment vaccination. The mean gestation day for T1 enrollment was approximately 55, with an estimated range between 40-75 days gestation.

T2 Vaccinations:

On Days 79, 92, and 93, 90 heifers, 200 cows and 189 cows, respectively, from the A&K herd were determined to meet the enrollment criteria for pregnancy status. These heifers and cows were bled and the assigned vaccine product or placebo was administered according to the randomization process. The mean gestation day for T2 enrollment was approximately 140, with an estimated range between 120-160 days gestation.

T3 Vaccinations:

On Days 177, 196, and 197, 126 heifers, 251 cows and 166 cows, respectively, from the W&W herd were determined to meet the enrollment criteria for pregnancy status. These heifers and cows were bled and the assigned vaccine product or placebo was administered according to the randomization process. The mean gestation day for T3 enrollment was approximately 210, with an estimated range between 195-225 days gestation.

Pregnancy Outcome and Post-Calving Observations:

All enrolled animals were followed through to calving. Calving results were recorded on the Calving Record Form. All trimester enrolled animals diagnosed as pregnant at the trimester vaccination and determined to be open at the end of the trial were counted as a fetal loss. Cows and heifers diagnosed as open were bled at the time of diagnosis and 1 to 4 weeks later. The protocol originally stated that the paired samples would be taken two weeks apart. The serum sample taken at the time of the trimester enrollment vaccination as well as the paired serum samples taken after fetal loss were all tested for levels of serum neutralizing antibody to IBR, BVD Type 1 and BVD Type 2 to determine if serum antibody levels had increased significantly between the first and second of the paired samples, which could indicate a potential fetal loss due to one of the agents.

Deaths at or just after calving diagnosed as due to dystocia (calving difficulties) were removed from the study. Deaths due to other causes unrelated to the study, such as deaths due to hypothermia, dam inflicted injuries or broken limbs were also removed from the study. However, fetuses and calves that died due to dystocia, hypothermia or injuries were subjected to necropsy and testing. The following tissues (if sampling was possible) were collected from the necropsied fetuses: lung, thymus, brain (cerebellum), liver, kidney, spleen, placenta, stomach contents, heart blood and pleural fluid.

The calves were observed daily for four weeks following birth. Any observed health problems or required treatments were recorded.

Diagnostic Testing:

Tissue samples were submitted to a laboratory for testing. Tests performed included general histology, fluorescent antibody (FA) tests specific for IBR and BVD, *Leptospira* FA, aerobic culture, mycology culture and serum neutralization for IBR, BVD 1 and BVD 2. When obtained, fetal and post-calving ear notch samples were submitted to the laboratory for BVD immunohistochemistry testing.

Tissue samples were also submitted to RTI for performance of virus isolations in tissue culture specific for IBR and BVD.

Serum Neutralization Tests on Adult Serum Samples:

Serum neutralization assays specific for antibody to IBR on blood samples taken from the adult heifers and cows were performed by Benchmark BioLabs, Lincoln, Nebr. according to a standard procedure for serum neutralization. Serum neutralization assays specific for antibody to BVD Type 1 and BVD Type 2 on blood samples taken from the adult heifers and cows were performed by Boehringer Ingelheim Vetmedica Research and Development according to the standard procedure for Serum Neutralization.

Additional Non-Study Related Treatments Administered to the Enrolled Animals:

Additional treatments administered to the trimester enrolled animals included the following Ivomec® Pour-On (Merial), Guardian® Scour Vaccine (Schering-Plough Animal Health), administered to the cows and heifers, and Alpha 7® Clostridial Bacterin (Boehringer Ingelheim Vetmedica) administered to the calves.

c. Alberta Site:

General Design and Sample Collection:

This was a controlled field safety study involving two groups of cross-bred beef cows. The study was designed to determine the safety of the administration of MLV vaccines containing IBR and BVD1 and BVD2 to previously vaccinated pregnant cattle. The two groups of cows were located on a ranch near Fort Macleod, Alberta Canada. One group of cows was vaccinated in trimester three and the second group was vaccinated in trimester two. Each of the trimester groups was considered to be a separate trial, with the data summarized separately. All cows were bred by natural service at pasture.

After confirmation of pregnancy by rectal palpation, a group of one hundred twenty cross-bred beef cows was vaccinated with the modified live 5-way vaccine (IBR, BVD 1, BVD 2, PI3 and BRSV, APHIS product code 1181.24) in trimester three. A second group of one hundred and forty cross-bred beef cows was vaccinated with the 5-way MLV vaccine rehydrated with Lepto bacterin in trimester two. Based on the VSM guideline, it was not necessary to include a placebo group.

At the time of trimester enrollment vaccination of Group 1 (third trimester vaccination), the cows were also vaccinated with an inactivated Rotavirus/Coronavirus/*E. coli* vaccine. This vaccine was administered as a separate shot in a separate site on the cow and had no affect on the outcome of the study. Following vaccination, each group of cows was housed either in a yard, at the ranch or pastured on range land. Each group of cows was observed daily to check for visual signs of fetal loss or other health problems. The investigator maintained a record of outcome of the pregnancy of all vaccinated cows in a calving record book as well as a daily activity calendar log.

Calves from 65 cows in group 1 and from 67 cows in group 2 were bled shortly after birth to obtain a pre-colostrum sample. If the investigator was unsure but suspected that a calf had suckled colostrum, the investigator did obtain a serum sample from the calf for testing and a note was made either in the in the calving record book or in the daily activity calendar. These calves were also indicated in the Investigator's "Research Data" calving/sampling spread sheet record for each study year.

Animal Selection and Identification:

Cattle selected for enrollment were physically normal, healthy breeding age female bovine, either cows or heifers. This herd had no history of infertility and no history of IBR and/or BVD related reproductive problems.

All cattle were identified with a unique number, using a plastic and/or metal ear tags. Calves were assigned a unique identification number and tagged, with a single tag, at birth based on the tag colour and on the sequence of it birth. The calf's tag was linked to the number of its dam in the calving records. In each of groups 1 and 2, all the cows received the same vaccination treatment. All calving events were observed except for the 2 fetal losses in Group 2 listed in "Calving Outcome" in the Results section below. The investigator selected calves born to cows from each group for serum collection based on his confidence that a calf was sampled before it suckled colostrum, with an objective to collect samples from at least 65 calves from each group. If the investigator was unsure that a calf had suckled, this was noted either in the "Remarks" section of the calving record book and/or in the calendar log of daily activities. Those calves were also indicated in the "Research Data" calving/sampling spread sheet record attached to the investigator's report for each study year.

Calving Records:

The investigator maintained a herd book for each of the two groups as well as a daily calendar log containing activities as part of the routine management of the herd. In addition to the identification of the dam, the date of birth and sex of the calf were recorded. These records also contain any notations applicable to herd health. To assist in herd management, a note on calving ease was made using a numeric scale (1 to 4), the calf's birth weight was estimated and the likely sire was also recorded. In the first year's calving season, the herd record book suggests a different, letter-based, scoring system for calving ease, but, for consistency, the numeric scale that had been used in the first year was used in the second year.

The record forms that were attached as a part of the study protocol were not used to record the results of the study. The investigator instead kept written records of the study in calving record books and daily activity logs. This is a deviation to the protocol, however, it did not affect the outcome of the study.

Serum Neutralization and Polymerase Chain Reaction (PCR):

Blood samples were allowed to clot at ambient temperature and then were processed within 36 hours by centrifugation to permit separation of the serum from the clotted blood cells. Aliquots of serum were transferred to three sterile storage tubes. Tubes were labeled and stored at ≤−20° C. until delivered by the study monitor to the testing laboratory. Delivery of a few of the samples to the processing laboratory was delayed approximately 12 hours beyond the 24 hours recommended by the study protocol. This is a deviation to the protocol. This delay did not affect the integrity of the serum samples and did not affect the outcome of the study. Serum neutralization titers for IBR, BVDV Type 1 (challenge virus, Singer) and Type 2 (Challenge virus, NVSL 125c) were determined on all sera at the Animal Health Laboratory, Guelph using a constant virus decreasing serum assay in appropriate cell cultures using <500 Tissue Culture Infective $Dose_{50}$ ($TCID_{50}$) challenge virus. The starting dilution was 1:4.

An RT PCR assay for BVD viruses was conducted on pre-colostral serum samples by the Animal Health Laboratory, University of Guelph, Guelph, Ontario. The RT PCR was conducted according to a published procedure. The serum from each calf was tested for gamma-glutamyl transpeptidase (GGT) to help distinguish a calf that had suckled from one that had not. The GGT testing was performed at the Animal Health Laboratory, Ontario Veterinary College, University of Guelph, Guelph, ON using an enzymatic calorimetric method with a Roche/Hitachi 911 Automatic Analyzer.

As there was only one treatment, the investigator and the laboratory technician who separated the serum from blood samples were not blinded to treatment group assignments. The individuals performing the laboratory examinations of post mortem samples and serum samples were unaware of treatment assignments.

d. Vaccine and Placebo Control Articles:

Vaccine and Placebo Control articles used in the trial at the Nebraska trial sites are shown below in Table G. The same serial of test vaccine was used for the pre-breeding vaccination and the trimester enrollment vaccinations.

TABLE G

| Test Vaccine | Serial Number(s) | Use |
|---|---|---|
| Infectious Bovine Rhinotracheitis-Bovine Viral Diarrhea-Parainfluenza 3-Respiratory Syncytial Vaccine, Modified Live Virus, Leptospira Canicola-Grippotyphosa-Hardjo-Icterohaemorrhagiae-Pomona Bacterin, APHIS Product Code 4469.23 | MK-270A-088 or MK-270B-088 | Pre-breeding and trimester vaccinations |
| Leptospira Canicola-Grippotyphosa-Hardjo-Icterohaemorrhagiae-Pomona Bacterin, APHIS Product Code 2665.00 (refer to Protocol Deviation 2, Addendum 3) | 184-087; 184-089; 184-090; | Trimester placebo control vaccinations |

Vaccine and Placebo Control articles used in the trial at the Alberta trial sites are shown below in Table H.

TABLE H

| Test Vaccine | Serial Number(s) | Use |
|---|---|---|
| Infectious Bovine Rhinotracheitis-Bovine Viral Diarrhea-Parainfluenza 3-Respiratory Syncytial Vaccine, Modified Live Virus, Leptospira Canicola-Grippotyphosa-Hardjo-Icterohaemorrhagiae-Pomona Bacterin, APHIS Product Code 1181.24 | 263-318A | Trimester vaccinations |
| Sterile Adjuvanted Diluent | 807-136 | Vaccine Rehydration |

e. Amendments, Deviations and Notes to File:

There was a single Amendment to the Study Protocol from the Nebraska site. The Amendment is outlined below in Table I.

TABLE I

| Amendment # | Sites Affected | Description | Effect on Outcome |
|---|---|---|---|
| 1 | A&K Ranch | Describes the decision to use artificial insemination for the A&K ranch | No effect on the outcome of the study |

There were a total of 14 Deviations to the Study Protocol from the Nebraska herds and 3 from the Alberta herd. The Deviations are outlined in the table below in Table J.

TABLE J

| Deviation # | Herds Affected | Description | Effect on Outcome |
|---|---|---|---|
| | | Protocol Deviations | |
| 1 | A&K first trimester | The last two cows for the day were assigned to treatment group based upon coin toss | No negative effect |
| 2 | All three Nebraska herds | The decision was made to use Lepto 5 bacterin as placebo based on a request by the herd owners | No negative effect |
| 3 | All three Nebraska herds | The decision was made to obtain baseline blood samples at the time of trimester vaccination | No negative effect |
| 4 | Raymond and A&K first trimester | Minimum gestation accepted for enrollment set to 45 days estimate based upon ultrasound estimates by the Site Investigator (45 days equal approximately 40-50 days) | No negative effect |
| 5 | A&K first trimester | Range between pregnancy check and enrollment was at 20 days, not the 7 days as stated in the protocol | No negative effect |
| 6 | First trimester enrollment | The protocol stated that a single herd would represent one trimester. A portion of the A&K herd was enrolled as 1st trimester, with the remainder of the herd enrolled as 2nd trimester. | No negative effect |
| 7 | A&K second trimester enrollment | Randomizations needed to be adjusted due to enrollment of non-qualified cow as well as to balance the outcome of the total number of cows enrolled as Group A and Group B | No negative effect |
| 8 | A&K second trimester enrollment | Adjustment of the enrollment of animals determined to be at 45 days gestation (40-50 days) at the time of initial pregnancy check | No negative effect |
| 9 | Williams 3rd trimester enrollment | Calves from cows and heifers enrolled in the third trimester were vaccinated with clostridial vaccine to prevent scours | No negative effect |
| 10 | All Nebraska herds/all three trimesters | First and second blood samples were not obtained within the two week time period for a number of the animals that had or were found to be open | No negative effect |
| 11 | All Nebraska herds/all three trimesters | First and second blood samples were not obtained within the two week time period for a number of the animals that had calf loss or were found to be open | No negative effect |
| 12 | A&K second trimester | The calf from cow #86 died due to dystocia. A blood sample was obtained at calving but was inadvertently listed and shipped with the blood samples from the Williams herd vaccinations. Cow #86 was enrolled in Group B, placebo. This sample was not tested. A second sample was not obtained. | No negative effect |
| 13 | Raymond first trimester | Calf 940Y was not submitted for necropsy after death at approximately 48 hours after birth. Cow was enrolled in Treatment Group A | Included in fetal losses for $2^{nd}$ trimester, Group A |

TABLE J-continued

| Deviation # | Herds Affected | Description | Effect on Outcome |
|---|---|---|---|
| 14 | Williams third trimester | Calf 5131 died approximately 2 hours after birth. The calf was ear notched but was not submitted for necropsy. Heifer 5131 was enrolled in Treatment Group A | Included in fetal losses for $3^{rd}$ trimester, Group A |
| | | Protocol Deviations Affecting the Alberta Site | |
| 1 | Ashley Herd, Alberta | The record forms provided in the appendix of the study protocol were not used. The investigator instead kept written records of the study in a calving record book and a calendar daily record. | No negative effect |
| 2 | Ashley Herd, Alberta | All cows in the $3^{rd}$ trimester group were vaccinated with Ecostar 2RC (Novartis Animal Health) at the time of trimester enrollment vaccination. | No negative effect |
| 3 | Ashley Herd, Alberta | Some blood samples were held for 36 hours prior to processing | No negative effect |

There was a total of 18 Notes to File that were written for the purpose of clarification of parts of the study for the Nebraska sites and 3 Notes to File for the Alberta site, as shown in the table below in Table K.

TABLE K

| Note to File Subject | Day | Herds Affected | Description | Effect on Outcome |
|---|---|---|---|---|
| | | Notes to File, Nebraska Trial Sites | | |
| Change of Ear Tag Numbers | 148 | Raymond first trimester enrollment | Replacement of ear tags, list of old and new tags for reference | No negative effect |
| Change of Ear Tag Numbers | 192 | A&K second trimester heifers | Replacement of ear tags, list of old and new tags for reference | No negative effect |
| Change of Ear Tag Numbers | 192 | Williams third trimester heifers | Replacement of ear tags, list of old and new tags for reference | No negative effect |
| Change of Ear Tag Numbers | 204 | Williams third trimester | Replacement of ear tags, list of old and new tags for reference | No negative effect |
| Fetal Shipments | 232 | Williams third trimester | Shipment of samples from three fetuses over a weekend | No negative effect |
| Duplicate Ear Tag Numbers for Heifers and Cows | 279 | A&K second trimester | A few mature cows and heifers were inadvertently given the same ear tag numbers. The tags of mature cows were changed to have the letter M added | No negative effect |
| Change of Ear Tag Numbers | 289 | Raymond first trimester | At the time of trimester enrollment vaccination ear tags were changed for 9 cows. The list provided gives a cross reference for pre-breeding vaccination | No negative effect |
| Assignment to groups for artificial insemination | 294 | A&K first and second trimester enrollment | The A&K ranch cows were divided into 3 groups A, B, C during breeding process. | No negative effect |
| Administration of colostrum to non-suckling calves | 294 | All three Nebraska herds | This note describes the administration of colostrum to weak calves to provide the initial feeding | No negative effect; caused positive results on necropsy serology |
| Administration of non-approved product for parasite control | 307 | Raymond first trimester | Cows were poured with Permectrin CDS Pour-on for parasite control | No negative effect |
| ID discrepancies on SDSU laboratory results | 344 | All three herds | Animal identifications were incorrect on diagnostic laboratory results. This list provides a cross reference | No negative effect |

TABLE K-continued

| Note to File Subject | Day | Herds Affected | Description | Effect on Outcome |
|---|---|---|---|---|
| Removal of cow 3028 prior to enrollment vaccination | 365 | Williams third trimester | Cow 3028 aborted during chute work on Day 197 prior to enrollment. The fetal samples were submitted for testing, the results are included in the raw data. Cow was not enrolled | No negative effect. |
| Cow 713 pregnancy checks | 365 | A&K second trimester | Cow number 713 was not ultrasounded as scheduled but was pregnancy checked and confirmed to be pregnant at enrollment vaccination on Day 458 and was enrolled in Treatment Group A | No negative effect |
| Ear notch not collected | 365 | A&K second trimester | At necropsy, an ear notch was not collected from calf 504Y at the time of death | No negative effect |
| Study record designation for A&K first trimester enrollment | 379 | A&K first trimester enrollment | The 82 cows enrolled in the first trimester were included in the data capture forms for the A&K ranch. First trimester cows that were enrolled were designated with a red dot in the study files | No negative effect |
| Cross-fostered calves | 379 | All Nebraska herds | Reference list for calves that were cross-fostered | No negative effect |
| Removal of heifer 577 prior to enrollment | 379 | A&K second trimester | Heifer 577 aborted prior to enrollment vaccination. The fetus was sampled and tested. The results are included in the raw data. Not enrolled in the trial. | The results indicated possible IBR exposure. Results could not be confirmed; not enrolled in the trial |
| Randomization of Raymond cows, first trimester | 428 | Raymond cows, first trimester | The Raymond herd was housed in two separate groups with approximately equal numbers in each group. A coin toss was used for group assignment | No negative effect |
| Notes to File, Alberta Trial Site | | | | |
| Clarification of death loss, Cow 190 | 394 | Alberta Ashley herd | $2^{nd}$ trimester enrollment Cow 190 (dam of calf 25Y) died of an esophageal abscess. Her calf was cross-fostered to cow 216. A serum sample was not taken from this calf | No negative effect |
| Clarification of death loss, Calf 28Y | 392 | Alberta Ashley herd | $2^{nd}$ trimester enrollment Cow 208 gave birth to calf 28Y. This calf was humanely destroyed after its jaw was fractured. A serum sample had been collected from 28Y. Calf 51Y, a co-twin born to Cow 45, was cross-fostered onto cow 208. Calf 51Y was not bled. | No negative effect |
| Clarification of notation on "Here BWF" identification | 397 | Alberta Ashley herd | a $2^{nd}$ trimester cow calved on Day 397. Her identification is noted as "Here BWF" and her calf was identified as 66Y. This cow had lost her plastic ear tag but had been amongst the group confirmed pregnant and vaccinated for the $2^{nd}$ trimester. Calf 66Y was bled. | No negative effect |

7. Results a. Nebraska Sites:

Ear Notch:

Ear notch results were all negative for both the enrollment testing of calves and heifers and for testing conducted on dead fetuses and calves. The negative results indicate that none of the enrolled cattle were persistently infected and that none of the fetal and calf losses in the trial were due to persistent infection with BVD.

Calving Outcome:

All cows and heifers were followed through calving and the calving outcome recorded for each case. Calving outcome was recorded as either Open (heifer or cow diagnosed as not pregnant, with no calf), Dead (calving resulted in a dead calf not diagnosed as dystocia), or Live (calving resulted in a live calf diagnosed as normal at calving). Calves that died at or immediately after calving due to calving difficulties (dystocia), weather related deaths (frozen in blizzard) or other non-study related causes (calf crushed when stepped on by dam) were removed from the trial. The animals that were removed were not included in the final study results. The Open and Dead cases were combined and included under the category Fetal Losses.

There were no calving losses/abortions that were diagnosed as due to either IBR or BVD. The total number of cows and heifers and a summary of the results that include all possible study related fetal losses from the first trimester are shown in the following tables.

TABLE L

Summary of the first trimester calving outcome results

| Treatment Group | Total Calf Losses/Total Enrolled | Percent Fetal Losses |
|---|---|---|
| A | 7/306 | 2.3 |
| B | 6/274 | 2.2 |
| Total | 13/580 | 2.2 |

TABLE M

Summary of the second trimester calving outcome results

| Treatment Group | Total Calf Losses/Total Enrolled | Percent Fetal Losses |
|---|---|---|
| A | 1/237 | 0.4 |
| B | 3/235 | 1.3 |
| Total | 4/472 | 0.8 |

TABLE N

Summary of the third trimester calving outcome results

| Treatment Group | Total Calf Losses/Total Enrolled | Percent Fetal Losses |
|---|---|---|
| A | 5/267 | 1.9 |
| B | 6/267 | 2.2 |
| Total | 11/534 | 2.1 |

Postpartum Observations:

Calves were observed for 4 weeks postpartum. All calf losses and treatments were recorded. Calves that were lost close to calving were included as a fetal loss and not as a post-calving loss. The results of post-calving observations for all three trimesters showed that the calf losses were low. The treatments consisted primarily of treatments for minor cases of scouring that cleared within 24 to 48 hours.

A summary of the post-calving treatments and post-calving losses for the first trimester are shown in the tables below.

TABLE O

Summary of the first trimester postpartum treatments

| Treatment Group | Postpartum Treatments/ Total Enrolled | Percent Calf Treatments |
|---|---|---|
| A | 6/299 | 2.0 |
| B | 1/268 | 0.4 |
| Total | 7/567 | 1.2 |

TABLE P

Summary of the first trimester postpartum calf deaths

| Treatment Group | Postpartum Deaths/ Total Enrolled | Percent Calf Deaths |
|---|---|---|
| A | 3/299 | 1 |
| B | 0/268 | 0.0 |
| Total | 3/567 | 0.5 |

A summary of the post-calving treatments and post-calving losses for the second trimester are shown in the following tables.

TABLE Q

Summary of the second trimester postpartum treatments

| Treatment Group | Postpartum Treatments/ Total Enrolled | Percent Calf Treatments |
|---|---|---|
| A | 6/236 | 2.5 |
| B | 2/232 | 0.9 |
| Total | 8/468 | 1.7 |

TABLE R

Summary of the second trimester postpartum calf deaths

| Treatment Group | Postpartum Deaths/ Total Enrolled | Percent Calf Deaths |
|---|---|---|
| A | 0/236 | 0.0 |
| B | 1/232 | 0.4 |
| Total | 1/468 | 0.2 |

A summary of the post-calving treatments and post-calving losses for the third trimester are shown in the following tables.

TABLE S

Summary of the third trimester postpartum treatments

| Treatment Group | Postpartum Treatments/ Total Enrolled | Percent Calf Treatments |
|---|---|---|
| A | 10/262 | 3.8 |
| B | 7/261 | 2.7 |
| Total | 17/523 | 3.3 |

TABLE T

Summary of the third trimester postpartum calf deaths

| Treatment Group | Postpartum Deaths/ Total Enrolled | Percent Calf Deaths |
|---|---|---|
| A | 3/262 | 1.1 |
| B | 1/261 | 0.4 |
| Total | 4/523 | 0.8 |

Laboratory Results:

Tissue Samples for Detection of IBR, BVD 1 and BVD 2:

With a few minor exceptions, a full necropsy with tissue sampling was performed on all available fetal and calf losses that occurred during the trial, including dystocia and hypothermia cases.

A necropsy was not performed and samples for testing were not obtained on calves 940Y or 5131 due to failure of the rancher to report the dead calf to the site investigator for necropsy. An ear notch sample was taken from calf 5131 and was reported as negative. Calf 940Y was from a cow enrolled in Group A of the Raymond first trimester herd. Calf 940Y died approximately 48 hours after birth. Calf 5131 was from a heifer enrolled in Group A of the Williams third trimester herd. Calf 5131 died approximately 2 hours after birth.

Animals that died due to a cause obviously unrelated to the study, for example euthanized due to broken leg, were not submitted for necropsy. Tissues and body fluid samples, as available, were submitted to a laboratory for analysis. Tests specific for detection of IBR and BVD were performed by the laboratory. In addition, RTI performed virus isolations on all submitted tissues.

All tests for IBR and BVD 1 and BVD 2 viral detection and isolation on all fetal and calf tissues were negative.

Heart blood and other body fluids, as available at necropsy, were tested for antibody to IBR, BVD 1 and BVD 2 by the laboratory. There was a total of six fetuses or calves that tested positive for antibody to IBR, BVD 1 and/or BVD 2. These are summarized in Table U.

TABLE U

Fetuses and calves with reported positive antibody results from necropsy fluid samples

| Fetus/Calf # | Herd/Trimester | Treatment Group | Diagnosis | IBR SN Titer | BVD 1 SN Titer | BVD 2 SN Titer |
|---|---|---|---|---|---|---|
| 577 | A&K 2nd/Not enrolled | Not Applicable | *Aspergillus* sp. abortion | 1:8 (heart blood) | <1:8 | <1:8 |
| 207Y | Raymond/1st | A | Weak calf, died at 24 hours (fed colostrum) | <1:4 | 1:64 (pleural fluid)<br>1:32 (heart blood) | 1:128 (pleural fluid)<br>1:64 (heart blood) |
| 86 | A&K/2nd | B | Died, dystocia | <1:4 | 1:16 (heart blood) | 1:32 (heart blood) |
| 5128 | Williams/3rd | A | Died, dystocia | <1:4 | <1:8 | 1:16 (pleural fluid) |
| 5013 | Williams/3rd | A | Enteritis, had suckled | 1:8 (pleural fluid) | 1:128 (pleural fluid) | 1:512 (pleural fluid) |
| 5020 | Williams/3rd | B | Euthanized after birth malformed had suckled | 1:4 (pleural fluid) | 1:64 (pleural fluid) | 1:32 (pleural fluid) |

Since the results on the pleural fluids on the BVD 1 and BVD 2 serum neutralizations for #86 and #5128 were borderline (one to two 2-fold dilutions above negative, with #86, one dilution above negative for only one BVD type), retests were requested to confirm the results. In both cases, attempts at retests were not successful due to the level of toxicity and/or contamination in the sample.

Serum Samples from Cows and Heifers Having Fetal Loss:

Serum samples were obtained from cows and heifers at the time of diagnosis of calf loss or status as open and again at approximately two weeks after the diagnosis. These serum samples as well as the serum sample from the animal that was obtained at enrollment vaccination were tested for the level of serum neutralizing antibody to IBR, BVD 1 and BVD 2. The cow/heifers tested are summarized in Table V below.

TABLE V

Serum neutralization results from heifers and cows with calf loss

| Animal # | Herd/Trimester | Treatment Group | Reason for Sampling |
|---|---|---|---|
| 522Y | Raymond/First | B | Stillborn calf |
| 4108 | A&K/First | A | Open |
| 210 | A&K/Second | B | Open |
| 018 | A&K/Second | B | Dead Calf (dystocia) |
| 391 | A&K/First | B | Dead Calf (dystocia) |
| 527 | A&K/Second | B | Dead Calf |
| 593 | A&K/Second | B | Dead Calf, pre-mature |
| 433 | A&K/First | B | Open |
| 220Y | Raymond/First | A | Open |
| 218Y | Raymond/First | A | Dead Calf (dystocia) |
| 243O | Raymond/First | B | Open |
| 10O | Raymond/First | B | Open |
| 166Y | Raymond/First | A | Open |
| 300W | Raymond/First | B | Open |
| 516Y | Raymond/First | B | Open |
| 925 | A&K/Second | A | Dead Calf (dystocia) |
| 859 | A&K/Second | B | Open |
| 630 | A&K/Second | A | Open |
| 950Y | Raymond/First | A | Stillborn Calf |
| 426Y | Raymond/First | A | Dead Calf (dystocia) |
| 813Y | Raymond/First | A | Open |
| 945Y | Raymond/First | A | Open |
| 620Y | Raymond/First | A | Open |
| 5127 | Williams/Third | B | Dead Calf (dystocia) |
| 5045 | Williams/Third | A | Dead Calf (dystocia) |
| 5075 | Williams/Third | B | Dead Calf (dystocia) |
| 5109 | Williams/Third | A | Dead Calf (dystocia) |

TABLE V-continued

Serum neutralization results from heifers and cows with calf loss

| Animal # | Herd/Trimester | Treatment Group | Reason for Sampling |
|---|---|---|---|
| 024 | Williams/Third | B | Stillborn Calf |
| 125 | Williams/Third | B | Open |
| 4032 | Williams/Third | B | Open |
| 4040 | Williams/Third | A | Open |
| 341 | Williams/Third | B | Calf died after birth - infected navel |
| 5131 | Williams/Third | A | Dead Calf - Premature |
| 5128 | Williams/Third | A | Dead Calf (dystocia) |
| 947 | A&K/Second | B | Live Calf; died with/in 48 hours |

TABLE V-continued

| Serum neutralization results from heifers and cows with calf loss | | | |
|---|---|---|---|
| Animal # | Herd/Trimester | Treatment Group | Reason for Sampling |
| 1045 | Williams/Third | A | Live Calf, died bacterial enteritis |
| 2056 | Williams/Third | B | Open |
| 4010 | Williams/Third | A | Stillborn Calf |
| 5012 | Williams/Third | B | Calf died, dystocia |
| 5020 | Williams/Third | B | Euthanized, malformed |
| 5030 | Williams/Third | B | Dead Calf (dystocia) |
| 5086 | Williams/Third | A | Died, stepped on by cow |
| 5103 | Williams/Third | A | Open |
| 577 | A&K/Not enrolled | Not Applicable | Aborted |
| 5041 | Williams/Third | A | Twins, premature |
| 5002 | Williams/Third | B | Euthanized, navel hernia |

The serological results for IBR, BVD 1 and BVD 2 were all within the levels that would be expected in a well vaccinated herd. There were a number of cows and heifers that showed a significant rise in titer after vaccination, but none of the animals showed a significant rise between the time of sampling at calf loss and the post-calving blood sampling, which would be indicative of a calf loss due to either IBR or BVD.

b. Statistical Analysis:

Based upon the guidelines published in VS Memorandum 800. 110, for each group, the calving rate, calf losses due to unknown causes, and the health status of the calves up to 4 weeks post partum were determined and summarized. The Clopper-Pearson 95% confidence interval for the aborting fractions due to IBR and BVD was calculated for each trimester group. All rate estimates and confidence intervals were calculated for each treatment group and for the groups combined. PROC FREQ of the SAS® System, version 9.1.3, was used to calculate the proportions. The rates (%) were obtained by multiplying the proportions by 100. The Clopper-Pearson confidence intervals were calculated using StatXact from Cytel Studio 7.

Abortion Rate Due to IBRV/BVDV:

For all three trimesters, no cows or heifers (0.0%) in either group were diagnosed as having aborted due to IBRV/BVDV. For the first trimester, the upper 95% confidence limits were 1.2%, 1.3%, and 0.6% respectively for group A, group B, and the groups combined. For the second trimester, the upper 95% confidence limits were 1.5%, 1.6%, and 0.8% respectively for group A, group B, and the groups combined. For the third trimester, the upper 95% confidence limits were 1.4%, 1.4%, and 0.7% respectively for group A, group B, and the groups combined.

Abortion Rate Due to Any Cause:

For all three trimesters, the estimated abortion rate due to any cause was less than 5% for both groups and for the groups combined. For the first trimester, the estimated rate was 2.3% for group A, 2.2% for group B, and 2.2% for the combined groups. For the second trimester, the rate was 0.4% for group A, 1.3% for group B, and 0.8% for the combined groups. For the third trimester, the rate was 1.9% for group A, 2.2% for group B, and 2.1% for the combined groups.

Post-Calving Treatment Rate:

The estimated rate of treatment for any cause for both treatment groups and groups combined was ≤3.8% for all three trimester groups. For the first trimester, the estimated rate was 2.0% for group A, 0.4% for group B, and 1.2% for the groups combined. For the second trimester, the estimated rate was 2.5% for group A, 0.9% for group B, and 1.7% for the groups combined. For the third trimester, the estimated rate was 3.8% for group A, 2.7% for group B, and 3.3% for the groups combined.

Post-Calving Death Rate:

The estimated rate of death by any cause for both treatment groups and groups combined was ≤1.1% for all three trimester groups. For the first trimester, the estimated rate was 1.0% for group A, 0.0% for group B, and 0.5% for the groups combined. For the second trimester, the estimated rate was 0.0% for group A, 0.4% for group B, and 0.2% for the groups combined. For the third trimester, the estimated rate was 1.1% for group A, 0.4% for group B, and 0.8% for the groups combined.

c. Alberta Site Results:

Calving Outcome:

In group one (third trimester), one cow (#119) gave birth to twins. One co-twin was dead at delivery and the second died shortly after birth. Both calves were subjected to a post mortem examination, and had no gross or histopathological or virological evidence of exposure to IBR or BVD viruses. In summary, for group 1, 120 cows were vaccinated with one pregnancy loss. This gives a 0.8% pregnancy loss for group 1, third trimester.

In group two (second trimester), cow 137 died of peritonitis as a sequel to surgical repair of a vaginal prolapse before she had an opportunity to give birth. Cow 115 was observed to abort a fetus, but the fetus had been consumed by wildlife so it was not available for post mortem examination. Three cows (#264, #132, #109) gave birth to calves that were either dead at birth or died shortly thereafter and were classified as stillbirths. All were subjected to a post mortem examination and had no gross or histopathological or virological evidence of exposure to IBR or BVD viruses (see attached post mortem reports Addendum 3). One cow (#216) aborted a fetus that was recovered. It was negative for exposure to IBR or BVD viruses on gross, histopathological and virological examination (see attached post mortem reports Addendum 3). Cow 161 had not calved and was determined to be not pregnant by rectal palpation. The loss of the fetus had not been observed and so it was not possible to conduct a post mortem examination.

In summary, among the 140 enrolled cows that finished the trial in group two, 6 cows either lost a fetus during gestation or gave birth to a stillborn calf. Four of these fetuses and calves were recovered and subjected to a post mortem examination. In each case, the post mortem examination showed no evidence of in utero exposure to IBRV, BVD 1 or BVD2. For the remaining two cows, no fetus was available for post mortem examination. This gives a 4.3% pregnancy loss for the second trimester group of cows.

Calf Treatments in First 45 Days of Life:

No calves born in the first or second calving season were treated for illness in their first 45 days of life.

Results on Calves that had Suckled Colostrum:

In group one, the investigator indicated that 5 of the 65 calves had been suspected to have suckled colostrum before a blood sample was collected (calves: 8Y, 16Y, 23R, 25Y, 46R). According to the GGT results, 4 calves (8R, 8Y, 25Y, 46R) had nursed (GGT>51 U/L) and each of these calves were seropositive for IBR, BVD1 and BVD2. These calves were seropositive as a result of having absorbed colostral antibody. Of the four calves that had laboratory tests indicating suckling, three had been identified by the investigator as having nursed. Calves 16Y and 23R, which were suspected to have suckled, were seronegative for IBR, BVD1 and BVD2 and negative for BVDV on RT-PCR and IBRV on virus isolation.

If calves 16Y and 23R did nurse, then nursing must have occurred immediately prior to the blood being drawn, with the time interval insufficient for antibody and GGT transfer and elevation. The negative antibody and virus test results indicate that these calves were not exposed to IBR, BVD1 or BVD2. In group two (second trimester), the investigator indicated that 3 of the 67 calves had been suspected to have suckled colostrum before a blood sample was collected (53R, 61R, 72R). Calves 53R and 72R were seronegative to IBR, BVD1 and BVD2 and negative for BVDV on RT-PCR and IBRV on virus isolation. If calves 53R and 72R did nurse, then nursing must have occurred immediately prior to the blood being drawn, with the time interval insufficient for antibody transfer and GGT elevation. The negative antibody and virus isolation results indicate that these calves were not exposed to IBR, BVD1 or BVD2. The investigator indicated that calf 61R was suspected to have suckled. Although the GGT results were below the upper limit of the normal range (51 U/L), the antibody testing indicated that the calf had low virus neutralizing activity against IBR (1:4), BVD1 (1:48) and BVD2 (1:6). Based on the investigator's observations and the test results having low positive antibody for all three viruses, suckling must have occurred very close to when the serum sample for 61R was obtained. Results of IBR virus isolation and BVD 1 and BVD 2 RT PCR testing on the serum from calf 61R were negative. Calf 37R was determined to have nursed unobserved because its GGT value was 2143 U/L (upper limit of normal range: 51 U/L). It was seropositive for IBR, BVD1 and BVD and negative for BVDV on RT-PCR and IBRV on virus isolation.

TABLE W

Summary of laboratory results of calves testing seropositive:

| Calf ID | GGT U/L | IBR VN | BVD1 VN | BVD2 VN | BVDV RT-PCR | IBRV Virus Isolation |
|---|---|---|---|---|---|---|
| First Calving Season | | | | | | |
| 8R | 1456 | 1:384 | 1:2048 | 1:256 | Neg | Neg |
| 8Y | 746 | 1:24 | 1:1024 | 1:256 | Neg | Neg |
| 25Y | 595 | 1:16 | 1:512 | 1:96 | Neg | Neg |
| 46R | 200 | 1:4 | 1:64 | 1:16 | Neg | Neg |
| Second Calving Season | | | | | | |
| 61R | 26 | 1:4 | 1:64 | 1:6 | Neg | Neg |
| 37R | 2143 | >256 | >4096 | >4096 | Neg | Neg |

Results on Enrolled Calves:

In group two, second trimester, two calves that were otherwise healthy, died by misadventure in the first 30 days of life. Calf 28Y was injured, likely from a cow's kick, causing a broken jaw. It was humanely destroyed and did not have a post mortem examination. Calf 28Y had been identified for blood collection at birth. At birth, calf 28Y was seronegative for IBR, BVD 1 and BVD2 and negative for BVDV on RT-PCR and IBRV on virus isolation. Calf #56R was swept down an embankment during a severe rain storm and was not available for post mortem examination. Calf 56R had been identified for blood collection at birth. At birth, calf 56R was seronegative for IBR, BVD1 and BVD2 and negative for BVDV on RT-PCR and IBRV on virus isolation.

In group two, the serum samples from two calves (49R, 98Y) were lost when, on two separate occasions, the centrifuge at the Fort Macleod Veterinary Clinic malfunctioned. The malfunction caused the clotted blood tube to break with complete loss of the serum sample. A total of 65 calves from cows in the third trimester (group 1) were bled shortly after calving. Based upon a combination of investigator observations, antibody testing for IBR and BVD 1 and BVD 2 and GGT testing, the results indicated that four of the calves may have suckled prior to sampling (8R, 8Y, 25Y, 46R). An additional two calves (16Y, 23R) were suspected of having suckled but were seronegative and had normal GGT results. Due to the question on the validity of the pre-colostral serum sampling, all six calves were removed from further consideration in the study. The remaining 59 calves from the third trimester group 1 were all negative for antibody to IBR, BVD 1 and BVD 2. All IBR virus isolations and BVD 1 and BVD 2 RT PCR test results from serum were negative for all calves. There were no post-calving losses due to health problems in this group. A total of 67 calves from cows in the second trimester (group 2) were bled shortly after calving. Based upon a combination of investigator observations, antibody testing for IBR and BVD 1 and BVD 2 and GGT testing, results indicated that two of the calves (37R, 61R) may have suckled prior to sampling. The investigator indicated there was evidence that an additional two calves (53R, 72R) may had suckled. Results of testing from these two calves were negative for both antibody and GGT, indicating that if suckling had occurred, the colostrum was consumed close enough to the blood sampling that passive transfer had not yet occurred. Due to the question of validity of the pre-colostral serum sampling, all four calves were removed from further consideration in the study. Two serum samples were lost due to malfunctions during the processing of the serum; therefore these two calves were also removed from further consideration in the study. The remaining 61 calves from the second trimester group 2 were all negative for antibody to IBR, BVD 1 and BVD 2. The blood samples from all calves were negative for IBR virus isolation and BVD 1 and BVD 2 testing by RT PCR. There were no post calving losses in this group due to health problems.

d. Discussion:

This study was completed in four working cow/calf herds, three located near Ainsworth, Nebr. and a fourth located in Alberta, Canada. Cows and heifers enrolled in the study were vaccinated prior to breeding and at the time of enrollment in the trial with vaccine containing field dose levels of cytopathic modified live IBR and BVD Type 1 and BVD Type 2 components (Boehringer Ingelheim).

For the non-serological Nebraska portion of the trial, data from a total of 580 cattle, 306 vaccinates and 274 placebo controls, were obtained for the first trimester. Data from a total of 472 cattle, 237 vaccinates and 235 placebo controls, were obtained for the second trimester. Data from a total of 534 cattle, 267 vaccinates and 267 controls were obtained for the third trimester.

All enrolled cattle were followed through calving and the calving outcome recorded. Any fetuses or calves recovered from enrolled cattle were subjected to full necropsy that included tests specific to detect IBR and BVD viral agents, both by histological techniques and by virus isolation. There were no positive results in any of the tests that would indicate IBR or BVD was involved in any of the calf losses.

Dystocia, the major cause of new born calf loss, is defined as a difficult or obstructive calving process. For the purposes of this trial, a diagnosis of dystocia as responsible for calf loss was made based upon observations made by the producer and/or Site Veterinarian. The observations were recorded either during calving or at the time of necropsy. Per the agreement made with the Center for Veterinary Biologics prior to the start of the study, calving losses diagnosed as due to dystocia were not included in the overall undiagnosed pregnancy loss rate for the enrolled cattle. After removal of calving losses due to dystocia, the overall undiagnosed calf losses for the cattle enrolled in the trial were below the 5% rate recommended in the guideline. The highest levels were seen in the first trimester group, with 2.3% and 2.2% for the vaccinates and placebo controls respectively. This is to be expected as the enrollment/trimester pregnancy check and vaccination for these cows and heifers was conducted in the first trimester. For the second and third trimester groups, the pregnancy check conducted at the time of enrollment presented the opportunity to eliminate any pregnancy losses that had occurred during the earlier parts of gestation. The level of pregnancy losses in all three trimesters are extremely low and prove the safety of the vaccination of these animals with the modified live vaccine component.

Heart blood and other body fluids, as available at necropsy, were tested for antibody to IBR, BVD 1 and BVD 2 by the laboratory. There were a total of six fetuses that tested positive for antibody, however, due to either site practices (forced feeding of colostrum) or testing problems due to sample toxicity/contamination and the inability to confirm the initial results, these results do not impact the outcome of the study.

Fetus from heifer 577 was reported to have a low levels of antibody to IBR in heart blood. This result was not confirmed. The heifer from the A&K herd aborted prior to the second (gestational) vaccination and was therefore not qualified for enrollment in the trial.

Three calves (207Y Group A $1^{st}$ trimester; 5013 Group A $3^{rd}$ trimester and 5020 Group B $3^{rd}$ trimester) died within approximately 48 hours of birth. Fluids from each of these calves showed relatively high antibody titers to IBR, BVD 1 and BVD 2. However, all three calves had either suckled or were force-fed (tubed) with colostrum prior to death, explaining the positive antibody results.

Fetus from cow 86, Group B, second trimester, died after birth by cesarean section. Death was due to dystocia. The calf presented with hydroperitoneum. Heart blood samples obtained at necropsy were reported as having low titers to BVD 1 and BVD 2. The diagnostic laboratory reported that this sample was found to be toxic to the cell cultures, and therefore the initial results could not be confirmed. The reported problems with toxicity of the serum sample and the inability to confirm the test results indicate that the original results should be considered suspect and, therefore do not impact the outcome of the study.

Fetus from heifer 5128, Group A, third trimester, died at birth due to dystocia. Testing for antibody on pleural fluid initially was reported as having a low titer to BVD 2, and negative for antibody to BVD Type 1. The diagnostic laboratory reported that this sample was found to be toxic to the cell cultures, and therefore the initial results could not be confirmed. The reported low antibody titer and the problems with toxicity of the pleural fluid sample and the inability to confirm the test results indicate that these results should be considered to be suspect and, therefore do not impact the outcome of the study.

In addition, blood samples were taken at the time that the enrollment vaccination (trimester vaccination) was administered. Paired blood samples were also obtained from cows and heifers at the time of diagnosis of pregnancy loss and at an interval of approximately two weeks after diagnosis. Those cattle diagnosed as open, with no recovery of fetal tissue, were of particular interest. The three samples (enrollment vaccination as well as paired samples) were tested to determine the level of antibody to IBR and BVD 1 and BVD 2 at the time of vaccination, at the time of diagnosis of pregnancy loss and at the interval post calf loss.

The serological results for IBR, BVD 1 and BVD 2 in these cattle were as expected for a well vaccinated herd. There were a number of cows and heifers that showed a significant rise in titer after vaccination, but none of the animals showed a significant rise between the time of sampling at the diagnosis of calf loss and the post-calving blood sampling, which would be indicative of a calf loss due to either IBR or BVD.

All calves at the Nebraska sites were followed for 4 weeks post partum. Rates of post partum illness, treatments and deaths in the enrolled calves in all three herds were very low. All three herds experienced minor illnesses that required treatment, most of which were episodes of scouring that persisted for 24 to 48 hours. The highest treatment rates were noted in the Williams herd (third trimester), in which the treatment rate was 3.8% in the vaccinates and 2.7% in the placebo controls. These treatment rates are low for working cow/calf herds.

The post-calving death rates in all three herds were very low and not above the rates that would be expected in normal working cow/calf herds. Necropsy results from all calf deaths were negative for virus pathogens in the post calving deaths.

At the Alberta site, the IBR, BVD 1 and BVD 2 serum neutralizing antibody status in pre-colostral serum samples was determined in a total of 61 calves from the second trimester and 59 calves from the third trimester. Six calves were removed from consideration in both the second and the third trimester due to either equipment malfunction or concerns on the validity of the pre-colostral sample status. The concerns over the validity of the samples were documented by the investigator in the study records. All serum samples from those calves having valid pre-colostral samples were negative for neutralizing antibody to IBR, BVD 1 and BVD 2.

8. Conclusion

The results of this study show no indication that vaccination of previously vaccinated pregnant cattle in the first, second or third trimester with the modified live IBR, BVD Type 1 and BVD 2 would result in deleterious effects to either the cow, heifer or the calves.

REFERENCES

The teachings and contents of all references (articles, patents, book portions, presentations, and the like) cited herein, including those listed below, are expressly incorporated by reference herein.

Baker, J. C. 1987. Bovine viral diarrhea virus: a review. J. Am. Vet. Med. Assoc. 190: 1449-1458.

Heinz, F. X., Collett, M. S., Purcell., R. H., Cold, E. A., Howard, C. R., Houghton, M., Moormann, R. J. M., Rice, C. M., and Thiel, H.-J. 2000. Familiy Flaviviridae. PP 859-878. In: Virus Taxonomy (van Regenmortel., H. H. V., Fauquet, C. M., and Bishop, D. H. L, Eds.). Academic Press, San Diego.

Lindenbach, B. D., and Rice, C. M. 2001. The pestiviruses. In Fields Virology, eds. Knipe, Moennig, V. and Plagemann, J. 1992. The pestiviruses. Adv. Virus Res. 41: 53-91.

Thiel, H.-J., Stark, R., Weiland, E., Rümenapf, T. & Meyers, G. 1991. Hog cholera virus: molecular composition of virions from a pestivirus. J. Virol. 65: 4705-4712.31.

The invention claimed is:

1. A method of preventing abortion in a pregnant cow, comprising administering a vaccine to the pregnant cow, wherein the vaccine comprises a modified live Infectious Bovine Rhinotracheitis (IBR) virus that has been passaged at least 4 times in bovine embryo kidney cells, 22 times in ovine cells and once in MDBK cells, modified live Bovine Viral Diarrhea Virus (BVDV) Type 1 of a Singer strain that has been passaged at least twice in bovine turbinate cells, modified live BVDV Type 2 of Strain 296 that has been passaged in bovine testicular cells at least six times, or in embryonic swine kidney cells at least 23 times, or in MDBK cells at least 23 times, and *Haemophilus somnus* bacterin wherein the pregnant cow was vaccinated with a therapeutically effective amount of a vaccine comprising IBR, BVDV Type I and BVDV Type 2 prior to pregnancy.

2. The method of claim 1, wherein the modified BVDV Singer strain is the one that is included in the BREED-BACK® FP5 vaccine.

3. The method of claim 1, wherein the modified live BVDV Type 2 Strain 296 is the one that is included in the BREED-BACK® FP5 vaccine.

4. The method of claim 1, wherein the modified live IBR is IBR Colorado 1 Strain.

5. The method of claim 4, wherein the modified live IBR Colorado 1 Strain is the one that is included in the BREED-BACK® FP5 vaccine.

6. The method of claim 1, wherein the vaccine further comprises an immunologically active component effective for treatment or prophylaxis of an infection caused by a *Leptospira* bacterium.

7. The method of claim 6, wherein the *Leptospira* bacterium is selected from the group consisting of: *Leptospira canicola, Leptospira grippotyphosa, Leptospira hardjo, Leptospira icterohaemorrhagiae*, and *Leptospira pomona.*

8. The method of claim 6, wherein the *Leptospira* bacterium comprises *Leptospira canicola, Leptospira grippotyphosa, Leptospira hardjo, Leptospira icterohaemorrhagiae*, and *Leptospira pomona.*

9. The method of claim 1, wherein the vaccine is selected from the group consisting of BREED-BACK™FP5-HS, EXPRESS™5-HS, EXPRESS™FP5-HS, BREED-BACK™FP10, EXPRESS™10, BREEDBACK™ FP10-HS, EXPRESS FP10-HS®, and combinations thereof.

10. The method of claim 1, further comprising the step of administering the vaccine to the pregnant cow during the first, second or third trimester of pregnancy.

11. The method of claim 1, wherein the vaccine prevents the incidence of one or more clinical signs of an infection caused by a microbe selected from the group consisting of Infectious Bovine Rhinotracheitis (IBR), Bovine Viral Diarrhea Virus (BVDV) Type 1, BVDV Type 2, and any combination thereof in a pregnant cow.

12. The method of claim 1, wherein the vaccine prevents the incidence of one or more clinical signs of an infection caused by a microbe selected from the group consisting of Infectious Bovine Rhinotracheitis (IBR), Bovine Viral Diarrhea Virus (BVDV) Type 1, BVDV Type 2, and any combination thereof in a fetus of a pregnant cow.

13. The method of claim 1, wherein the pregnant cow is a pregnant heifer.

* * * * *